US009163041B2

(12) United States Patent
Wan

(10) Patent No.: US 9,163,041 B2
(45) Date of Patent: *Oct. 20, 2015

(54) METAL UTILIZATION IN SUPPORTED, METAL-CONTAINING CATALYSTS

(75) Inventor: Kam-To Wan, Town and Country, MO (US)

(73) Assignee: Monsanto Technology LLC, St. Louis, MO (US)

( * ) Notice: Subject to any disclaimer, the term of this patent is extended or adjusted under 35 U.S.C. 154(b) by 256 days.

This patent is subject to a terminal disclaimer.

(21) Appl. No.: 13/557,700

(22) Filed: Jul. 25, 2012

(65) Prior Publication Data

US 2013/0023406 A1    Jan. 24, 2013

Related U.S. Application Data

(63) Continuation of application No. 12/434,360, filed on May 1, 2009, now Pat. No. 8,252,953.

(60) Provisional application No. 61/049,465, filed on May 1, 2008, provisional application No. 61/049,508, filed on May 1, 2008.

(51) Int. Cl.
*B01J 23/75* (2006.01)
*B01J 23/745* (2006.01)
(Continued)

(52) U.S. Cl.
CPC ............... *C07F 9/3813* (2013.01); *B01J 21/18* (2013.01); *B01J 23/42* (2013.01); *B01J 23/70* (2013.01); *B01J 23/74* (2013.01); *B01J 23/745* (2013.01); *B01J 23/75* (2013.01)

(58) Field of Classification Search
CPC ......... C07F 9/3813; B01J 21/18; B01J 23/42; B01J 23/70; B01J 23/72; B01J 23/74; B01J 23/745; B01J 23/75

USPC ............................. 502/182, 184, 185; 526/17
IPC ............ B01J 23/24,23/38, 23/42, 23/44, 23/72, B01J 23/745, 23/75, 23/89
See application file for complete search history.

(56) References Cited

U.S. PATENT DOCUMENTS 2,384,817 A    9/1945 Chitwood
3,340,097 A    9/1967 Hess et al.
(Continued)

FOREIGN PATENT DOCUMENTS

DE    19600741 A1    7/1996
EP    0055695 A1    7/1982
(Continued)

OTHER PUBLICATIONS

Vertes, CS., et al., "Mossbauer Spectroscopy Studies of Sn—Pt/Al2O3 Catalysts Prepared by Controlled Surface Reactions," Applied Catalysis, 1991, pp. 149-159, vol. 68.
(Continued)

*Primary Examiner* — Jun Li
(74) *Attorney, Agent, or Firm* — Senniger Powers LLP; Joseph A. Schaper

(57) ABSTRACT

Generally, the present invention relates to improvements in metal utilization in supported, metal-containing catalysts. For example, the present invention relates to methods for directing and/or controlling metal deposition onto surfaces of porous substrates. The present invention also relates to methods for preparing catalysts in which a first metal is deposited onto a support (e.g., a porous carbon support) to provide one or more regions of a first metal at the surface of the support, and a second metal is deposited at the surface of the one or more regions of the first metal. The invention further relates to use of catalysts prepared as detailed herein in catalytic oxidation reactions, such as oxidation of a substrate selected from the group consisting of N-(phosphonomethyl)iminodiacetic acid or a salt thereof, formaldehyde, and/or formic acid.

20 Claims, 93 Drawing Sheets

(51) Int. Cl.
    *B01J 21/18*     (2006.01)
    *C07F 9/38*     (2006.01)
    *B01J 23/70*     (2006.01)
    *B01J 23/42*     (2006.01)
    *B01J 23/74*     (2006.01)

(56) References Cited

U.S. PATENT DOCUMENTS

| | | |
|---|---|---|
| 3,799,758 A | 3/1974 | Franz et al. |
| 3,835,000 A | 9/1974 | Frazier et al. |
| 3,871,998 A | 3/1975 | Rase et al. |
| 3,927,080 A | 12/1975 | Gaertner |
| 3,950,402 A | 4/1976 | Franz |
| 3,954,848 A | 5/1976 | Franz |
| 3,956,370 A | 5/1976 | Parry et al. |
| 3,969,398 A | 7/1976 | Hershman |
| 4,026,950 A | 5/1977 | Le Ludec |
| 4,147,719 A | 4/1979 | Franz |
| 4,186,110 A | 1/1980 | Jalan et al. |
| 4,190,605 A | 2/1980 | Muench et al. |
| 4,225,727 A | 9/1980 | Kamiyama et al. |
| 4,264,776 A | 4/1981 | Hershman et al. |
| 4,325,842 A | 4/1982 | Slaugh et al. |
| 4,325,843 A | 4/1982 | Slaugh et al. |
| 4,326,992 A | 4/1982 | Slaugh et al. |
| 4,333,916 A | 6/1982 | Iwai et al. |
| 4,345,038 A | 8/1982 | McCandlish et al. |
| 4,351,962 A | 9/1982 | Gradeff et al. |
| 4,415,479 A | 11/1983 | Puskas et al. |
| 4,476,102 A | 10/1984 | McCandish et al. |
| 4,486,356 A | 12/1984 | Bakel |
| 4,492,770 A | 1/1985 | Blanchard et al. |
| 4,507,250 A | 3/1985 | Bakel |
| 4,522,708 A | 6/1985 | Leclercq et al. |
| 4,525,294 A | 6/1985 | Sartori et al. |
| 4,579,689 A | 4/1986 | Hershman et al. |
| 4,582,650 A | 4/1986 | Felthouse |
| 4,624,937 A | 11/1986 | Chou |
| 4,654,429 A | 3/1987 | Balthazor et al. |
| 4,696,771 A | 9/1987 | Floyd |
| 4,696,772 A | 9/1987 | Chou |
| 4,775,498 A | 10/1988 | Gentilcore |
| 4,782,183 A | 11/1988 | Goto et al. |
| 4,794,054 A | 12/1988 | Ito et al. |
| 4,810,426 A | 3/1989 | Fields, Jr. et al. |
| 4,851,131 A | 7/1989 | Grabiak et al. |
| 4,921,991 A | 5/1990 | Lacroix |
| 4,970,128 A | 11/1990 | Itoh et al. |
| 4,978,649 A | 12/1990 | Surovikin et al. |
| 5,023,369 A | 6/1991 | Fields, Jr. |
| 5,024,905 A | 6/1991 | Itoh et al. |
| 5,077,431 A | 12/1991 | Fields, Jr. |
| 5,079,107 A | 1/1992 | Jalan |
| 5,087,740 A | 2/1992 | Smith |
| 5,091,561 A | 2/1992 | Riley et al. |
| 5,095,140 A | 3/1992 | Fields, Jr. |
| 5,096,866 A | 3/1992 | Itoh et al. |
| 5,112,787 A | 5/1992 | Falke et al. |
| 5,162,563 A | 11/1992 | Nishihira et al. |
| 5,178,971 A | 1/1993 | Itoh et al. |
| 5,179,228 A | 1/1993 | Ramon et al. |
| 5,189,005 A | 2/1993 | Watanabe et al. |
| 5,225,391 A | 7/1993 | Stonehart et al. |
| 5,292,936 A | 3/1994 | Franczyk |
| 5,338,716 A | 8/1994 | Triplett et al. |
| 5,356,849 A | 10/1994 | Matviya et al. |
| 5,367,112 A | 11/1994 | Franczyk |
| 5,372,981 A | 12/1994 | Witherspoon |
| 5,410,085 A | 4/1995 | Birkenstock et al. |
| 5,427,761 A | 6/1995 | Grindatto et al. |
| 5,439,859 A | 8/1995 | Durante et al. |
| 5,500,485 A | 3/1996 | Hodgkinson |
| 5,585,083 A | 12/1996 | Kielin et al. |
| 5,602,276 A | 2/1997 | Stern et al. |
| 5,606,107 A | 2/1997 | Smith |
| 5,627,125 A | 5/1997 | Ebner et al. |
| 5,658,839 A | 8/1997 | De Agudelo et al. |
| 5,688,994 A | 11/1997 | Baysdon et al. |
| 5,689,000 A | 11/1997 | Ebner |
| 5,739,390 A | 4/1998 | Franczyk |
| 5,759,944 A | 6/1998 | Buchanan et al. |
| 5,783,737 A | 7/1998 | Metivier |
| 5,876,867 A | 3/1999 | Itoh et al. |
| 5,882,619 A | 3/1999 | Heineke et al. |
| 5,916,840 A | 6/1999 | Ebner |
| 5,989,648 A | 11/1999 | Phillips |
| 6,005,140 A | 12/1999 | Morgenstern et al. |
| 6,153,753 A | 11/2000 | Johnson et al. |
| 6,278,017 B1 | 8/2001 | Stern et al. |
| 6,376,708 B1 | 4/2002 | Morgenstern et al. |
| 6,417,133 B1 | 7/2002 | Ebner et al. |
| 6,436,816 B1 | 8/2002 | Lee et al. |
| 6,528,201 B1 | 3/2003 | Hitomi |
| 6,528,680 B1 | 3/2003 | Aust et al. |
| 6,586,621 B2 | 7/2003 | Leiber et al. |
| 6,670,301 B2 | 12/2003 | Adzic et al. |
| 6,689,505 B1 | 2/2004 | Albers et al. |
| 6,689,711 B2 | 2/2004 | Lefebvre |
| 6,696,384 B2 | 2/2004 | McCrae et al. |
| 6,706,662 B2 | 3/2004 | Morgenstern et al. |
| 6,764,874 B1 | 7/2004 | Zhang et al. |
| 6,913,739 B2 | 7/2005 | Shore et al. |
| 6,956,005 B2 | 10/2005 | Leiber |
| 6,963,009 B2 | 11/2005 | Leiber et al. |
| 7,015,351 B2 | 3/2006 | Haupfear et al. |
| 7,060,385 B2 | 6/2006 | Kato et al. |
| 7,309,675 B1 | 12/2007 | Renner et al. |
| 7,329,778 B2 | 2/2008 | Morgenstern et al. |
| 2001/0002424 A1 | 5/2001 | Siebenhaar et al. |
| 2002/0016503 A1 | 2/2002 | Leiber et al. |
| 2002/0068836 A1 | 6/2002 | Haupfear et al. |
| 2002/0121460 A1 | 9/2002 | Moy et al. |
| 2003/0004054 A1* | 1/2003 | Ito et al. ........... 502/178 |
| 2003/0171611 A1 | 9/2003 | Leiber |
| 2003/0228972 A1 | 12/2003 | Birss et al. |
| 2003/0229246 A1 | 12/2003 | Leiber et al. |
| 2005/0142428 A1 | 6/2005 | Daimon et al. |
| 2010/0130774 A1* | 5/2010 | Wan et al. ........... 562/17 |

FOREIGN PATENT DOCUMENTS

| | | |
|---|---|---|
| EP | 0098034 A2 | 4/1983 |
| EP | 0019445 B1 | 5/1983 |
| EP | 0162035 A2 | 11/1985 |
| EP | 0408528 A1 | 1/1991 |
| EP | 0595124 A1 | 5/1994 |
| EP | 0680948 A1 | 11/1995 |
| EP | 0801978 A1 | 10/1997 |
| EP | 1067108 A2 | 1/2001 |
| EP | 1236509 A1 | 9/2002 |
| EP | 1524711 A2 | 4/2005 |
| EP | 1653535 A1 | 5/2006 |
| FR | 2798079 A1 | 9/1999 |
| FR | 2798135 A1 | 9/1999 |
| GB | 1468109 | 3/1977 |
| GB | 1601715 | 11/1981 |
| WO | 9532150 A1 | 11/1995 |
| WO | 9619485 A1 | 6/1996 |
| WO | 9835930 A1 | 8/1998 |
| WO | 9941260 A1 | 8/1999 |
| WO | 9943430 | 9/1999 |
| WO | 0001707 A1 | 1/2000 |
| WO | 0009517 | 2/2000 |
| WO | 0062926 A1 | 10/2000 |
| WO | 0107447 A1 | 2/2001 |
| WO | 0128679 A1 | 4/2001 |
| WO | 0192272 A2 | 12/2001 |
| WO | 02098557 A1 | 12/2002 |
| WO | 03068387 A1 | 8/2003 |
| WO | 2006031198 A1 | 3/2006 |
| WO | 2006031938 A2 | 3/2006 |
| WO | 2006124959 A2 | 11/2006 |

(56) References Cited

FOREIGN PATENT DOCUMENTS

| WO | 2008025750 A1 | 3/2008 | |
|---|---|---|---|
| WO | WO2008025751 A1 * | 3/2008 | B01J 23/38 |

OTHER PUBLICATIONS

Wang, H., et al., "Effect of the Pre-Treatment of Carbon Black Supports on the Activity of Fe-Based Electrocatalysts for the Reduction of Oxygen," Journal of Physical Chemistry B, 1999, pp. 2042-2049, vol. 103, American Chemical Society.
Watanbe, M., et al., "Electrocatalysis by Ad-Atoms: Part XIII. Preparation of Ad-electrodes with Tin Ad-Atoms for Methanol, Formaldehyde and Formic Acid Fuel Cells," J. Electroanal. Chem., 1985, pp. 367-375, vol. 191.
Weng, L.T., et al., "Characterization of Electrocatalysts for Oxygen Reduction by TOF SIMS," Secondary Ion Mass Spectrometry, Proceedings of the International Conference on Secondary Ion Mass Spectrometry, 9th, Yokohama, 1994, pp. 442-445, Wiley, Chicester, United Kingdom.
Weng, L.T., et al., "Surface Characterization by Time-of-Flight SIMS of a Catalyst for Oxygen Electroreduction: Pyrolyzed Cobalt Phthalocyanine-On-Carbon Black," Applied Surface Science, 1995, pp. 9-21, vol. 84, Elsevier Science B.V.
Autolab Application Note, "A Simple Experimental Protocol for Platinum Deposition on Gold Electrodes," Appl-040-1.
CRC Handbook of Chemistry and Physics, 79th Edition, 1998, "Ionization Potentials of Atoms and Atomic Ions," pp. 10-175 to 10-176, D.R. Lide, Ed., CRC Press, Boca Raton, FL.
English Language Abstract of AU5828580.
Webb et al., "Analytical Methods in Fine Particle Technology," Chapter 6, pp. 232-235, First Edition, 1997 printing, Micromeritics Instrument Corp; Atlanta, Georgia.
Adzic et al., "Low Pt Loading Electrocatalysts," Materials Science Department, Brookhaven National Laboratory, Upton, NY 11973-5000; http://www1.eere.energy.gov/hydrogenandfuelcells/pdfs/merit03/81_bnl_radoslav_adzic.pdf; accessed Jan. 17, 2008, 22 pages.
Ku Yu et al., "Underpotential Deposition and Galvanic Replacement for Fuel Cell Catalysis," Apr. 24th, 2007; inbt.jhu.edu/igert/if_UPD_presentationre2.ppt; accessed Jan. 17, 2008, 29 pages.
Partial International Search Report, PCT/US2009/042562, dated Nov. 13, 2009, 8 pages.
International Search Report, PCT/US2009/042562, dated Mar. 19, 2010, 2 pages.
Qian et al., "PtM/C Catalyst Prepared Using Reverse Micelle Method for Oxygen Reduction Reaction in PEM Fuel Cells", Journal of Physical Chemistry, 2008, 112: 1146-1157.
Akita et al., "Analytical TEM observation of Au—Pd nanoparticles prepared by sonochemical method", Catalysis Today, 2008, vol. 131, pp. 90-97.
Alvarez-Merino, M., et al., "Tungsten Catalysts Supported on Activated Carbon," Journal of Catalysis, 2000, pp. 363-373, vol. 192, Academic Press.
Alves, M.C.M., et al., "Characterization of New Systems for the Catalytic Electroreduction of Oxygen by Electrochemistry and X-Ray Absorption Spectroscopy," NATO ASI Series, Series C: Mathematical and Physical Sciences, Synchrotron Techniques in Interfacial electrochemistry, 1994, pp. 281-293, vol. 432, Kluwer Academic Press, the Netherlands.
Andrew, M.R. et al., "The Characterization of Pt/Sn Catalyst for the Electrochemical Oxidation of Methanol," Journal of Applied Electrochemistry, 1976, pp. 99-106, vol. 6.
Arico, A.S., et al., "Methanol Oxidation on Carbon-Supported Pt—Sn Electrodes in Silicotungstic Acid," Electrochimica Acta., 1994, pp. 691-700, vol. 30, No. 5.
Balakrishnan, K., et al., "A Chemisorption and XPS Study of Bimetallic Pt—Sn/Al2O3 Catalysts," Journal of Catalysis, 1991, pp. 287-306, vol. 127.

Bett, J.S., et al., "Platinum-macrocycle Co-catalysts for the Electrochemical Oxidation of Methanol," Electrochimica Acta, 1998, pp. 3645-3655, vol. 43, No. 24, Elsevier Science Ltd., Great Britain.
Birss, V.I., et al., "Non-Noble Metal Catalysts for PEM Oxygen Reduction Based on Sol Gel Derived Cobalt Nigrogen Compounds," Electrochemical Society Proceedings, 2002, pp. 89-98, vol. 2002-31, Electrochemical Society.
Bouwkamp-Wijnoltz, A.L., et al., "Electrochemical Reduction of Oxygen: An Alternative Method to Prepare Active CoN4 Catalysts," Electrochimica Acta., 1999, pp. 379-386, vol. 45.
Bouwkamp-Wijnoltz, A.L., et al., "On Active-Site Heterogeneity in Pyrolyzed Carbon-Supported Iron Porphyrin Catalysts for the Electrochemical Reduction of Oxygen: An In Situ Mossbauer Study," J. Phys. Chem., 2002, pp. 12993-13001, vol. 106, No. 50.
Bridgewater, A.J. et al., "Reactions of Carbon Monoxide with Hydrogen Over Molybdenum/Charcoal Catalysts," Journal of Catalysis, 1982, pp. 116-125, vol. 78.
Burch, R., "The Oxidation State of Tin and the Interaction Between Platinum and Tin," Journal of Catalysis, 1981, pp. 348-359.
Cameron, "Carbon as Supports for Precious Metal Catalysts," Catalysis Today, 1990, pp. 113-137, vol. 7.
Campbell, S., et al., "Effect of Bi and Sn Adatoms on Formic Acid and Methanol Oxidation at Well Defined Platinum Surfaces," Journal of Chemical Society, Faraday Trans., 1992, pp. 833-841, vol. 88, No. 6.
Cathro, K.J., "The Oxidation of Water-Soluble Organic Fuels Using Platinum-Tin Catalysts," J. Electrochem. Soc.: Electrochemical Technology, 1969, pp. 1608-1611, vol. 116, No. 11.
Collman, J.P., et al., "Electrode Catalysis of the Four-Electron Reduction of Oxygen to Water by Dicobalt Face-to-Face Prophyrins," Journal of American Chemical Society, 1980, pp. 6027-6036, vol. 102, American Chemical Society.
Coloma, F., et al., "Preparation of Platinum Supported on Pregraphitized Carbon Blacks," Langmuir, 1994, pp. 750-755, vol. 10.
Coloma, F., et al., "Heat-Treated Carbon Blacks as Supports for Platinum Catalysts," Journal of Catalysis, 1995, pp. 299-305, vol. 154.
Cote, R. et al., "Non-Noble Metal-Based Catalysts for the Reduction of Oxygen in Polymer Electrolyte Fuel Cells," Journal of New Materials for Electrochemical Systems I, 1998, pp. 7-16.
Dandekar A. et al., "Carbon-Supported Copper Catalysts," Journal of Catalysis, 1999, pp. 131-154, vol. 183, Academic Press.
Deng, C.Z., et al., "Sputtered Cobalt—Carbon—Nitrogen Thin Films as Oxygen Reduction Electrocatalysts," J. Electrochem. Soc., 1998, pp. 3507-3512, vol. 145, No. 10.
Dignard-Bailey, L., et al., "Graphitization and Particle Size Analysis of Pyrolyzed Cobalt Phthalocyanine/Carbon Catalysts for Oxygen Reduction in Fuel Cells," Journal of Materials Research, 1994, pp. 3203-3209, vol. 9, No. 12, Materials Research Society.
Dubinin, M.M., "Macroporous Structures of Carbonaceous Adsorbents," Carbon, 1982, pp. 195-200, vol. 20, No. 3.
Durand, R.R., et al., "Catalysis of Dioxygen Reduction at Graphite Electrodes by an Adsorbed Cobalt(II) Porphyrin," Journal of Electroanalytical Chemistry, 1982, pp. 273-289, vol. 134, No. 2, Elsevier Sequoia S.A., Lausanne, The Netherlands.
Ewen, R.J., et al. "X-Ray Photoelectron Spectroscopy of Clean and Gas-Doped Films of Phthalocyanines," Journal of Physics Condensed Matter, 1991, pp. S303-S310, vol. 3, IOP Puplication Ltd., An Institute of Physics Journal, United Kingdom.
Faubert, G. et al., "Heat-Treated Iron and Cobalt Tetraphenylporphyrins Adsorbed on Carbon Black: Physical Characterization and Catalytic Properties of these Materials for the Reduction of Oxygen in Polymer Electrolyte Fuel Cells," Electrochimica Acta, 1996, pp. 1689-1701, vol. 41, No. 10, Elsevier Science Ltd., Great Britain.
Faubert, G. et al., "Activation and Characterization of Fe-Based Catalysts for the Reduction of Oxygen in Polymer Electrolyte Fuel Cells," Electrochimica Acta., 1998, pp. 1969-1984, vol. 43, No. 14-15, Elsevier Science Ltd., Great Britain.
Faubert, G. et al., "Iron Catalysts Prepared by High-Temperature Pyrolysis of Tetraphenyprophyrins Adsorbed on Carbon Black for

(56) References Cited

OTHER PUBLICATIONS

Oxygen Reduction in Polymer Electrolyte Fuel Cells," Electrochimica Acta., 1998, pp. 341-353, vol. 43, No. 3-4, Elsevier Science Ltd. Great Britain.

Faubert, G. et al., "Oxygen Reduction Catalysts for Polymer Electrolyte Fuel Cells from the Pyrolysis of Fell Acetate Absorbed on 3,4,9,10-Perylenetetracaroxylic Dianhydride," Electrochimica Acta, 1999, pp. 2589-2603, vol. 44, Elsevier Science Ltd.

Franco et al., "Synthesis and Characterization of PtRu/C Catalysts Obtained by Colloidal and Deposition Methods for Fuel Cell Applications," Materials Research, 2005, pp. 117-120, vol. 8, No. 2.

Franklin, T., et al., "The effect of Anionic Poisons on the Catalytic Oxidation of Formaldehyde on Platinum," Journal of Catalysis, 1976, pp. 360-366, vol. 42.

Franz, J.E., et al., "Glyphosate: An Unique Global Herbicide, Chapter 8—Methods of Preparing Glyphosate", American Chemical Society, 1997, pp. 233-262, Washington, D.C.

Fusy et al., "Growth and Reactivity of Evaporated Platinum Films on Cu(111): a Study by AES, RHEED and Adsorption of Carbon Monoxide and Xenon," Applied Surface Science, 1996, pp. 211-220, vol. 93.

Gallezot, P., et al., "Catalytic Oxidations with Air for Clean and Selective Transformations of Polyols," Catalysis of Organic Reactions, 1994, pp. 331-340, (Scaros et al., eds. Marcel Dekker, Inc., New York, NY).

Gokagac, G., et al., "Characterisation of Carbon-Supported Pt—Sn Bimetallic Catalysts for the Electrochemical Oxidation of Methanol," Journal of Chemical Society, 1993, pp. 151-157, vol. 89, No. 1, Faraday Trans.

Granger, P., et al., "Kinetics of No and Co Reaction Over Platinum Catalysts," Journal of Catalysis, 1998, pp. 304-314, Academic Press.

Grasselli, R., et al., "Selective Oxidation of Hydrocarbons with Heterogeneous Catalysts Containing Tellurium," Proc. Int. Symp. Uses Selenium Tellurium, 1989, 4th, pp. 609-632, Selenium—Tellurium Dev. Assoc., Darien, Conn.

Gupta, S., et al., "Methanol-Tolerant Electrocatalysts for Oxygen Reductin in a Polymer Electrolyte Membrane Fuel Cell," J. Appl. Electrochem., 1998, pp. 673-682, vol. 28, No. 7.

He, P., et al., "Oxygen Reduction Catalysts for Polymer Electrolyte Fuel Cells From the Pyrolysis of Various Transition Metal Acetates Adsorbed on 3,4,9,10-Peryleneetracarboxylic Dianhydride," Journal of New Material for Electrochemical Systems, 1999, pp. 243-251, vol. 2, Journal of New Material Electrochemcial Systems.

Hirai, T., et al., "The Influence of Catalyst-Supporting Methods on Electrochemical Activity and the Resultant Stability of Air Electrodes Activated with Iron Pythalocyanine," Journal of Applied Electrochemistry, 1985, pp. 441-445, Chapman and Hall Ltd.

Jasinski, R., "Cobalt Phthalocyanine as a Fuel Cell Cathode," Journal of the Electrochemical Society, 1965, pp. 526-528, vol. 112, No. 5.

Kijenski et al., "Platinum Deposited on Monolayer Supports in Selective Hydrogenation of Furfural to Furfuryl Alcohol," Applied Catalysis A: General, Jul. 10, 2002, pp. 171-182, vol. 233, issues 1-2.

Kim, T.K., et al., "Preparation of Carbon-Supported Platinum Catalysts: Adsorption Mechanism of Anionic Platinum Precursor onto Carbon Support," Carbon, 1992, pp. 467-475, vol. 30, No. 3.

Kim, K.T., et al., "Surface and Catalytic Properties of Iron—Platinum/Carbon Electrocatalysts for Cathodic Oxygen Reduction in PAFC," J. Electrochem. Soc., 1993, pp. 31-36, vol. 140, No. 1.

Kim, D.W., et al., "CoMo Bimetallic Nitride Catalysts for Thiophene HDS," Catalysis Letters, 1997, pp. 91-95, vol. 43, No. 1-2, J.C. Baltzer AG, Science Publishers.

Kim et al., "Platinum Nanofilm Formation by EC-ALE via Redox Replacement of UPD Copper: Studies Using in-Situ Scanning Tunneling Microscopy," J. Phys. Chem. B, 2006, pp. 17998-18006, vol. 110.

Kimura, H., et al., "Palladium Based Multi-Component Catalytic Systems for the Alcohol to Carboxylate Oxidation Reaction," Applied Catalysis A: General, 1993, pp. 143-169, vol. 95.

Kimura, H., "Selective Oxidation of Glycerol on a Platinum—bismuth Catalyst by Using a Fixed Bed Reactor," Applied Catalysis A: General, 1993, pp. 147-158, vol. 105.

Krulik et al., "Metallic Coatings," Kirk-Othmer Encyclopedia of Chemical Technology Fourth Edition, pp. 258, 272, and 291, vol. 16.

Lalande, G., et al., "Rotating Disk Electrode Measurements on the Electrocatalytic Activity of Heat-Treated Carbon Supported Cobalt Phthalocyanine Catalysts for Oxygen Reduction," Electrochemical Society Proceedings, 1994, pp. 418-429, Electrochemical Society.

Lalande, G., et al., "Catalytic Activity and Stability of Heat-Treated Iron Phthalocyanines for the Electroreduction of Oxygen in Polymer Electrolyte Fuel Cells," Journal of Power Sources, 1996, pp. 227-237, vol. 61, Elsevier Science S.A.

U.S. Pat. No. 6,337,298, 01/2002, Ebner et al. (withdrawn).

Lalande, G., et al., "Chromium-Based Electrocatalysts for Oxygen Reduction in Polymer Electrolyte Fuel Cells," New Materials for Fuel Cell and Modern Battery Systems II, Proceedings of the International Symposium on New Materials for Fuel Cell and Modern Battery Systems, 2nd Montreal, 1997, pp. 768-777, Ecole Polytechnique De Montreal, Montreal Que.

Lalande, G., et al., "Electroreduction of Oxygen in Polymer Electrolyte Fuel Cells by Activated Carbon Coated Cobalt Nanocrystallites Produced by Electric Arc Discharge," Chemistry of Materials, 1997, pp. 784-790, vol. 9, No. 3, American Chemical Society.

Lalande, G., et al., "Is Nitrogen Important in the Formulation of Fe-based Catalysts for Oxygen Reduction in Solid Polymer Fuel Cells?," Electrochimica Acta., 1997, pp. 1379-1388, vol. 42, No. 9, Great Britain.

Lefevre, M., et al., "Functionalities of Fe-Based Catalyst Evidenced by ToF-SIMS in Relation with the Electroreduction of Oxygen in Polymer Electrolyte Fuel Cells," Secondary Ion Mass Spectrometry, SIMS XII, Proceedings of the International Conference on Secondary Ion Mass Spectrometry, 1999, pp. 447-450, Elsevier Science, Amsterdam, Netherlands.

Lefevre, M., et al., "O2 Reduction in PEM Fuel Cells: Activity and Active Site Structural Information for Catalysts Obtained by the Pyrolysis at High Temperature of Fe Precursors," Journal of Physical Chemistry B, 2000, pp. 11238-11247, vol. 104, American Chemical Society.

Lefevre, M., et al., "Molecular Oxygen Reduction in PEM Fuel Cells: Evidence for the Simultaneous Presence of Two Active Sites in Fe-Based Catalysts," Journal of Physical Chemistry, 2002, pp. 8705-8713, vol. 106, No. 34.

Levy, R.B., et al., "Platinum-Like Behavior of Tungston Carbide in Surface Catalysis," Science 1973, pp. 547-549, vol. 181.

Liang, C., et al., "Activated Carbon Supported Bimetallic CoMo Carbides Synthesized by Carbothermal Hydrogen Reduction," Carbon, 2003, pp. 1833-1839, vol. 41, Elsevier Science.

Lin, W.-F., et al., "On-Line FTIR Spectroscopic Investigations of Methanol Oxidation in a Direct Methanol Fuel Cell," J. Electrochem. Soc., 1997, pp. 1917-1922, vol. 144, No. 6.

Lin, C.A., et al., "Characterization of Boron—Nitride-Supported Pt Catalysts for the Deep Oxidation of Benzene," Journal of Catalysis, 2002, pp. 39-45, vol. 210, Elsevier Science, USA.

Luk'yanova, Z.V., et al., "Determination of the Surface Area of Platinum in Adsorption Catalysts from the Amount of 'Soluble' Platinum," Russian Journal of Physical Chemistry, 1979, pp. 225-227, vol. 53, No. 2.

Maier, L., "Organic Phosphorus Compounds 95. A Simple Method for the Preparation of N-Dihydroxyphosphonylmethyl-Glycine(Glyphosate)," Phosphorus, Sulfur, and Silicon, 1991, pp. 65-67, vol. 61.

Mallat, T., "Preparation of Promoted Platinum Catalysts of Designed Geometry and the Role of Promoters in the Liquid-Phase Oxidation of 1-Methoxy-2-Propanol," Journal of Catalysis, 1993, pp. 237-253, vol. 342.

Mallat, T., et al., "Oxidation of Alcohols with Molecular Oxygen on Platinum Metal Catalysts in Aqueous Solutions," Catalysis Today, 1994, pp. 247-284, vol. 19.

Margitfalvi, J., et al., "Supported Bimetallic Catalysts Prepared by Controlled Surface Reactions," Ch. 11, pp. 373-409.

(56) References Cited

OTHER PUBLICATIONS

Markusse, A.P., et al., "Platinum Deactivation: in situ EXAFS During Aqueous Alcohol Oxidation Reaction," Catalysts Letters, 1998, pp. 141-145.

Merlen, E., et al., "Characterization of Bimetallic Pt—Sn/Al2O3 Catalysts: Relationship Between Particle Size and Structure," Journal of Catalysis, 1996, pp. 178-188, vol. 159.

Milad, I.K., et al., "A Comparison of Bulk Metal Nitride Catalysts for Pyridine Hydrodenitrogenation," Catalysis Letters, 1998, pp. 113-119, vol. 52, No. 1-2, J.C. Baltzer AG, Science Publishers.

Mordenti, D., et al., "New Synthesis of Mo2C 14 nm in Average Size Supported on a High Specific Surface Area Carbon Material," Journal of Solid State Chemistry, 1998, pp. 114-120, vol. 141, Academic Press.

Mukerjee, S., et al., "An In Situ X-Ray Absorption Spectroscopy Investigations of the Effect of Sn Additions to Carbon-Supported Pt Electrocatalysts," Journal of the Electrochemical Society, 1999, pp. 600-606, vol. 146, No. 2.

Murav'ev, V.I., "Carbonitriding in a Fluidized Bed of Carbon-Graphite Materials," Metal Science and Heat Treatment, 1976, pp. 492-495, vol. 18, No. 5-6, Consultants Bureau, New York.

Nagai, M., et al., "Catalytic Activity and Surface Properties of Nitride Molybdena-Alumnia for Carbazole Hydrogenitrogenation," Journal of Catalysis, 2000, pp. 128-137, vol. 191, Academic Press.

Nhut, J.M., et al., "Synthesis and Catalytic Uses of Carbon and Silicon Nanostructures," Catalysis Today, 2002, pp. 12-32, vol. 76, Elsevier Science B.V.

Nishihara, H., et al., "Electrochemical Olefin Epoxidation with Manganese meso-Tetraphenylporphyrin Catalyst and Hydrogen Peroxide Generation at Polymer-Coated Electrodes," Inorganic Chemistry, 1990, pp. 1000-1006, vol. 29, No. 5, American Chemical Society.

Ohta, R., et al., "Origin of N 1s Spectrum in Amorphous Carbon Nitride Obtained by X-Ray Photoelectron Spectroscopy," Thin Solid Films, 2003, pp. 296-302, vol. 434, Elsevier.

Okada, T., et al., "Oxygen Reduction of Heat-Treated Catalysts Based on Cobalt-Porphyrin Ion Complexes," J. Electrochem. Soc., 1998, pp. 815-822, vol. 145, No. 3.

Okada, T., et al., "Oxygen Reduction Characteristics of Graphite Electrodes Modified with Cobalt Di-Quinolyldiamine Derivatives," Electrochimica Acta, 2000, pp. 4419-4428, vol. 45, Elsevier Science Ltd., Great Britain.

Fournier, J. et al., "Activation of Various Fe-Based Precursors on Carbon Black and Graphite Supports to Obtain Catalysts for the Reduction of Oxygen in Fuel Cells," J. Electrochem. Soc., 1997, pp. 218-226, vol. 144, No. 1.

Oyama, S.T., et al. "Preparation and Characterization of Early Transition-Metal Carbides and Nitrides," Industrial & Engineering Chemistry Research, 1988, pp. 1639-1648, vol. 27, No. 9, American Chemical Society.

Oyama, S.T., "Preparation and Catalytic Properties of Transition Metal Carbides and Nitrides," Catalysis Today, 1992, pp. 179-200, vol. 15, Elsevier Science Publishers, B.V., Amsterdam.

Park, S., et al., "Electrocatalytic Pathways on Carbon-Supported Platinum Nanoparticles: Comparison of Particle-Size-Dependent Rates of Methanol, Formic Acid, and Formaldehyde Electroxidation," Langmuir, 2002, pp. 5792-5798, vol. 18.

Pinel, C., et al., "Effect of the Nature of Carbon Catalysts on Glyphosate Synthesis," Academic Press, 1999, pp. 515-519.

Ponec, V., et al., "Preparation and Characterization of Metal and Alloy Catalysts," Studies in Surface Science and Catalysis; Catalysis by Metal and Alloys, Ch. 7, pp. 299-391, vol. 95 (Delman, B., et al., eds, Elscvier Science B. V., Amsterdam, Netherlands.

Prado-Burgette, C., et al., "Effect of Carbon Support and Mean Pt Particle Size on Hydrogen Chemisorption by Carbon-Supported Pt Catalysts," Journal of Catalysis, 1991, pp. 397-404, vol. 128.

Prado-Burgette, C., et al., "The Effect of Oxygen Surface Groups of the Support on Platinum Despersion in Pt/Carbon Catalysts," Journal of Catalysis, pp. 98-106, vol. 115.

Riley, D., et al., "Homogeneous Catalysts for Selective Molecular Oxygen Driven Oxidative Decarboxylations," J. Am. Chem. Soc., 1991, pp. 3371-3378, vol. 113.

Riley, D., et al., "Vanadium (IV, V) Salts as Homogeneous Catalysts for the Oxygen Oxidation of N-(Phosphonomethyl)Iminodiacetic Acid to N-(Phosphonomethyl)Glycine," Inorg. Chem., 1991, pp. 4191-4197, vol. 30.

Rodriguez-Reinoso, F., et al., "Platinum Catalysts Supported on Activated Carbons," Journal of Catalysis, 1986, pp. 171-183, vol. 99.

Sedunov, V.K., et al., "Structure and Phase Composition of Surface Zones of Carburized and Carbonitrided Layers," Metal Science and Heat Treatment, 1977, pp. 742-745, vol. 19, No. 9-10, Consultants Bureau, New York.

Shekhobalova, V.I., et al., "Deactivation Mechanism of Platinum Catalysts During the Liquid-Phase Decomposition of Hydrogen Peroxide," Russian Journal of Physical Chemistry, 1979, pp. 1308-1309, vol. 53, No. 9.

Shekhobalova, V.I., et al., "Relationship Between the Shape of the Kinetic Curves for the Catalytic Decomposition of Hydrogen Peroxide and the Amount of 'Soluble' Metal in the Catalyst," Russian Journal of Physical Chemistry, 1979, pp. 917-918, vol. 53, No. 6.

Shekhobalova, V.I., et al., "Effect of Small Additions of Ki on the Properties of Pt Adsorption Catalysts," Russian Journal of Physical Chemistry, 1984, p. 1759, vol. 58, No. 11.

Singh, A., et al., "X-Ray Photoelectron Spectroscopy of Nitrogen-Implanted Cemented Tungsten Carbide(WC—Co)," Journal of Materials Science Letters, 1990, pp. 1101-1102, vol. 9, Chapman and Hall Ltd.

Takano, I., et al., "Nitrogenation of Various Transition Metals by N2+-Ion Implantation," Applied Surface Science, 1989, pp. 25-32, vol. 37, Elsevier Science Publishers B.V., North-Holland, Amsterdam.

Toda, T., et al., "Enhancement of the Electroreduction of Oxygen on Pt Alloys with Fe, Ni, and Co," Journal of the Electrochemical Society, 1999, pp. 3750-3756, vol. 146, No. 10.

Torrens, M.A., "Mossbauer Studies on Oxo-Bridged Iron (III) Porphines," Journal of the American Chemical Society, 1972, pp. 4160-4162, vol. 94, No. 12.

Van Dam, H.E., et al., "Preparation of Platinum on Activated Carbon," Journal of Catalysis, 1991, pp. 335-349, vol. 131.

Van Der Putten, A., et al., "Oxygen Reduction on Pyrolysed Carbon-Supported Transition Metal Chelates," Journal of Electroanalytical Chemistry and Interfacial Electrochemistry, 1986, pp. 233-244, vol. 205, Elsevier Sequoia S. A. Lausanne, The Netherlands.

Van Veen, J.A.R., et al., "Effect of Heat Treatment on the Performance of Carbon-supported Transition-metal Chelates in the Electrochemical Reduction of Oxygen," J. Chem Soc., Faraday Trans. 1, 1981, pp. 2827-2843, vol. 77, The Royal Society of Chemistry, United Kingdom.

Van Veen, J.A.R., et al., "On the Effect of a Heat Treatment on the Structure of Carbon-Supported Metalloprophyrins and Phthalocyanines," Electrochimica Acta, 1988, pp. 801-804, vol. 33, No. 6, Pergamon Press plc., Great Britain.

* cited by examiner

Mechanism One: *In-Situ* Coupling

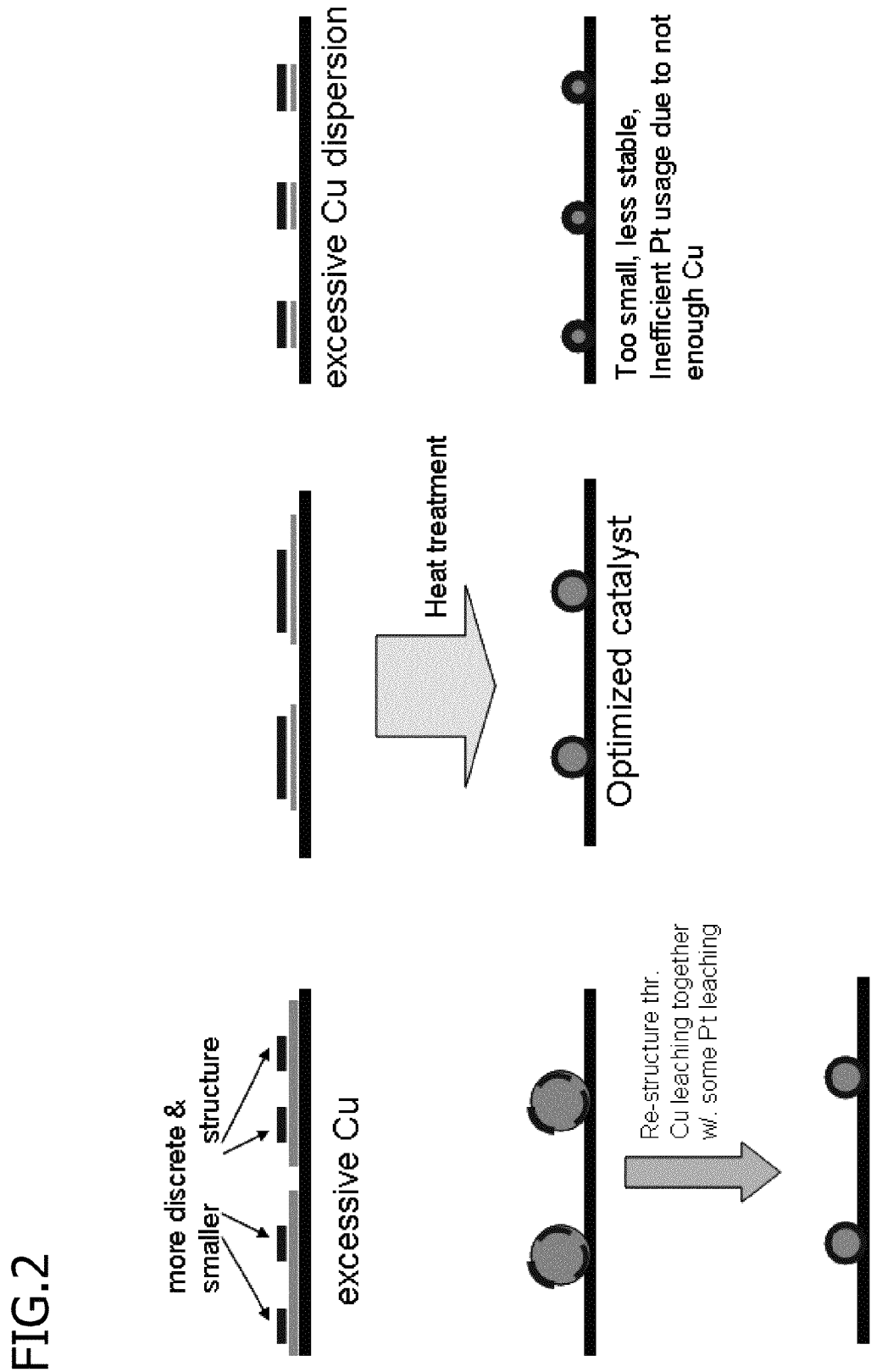

FIG. 128
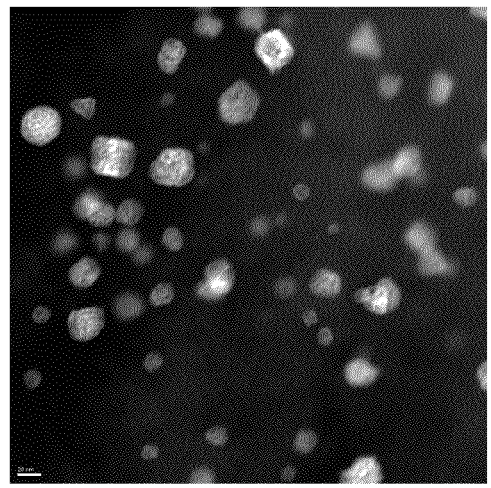
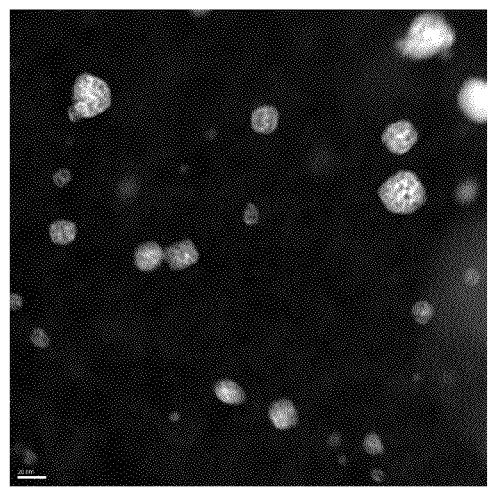
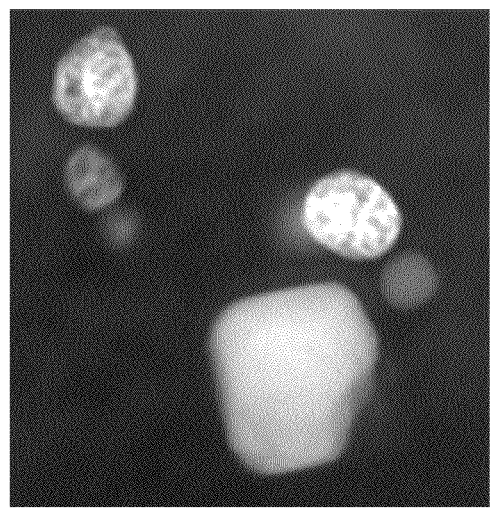

Cu (001)

METAL UTILIZATION IN SUPPORTED, METAL-CONTAINING CATALYSTS

REFERENCE TO RELATED APPLICATIONS

This application is a continuation of U.S. patent application Ser. No. 12/434,360, filed May 1, 2009, which issued as U.S. Pat. No. 8,252,953 on Aug. 28, 2012, and which claims the benefit of U.S. Provisional Application Ser. No. 61/049,465, filed May 1, 2008 and U.S. Provisional Application Ser. No. 61/049,508, filed May 1, 2008, the entire contents of which are incorporated herein by reference.

FIELD OF THE INVENTION

Generally, the present invention relates to improvements in metal utilization in supported, metal-containing catalysts. For example, the present invention relates to methods for directing and/or controlling metal deposition onto surfaces of porous substrates. More particularly, some embodiments of the present invention relate to methods for treating porous substrates (e.g., porous carbon substrates or porous metal substrates) to provide treated substrates having one or more desirable properties (e.g., a reduced surface area attributable to pores having a nominal diameter within a predefined range) that may be utilized as supports for metal-containing catalysts.

The present invention also relates to methods for preparing catalysts in which a first metal is deposited onto a support (e.g., a porous carbon support) to provide one or more regions of a first metal at the surface of the support, and a second metal is deposited at the surface of the one or more regions of the first metal. Generally, the electropositivity of the first metal (e.g., copper or iron) is greater than the electropositivity of the second metal (e.g., a noble metal such as platinum) and the second metal is deposited at the surface of the one or more regions of the first metal by displacement of the first metal.

The present invention further relates to treated substrates, catalyst precursor structures and catalysts prepared by these methods.

The invention further relates to use of catalysts prepared as detailed herein in catalytic oxidation reactions, such as oxidation of a substrate selected from the group consisting of N-(phosphonomethyl)iminodiacetic acid or a salt thereof, formaldehyde, and/or formic acid.

BACKGROUND OF THE INVENTION

N-(phosphonomethyl)glycine (known in the agricultural chemical industry as glyphosate) is described in Franz, U.S. Pat. No. 3,799,758. Glyphosate and its salts are conveniently applied as a post-emergent herbicide in aqueous formulations. It is a highly effective and commercially important broad-spectrum herbicide useful in killing or controlling the growth of a wide variety of plants, including germinating seeds, emerging seedlings, maturing and established woody and herbaceous vegetation, and aquatic plants.

Various methods for producing glyphosate are known in the art, including various methods utilizing carbon-supported noble metal-containing catalysts. See, for example, U.S. Pat. No. 6,417,133 to Ebner et al. and Wan et al. International Publication No. WO 2006/031938. Generally, these methods include the liquid phase oxidative cleavage of N-(phosphonomethyl)iminodiacetic acid (i.e., PMIDA) in the presence of a carbon-supported noble metal-containing catalyst. Along with glyphosate product, various by-products may form, such as formaldehyde, formic acid (which is formed by the oxidation of the formaldehyde by-product); aminomethylphosphonic acid (AMPA) and methyl aminomethylphosphonic acid (MAMPA), which are formed by the oxidation of N-(phosphonomethyl)glycine; and iminodiacetic acid (IDA), which is formed by the de-phosphonomethylation of PMIDA. These by-products may reduce glyphosate yield (e.g., AMPA and/or MAMPA) and may introduce toxicity issues (e.g., formaldehyde). Thus, significant by-product formation is preferably avoided.

It is generally known in the art including, for example, as described in Ebner et al. U.S. Pat. No. 6,417,133 and by Wan et al. in International Publication No. WO 2006/031938, that carbon primarily catalyzes the oxidation of PMIDA to glyphosate and the noble metal primarily catalyzes the oxidation of by-product formaldehyde to carbon dioxide, and water. The catalysts of Ebner et al. U.S. Pat. No. 6,417,133 and Wan et al. WO 2006/031938 have proven to be highly advantageous and effective catalysts for the oxidation of PMIDA to glyphosate and the oxidation of by-products formaldehyde and formic acid to carbon dioxide and water without excessive leaching of noble metal from the carbon support. These catalysts are also effective in the operation of a continuous process for the production of glyphosate by oxidation of PMIDA. Even though these catalysts are effective in PMIDA oxidation and are generally resistant to noble metal leaching under PMIDA oxidation conditions, there exist opportunities for improvement.

For example, the distribution and/or size of the pores of the porous substrates utilized in noble metal-containing catalysts may impact catalyst performance and metal utilization. Methods to introduce compounds (i.e., pore blocking compounds) within pores of substrates to modify metal deposition are known in the art. See, for example, U.S. Pat. No. 5,439,859 to Durante et al.

One object of the present invention is development of catalysts effective for the oxidation of PMIDA, formaldehyde, and/or formic acid that more efficiently utilize the costly noble metal, and methods for their preparation. More efficient metal usage may provide catalysts more active than conventional catalysts. Another object of the present invention is development of methods for preparing effective catalysts that require a reduced proportion of costly noble metal as compared to conventional catalysts, while still exhibiting suitable activity.

SUMMARY OF THE INVENTION

This invention provides catalysts and methods for preparing catalysts that are useful in heterogeneous oxidation reactions, including the preparation of glyphosate by the oxidation of PMIDA.

Briefly, therefore, the present invention is directed to oxidation catalysts comprising a particulate carbon support, a first metal, and a second metal, the support having at its surface particles comprising the first metal and the second metal.

In at least one embodiment, the second metal distribution within at least one of the particles as characterized by energy dispersive x-ray (EDX) line scan analysis as described in Protocol B produces a second metal signal that varies by no more than about 25% across a scanning region having a dimension that is at least about 70% of the largest dimension of the at least one particle. In a further embodiment, the second metal distribution within at least one of the particles as characterized by EDX line scan analysis as described in Protocol B produces a second metal signal that varies by no more than about 20% across a scanning region having a dimension that is at least about 60% of the largest dimension of the at least one particle. In another embodiment, the second metal distribution within at least one of the particles as characterized by EDX line scan analysis as described in Protocol B produces a second metal signal that varies by no more than about 15% across a scanning region having a dimension that is at least about 50% of the largest dimension of the at least one particle.

The present invention is also directed to an oxidation catalyst comprising a particulate carbon support, copper, and platinum, the support having at its surface particles comprising copper and platinum. The platinum distribution within at least 70% (number basis) of the particles as characterized by EDX line scan analysis as described in Protocol B produces a platinum signal that varies by no more than about 25% across a scanning region having a dimension that is at least about 70% of the largest dimension of said particles.

The present invention is further directed to an oxidation catalyst comprising a particulate carbon support, a first metal, and a noble metal, the support having at its surface metal particles comprising the first metal and the noble metal. The catalyst is characterized as chemisorbing at least 975 µmoles CO per gram of catalyst per gram noble metal during Cycle 2 of static carbon monoxide chemisorption analysis as described in Protocol A.

The present invention is also directed to an oxidation catalyst comprising a particulate carbon support, a first metal, and a noble metal, the support having at its surface metal particles comprising the first metal and the noble metal, wherein the metal particles comprise a core comprising the first metal and a shell at least partially surrounding the core and comprising the noble metal, wherein at least about 70% of the noble metal is present within the particle shell.

In a further embodiment, the present invention is directed to an oxidation catalyst comprising a particulate carbon support, platinum, and copper, the support having at its surface metal particles comprising platinum and copper, wherein the atom percent of platinum at the surface of the particles is at least about 10%.

In a still further embodiment, the present invention is directed to an oxidation catalyst comprising a particulate carbon support, a first metal, and a noble metal, the support having at its surface metal particles comprising the first metal and the noble metal, wherein the metal particles comprise a core comprising the first metal and a shell at least partially surrounding the core and comprising the noble metal; and the catalyst is characterized as chemisorbing at least 975 µmoles CO per gram of catalyst per gram noble metal during Cycle 2 of static carbon monoxide chemisorption analysis as described in Protocol A.

In another embodiment, the present invention is directed to an oxidation catalyst comprising a particulate carbon support, platinum, and copper, the support having at its surface metal particles comprising platinum and copper, wherein the atom percent of platinum at the surface of the particles is at least about 5%; and the catalyst is characterized as chemisorbing at least 500 µmoles CO per gram of catalyst per gram noble metal during Cycle 2 of static carbon monoxide chemisorption analysis as described in Protocol A.

In a still further embodiment, the present invention is directed to an oxidation catalyst comprising a particulate carbon support, a first metal, and a noble metal, the support having at its surface metal particles comprising the first metal and the noble metal, wherein the metal particles comprise a core comprising the first metal and a shell at least partially surrounding the core and comprising the noble metal; the noble metal constitutes less than 5% by weight of the catalyst; and the catalyst is characterized as chemisorbing at least about 800 µmoles CO per gram of catalyst per gram noble metal during Cycle 2 of static carbon monoxide chemisorption analysis as described in Protocol A.

The present invention is also directed to an oxidation catalyst comprising a particulate carbon support having metal particles at a surface thereof comprising a first metal and a second metal, wherein the electropositivity of the first metal is greater than the electropositivity of the second metal and the second metal is deposited by displacement of first metal ions of one or more regions of first metal of a catalyst precursor structure; and the weight ratio of the second metal to the first metal is at least about 0.25:1.

The present invention is also directed to processes for oxidizing a substrate selected from the group consisting of N-(phosphonomethyl)iminodiacetic acid or a salt thereof, formaldehyde, and formic acid. Generally, the process comprises contacting the substrate with an oxidizing agent in the presence of an oxidation catalyst prepared by the methods detailed herein and/or as described herein. For example, in one embodiment the catalyst comprises a first metal, a noble metal, and a porous carbon support, the catalyst comprising one or more first metal regions at the surface of the carbon support and one or more noble metal regions at the surface of the one or more first metal regions, wherein the first metal has an electropositivity greater than the electropositivity of the noble metal.

The present invention is further directed to various methods for preparing a catalyst comprising a first metal, a second metal, and a porous support having a surface comprising pores of a nominal diameter within a predefined range and pores of a nominal diameter outside the predefined range.

In one embodiment, the method comprises disposing a pore blocking agent within pores of the porous support having a nominal diameter within the predefined range, the pore blocking agent having at least one dimension relative to the openings of the pores having a nominal diameter within the predefined range such that the pore blocking agent is preferentially retained within the pores; contacting the support with a first metal deposition bath comprising an aqueous medium and ions of the first metal, thereby depositing the first metal at the surface of the porous support within the pores having a nominal diameter outside the predefined range to form a catalyst precursor structure having one or more regions of the deposited first metal at the surface of the support among the pores of a nominal diameter outside the predefined range; and contacting the catalyst precursor structure with a second metal deposition bath comprising ions of the second metal, thereby depositing the second metal at the surface of the catalyst precursor structure.

In another embodiment, the method comprises contacting the support and a first metal deposition bath comprising an aqueous medium, ions of the first metal, and a coordinating agent that forms a coordination compound with the first metal having at least one dimension larger than the nominal diameter of the pores within the predefined range, thereby depositing the first metal at the surface of the support within the pores having a nominal diameter outside the predefined range to form a catalyst precursor structure having one or more regions of the deposited first metal at the surface of the support; and contacting the catalyst precursor structure with a second metal deposition bath comprising ions of the second metal, thereby depositing the second metal at the surface of the catalyst precursor structure.

The present invention is also directed to methods for preparing catalysts comprising a first metal, a second metal, and a porous carbon support.

In one embodiment, the method comprises contacting the porous carbon support with a first metal deposition bath comprising ions of the first metal, thereby depositing the first metal at the surface of the porous carbon support to form a catalyst precursor structure having one or more regions of the deposited first metal at the surface of the support, wherein the first metal has an electropositivity greater than the electropositivity of the second metal; contacting the catalyst precursor structure with a second metal deposition bath comprising ions of the second metal, thereby depositing the second metal at the surface of the catalyst precursor structure by displacement of the first metal from one or more of the regions; and heating the catalyst precursor structure having the first and second metals deposited at the surface of the catalyst precursor structure to a temperature of at least about 500° C. in a non-oxidizing environment.

In a further embodiment, the method comprises contacting the porous carbon support with a first metal deposition bath comprising ions of the first metal, thereby depositing the first metal at the surface of the porous carbon support to form a catalyst precursor structure having one or more regions of the deposited first metal at the surface of the support, wherein the carbon support has a Langmuir surface area of at least about 500 m$^2$/g and the first metal has an electropositivity greater than the electropositivity of the second metal; and contacting the catalyst precursor structure with a second metal deposition bath comprising ions of the second metal, thereby depositing the second metal at the surface of the catalyst precursor structure by displacement of the first metal from one or more of the regions.

The present invention is also directed to methods for preparing a catalyst comprising a first metal, a noble metal, and a porous support. In one embodiment, the method comprises contacting the support and a first metal deposition bath comprising an aqueous medium, ions of the first metal and a coordinating agent that forms a coordination compound with the first metal, thereby depositing the first metal at the surface of the support to form a catalyst precursor structure having one or more regions of the deposited first metal at the surface of the support, wherein the first metal has an electropositivity greater than the electropositivity of the noble metal; and contacting the catalyst precursor structure with a noble metal deposition bath comprising ions of the noble metal, thereby depositing the noble metal at the surface of the catalyst precursor structure by displacement of the first metal from one or more of the regions.

In a further embodiment, the method comprises contacting the support with a first metal deposition bath comprising an aqueous medium and ions of the first metal, thereby depositing first metal at the surface of the support to form a catalyst precursor structure having one or more regions of the deposited first metal at the surface of the support, wherein the first metal has an electropositivity greater than the electropositivity of the noble metal; and contacting the catalyst precursor structure with a noble metal deposition bath comprising ions of the noble metal, thereby depositing the noble metal at the surface of the catalyst precursor structure by displacement of the first metal from one or more of the regions, wherein substantially all the noble metal is deposited by the displacement, or the noble metal ions consist essentially of noble metal ions having an oxidation number of 2.

In another embodiment, the method comprises contacting the support with a first metal deposition bath comprising an aqueous medium, ions of the first metal, and a pore blocking agent, thereby disposing the pore blocking agent within pores of the substrate having a nominal diameter within a predefined range, wherein the pore blocking agent has at least one dimension relative to the opening of the pores of the predefined range sufficient such that the pore blocking agent is preferentially retained within the pores, and depositing first metal at the surface of the support within pores having a nominal diameter outside the predefined range, thereby forming a catalyst precursor structure having one or more regions of the deposited first metal at the surface of the support, wherein the first metal has an electropositivity greater than the electropositivity of the noble metal; and contacting the catalyst precursor structure with a noble metal deposition bath comprising ions of the noble metal, thereby depositing the noble metal at the surface of the catalyst precursor structure by displacement of the first metal from one or more of regions.

The present invention is also directed to methods for preparing a catalyst comprising a first metal, a noble metal, and a porous support having a surface comprising pores of a nominal diameter within a predefined range and pores of a nominal diameter outside the predefined range. In one embodiment, the method comprises contacting the support and a first metal deposition bath comprising an aqueous medium, ions of the first metal and a coordinating agent that forms a coordination compound with the first metal having at least one dimension larger than the nominal diameter of the pores within the predefined range, thereby depositing the first metal at the surface of the support within the pores having a nominal diameter outside the predefined range to form a catalyst precursor structure having one or more regions of the deposited first metal at the surface of the support; and contacting the catalyst precursor structure with a noble metal deposition bath comprising ions of the noble metal, thereby depositing the noble metal at the surface of the catalyst precursor structure.

The present invention is also directed to methods for preparing catalysts comprising copper, platinum, and a porous carbon support.

In one embodiment, the method comprises contacting the support with a copper deposition bath comprising copper ions and a coordinating agent in the absence of an externally applied voltage, thereby depositing copper at the surface of the porous carbon support to form a catalyst precursor structure having one or more regions of deposited copper at the surface of the support; and contacting the catalyst precursor structure and a platinum deposition bath comprising platinum ions, thereby depositing platinum at the surface of the catalyst precursor structure by displacement of copper from one or more of the regions.

In another embodiment, the method comprises contacting the support and a copper deposition bath comprising copper ions in the absence of an externally applied voltage, thereby depositing copper at the surface of the carbon support to form a catalyst precursor structure having one or more regions of deposited copper at the surface of the support, wherein the carbon support has a Langmuir surface area of at least about 500 m$^2$/g prior to deposition of copper thereon; and contacting the catalyst precursor structure and a platinum deposition bath comprising platinum ions, thereby depositing platinum at the surface of the catalyst precursor structure by displacement of copper from one or more of the regions.

In a further embodiment, the method comprises contacting the support and a copper deposition bath comprising copper ions in the absence of an externally applied voltage, thereby depositing copper at the surface of the carbon support to form a catalyst precursor structure having one or more regions of deposited copper at the surface of the support; contacting the catalyst precursor structure and a platinum deposition bath comprising platinum ions, thereby depositing platinum at the surface of the catalyst precursor structure by displacement of copper from one or more of the regions; and heating the surface of the catalyst precursor having platinum at the surface of the one or more copper regions to a temperature of at least about 500° C. in a non-oxidizing environment.

The present invention is also directed to methods for preparing catalysts comprising iron, platinum, and a porous carbon support.

In one embodiment, the method comprises contacting the support with an iron deposition bath comprising iron ions and a coordinating agent in the absence of an externally applied voltage, thereby depositing iron at the surface of the porous carbon support to form a catalyst precursor structure having one or more regions of deposited iron at the surface of the support; and contacting the catalyst precursor structure and a platinum deposition bath comprising platinum ions, thereby depositing platinum at the surface of the catalyst precursor structure by displacement of iron from one or more of the regions.

In another embodiment, the method comprises contacting the support and an iron deposition bath comprising iron ions in the absence of an externally applied voltage, thereby depositing iron at the surface of the carbon support to form a catalyst precursor structure having one or more regions of deposited iron at the surface of the support, wherein the carbon support has a Langmuir surface area of at least about 500 m$^2$/g prior to deposition of iron thereon; and contacting the catalyst precursor structure and a platinum deposition bath comprising platinum ions, thereby depositing platinum at the surface of the catalyst precursor structure by displacement of iron from one or more of the regions.

In a further embodiment, the method comprises contacting the support and an iron deposition bath comprising iron ions in the absence of an externally applied voltage, thereby depositing iron at the surface of the carbon support to form a catalyst precursor structure having one or more regions of deposited iron at the surface of the support; contacting the catalyst precursor structure and a platinum deposition bath comprising platinum ions, thereby depositing platinum at the surface of the catalyst precursor structure by displacement of iron from one or more of the regions; and heating the surface of the catalyst precursor having platinum at the surface of the one or more iron regions in a non-oxidizing environment.

The present invention is also directed to methods for treating a porous substrate to prepare a modified porous substrate having a reduced surface area attributable to pores having a nominal diameter within a predefined range.

In one embodiment, the method comprises disposing a pore blocking agent within pores of the porous substrate having a nominal diameter within the predefined range, the pore blocking agent having at least one dimension relative to the opening of the pores having a nominal diameter within the predefined range sufficient such that the pore blocking agent is preferentially retained within the pores.

In another embodiment, the method comprises introducing a pore blocking compound into the pores of the porous substrate, the pore blocking compound being susceptible to a conformational change such that the pore blocking compound is retained within pores of the porous substrate having a diameter within the predefined range.

In a further embodiment, the method comprises introducing into the pores having a nominal diameter within a predefined range compounds capable of forming a pore blocking compound having at least one dimension such that the pore blocking compound is retained within the pores having a nominal diameter within a predefined range.

The present invention is also directed to methods for treating porous substrates having micropores and larger diameter pores to prepare a modified porous substrate having a reduced micropore surface area.

In one embodiment, the method comprises disposing a pore blocking agent within micropores of the porous substrate, the pore blocking agent having at least one dimension relative to the micropore openings such that the pore blocking agent is preferentially retained within the pores.

In another embodiment, the method comprises introducing a pore blocking compound into the micropores of the porous substrate, the pore blocking compound being susceptible to a conformational change such that the pore blocking compound is retained within micropores of the porous substrate.

In a further embodiment, the method comprises introducing into the micropores of the substrate compounds capable of forming a pore blocking compound having at least one dimension such that the pore blocking compound is retained within the micropores.

In a still further embodiment, the method comprises introducing a pore blocking composition into the micropores of the porous substrate, the pore blocking composition comprising a substituted cyclohexane derivative.

The present invention is also directed to methods for preparing a catalyst comprising a metal at the surface of a porous substrate wherein the metal is preferentially excluded from pores of the porous substrate having a nominal diameter within a predefined range. In one embodiment, the method comprises (i) introducing one or more precursors of a pore blocking compound into pores of the porous substrate, wherein: at least one of the pore blocking compound precursors is susceptible to a conformational change to form a pore blocking compound that is retained within pores of the porous substrate having a nominal diameter within the predefined range, or at least two pore blocking compound precursors are capable of forming a pore blocking compound having at least one dimension such that the pore blocking compound is retained within pores of the porous substrate having a nominal diameter within a predefined range; (ii) preferentially removing the pore blocking compound from the pores of the porous substrate having a nominal diameter outside the predefined range to prepare a modified porous substrate having a reduced surface area attributable to pores having a nominal diameter within the predefined range; and (iii) contacting the surface of the modified porous substrate with a solution containing the metal.

In another embodiment, the present invention is directed to a porous substrate having a pore blocking compound within pores of the porous substrate having a nominal diameter within a predefined range. The pore blocking compound is retained within the pores having a nominal diameter within a predefined range due to the pore blocking compound having at least one dimension that is greater than openings of the pores having a nominal diameter within a predefined range, or the pore blocking compound exhibiting a conformation that prevents the pore blocking compound from exiting through openings of pores having a nominal diameter within the predefined range.

The present invention is directed to treated porous substrates having a pore blocking compound within micropores of the porous substrate. In one embodiment, the micropore surface area of the treated substrate is no more than about 70% of the micropore surface area of the porous substrate prior to treatment. In another embodiment, the pore blocking compound is selected from the group consisting of the condensation product of a substituted cyclohexane derivative and a glycol, the condensation product of a di-substituted cyclohexane derivative and a glycol, and combinations thereof.

Other objects and features will be in part apparent and in part pointed out hereinafter.

BRIEF DESCRIPTION OF THE DRAWINGS

FIG. 2 depicts heat treatment of a first and second metal-impregnated support in accordance with the present invention.

FIG. 128 provides STEM micrographs described in Example 57.

DETAILED DESCRIPTION OF THE PREFERRED EMBODIMENTS

Figure 1A:
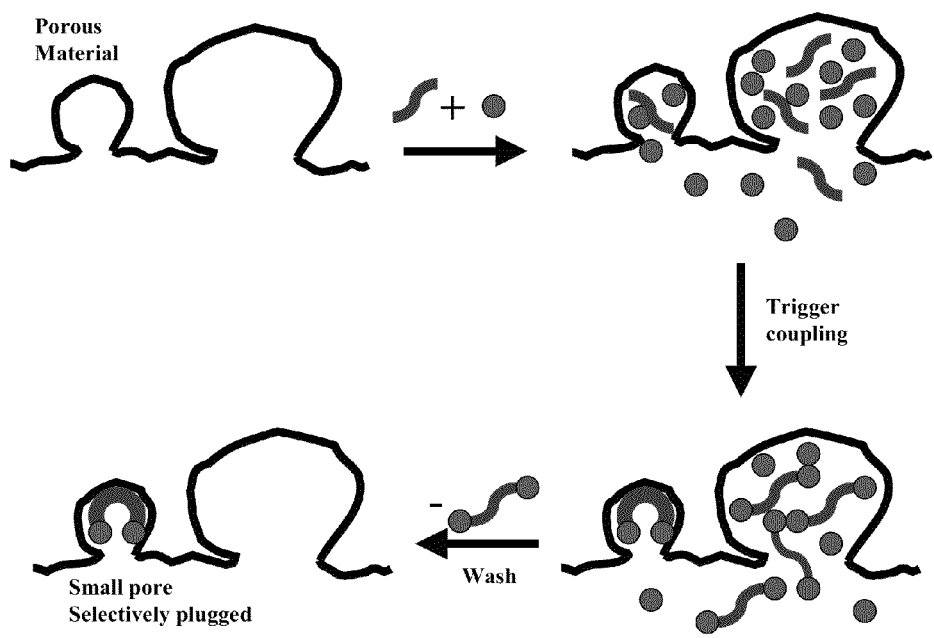
FIGS. 1A-1C are graphical representations of pore blockers in accordance with the present invention.

Described herein are catalyst preparation methods providing improvements in metal utilization in supported, metal-containing catalysts. Generally, various embodiments of the present invention include controlling and/or directing metal deposition onto the surface of a porous substrate. Controlling or directing metal deposition can be used to address one or more problems associated with the preparation of conventional supported, metal-containing catalysts.

For example, one potential drawback associated with conventional platinum on carbon catalysts is the susceptibility of relatively small platinum-containing particles to leaching during liquid phase catalytic oxidation reactions as compared to larger metal-containing particles. Excessive leaching of metal particles results in metal loss and represents inefficient metal usage. Furthermore, in the case of PMIDA oxidation, these relatively small platinum-containing crystallites are believed to contribute to undesired by-product formation (e.g., IDA). Relatively small platinum-containing crystallites are also believed to be more susceptible to deactivation than larger particles (e.g., by deactivation of metal-containing active sites in the presence of the reaction medium and/or by coking of the catalyst). It is believed that a significant portion of the relatively small metal particles are at the surface of the carbon support within relatively small pores and that the small pores may act to trap and prevent these relatively small platinum crystallites from agglomerating into larger particles that are generally more resistant to leaching and generally do not promote IDA formation. In addition, metal deposited at the surface of a porous substrate within the relatively small pores is believed to be less accessible to reactants than metal deposited within larger pores, and thereby contributes less to catalyst activity.

Various methods described herein for directing and/or controlling metal deposition generally involve treating porous substrates by disposing or introducing one or more pore blocking compounds within pores of a predefined size range. The methods described herein may be used to selectively block pores within a certain size domain without significantly affecting other pores of the substrate so as to provide advantageous catalytic surface area. As detailed herein, including the Examples, various embodiments of the present invention provide a porous substrate including a pore blocking compound disposed and preferentially retained within relatively small pores (e.g., micropores, or pores having a nominal diameter of less than about 20 Å). The presence of the pore blocking compound within the pores of the substrate may be indicated by a reduced proportion of surface area attributable to the relatively small pores (e.g., a reduced proportion of micropore surface area) and/or by a reduced contribution to the porosity of the substrate by the relatively small pores. It is believed that the presence of the pore blocking compound within the micropores of the treated substrate reduces, and preferably substantially prevents, metal deposition at the substrate surfaces within these pores, thereby directing metal deposition to other surfaces of the substrate and within larger pores. The presence of the pore blocker is thus currently believed to reduce formation of small metal crystallites within the micropores that are resistant to agglomeration, readily leached and/or deactivated, and represent inefficient metal usage.

In addition to or separate from the effect of controlling or directing the location of metal deposition (e.g., by disposing within or introducing a pore blocking compound into pores of a substrate), the manner of metal deposition may promote more efficient metal usage as well. For example, various catalysts described herein include and/or are prepared from a support having one or more regions of a first metal at the surface of the support, and a second metal at the surface of the one or more regions of the first metal.

The first metal is selected to have a greater electropositivity than the second metal and the second metal is deposited at the surface of the one or more regions of the first metal by displacement of the first metal from the one or more regions at the surface of the support. More particularly, the second metal may be deposited by near atom-for-atom replacement of the first metal by the second metal. It is currently believed that metal deposition in this manner promotes formation of a relatively thin layer comprising second metal atoms and may in fact form a near monolayer of second metal atoms deposited at the surface of the first metal regions (e.g., a layer of second metal atoms at the surface of the one or more regions of first metal no more than about 3 atoms thick). Heating the carbon support having the first and second metals thereon forms metal particles comprising the first and second metal. The metal particles formed contain the second metal in a form that represents more efficient second metal utilization. For example, the composition of a significant fraction of the metal particles is generally rich in first metal content, thereby providing a relatively low proportion of unexposed second metal throughout the particles (e.g., a first metal-rich bimetallic alloy). Additionally or alternatively, metal particles formed upon subsequent heating may have a relatively thin shell comprising the second metal (e.g., a layer no more than about 3 atoms thick) at least partially surrounding a core predominantly comprising the first metal.

I. Porous Substrate Treatment

Disposing within and/or introducing a pore blocking agent or compound (also referred to herein as a pore blocker) into pores of a porous substrate generally comprises contacting the substrate with the agent or compound, or a precursor (or precursors) thereof. In one embodiment, the pore blocking compound is preferentially retained within pores of the substrate within a selected size domain (e.g., micropores) by virtue of having at least one dimension larger than the openings of the pores, thereby inhibiting the agent from exiting the selected pores. In various embodiments, the pore blocking agent may be formed from one or more pore blocking agent precursors introduced into the substrate pores. Additionally or alternatively, and regardless of whether the pore blocking agent is introduced into the pores or formed in situ (i.e., formed from one or more agent precursors introduced into the pores), the agent may be retained within pores of the substrate within a selected size domain by virtue of an induced conformational change in the pore blocking agent such that the pore blocking agent is dimensionally inhibited from exiting the selected pores. A conformational change in the pore blocking agent may be induced within selected pores by virtue of interactions between the pore blocking agent and the walls of the pores. In accordance with one embodiment, a pore blocking agent is disposed within and preferentially retained within micropores of the porous substrate to produce a treated substrate for metal deposition exhibiting a reduced proportion of micropore surface area.

It is to be understood that reference to one or more precursors contemplates compositions that ultimately function as a pore blocking agent upon entry into pores (e.g., by virtue of at least one dimension of the compound and/or by virtue of a conformational change in the compound after entry into the pores). Additionally or alternatively, reference to one or more precursors may refer to one or more compounds that combine or react to form the pore blocking agent once disposed within and/or introduced into the pores of the substrate. Regardless of whether a compound that ultimately functions as the pore blocker is introduced into or disposed within the pores of the substrate, or whether components that combine to form the pore blocker are introduced into or disposed within the pores, the mechanism by which the pore blocker is believed to function (i.e., by virtue of having at least one dimension larger than pore openings, either initially or following a conformational change) is the same.

In various embodiments the pore blocker comprises a compound having at least one dimension such that, after entry into pores, the pore blocker is preferentially retained within those pores falling within a selected size domain. Of course, it is to be understood that the pore blocker likewise typically has at least one dimension that permits entry into the pores, but it is currently believed that the pore blocker typically assumes an orientation and/or conformation within the pores such that the dimension greater than the pore opening prevents the pore blocking compound from exiting the pore.

As noted above, in accordance with one embodiment, the pore blocker is preferentially retained within substrate micropores. However, this does not exclude the pore blocker or precursor(s) thereof from also entering pores of a size that are not within this predefined range upon contact with the porous substrate. For example, pore blocker may enter pores having a nominal diameter greater than about 20 Å (e.g., pores having a nominal diameter of from about 20 Å to about 3000 Å, commonly referred as meso- and macropores), but the pore blocker tends to subsequently exit and not be preferentially retained within these pores, although the pore blocking agent may remain in a minor portion of pores outside the micropore range.

A. Porous Substrate

Generally, the porous substrate or supporting structure for the catalytic metal-containing active phase may comprise any material suitable for deposition of one or more metals thereon. Preferably, the porous substrate is in the form of a carbon support. In general, the carbon supports used in the present invention are well known in the art including, for example, those detailed in U.S. Pat. No. 6,417,133 to Ebner et al. and by Wan et al. in WO 2006/031938 (the entire contents of which are incorporated herein by reference for all relevant purposes). Activated, non-graphitized carbon supports are preferred for noble metal on carbon catalysts used for PMIDA oxidation and provide the catalyst with robust mechanical integrity and high surface area for the metal-containing active phase. However, activated, non-graphitized carbon supports are not necessarily preferred in all instances and it should be understood that suitable catalysts for various other applications may be prepared utilizing carbon supports that are not activated and/or non-graphitized. In various particularly preferred embodiments, the supports are in the form of particulates (e.g., powders).

In various preferred embodiments (e.g., catalysts used for PMIDA oxidation), the carbon support contains a relatively low proportion of oxygen-containing functional groups (e.g., carboxylic acids, ethers, alcohols, aldehydes, lactones, ketones, esters, amine oxides, and amides). These functional groups may increase noble metal leaching and potentially increase noble metal agglomeration and particle growth during liquid phase oxidation reactions and thus reduce the ability of the catalyst to oxidize oxidizable substrates (e.g., PMIDA and/or formaldehyde). As used herein, an oxygen-containing functional group is "at the surface of the carbon support" if it is bound to an atom of the carbon support and is able to chemically or physically interact with compositions within the reaction mixture or with the metal atoms deposited on the carbon support. As described in U.S. Pat. No. 6,417,133 and by Wan et al. in WO 2006/031938, many of the oxygen-containing functional groups that reduce noble metal resistance to leaching and sintering and reduce the activity of the catalyst desorb from the carbon support as carbon monoxide when the catalyst is heated at a high temperature (e.g., 900° C.) in an inert atmosphere (e.g., helium or argon). Thus, measuring the amount of CO desorption from a fresh catalyst (i.e., a catalyst that has not previously been used in a liquid phase oxidation reaction) under high temperatures is one method that may be used to analyze the surface of the catalyst to predict noble metal retention and maintenance of catalyst activity. One way to measure CO desorption is by using thermogravimetric analysis with in-line mass spectroscopy ("TGA-MS"). Preferably, no more than about 1.2 mmole of carbon monoxide per gram of catalyst desorb from the catalyst of the present invention when a dry, fresh sample of the catalyst, after being heated at a temperature of about 500° C. for about 1 hour in a hydrogen atmosphere and before being exposed to an oxidant following the heating in the hydrogen atmosphere, is heated in a helium atmosphere is subjected to a temperature which is increased from about 20° C. to about 900° C. at about 10° C. per minute, and then held constant at about 900° C. for about 30 minutes. More preferably, no more than about 0.7 mmole of carbon monoxide per gram of fresh catalyst desorb under those conditions, even more preferably no more than about 0.5 mmole of carbon monoxide per gram of fresh catalyst desorb, and most preferably no more than about 0.3 mmole of carbon monoxide per gram of fresh catalyst desorb. A catalyst is considered "dry" when the catalyst has a moisture content of less than about 1% by weight. Typically, a catalyst may be dried by placing it into a $N_2$ purged vacuum of about 25 inches of Hg and a temperature of about 120° C. for about 16 hours.

As further described in U.S. Pat. No. 6,417,133 and by Wan et al. in WO 2006/031938, measuring the number of oxygen atoms at the surface of a fresh catalyst support is another method to analyze the catalyst to predict noble metal retention and maintenance of catalytic activity. Using, for example, x-ray photoelectron spectroscopy, a surface layer of the support which is about 50 Å in thickness is analyzed. Preferably, this analysis for a support suitable for use in connection with the oxidation catalysts described herein indicates a ratio of carbon atoms to oxygen atoms at the surface of the support of at least about 20:1. More preferably, the ratio is at least about 30:1, even more preferably at least about 40:1, even more preferably at least about 50:1, and most preferably at least about 60:1. In addition, the ratio of oxygen atoms to metal atoms at the surface preferably is less than about 8:1. More preferably, the ratio is less than about 7:1, even more preferably less than about 6:1, and most preferably less than about 5:1.

Typically, a support that is in particulate form may comprise a broad size distribution of particles. For powders, preferably at least about 95% of the particles are from about 2 to about 300 μm in their largest dimension, more preferably at least about 98% of the particles are from about 2 to about 200 μm in their largest dimension, and most preferably about 99% of the particles are from about 2 to about 150 μm in their largest dimension with about 95% of the particles being from about 3 to about 100 μm in their largest dimension. Particles greater than about 200 μm in their largest dimension tend to fracture into super-fine particles (i.e., less than 2 μm in their largest dimension), which may be more difficult to recover.

In the following discussion, specific surface areas of carbon supports and catalysts are typically provided in terms of the well-known Langmuir method using $N_2$. It is to be understood that these values generally correspond to those measured by the likewise well-known Brunauer-Emmett-Teller (B.E.T.) method using $N_2$.

The specific surface area of the carbon support prior to any treatment (e.g., disposing or introducing a pore blocking compound within pores of a substrate) in accordance with the present invention is generally at least about 500 $m^2/g$, at least about 750 $m^2/g$, at least about 1000 $m^2/g$, or at least about 1250 $m^2/g$. Typically, the specific surface area of the carbon support is from about 10 to about 3000 $m^2/g$, more typically from about 500 to about 2100 $m^2/g$, and still more typically from about 750 to about 1900 $m^2/g$ or from about 1000 to about 1900 $m^2/g$. In certain embodiments, the preferred specific surface area is from about 1000 to about 1700 $m^2/g$, 1000 to about 1500 $m^2/g$, from about 1100 to about 1500 $m^2/g$, from about 1250 to about 1500 $m^2/g$, from about 1200 to about 1400 $m^2/g$, or about 1400 $m^2/g$. Further in accordance with the present invention, the porous carbon support generally has a pore volume of at least about 0.1 ml/g, at least about 0.2 ml/g, or at least about 0.4 ml/g. Typically, the porous carbon support has a pore volume of from about 0.1 to about 2.5 ml/g, more typically from about 0.2 to about 2.0 ml/g and, still more typically, of from about 0.4 to about 1.5 ml/g.

It is to be noted that the present discussion focuses on pore blocking treatment to reduce micropore surface area of porous carbon substrates or supports for use in noble metal-containing catalysts suitable for use in PMIDA oxidation. However, it is to be understood that methods for treating a porous substrate by introduction of a pore blocking compound as described herein are generally applicable to preferentially blocking other pore size domains, other types of porous catalyst supports and/or porous carbon substrates used as supports for metals other than noble metals. For example, the methods of the present invention are suitable for treatment of porous Raney metals or alloys often referred to as sponges, such as those described in U.S. Pat. No. 7,329,778 to Morgenstern et al. and used as supports for copper-containing catalysts used in the dehydrogenation of primary amino alcohols. By way of further example, the methods of the present invention are also suitable for treatment of other non-carbon porous supports such as, for example, silicon dioxide ($SiO_2$), aluminum oxide ($Al_2O_3$), zirconium oxide ($ZrO_3$), titanium oxide ($TiO_2$), and combinations thereof.

B. Pore Blocking

In accordance with the present invention, the pore blocker used to selectively block micropores may be selected from a variety of compounds including, for example, various sugars (e.g., sucrose), 5- or 6-member ring-containing compounds (e.g., 1,3- and 1,4-disubstituted cyclohexanes), and combinations thereof. Compounds suitable for use in connection with selective blocking of micropores include 1,4-cyclohexanedimethanol (1,4-CHDM), 1,4-cyclohexanedione bis(ethylene ketal), 1,3- or 1,4-cyclohexanedicarboxylic acid, 1,4-cyclohexane dione monoethylene acetal, and combinations thereof.

In various embodiments, the pore blocker may comprise the product of a reaction (e.g., a condensation reaction) between one or more pore blocking compound precursors. Once formed, the resulting pore blocking compound may be preferentially retained within selected pores of the substrate by virtue of having at least one dimension that prevents the pore blocking compound from exiting the pores.

For example, it has been observed that the coupling product of a cyclohexane derivative and a glycol may be utilized as a micropore pore blocking agent for particulate carbon substrates used to support a noble metal or other metal catalyst. More particularly, the pore blocking agent may be the coupling product of a di-substituted, tri-substituted, or tetra-substituted cyclohexane derivative and a glycol. In particular, the cyclohexane derivative may be selected from the group consisting of 1,4-cyclohexanedione, 1,3-cyclohexanedione, 1,4-cyclohexanebis(methylamine), and combinations thereof. The glycol is generally selected from the group consisting of ethylene glycol, propylene glycol, and combinations thereof.

Generally, the substrate is contacted with a liquid comprising the pore blocking agent or one or more precursor(s) of the pore blocking agent. Typically, the substrate to be treated is contacted with a mixture or solution comprising one or more pore blocking compounds or precursor(s) dispersed or dissolved in a liquid contacting medium (e.g., deionized water). For example, the substrate may be contacted with a mixture or solution including a cyclohexane derivative and a glycol, or a liquid contacting medium consisting essentially of the cyclohexane derivative and glycol. The substrate may also be sequentially contacted with liquids or liquid media comprising one or more of the precursors. The composition of the liquid including the pore blocking agent or a precursor(s) thereof contacted with the porous substrate is not narrowly critical and may be readily selected and/or optimized by one skilled in the art.

As noted, regardless of whether a compound that ultimately functions as a pore blocker is introduced into pores of the substrate or precursors that form the blocking compound are introduced into the substrate, pore blockers may be preferentially retained within selected substrate pores (e.g., micropores) by virtue of the conformational arrangement assumed by the pore blocking agent once disposed or formed within the pores. For example, it is currently believed that various pore blocker molecules transform from a more linear chair conformation to a bulkier boat conformation, which conduces trapping of the compound within the micropores. In particular, it is currently believed that various pore blocking agents including a hydrophilic end group will favor a boat conformation within the micropore(s) of a porous carbon support because of the nature of the carbon support (i.e., the boat conformation will be favored by a pore blocking compound having hydrophilic end groups because of the relatively hydrophobic nature of the carbon support surface). Examples of pore blocking compounds including a hydrophilic end group include 1,4-cyclohexanedicarboxylic acid and 1,4-cyclohexanedimethanol (CHDM).

A conformational change of a pore blocker also may be promoted or induced by manipulating the liquid medium comprising the pore blocking agent in contact with the substrate including, for example, adjusting the pH and/or adjusting the temperature of the liquid medium.

Figure 1B:
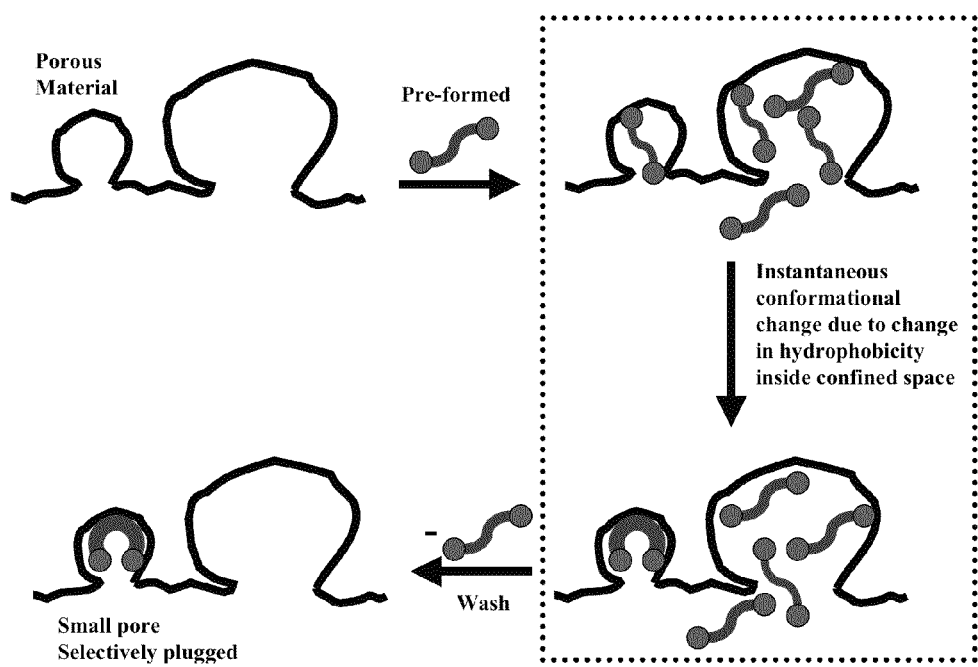
Figure 1C:
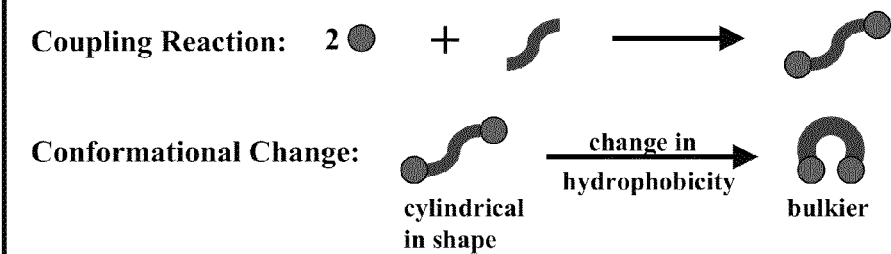
Figure 1D:
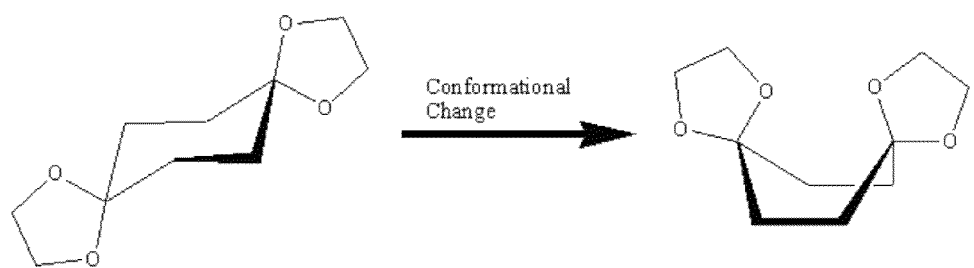
FIG. 1D illustrates a conformational change of a pore blocker in accordance with the present invention.

FIGS. 1A-1C provide graphical representations of preformed pore blockers and pore blocker molecules formed from precursors within the pore (i.e., in situ coupling) that undergo a conformational change within the pore to selectively block or plug smaller pores. Conformational change of a cyclohexane pore blocker is shown generally in FIG. 1D. These depictions are for illustrative purposes and are not intended to limit the present invention.

As noted, it is believed that contacting the substrate with the pore blocking agent or precursors results in pore blocking agent being introduced into or disposed within substrate micropores, and within larger pores outside this predefined range. In order to provide a treated substrate in which the micropores within the predefined range are preferentially blocked, the substrate is subsequently contacted with a washing liquid to remove the blocking agent from pores outside the micropore domain (i.e., those pores in which the pore blocking agent will not be preferentially retained by virtue of the agent having at least one dimension larger than the pore opening). The precise composition of the washing liquid and manner of its contact with the substrate are not narrowly critical, but the substrate may suitably be contacted with deionized water for this purpose.

C. Treated Substrates

As noted, the substrate treatment method of the present invention is suitable for introducing a pore blocking agent into the micropores of porous substrates (e.g., a particulate carbon support) and preferentially retaining the pore blocking agent in the micropores. Preferential retention of the pore blocking agent within micropores may be represented by the proportion of micropores in which the agent is retained. Typically, the pore blocking compound remains in at least about 2%, at least about 5%, at least about 10%, or at least about 20% of the micropores, basis the total number of substrate micropores.

Preferential retention of the pore blocking compound within micropores may also be indicated by the treated substrate surface area provided by micropores and provided by larger pores. It is believed that the presence of the pore blocking compound within micropores will cause at least a portion of these "blocked" pores to appear as a non-porous portion of the treated substrate during surface area measurement methods (e.g., the well-known Langmuir surface area measuring method), thereby reducing the proportion of surface area that would otherwise be attributable to the micropores if they were not blocked. This preferential blocking of the targeted pores results in a reduction in the surface area provided by the micropores (i.e., micropore surface area). For example, in various embodiments, the micropore surface area of the treated substrate is generally no more than about 70%, no more than about 60%, or no more than about 50% of the micropore surface area of the substrate prior to treatment by contact with the pore blocker. Preferably, the micropore surface area of the treated substrate is no more than about 40%, more preferably no more than about 30% and, still more preferably, no more than about 20% of the micropore surface area of the substrate prior to treatment.

D. Methods for Preparing Catalysts Using Treated Substrates

As detailed herein, catalysts may be prepared by a process generally comprising depositing one or more noble metals and optionally one or more promoter metals at the surface of a treated (i.e., pore blocked) substrate such as a porous carbon support and heating the carbon support having the noble metal and optional promoter(s) deposited thereon in a non-oxidizing environment.

The noble metal is generally selected from the group consisting of platinum, palladium, ruthenium, rhodium, iridium, silver, osmium, gold, and combinations thereof. In various preferred embodiments, the noble metal comprises platinum and/or palladium. In still further preferred embodiments, the noble metal is platinum. One or more promoter metals is generally selected from the group consisting of tin, cadmium, magnesium, manganese, nickel, aluminum, cobalt, bismuth, lead, titanium, antimony, selenium, iron, rhenium, zinc, cerium, zirconium, tellurium, germanium, and combinations thereof at a surface of the porous substrate and/or a surface of the noble metal.

The noble metal may be deposited in accordance with conventional methods known in the art including, for example, liquid phase deposition methods such as reactive deposition techniques (e.g., deposition via reduction of noble metal compounds and deposition via hydrolysis of noble metal compounds), ion exchange techniques, excess solution impregnation, and incipient wetness impregnation; vapor phase methods such as physical deposition and chemical deposition; precipitation; electrochemical deposition; and electroless deposition as described in U.S. Pat. No. 6,417,133 and by Wan et al. in International Publication No. WO 2006/031938. In various preferred embodiments, the noble metal is deposited via a reactive deposition technique comprising contacting the carbon support with a solution comprising a salt of the noble metal, and then hydrolyzing the salt. An example of a relatively inexpensive suitable platinum salt is hexachloroplatinic acid ($H_2PtCl_6$).

A promoter(s) may be deposited onto the surface of the treated carbon support before, simultaneously with, or after deposition of the noble metal onto the surface. Methods to deposit a promoter metal are generally known in the art, and include the methods noted above regarding noble metal deposition.

After the carbon support has been impregnated with the noble metal(s) and optional promoter(s), the surface of the catalyst is preferably heated to elevated temperatures, for example, in a heat treatment or calcining operation. For example, calcining may be carried out by placing the catalyst in a kiln (e.g., rotary kilns, tunnel kilns, and vertical calciners) through which a heat treatment atmosphere is passed.

Generally, the surface of the treated support impregnated with one or more metals is heated to a temperature of at least about 700° C., at least about 800° C., at least about 850° C., at least about 900° C., or at least about 950° C. Typically, the metal-impregnated support is heated to a temperature of from about 800° C. to about 1200° C., preferably from about 850° C. to about 1200° C., more preferably from about 900° C. to about 1200° C., even more preferably from about 900° C. to about 1000° C. and especially from about 925° C. to about 975° C.

The period of time that the impregnated support is subjected to elevated temperatures (including the time at which the support is heated at the maximum temperature) is not narrowly critical. Typically, in commercial scale apparatus, the metal-impregnated support is heated at the maximum heat treatment temperature for at least about 10 minutes (e.g., at least about 30 minutes).

Preferably, the metal-impregnated support is heated in a non-oxidizing environment. The non-oxidizing environment may comprise or consist essentially of inert gases such as $N_2$, noble gases (e.g., argon, helium) or mixtures thereof. In certain embodiments, the non-oxidizing environment comprises a reducing environment and includes a gas-phase reducing agent such as, for example, hydrogen, carbon monoxide, or combinations thereof. The non-oxidizing environment in which the catalyst is heated may include other components such as ammonia, water vapor, and/or an oxygen-containing compound as described, for example, by Wan et al. in International Publication No. WO 2006/031938. In one embodiment, heat treatment following metal deposition preferably comprises high-temperature gas-phase reduction to remove oxygen-containing functional groups from the surface of the catalyst, thereby attaining a catalyst exhibiting the carbon monoxide desorption and/or carbon atom to oxygen atom surface ratio characteristics as described in Ebner et al. U.S. Pat. No. 6,417,133.

In various preferred embodiments, the noble metal is alloyed with at least one promoter to form alloyed metal particles. For example, noble metal particles at a surface of the carbon support may comprise noble metal atoms alloyed with promoter metal atoms. In various other preferred embodiments, the noble metal is alloyed with two promoters (e.g., iron and cobalt). Catalysts comprising a noble metal alloyed with one or more promoters often exhibit greater resistance to metal leaching and further stability (e.g., from cycle to cycle) with respect to formaldehyde and formic acid oxidation. It is to be understood that the term alloy as used herein generally encompasses any metal particle comprising a noble metal and at least one promoter (e.g., intermetallic compounds, substitutional alloys, multiphasic alloys, segregated alloys, and interstitial alloys as described by Wan et al. in International Publication No. WO 2006/031938).

Subjecting the metal-impregnated support to heat treatment generally provides agglomeration and/or sintering of metal particles at the surface of the support. Utilizing treated substrates having blocked micropores results in impregnated supports having a reduced proportion of relatively small metal-containing particles at the support surface within the micropore domain, which are generally more susceptible to leaching and/or deactivation, as compared to larger-sized noble metal-containing particles. Additionally or alternatively, metal-containing particles at the substrate surface outside the micropore domain are generally more accessible to reactants. By virtue of either or both of these effects, treated substrates of the present invention are believed to provide more efficient metal usage (e.g., an increase in effective catalytic metal surface area per unit weight) in the catalyst.

It is to be noted that persistence of the pore blocker in the treated substrate following post-metal deposition heat treatment is not critical to provide the above-noted advantages. In fact, it is currently believed that the pore blocker is most likely decomposed and/or otherwise removed from the substrate surface during calcining. But it is further currently believed that one or more of the above-noted advantages are achieved so long as the pore blocker is preferentially retained with the selected pores at the support surface during metal deposition in order to promote the desired metal dispersion.

E. Catalysts Prepared Using Treated Substrates

Substrates treated in accordance with the present method (i.e., pore blocked substrates) may be utilized as supports for metal-containing catalysts including, for example, catalysts including one or more noble metals (e.g., a noble metal such as platinum) deposited on a particulate carbon support. In addition, noble metal-containing catalysts prepared using substrates treated by the present invention may include one or more promoter(s) and may be prepared in a manner to exhibit one or more of the properties as described, for example, in U.S. Pat. No. 6,417,133, International Publication No. WO 2006/031938, and U.S. Pat. No. 6,956,005, the entire contents of which are incorporated herein by reference for all relevant purposes.

Generally, the noble metal constitutes less than about 8% by weight of the catalyst, typically less than about 7% by weight of the catalyst, more typically less than about 6% by weight of the catalyst. In various embodiments, the noble metal typically constitutes from about 1% to about 8% by weight of the catalyst, more typically from about 2% to about 7% by weight of the catalyst and, still more typically, from about 3% to about 6% by weight of the catalyst.

As noted, particulate carbon supports treated in accordance with the present invention to preferentially block micropores provide more efficient metal usage. Accordingly, effective catalysts may be prepared that contain noble metal in an amount below the above-noted limits and/or at or near the lower limits of one or more of the above-noted ranges. For example, in various embodiments, the noble metal constitutes less than about 5% by weight of the catalyst, less than about 4% by weight of the catalyst, or even less than about 3% by weight of the catalyst. By way of further example, in various embodiments the noble metal typically constitutes from about 1% to about 5% by weight of the catalyst, more typically from about 1.5% to about 4% by weight of the catalyst and, still more typically, from about 2% to about 3% by weight of the catalyst. However, it should be understood that the present invention does not require that a treated substrate be used for preparation of a noble metal-containing catalyst including a reduced proportion of noble metal as compared to conventional catalysts. Namely, preparation of a catalyst including a treated porous substrate that provides more efficient metal usage at conventional noble metal loadings likewise represents an advance in the art (e.g., treated substrates of the present invention are currently believed to provide a reduced proportion of relatively small metal particles that are susceptible to leaching and represent inefficient metal usage, thereby contributing to improvements in catalytic activity and reduced undesired by-product (e.g., IDA) formation).

Generally, in accordance with some embodiments, at least one promoter (e.g., iron) constitutes less than about 2% by weight of the catalyst, less than about 1.5% by weight of the catalyst, less than about 1% by weight of the catalyst, less than about 0.5% by weight of the catalyst, or about 0.4% by weight of the catalyst. Typically, at least one promoter constitutes less than about 1% by weight of the catalyst, preferably from about 0.25% to about 0.75% by weight of the catalyst and, more preferably, from about 0.25% to about 0.6% by weight of the catalyst. In various preferred embodiments, the catalyst includes iron as a promoter. Additionally or alternatively, the catalyst includes cobalt as a promoter.

In various particularly preferred embodiments, the catalyst comprises both iron and cobalt promoters. Use of iron and cobalt generally provides benefits associated with use of iron (e.g., activity and stability with respect to formaldehyde and formic acid oxidation). However, as compared to the presence of iron alone as a promoter, the presence of cobalt tends to reduce formation of certain by-products during oxidation of a PMIDA substrate (e.g., IDA). Moreover, IDA formation is believed to be directly related to total iron content of the catalyst. Thus, in various iron/cobalt co-promoter embodiments, iron content is essentially replaced by cobalt to reduce formation of IDA and other by-products while nevertheless providing sufficient activity towards oxidation of formaldehyde and formic acid. For example, as compared to a platinum on carbon catalyst containing 0.5% by weight iron in the absence of cobalt, a similar catalyst containing 0.25% by weight iron and 0.25% by weight cobalt typically provides comparable activity for PMIDA, formaldehyde and formic acid oxidation, while minimizing by-product formation.

In iron/cobalt co-promoter embodiments, the amount of each promoter at the surface of the carbon support (whether associated with the carbon surface itself, noble metal, or a combination thereof) is typically at least about 0.05% by weight, at least about 0.1% by weight or at least about 0.2% by weight. Furthermore, the amount of iron at the surface of the carbon support is typically from about 0.1 to about 4% by weight of the catalyst, preferably from about 0.1 to about 2% by weight of the catalyst, more preferably from about 0.1 to about 1% by weight of the catalyst and, even more preferably, from about 0.1 to about 0.5% by weight of the catalyst. Similarly, the amount of cobalt at the surface of the carbon support is typically from about 0.1 to about 4% by weight of the catalyst, preferably from about 0.1 to about 2% by weight of the catalyst, more preferably from about 0.2 to about 1% by weight of the catalyst and, even more preferably, from about 0.2 to about 0.5% by weight of the catalyst. In such an embodiment, the weight ratio of iron to cobalt in the catalyst is generally from about 0.1:1 to about 1.5:1 and preferably from about 0.2:1 to about 1:1. For example, the catalyst may comprise about 0.1% by weight iron and about 0.4% by weight cobalt or about 0.2% by weight and about 0.2% by weight cobalt.

As understood by those skilled in the art, the metal content of the catalysts can be freely controlled within the ranges described herein (e.g., by adjusting the concentration and relative proportions of the metal source(s) used in a liquid phase reactive deposition bath).

II. First and Second Metal-Containing Catalysts

Various preferred embodiments of the present invention are directed to catalysts that comprise and/or are prepared from a porous substrate or support having one or more regions of a first metal at its surface, and a second metal at the surface of the one or more regions of the first metal. In such embodiments, the first metal is selected to have an electropositivity greater than the electropositivity of the second metal (i.e., the first metal is higher than the second metal in the electromotive series). Oxidation of the first metal provides electrons for reduction of second metal ions present in the deposition bath to thereby deposit second metal atoms at the surface of the one or more regions of the first metal. The first metal oxidation and second metal reduction and deposition occur substantially simultaneously and second metal atoms are deposited at the surface of the one or more regions of the first metal by displacement of first metal ions from the one or more regions into the deposition bath. Metal deposition in this manner may be referred to as spontaneous, or redox displacement deposition. (See, for example, U.S. Pat. No. 6,670,301 to Adzic et al. and U.S. Pat. Nos. 6,376,708, 6,706,662 and 7,329,778 to Morgenstern et al.) Preferably, the sacrificial first metal is less expensive than the second metal.

As detailed herein, deposition of the second metal by displacement deposition is preferably conducted and controlled in a manner that provides preferential deposition of the second metal at the surface of the one or more regions of the first metal. That is, the second metal is preferentially deposited at the surface of the first metal region(s) by displacement deposition over deposition of the second metal at the support surface and/or deposition of the second metal at the surface of already-deposited second metal.

Without being bound to a particular theory, it is currently believed that the source of second metal ions may promote preferential deposition of the second metal onto the one or more regions of first metal. More particularly, it is currently believed that second metal sources that provide second metal ions at lower oxidation numbers (e.g., +2) provide slower, more controlled metal deposition as compared to sources that provide noble metal ions at higher oxidation numbers (e.g., +4). Second metal ions at such higher oxidation numbers are believed to be more readily reduced in the presence of electrons generated by oxidation of the first metal which provides a greater driving force for deposition of the second metal. This greater driving force is believed to increase the rate of second metal deposition which, in turn, is believed to promote less discriminate deposition of the second metal. More particularly, the greater driving force for deposition of second metal ions is believed to promote deposition of second metal atoms onto the support and/or onto the surface of already-deposited second metal atoms. Accordingly, it is currently believed that as the oxidation state of second metal ions decreases, preferential (e.g., selective) deposition of the noble metal directed onto one or more regions of first metal by displacement of first metal atoms over deposition onto the carbon support and/or already-deposited second metal atoms generally increases.

In addition, it is currently believed that deposition of second metal atoms utilizing sources that provide ions at relatively low oxidation numbers proceeds in a manner that generally reduces the complexity of the displacement deposition process to promote the desired preferential deposition of the second metal directed onto the first metal regions. For example, displacement deposition utilizing sources that provide second metal ions at relatively low oxidation numbers proceeds readily in the absence of precise control of concentration of the second metal source and/or deposition time.

In accordance with the present invention, it is currently believed that a significant fraction, if not substantially all, of the second metal deposited by controlled displacement of a first metal provides domains or regions at the surface of one or more regions of the first metal characterized as comprising a relatively thin layer of second metal atoms (e.g., no more than about 5 atoms thick, or no more than about 3 atoms thick), rather than agglomerating to form metal-containing particles. In certain preferred embodiments, preparation of the catalyst by the present method may provide a near monolayer of second metal (e.g., a layer of second metal atoms no more than about 3 atoms in thickness, no more than about 2 atoms in thickness, and preferably from about one to about two atoms in thickness).

Further in accordance with the present invention, it is currently believed that deposition of the second metal by displacement of first metal atoms from one or more regions of first metal provides a structure (e.g., a catalyst precursor structure) that, upon heat treatment at elevated temperatures, provides metal particles that include the second metal in a form that represents more efficient second metal utilization. In various embodiments, the metal particles are typically first metal-rich (i.e., contain an excess of first metal atoms over second metal atoms) and it is currently believed that the particles include one or more bimetallic alloys. In contrast, conventional noble metal-containing catalysts typically include particles comprising an atomic excess of noble metal atoms. In this manner, the first metal-rich particles are believed to include the noble (i.e., second) metal in a form that represents a reduced proportion of noble metal distributed throughout the particle and, accordingly, represents reduced unexposed, and potentially unutilized noble metal atoms throughout the particle structure. But an excess of first metal is not required to provide an improvement in metal utilization. However, to the extent that the proportion of first metal to second metal is increased, improvements in second metal utilization may be realized. Accordingly, various embodiments of the present invention contemplate selecting first and second metal combinations that are amenable to forming alloys that include at least an equivalent atomic proportion of first metal ($M_1$) to second metal ($M_2$). More particularly, in various embodiments there is a preference for selecting first and second metal combinations that provide bimetallic alloys of first and second metal, $M_{1x}M_{2y}$, where the atomic ratio of x:y is greater than or equal to 1. Further in accordance with these and various other preferred embodiments, the metal particles include bimetallic alloys in which the atomic ratio of x:y is greater than about 2, or greater than about 3. For example, in the case of copper and platinum first and second metals, respectively, the metal particles at the surface of the support may include CuPt and/or $Cu_3Pt$ bimetallic alloys. By way of further example, in the case of tin and platinum first and second metals, respectively, at least some of the metal particles may include $Pt_2Sn_3$, $PtSn_2$, and/or $PtSn_4$ bimetallic alloys. In the case of iron and platinum first and second metals, respectively, the metal particles at the surface of the support may include, for example, $Fe_3Pt$, FePt, $Fe_{0.75}Pt_{0.25}$.

Additionally or alternatively, it is also currently believed that at least some of the supported metal particles produced upon calcination of a catalyst precursor structure prepared by displacement deposition of a noble (i.e., second) metal as detailed herein include a relatively thin layer or shell comprising second metal atoms (e.g., a layer of second metal atoms no more than about 3 atoms thick) at least partially surrounding a core comprising the first metal. The core generally comprises a relatively high concentration of first metal (e.g., greater than about 50 atom percent). The combination of a first metal-rich core and second metal-containing shell provides a relatively low proportion of unexposed second metal and, thus, provides improvements in exposed metal surface area per unit metal weight. It is currently believed that particles exhibiting such a core-shell arrangement may generally provide a greater improvement in second metal utilization over conventional supported noble metal catalysts as compared to particles generally characterized as first metal-rich (i.e., a greater increase in exposed second metal surface area per unit second metal weight). Thus, as the fraction of core-shell particles at the surface of the support increases, metal utilization in the catalyst likewise increases. Accordingly, in various preferred embodiments, the catalyst includes a predominant fraction of metal particles exhibiting a core-shell arrangement. However, it is to be noted that improvements in metal utilization are nonetheless provided by virtue of the presence of metal particles generally rich in first metal content, regardless of the presence of any particles characterized as exhibiting a core-shell arrangement.

It is to be noted that reference to a porous substrate such as a carbon support having first and second metals deposited thereon (i.e., a first and second metal-containing support) as a catalyst precursor structure does not exclude catalytic activity of these impregnated supports in the absence of subsequent heat treatment. In fact, experimental evidence indicates that metal-impregnated supports prepared in this manner may function as effective catalysts. Accordingly, elsewhere herein (including the claims) porous substrates having a first metal deposited thereon (e.g., a first metal-impregnated support) are likewise referred to as catalyst precursor structures. But in various preferred embodiments, the first and second metal-impregnated support is heated at elevated temperatures to provide the catalyst (sometimes referred to herein as a finished catalyst).

Experimental evidence indicates that catalysts (i.e., both catalyst precursor structures and finished catalysts) prepared as detailed herein utilizing a noble metal and a first, sacrificial metal layer are at least as active as conventional noble metal on carbon catalysts on a per unit metal weight basis. Without being bound to a particular theory, it is currently believed that active sites or domains of second metal provided by the method of the present invention provide an increase in catalytic surface area per unit metal weight as compared to conventional metal-containing catalysts prepared by methods that do not include displacement deposition of the second metal onto one or more regions of a first, sacrificial metal.

Conventional noble metal on carbon catalysts generally include noble metal-containing particles at the surface of the support formed by agglomeration and/or sintering of noble metal atoms and/or noble metal-containing particles. This agglomeration typically occurs during post-deposition heat treatment of a noble metal-impregnated support at relatively high temperatures. Metal particles of conventional noble metal catalysts formed by agglomeration of deposited metal at the surface of a support, typically include the noble metal distributed throughout the entire particle (e.g., the particles exhibit a composition profile of relatively constant noble metal concentration throughout). Particle stability (e.g., resistance to leaching and/or deactivation under reaction conditions) generally increases with increased particle size, but exposed metal catalytic surface area per unit metal weight typically decreases in larger particles. Thus, despite the increased stability, an abundance of relatively large noble metal-containing particles and the attendant lower catalytic metal surface area per unit metal weight represents less efficient metal usage. Advantageously, first metal-rich particles and/or metal particles comprising a noble (i.e., second) metal-containing shell and first metal-containing core prepared in accordance with various embodiments of the present invention generally represent more efficient metal usage. For example, as noted, the first metal-rich particles are believed to include the second metal in a form (e.g., a bimetallic alloy including an atomic excess of first metal) that provides a reduced proportion of unexposed second metal.

Additionally or alternatively, and as detailed elsewhere herein, larger, more stable metal particles in accordance with the present invention are not associated with an unacceptable decrease in effective catalytic second metal surface area since an increase in particle size is generally associated with an increase in the size of the first metal-rich core. For example, experimental evidence indicates relatively constant thickness of the second metal-containing shell over a range of particle sizes. Accordingly, as particle size increases, the fraction (atom and/or weight) of the particle provided by the first metal-rich core generally increases while the fraction of the particle provided by the second metal-containing shell generally decreases. However, the exposed second metal surface area increases with increased particle size. For example, as compared to a particle including a core 1 nm in diameter, at constant second metal shell thickness, a particle including a core 10 nm in diameter may provide up to a 100-fold increase in exposed surface area of the second metal-containing shell.

One mechanism for deactivation of conventional noble metal on carbon catalysts prepared by deposition of noble metal in the absence of a sacrificial metal involves overoxidation of platinum as a result of charge build-up among the active sites comprising particles of agglomerated noble metal atoms. It is currently believed that metal-containing particles in which a second metal-containing shell at least partially surrounds a first metal-containing core result in reduced overoxidation of the catalyst. In this manner, the form of the catalyst provides an improvement in activity. With regard to a catalyst precursor structure, it is currently believed that preferential deposition of second metal by displacement of first metal to form domains or active sites less prone to agglomeration to form metal-containing particles than metal deposited in the absence of a sacrificial metal provides greater dispersion of charge among the active sites and, thus, reduced catalyst deactivation by over-oxidation of the metal.

It is to be noted that a certain degree of agglomeration of second metal to form primarily second metal-containing particles may occur in first and second metal-containing catalysts prepared in accordance with the present invention. However, it is currently believed that any such agglomeration occurs to a lesser extent than observed in catalysts prepared without a first, sacrificial metal and, in any event, second metal agglomeration is not believed to occur to any significant degree that prevents achieving the above-noted benefits of improved metal utilization.

It is also currently believed that the above-described methods utilizing a first, sacrificial metal layer may be utilized in conjunction with the methods for treating porous substrates detailed elsewhere herein. For example, a first metal may be deposited onto a porous support first treated in accordance with the methods detailed herein (e.g., a substrate having a pore blocking compound disposed and/or preferentially retained within its micropores), followed by deposition of a second metal onto one or more regions of the deposited first metal. In this manner, it is currently believed that deposition of both the one or more regions of the first metal, and subsequent deposition of the second metal thereon are preferentially directed outside the relatively small pore (e.g., micropore) domain of the substrate, thereby providing advantageous dispersion of the first and second metals and contributing to one or more of the above-noted benefits with respect to metal utilization.

A. First Metal

In those embodiments of the present invention in which the catalyst or precursor includes one or more regions of a first metal at the surface of the support, the first metal is generally selected from the group consisting of vanadium, tungsten, molybdenum, gold, osmium, iridium, tantalum, palladium, ruthenium, antimony, bismuth, arsenic, mercury, silver, copper, titanium, tin, lead, germanium, zirconium, cerium, nickel, cobalt, iron, chromium, zinc, manganese, aluminum, beryllium, magnesium, lithium, barium, cesium, and combinations thereof. In various preferred embodiments, the first metal is selected from the group consisting of copper, iron, tin, nickel, cobalt, and combinations thereof. In various other preferred embodiments, the first metal comprises copper, tin, nickel, or a combination thereof. In various other preferred embodiments, the first metal is tin or the first metal is copper. In still further embodiments, the first metal comprises cobalt, copper, iron and combinations thereof. In various preferred embodiments, the first metal is copper. In various other preferred embodiments, the first metal is iron. In still further preferred embodiments, the first metal is cobalt.

Generally, the support is contacted with a deposition bath comprising ions of the first metal and one or more other components to deposit the first metal at the surface of the support. At least two events occur during deposition of the first metal at the surface of the support: (1) nucleation (i.e., deposition of first metal atoms at the surface of the support) and (2) particle growth (i.e., agglomeration of deposited first metal atoms). As used herein, the term region(s) of first metal refers to a group of agglomerated first metal atoms at the surface of the support. It is currently believed that the sizes, or dimensions of these regions (i.e., the proportion of support surface area over which a region of first metal is deposited) may directly impact the effectiveness/suitability of the catalyst.

For example, the proportion of deposition, or exchange sites for second metal deposition decreases along with decreasing dimensions of first metal regions. In addition, resistance to leaching and/or deactivation under reaction conditions generally decreases as one or more dimensions of the first metal region size decrease. Thus, it is preferred that the dimensions of the first metal regions are sufficiently resistant to metal leaching and provide a sufficient proportion of sites for second metal deposition. Accordingly, one or more conditions of first metal deposition are preferably controlled to provide a suitable balance between nucleation and agglomeration (i.e., particle growth) and, thus, provide first metal regions of suitable dimensions that provide sufficient exchange sites for deposition of second metal, are stable themselves and, thus, promote deposition of stable domains, or regions of second metal. For example, as detailed elsewhere herein, first and second metal-containing supports preferably include an excess of first metal, which contributes to providing the second metal in a form that promotes more efficient metal utilization.

In addition to achieving a desirable balance between nucleation and agglomeration, the location, or dispersion of the one or more regions of first metal at the support surface may impact metal utilization. That is, the considerations noted above generally concerning deposition of metal among relatively small pores generally likewise apply to deposition of one or more first metal regions and the dispersion of these regions among the pores of porous substrates is currently believed to affect catalyst performance. Accordingly, one or more conditions of first metal deposition are generally controlled and/or selected to provide a desired dispersion of first metal regions. Thus, generally, conditions of first metal deposition preferably promote deposition of the first metal at the support surface to provide regions of first metal at the support having one or more dimensions that provide a suitable proportion of exchange sites for deposition of second metal at the surface of the first metal regions. More particularly, it is currently believed that the dimensions of the first metal regions preferably provide a suitable excess of deposited first metal with respect to the desired proportion of second metal to be deposited. For example, as detailed elsewhere herein, supports having first and second metals deposited thereon in accordance with the present invention may be characterized by a minimum atom ratio of first metal to second metal.

1. Coordinating Agents/Pore Blocking

In various preferred embodiments, preferential deposition of the first metal outside relatively small pores (e.g., the micropore domain) of the substrate may be promoted by the presence of one or more components of the first metal deposition bath. More particularly, dispersion of first metal in this manner may be promoted by the presence of one or more components of the deposition bath referred to herein as coordinating agent(s).

It is currently believed that a component of the first metal deposition bath may function as a coordinating agent by forming one or more coordination bonds with the first metal and that the thus formed coordination compound may be unable to enter certain relatively small pores of the substrate, thereby preventing coordinated first metal from depositing among those portions of the substrate surface. It is to be understood that the precise form of any coordination bond(s) between the compound and metal, or the precise form of any coordination compound thus formed are not narrowly critical. However, it is currently believed that a coordination compound generally includes an association or bond between the first metal ion and one or more binding sites of one or more ligands. The coordination number of a metal ion of a coordination compound generally corresponds to the number of other ligand atoms linked thereto. Ligands may be attached to the central metal ion by one or more coordinate covalent bonds in which the electrons involved in the covalent bonds are provided by the ligands (i.e., the central metal ion can be regarded as an electron acceptor and the ligand can be regarded as an electron donor). The typical donor atoms of the ligand include, for example, oxygen, nitrogen, and sulfur. The ligands can provide one or more potential binding sites; ligands offering two, three, four, etc., potential binding sites are termed bidendate, tridendate, tetradentate, etc., respectively. Just as one central atom can coordinate with more than one ligand, a ligand with multiple donor atoms can bind with more than one central atom. Coordinating compounds including a metal ion bonded to two or more binding sites of a particular ligand are typically referred to as chelates.

Additionally or alternatively, a coordinating agent as described herein may promote dispersion of the first metal at the support surface by virtue of the coordination bonds between the coordinating agent and metal to be deposited retarding or delaying reduction of the metal ions and metal deposition at the support surface while promoting dispersion of the first metal over the support surface. The strength of coordination between the coordinating agent and metal generally influences the effectiveness of the agent for promoting dispersion of the first metal over the support surface. Unless the strength of coordination reaches a minimum threshold, the effect of the agent on dispersion will not be noticeable to any significant degree and the degree of coordination that prevails in the deposition bath will essentially mimic water solvation. As the strength of coordination between the agent and metal increases, a greater concentration of reducing agent may be utilized and/or a relatively strong reducing agent (e.g., metal hydride) may be included in the deposition bath to promote reduction of the coordination complex and/or first metal reduction and deposition. Coordinating agent and/or ligand(s) derived therefrom present in the deposition bath may effectively function as a pore blocking compound during and/or after first metal deposition. For example, once the coordination bond(s) between the first metal and the coordinating agent have been broken, the agent or ligand(s) may be disposed within micropores of the support.

In accordance with the foregoing regarding deposition bath components that may function as coordinating agents, in these and various other preferred embodiments, such components of the first metal deposition bath may promote desirable dispersion of the one or more regions of first metal by virtue of a pore blocking function. That is, in addition to preventing entry of coordinated first metal into certain pores of the substrate, components of the first metal deposition bath described as coordinating agents may themselves be deposited among certain, relatively small pores of the porous substrate, thereby inhibiting, and preferably substantially preventing, deposition of first metal within the relatively small pores. Generally, these compounds are believed to function as pore blocking compounds during first metal deposition and that preferential deposition of first metal and pore blocking may occur substantially simultaneously to provide a first metal-impregnated substrate.

But it is to be understood that treating a porous substrate in accordance with the methods detailed above to dispose within and/or introduce a pore blocking compound into pores of the substrate, followed by metal deposition, likewise provides suitable substrates.

A variety of compounds that function as coordinating agents and/or pore blocking compounds may be included in the first metal deposition bath to provide one or more of the above-noted effects. Generally, these compounds are selected from the group consisting of various sugars, 5- or 6-member ring-containing compounds (e.g., 1,3- and 1,4-disubstituted cyclohexanes), polyols, Rochelle salts, acids, amines, citrates, and combinations thereof. For example, the compound may be selected from the group consisting of sucrose, sorbitol, mannitol, xylitol, Rochelle salts (potassium sodium tartrates), ethylenediaminetetraacetic acid (EDTA), N-hydroxyethylethylenediaminetetraacetic acid (HEDTA), nitrilotriacetic acid (NTA), N,N,N',N'-tetrakis(2-hydroxypropyl)ethylenediamine, and combinations thereof.

It is to be noted that the advantageous effects provided by the presence of these compounds referred to herein as coordinating agents or pore blockers are based in part on experimental evidence. While it is currently believed that one or more of these compounds provide either or both of the coordinating and pore blocking functions, it should be understood that the present invention is not dependent on either or both of these theories and does not require one or more compounds providing either or both of these functions.

In various preferred embodiments (e.g., those in which the first metal is copper or iron), the deposition bath comprises sucrose that is believed to function as a coordinating agent and/or pore blocking compound. In addition to these effect(s) in accordance with the preceding discussion, its presence may offer other advantages. For example, as detailed elsewhere herein, first metal deposition may proceed more readily at higher pH. The coordinating effect of sucrose allows for deposition of the first metal at higher pH since the coordinating effect reduces the risk of excessive first metal precipitation at higher pH.

Generally, the coordinating agent/pore blocker, or a combination of agents/blockers, is present in the first metal deposition bath at a concentration of at least about 10 g/L, at least about 20 g/L, or at least about 30 g/L. Preferably, this component of the first metal deposition bath is present at a concentration of from about 10 g/L to about 115 g/L, from about 25 g/L to about 100 g/L, or from about 40 g/L to about 85 g/L. Further in accordance with these and various other preferred embodiments, the weight ratio of coordinating agent to first metal in the deposition bath is generally at least about 3:1, typically at least about 5:1 and, more typically, at least about 8:1. For example, generally the weight ratio of coordinating agent to first metal in the deposition bath is generally from about 3:1 to about 20:1, typically from about 5:1 to about 15:1 and, more typically, from about 8:1 to about 12:1.

2. Electroless Plating of First Metal

Generally and in accordance with the foregoing, deposition of first metal at the surface of the support may be conducted in accordance with conventional methods known in the art. Thus, typically first metal deposition is conducted by electroless plating in which the support is contacted with a deposition bath generally comprising a source of the first metal in the absence of an externally applied voltage. The deposition bath generally comprises a reducing agent that reduces ions of the first metal to form metal atoms that are deposited at the surface of the support.

Generally, the source of the first metal is a first metal salt including, for example, first metal sulfates, first metal nitrates, first metal chlorides, first metal tartrates, first metal phosphates, and combinations thereof. The concentration of first metal in the deposition bath is generally selected in view of the desired first metal content. Typically, the source of first metal is present in the deposition bath at a concentration of at least about 0.25 g/L, at least about 1 g/L, at least about 2.5 g/L, or at least about 4 g/L. For example, the first metal source may be present in the deposition bath at a concentration of from about 1 to about 20 g/L, from about 2.5 to about 12.5 g/L, or from about 4 to about 10 g/L.

3. Copper Deposition

The following discussion focuses on deposition of copper as the first metal onto a porous carbon support. However, as detailed elsewhere herein, it should be understood that the present invention likewise contemplates deposition of first metals other than copper onto carbon supports, and deposition of copper and other first metals onto non-carbon supports.

(a) Sources of Copper

Sources of copper ions suitable for use in the methods of the present invention include copper salts such as the nitrate, sulfate, chloride, acetate, oxalate, and formate salts of copper, and combinations thereof. Salts containing copper in the divalent state (i.e., Cu(II)) are generally preferred including, for example, copper sulfate.

(b) Copper Loading in Deposition Bath

First metal loading in the deposition bath may affect the quality (e.g., resistance to leaching) and/or suitability (e.g., dispersion of first metal over a sufficient portion of support surface) of first metal deposition. More particularly, the relative proportions of first metal and support are currently believed to impact first metal deposition. Agglomeration, or particle growth, and the dimensions of the resulting regions of first metal may increase with increased copper loading. As noted above, the dimensions of the first metal regions are preferably controlled to promote a suitable balance between dispersion and stability of the first and second metals. Accordingly, the concentration of copper in the deposition bath satisfies the above-noted limits and/or is within the above-noted ranges.

For example, typically copper is present in the first metal deposition bath at a concentration of at least about 0.25 g/L, more typically at least about 1 g/L, still more typically at least about 2 g/L, and even more typically at least about 3 g/L (e.g., at least about 5 g/L). Preferably, copper is present in the first metal deposition bath at a concentration of from about 0.25 to about 15 g/L, more preferably from about 1 to about 12 g/L and, still more preferably, from about 2 to about 10 g/L.

(c) Reducing Agents

Suitable reducing agents include those generally known in the art including, for example, sodium hypophosphite ($NaH_2PO_2$), formaldehyde ($CH_2O$) and other aldehydes, formic acid (HCOOH), salts of formic acid, salts of borohydride (e.g., sodium borohydride ($NaBH_4$)), salts of substituted borohydrides (e.g., sodium triacetoxyborohydride (Na$(CH_3CO_2)_3BH$)), sodium alkoxides, hydrazine ($H_2NNH_2$), and ethylene glycol. In various preferred embodiments, formaldehyde is the preferred reducing agent. For copper deposition in non-aqueous deposition baths, gaseous hydrogen is often the preferred reducing agent since it is generally readily soluble in organic solvents.

The manner of addition of reducing agent to the deposition bath is not narrowly critical, but in various embodiments the reducing agent is added at a relatively slow rate (e.g., over a period of from about 5 minutes to 3 hours, or over a period of from about 15 minutes to about 1 hour) to a slurry of the support and first metal in water or an alcohol and under an inert atmosphere (e.g., $N_2$). If the reducing agent is instead first added to the copper salt, it preferably may be added to a solution which contains the copper salt and also a coordinating agent (e.g., chelator). The presence of the chelator inhibits the reduction of the copper ions before the copper-salt solution is combined with the support and which, as detailed herein, may likewise promote advantageous deposition of first metal throughout the surface of the support.

Typically, in the case of formaldehyde as the reducing agent, the reducing agent is present in the first metal deposition bath at a concentration of at least about 1 g/L, more typically at least about 2 g/L and, still more typically, at least about 5 g/L. For example, in the case of formaldehyde as the reducing agent, preferably formaldehyde is present in the deposition bath at a concentration of from about 1 to about 20 g/L, more preferably from about 2 to about 15 g/L and, still more preferably, from about 5 to about 10 g/L.

Additionally or alternatively, in the case of a formaldehyde reducing agent, generally formaldehyde and the first metal (e.g., copper) are present in the deposition bath at a weight ratio of formaldehyde to first metal of at least about 0.5:1, and typically at least about 1:1. For example, in various embodiments, the weight ratio of formaldehyde to first metal in the deposition bath is from about 0.5:1 to about 5:1, from about 1:1 to about 3:1, or from about 1:1 to about 2:1.

(d) Temperature

The temperature of the deposition bath may affect nucleation and agglomeration (e.g., particle growth) that occur during first metal deposition. For example, generally nucleation (i.e., metal deposition) and agglomeration increase with increasing deposition bath temperature.

Thus, preferably the temperature of the deposition bath does not reach a level that promotes metal agglomeration and/or metal leaching under reaction conditions to an undesired degree. Reducing the temperature of the plating bath generally suppresses nucleation to a greater degree than agglomeration. Accordingly, the temperature of the plating bath is preferably high enough so that nucleation is not retarded to an unacceptable degree. In accordance with the present invention, it is currently believed that first metal deposition baths having a temperature of from about 5° C. to about 60° C. generally address these concerns and provide suitable deposition of the first metal. Preferably, the temperature of the first metal deposition bath is from about 10° C. to about 50° C.; more preferably, the temperature of the first metal deposition bath is from about 20° C. to about 45° C. It is to be noted that reference to the temperature of the first metal deposition bath may refer to the temperature of the bath prior to and/or during contact of the deposition bath and the support.

(e) Agitation

Preferably the first metal deposition bath is agitated to promote dispersion of the first metal over the surface of the support. Agitation may also promote diffusion of the reducing agent throughout the support. Experimental evidence indicates that sufficient agitation may contribute to improvements in catalytic activity. However, excessive agitation of the deposition bath may cause dispersion of copper to a degree that provides first metal regions that may be less resistant to leaching than less dispersed regions. For example, undesirably high dispersion may result in deposition of a portion of first metal within the relatively small pores of the support that is less prone to agglomeration to form first metal regions generally resistant to leaching.

In addition, it is currently believed that the type of agitator may impact deposition of the first metal. Experimental evidence indicates that the first metal (e.g., copper) may deposit onto the agitator surface resulting in reduced first metal deposition onto the carbon support and, therefore, reduced sites for deposition of second metal. For example, first metal may deposit onto the surface of agitators that include or are constructed of metal (e.g., coated metal agitators). Thus, in various preferred embodiments, the agitator is constructed of material that generally prevents, and preferably substantially completely prevents first metal deposition at the surface of the agitator. For example, the agitator may preferably be constructed of glass, or various other materials that preferably avoid first metal deposition at the agitator surface.

(f) Deposition pH

Copper deposition is generally more effective at higher pH (e.g., greater than about 8, greater than about 9, or greater than about 10). In fact, as deposition bath pH increases, copper deposition through reduction and precipitation onto the support may proceed at a rate that may hinder sufficient dispersion of the first metal over the support surface. In addition to the above-noted benefits, the presence of a coordinating agent such as sucrose is currently believed to retard copper precipitation at high pH and thereby promote sufficient dispersion of the metal over the surface of the support. Formation of a coordination complex between the first metal and a coordinating agent is generally enhanced at the above-noted pH levels. However, at certain levels the pH of the deposition bath may negatively impact solvation of first metal ions and first metal reduction and deposition. Accordingly, in various preferred embodiments in which a coordinating agent is present in the deposition bath, the pH of the deposition bath is from about 8 to about 13, or from about 9 to about 12.

4. Iron Deposition

In various preferred embodiments, the first metal is iron. Generally, deposition of iron at the surface of the support may be conducted in accordance with conventional methods known in the art (e.g., electroless plating). Thus, typically iron deposition is conducted by a process comprising contacting the support with a deposition bath comprising a source of the first metal in the absence of an externally applied voltage. For example, iron may be deposited via electroless deposition using methods generally known in the art including, for example, those described in U.S. Pat. No. 6,417,133 and by Wan et al. in International Publication No. WO 2006/031938. In various embodiments, as detailed below, the deposition bath comprises a reducing agent that reduces ions of the first metal that are deposited at the surface of the support.

(a) Sources of Iron

Suitable sources of iron include iron salts such as the nitrate, sulfate, chloride, acetate, oxalate, and formate salts, and combinations thereof. In various preferred embodiments, the source of iron comprises iron chloride (i.e., $FeCl_3$), iron sulfate (i.e., $Fe_2(SO_4)_3$), or a combination thereof.

The concentration of iron source in the deposition bath is not narrowly critical and is generally selected in view of the desired metal content and/or the composition of the source. Often, the source of iron is present in the deposition bath at a concentration of at least about 5 g/L and more typically from about 5 to about 20 g/L. In various embodiments, the entire proportion of the source of iron is introduced into the deposition bath prior to, during, or after addition of the carbon support to the deposition bath and/or the vessel containing deposition bath. Additionally or alternatively (including as described in the working Examples), the source of iron may be metered, or pumped into the deposition bath and/or a vessel containing the carbon support. In this regard it is to be understood that metered addition of the source of iron is controlled to provide deposition of a suitable proportion of iron at the support surface, regardless of the concentration of iron source in the deposition bath at any point(s) during iron deposition.

(b) Iron Loading in Deposition Bath

As with other first metals (e.g., copper as described above), iron loading in the deposition bath may affect the quality and/or dispersion of iron deposition over a sufficient portion of the support surface. The concentration of iron in the deposition bath is generally controlled to address these concerns and others (e.g., agglomeration of first metal). For example, typically iron is present in the first metal deposition bath at a concentration of at least about 2 g/L, more typically at least about 3 g/L and, still more typically, at least about 4 g/L. Preferably, iron is present in the deposition bath at a concentration of from about 2 to about 8 g/L, more preferably from about 3 to about 6 g/L and, still more preferably, from about 4 to about 5 g/L.

(c) Reducing Agents

To provide a driving force for deposition of a second metal thereon, preferably iron is deposited in an at least partially reduced state, e.g., as $Fe^{+2}$ and/or its fully reduced state as $Fe^0$. Thus, in various embodiments, the iron first metal deposition bath comprises a reducing agent. Any reducing agent is generally utilized under the conditions set forth above regarding copper deposition (e.g., concentration of reducing agent, etc.). Suitable reducing agents include sodium hypophosphite ($NaH_2PO_2$), formaldehyde ($CH_2O$), formic acid (HCOOH), salts of formic acid, sodium borohydride ($NaBH_4$), sodium triacetoxyborohydride ($Na(CH_3CO_2)_3BH$)), sodium alkoxides, hydrazine ($H_2NNH_2$), and ethylene glycol. In view of the greater electropositivity of iron as compared to copper, stronger reducing agents for iron first metal deposition may be preferred as compared to those preferred for copper first metal deposition. Thus, in various preferred embodiments the reducing agent is sodium borohydride or ethylene glycol.

In those embodiments in which the reducing agent is sodium borohydride and/or ethylene glycol, the molar ratio of reducing agent to iron deposited is generally at least 1, typically at least about 2, and more typically at least about 3. Typically in accordance with these embodiments, the molar ratio of sodium borohydride to iron deposited is form about 1 to about 5 and, more typically, from about 2 to about 4.

(d) Temperature

As with copper deposition, the temperature of the deposition bath affects iron nucleation and agglomeration. Generally, the temperature of the deposition bath is sufficient to provide suitable nucleation and agglomeration, but preferably not at a level that promotes first metal agglomeration to an undesired degree. Generally, iron deposition bath temperatures ranging from about 5° C. to about 60° C. may be utilized to provide suitable catalysts. Often, the temperature of the iron deposition bath is above ambient conditions in order to provide sufficient nucleation and, more particularly, suitable dispersion of first metal over the support surface. Thus, typically the temperature of the iron deposition bath is from about 25° C. to about 60° C. and, more typically, from about 25° C. to about 45° C.

(e) Agitation

The iron first metal deposition bath is typically agitated to promote dispersion of iron over the surface of the support. As in copper deposition, agitation may also promote diffusion of the reducing agent throughout the support. Any agitation during first metal deposition is generally conducted in accordance with the above description regarding copper deposition.

(f) Deposition pH

As with copper deposition, iron deposition generally proceeds more readily as deposition pH increases. Thus, typically the iron deposition pH is at least about 8, at least about 9, or at least about 10. Also as with iron deposition, the presence of a coordinating agent (e.g., sucrose) is currently believed to retard iron precipitation at high pH and thereby promote sufficient dispersion of the metal over the surface of the support. As noted, formation of a coordination complex between the first metal and a coordinating agent is generally enhanced at the above-noted pH levels. But at certain pH levels, deposition bath pH may negatively impact solvation or iron ions and first metal reduction and deposition. Thus, in various preferred embodiments the pH of the iron deposition bath is from about 8 to about 13, or from about 9 to about 12.

5. First Metal Deposition Atmosphere

Regardless of the precise conditions of first metal deposition and the dispersion of first metal deposited at the support surface, oxidation of deposited first metal may reduce the proportion of first metal exchange sites available for second metal deposition. Accordingly, in various preferred embodiments, the first metal is deposited onto the support in the presence of a non-oxidizing environment (e.g., a nitrogen atmosphere). Additionally or alternatively, water and/or other deposition bath components are degassed to remove dissolved oxygen using methods known to those skilled in the art.

B. Second Metal

Conventional noble metal-containing catalysts are generally prepared by depositing a noble metal at the surface of a support, typically a porous carbon support. Agglomeration of noble metal into particles, thereby reducing exposed metal catalytic surface area, has been observed with these methods. In particular, an abundance of relatively large metal-containing particles may represent inefficient usage of the metal by virtue of these particles providing a relatively low exposed catalytic surface area per unit metal.

In accordance with various embodiments of the present invention, noble metal-containing catalysts are prepared by a method in which the noble metal is deposited in a manner that increases the exposed metal catalytic surface area per unit weight of metal. More particularly, the noble metal is deposited at the surface of one or more regions of first metal by displacement of first metal from the regions. It is currently believed that deposition of the noble metal utilizing a first, sacrificial metal results in reduced noble metal agglomeration. For example, as noted elsewhere herein, deposition of the noble metal in this manner provides a catalyst precursor structure in which the noble metal deposited at the surface of one or more regions of a first metal is less prone to agglomeration than noble metal deposited directly onto the surface of a porous support. It is further currently believed that, upon heat treatment of supports having thereon noble metal deposited in this manner, metal particles are formed that provide improved noble (second) metal utilization (e.g., greater exposed metal catalytic surface area per unit metal weight).

Generally, the second metal is deposited onto a first metal-impregnated support by contact of the metal-impregnated support and a second metal deposition bath. More particularly, the second metal is generally deposited via electroless deposition in which the first metal-impregnated support and second metal deposition bath are contacted in the absence of an externally applied voltage.

As noted, in various embodiments, the second metal is a noble metal. Typically, the noble metal is selected from the group consisting of platinum, palladium, ruthenium, rhodium, iridium, silver, osmium, gold, and combinations thereof. In various preferred embodiments, the noble metal comprises platinum. In still other preferred embodiments, the noble metal comprises more than one metal (e.g., platinum and palladium or platinum and gold).

The following discussion focuses on deposition of platinum as the second metal, but it is to be understood that the present invention likewise contemplates utilizing any or all of the above-noted noble metals as the second metal. In addition, suitability of a combination of metals for use in displacement deposition of a second metal onto one or more regions of a first metal generally depends on their relative electropositivities. Thus, the present invention is not limited to deposition of noble metals as the second metal. For example, two metals designated as candidate first metals elsewhere herein may provide the first and second metals so long as their relative electropositivities allow displacement deposition of the second metal onto one or more regions of the first metal.

Suitable sources of platinum include those generally known in the art for use in liquid phase deposition of platinum and include, for example, $H_2PtCl_4$, $H_2PtCl_6$, $K_2PtCl_4$, $Na_2PtCl_6$, and combinations thereof. Thus, in various embodiments, the second metal deposition bath comprises a source of platinum including a platinum salt comprising platinum at an oxidation state of +2 and/or +4. As noted, in various preferred embodiments, the source of platinum provides platinum ions exhibiting an oxidation state of +2. However, it is to be understood that effective catalysts may be prepared utilizing sources of platinum that provide platinum ions having other oxidation states (e.g., +4), and sources of platinum that provide platinum ions that comprise platinum ions exhibiting oxidation states other than +2. Similarly, sources of noble metals other than platinum and second metal sources generally that provide metal ions at lower oxidation states are likewise preferred. For example, it is currently believed that palladium provided by $Na_2PdCl_4$ and $PdCl_2$ may be utilized to prepare active catalyst comprising palladium as the second metal.

Generally, the source of platinum is present in the second metal deposition bath in a proportion that provides a molar concentration of second metal ions less than the concentration of first metal ions in the first metal deposition bath. Typically, the molar ratio of copper ions in the first metal deposition bath to noble metal ions in the second metal deposition bath is greater than 1, more typically at least about 2 and, even more typically at least about 3 (e.g., at least about 5). In various preferred embodiments, the molar ratio of copper ions in the first metal deposition bath to noble metal ions in the second noble metal deposition bath is typically greater than 1 to about 20, more typically from about 2 to about 15, still more typically from about 3 to about 10 and, even more typically, from about 5 to about 7.5.

Generally, the first metal-impregnated support is not subjected to elevated temperatures prior to contact with the second metal deposition bath. That is, the catalyst precursor structure is preferably not subjected to temperatures that would promote formation of metal-containing particles (e.g., through agglomeration of first metal particles). For example, the first and second metal-impregnated support is generally subjected to temperatures of no more than about 200° C., no more than about 150° C., and preferably no more than about 120° C. prior to contact with the second metal deposition bath.

Typically, the metal-impregnated support and second metal deposition bath are contacted at a temperature of at least about 5° C., typically at least about 10° C. and, more typically, at least about 15° C. Preferably, the first metal-impregnated support and the second metal deposition bath are contacted at a temperature of from about 10° C. to about 60° C., from about 20° C. to about 50° C., or from about 25° C. to about 45° C.

Often, the second metal deposition bath has a pH less than the pH of the first metal deposition bath and is from about 1 to about 12 or from about 1.5 to about 10. In accordance with various embodiments, the pH of the deposition bath is from about 2 to about 7 or from about 3 to about 5. Such pH conditions have been observed to be suitable for deposition of a noble (second) metal onto one or more regions of copper first metal. In various preferred embodiments, the first metal is iron. As compared to copper, iron may be more readily leached from the surface of the support as the pH of the deposition bath decreases. Thus, in accordance with those embodiments in which the first metal is iron, the pH of the noble (second) metal deposition bath is typically from about 4 to about 9, and preferably from about 5 to about 8 (e.g., about 7).

As noted above, preferably the first metal is deposited in an environment that avoids oxidation of deposited first metal that may reduce the proportion of first metal exchange sites available for second metal deposition. Likewise, in various preferred embodiments, the second metal is also deposited onto the first metal-impregnated support in a non-oxidizing environment (e.g., a nitrogen atmosphere) to avoid oxidation of deposited first and second metal.

C. First and Second Metal-Impregnated Support

As noted, preferably the first metal deposited at the support surface provides suitable exchange sites for deposition of second metal at the surface of one or more regions of first metal and, more particularly, an excess of exchange sites for second metal deposition. Accordingly, typically the atom ratio of first metal to second metal of the first and second metal-impregnated support (i.e., catalyst precursor structure) is at least about 1.5, more typically at least about 2 and, still more typically, at least about 3 (e.g., at least about 4 or at least about 5). Preferably, the atom ratio of first metal to second metal of the first and second metal-impregnated support is from about 1.5 to about 15 more preferably from about 2 to about 15, still more preferably from about 3 to about 10 and, even more preferably, from about 4 to about 8.

As noted, heat treatment of the impregnated support provides first and noble (second) metal-containing particles at the support surface including the noble (second) metal in a form that provides advantageous metal utilization. An excess of first metal atoms to second metal atoms on the impregnated support is believed to result in formation of such particles. For example, the excess of first metal to second metal atoms on the impregnated support provides first metal-rich particles that include a relatively low proportion of unexposed noble (second) metal throughout the particles (e.g., a bimetallic alloy having an excess of first metal atoms).

Additionally or alternatively, and as generally depicted in FIG. 2, heat treatment of the first and second metal-impregnated support may form metal particles comprising a core and a shell at least partially surrounding the core. It is currently believed that the composition of the core and shell indicate improvements in metal utilization and, more particularly, improvements in second metal (e.g., noble metal) utilization. For example, the core of these particles is generally first metal-rich, thereby providing a relatively low proportion of unexposed second metal throughout the particles.

As the atom ratio of first metal to second metal in the catalyst precursor increases, the extent to which the first metal-rich core is surrounded by a second metal-containing shell may decrease. For example, a relatively high excess of first metal exchange sites for second metal deposition may result in a portion of exchange sites that do not participate in displacement deposition of noble (second) metal. Such particles may be prepared from catalyst precursors in which the atom ratio is near or above the above-noted upper limit of first metal to second metal atom ratios (e.g., about 10 or higher). Although less preferred, it should be understood that a decrease in the degree to which the core is surrounded by a second metal-containing shell does not necessarily indicate a lack of improved second metal utilization. These particles may nonetheless provide improved metal utilization based on, for example, a first metal-rich core that provides a relatively low proportion of unexposed, and potentially unutilized noble (second) metal. However, it is currently believed that the structure of the particles may shift toward increased coverage of the first metal-rich core by the second metal-containing shell. More particularly, this shift in form of the particles may comprise leaching of first metal from the metal particle at the support surface during use of the catalyst in liquid phase reactions. Second metal may likewise be removed or leached from the particles, but it is currently believed that first metal is removed from the particles to a greater degree than second metal. Accordingly, the atom ratio of first metal to second metal approaches more preferred ranges and it is currently believed that as a result of this removal the structure of particles shifts to more preferred (i.e., more extensive) coverage of the first metal-rich core by the second metal-containing shell. After a period of use, the leaching of first metal from the metal particles on the support surface generally decreases. Following such a period of use, it is currently believed that catalysts comprising particles having a more preferred ratio of first metal to second metal atoms with the attendant shift in structure, thereafter exhibit performance characteristics comparable to catalysts prepared using the more preferred ratios of first metal to second metal atoms. This "self-correcting" behavior has been observed, for example, in connection with catalysts in which the first metal is copper and the second metal is platinum.

D. Heat Treatment of First and Second Metal-Impregnated Supports

As noted, it is to be understood that the metal-impregnated support of the present invention is a suitable catalyst as described in the working examples detailed herein. However, typically in accordance with various preferred embodiments, the metal-impregnated support is treated at elevated temperatures generally as detailed elsewhere herein (e.g., in the presence of a non-oxidizing environment at temperatures in excess of about 800° C.) to form a finished catalyst. Typically, the metal-impregnated support is heated to temperatures from about 400° C. to about 1000° C., more typically from about 500° C. to about 950° C., still more typically from about 600° C. to about 950° C. and, even more typically, from about 700° C. to about 900° C. Subjecting metal-impregnated supports to such temperatures provides finished catalysts exhibiting reduced metal leaching and improved metal utilization as detailed elsewhere herein (e.g., catalysts comprising first metal-rich particles and/or particles including a first metal-rich core at least partially surrounded by a second metal-rich shell).

Stable metal particles (i.e., resistant to leaching) are currently believed to be readily formed in the case of first and second metal-impregnated supports in which the first metal is iron and the second metal is platinum. Iron and platinum-impregnated supports (i.e., iron-platinum catalyst precursors) have been observed to exhibit suitable stability during reaction testing. Preferably, however, the iron-platinum catalyst precursor is subjected to elevated temperatures to prepare a finished catalyst. It is currently believed that heating the iron-platinum impregnated support improves activity. But, in view of the advantageous stability of the iron and platinum-impregnated supports, suitable catalysts may be prepared therefrom by heating the catalyst precursor to temperatures within, but at or near the lower limits of the above-noted ranges. Thus, in accordance with certain embodiments, platinum-iron impregnated supports are subjected to a maximum temperature of from about 400° C. to about 750° C., or from about 500° C. to about 650° C. to prepare a finished catalyst.

As noted, the degree of first and second metal alloying generally increases with increasing temperature to which the metal-impregnated support is subjected. Accordingly, subjecting the iron/platinum-impregnated support to a relatively low maximum temperature is currently believed to provide a relatively low degree of iron and platinum alloying. Although catalysts of the present invention include the first and second metals in a form that represents efficient metal utilization (e.g., a first metal-rich alloy), alloy formation unavoidably results in unexposed noble (second) metal. Thus, preparing iron and platinum-containing catalysts by subjecting the metal-impregnated support to relatively low temperature may contribute to improved metal utilization. However, in this regard it is to be noted that preparing iron and platinum-containing catalysts by subjecting the supports to higher temperatures, e.g., in the ranges noted above such as 700° C. or higher, is likewise currently believed to provide catalysts that represent more efficient metal utilization.

E. Iron and Platinum Deposition Protocols

Suitable iron and platinum-containing catalysts generally may be prepared in accordance with the above discussion regarding iron (first metal) and platinum (second metal) deposition, both in accordance with the above discussions concerning first and second metals generally, and specifically iron and platinum. However, in accordance with the present invention it has been discovered that advantageous catalysts are provided by combinations of particular features of iron (first metal) and platinum (second metal) deposition.

For example, in various preferred embodiments, the iron (first metal) deposition bath comprises ethylene glycol as a reducing agent, but does not comprise a separate coordinating agent (e.g., sucrose). However, it is to be understood that the ethylene glycol reducing agent may, in fact, function as a coordinating agent to a certain degree.

In still other preferred embodiments, the iron deposition bath comprises both a reducing agent and a coordinating agent. In various such embodiments, ethylene glycol is the reducing agent and sucrose is the coordinating agent. In further such embodiments, ethylene glycol and sodium borohydride are utilized as reducing agents for iron deposition, and the iron deposition bath also comprises sucrose as a coordinating agent.

In various other preferred embodiments, the iron (first metal) deposition bath comprises sodium borohydride as a reducing agent generally in accordance with the above discussion. The iron deposition bath does not comprise a separate coordinating agent (e.g., sucrose).

F. First and Second Metal-Containing Catalysts

As noted, first and noble (second) metal-impregnated supports typically contain an excess of first metal atoms over second metal atoms. In accordance with these and various other embodiments, generally the first metal constitutes at least about 1% by weight, at least about 1.5% by weight, or at least about 2% by weight of the catalyst. Typically the first metal constitutes at least about 3% by weight, at least about 4% by weight, or at least about 5% by weight of the catalyst. For example, preferably the first metal constitutes from about 3% to about 25% by weight of the catalyst, more preferably from about 4% to about 20% by weight of the catalyst and, still more preferably, from about 5% to about 15% by weight of the catalyst. In various other embodiments (e.g., those in which iron is the first metal), the first metal constitutes from about 1% to about 10% by weight, more preferably from about 1.5% to about 8% by weight and, still more preferably, from about 2% to about 5% (e.g., about 4%) by weight of the catalyst.

In accordance with the foregoing, catalysts of various embodiments of the present invention generally contain at least about 1% by weight noble (second) metal, at least about 2% by weight noble metal, or at least about 3% by weight noble metal. Typically, the catalysts contain less than about 8% by weight noble metal, more typically less than about 7% by weight noble metal and, still more typically, less than about 6% by weight noble metal. In accordance with various preferred embodiments, the catalysts contain less than about 5% or less than about 4% by weight noble metal (e.g., from about 1% to about 3% by weight noble metal). Catalysts prepared as detailed herein more efficiently utilize the noble (second) metal as compared to conventional catalysts, thereby providing catalysts at least as active or even more active than conventional noble metal-containing catalysts. For example, catalysts can be prepared that include metal loadings similar to conventional noble metal-containing catalysts, but are generally more active and, in various preferred embodiments, much more active than conventional noble metal-containing catalysts. In this manner, catalytic activity can be increased without an increase in noble metal loading, which may be undesired due to processing limitations. In various embodiments, active catalysts can be prepared that contain from about 3% to about 6% by weight noble metal, or from about 4% to about 5% by weight noble metal.

By way of further example, more efficient metal usage by catalysts of the present invention allows preparation of catalysts that include a reduced proportion of second metal as compared to conventional noble metal-containing catalysts, but that are at least as active and, in various preferred embodiments, more active than conventional noble metal-containing catalysts. In this manner, catalysts of the present invention can provide activities equivalent to those provided by conventional noble metal-containing catalysts at lower noble metal loadings, or greater catalytic activities at equivalent noble metal loadings. For example, in various embodiments, active catalysts may be prepared that contain from about 1% to about 5% by weight, from about 1.5% to about 4% by weight, or from about 2% to about 3% by weight noble metal.

In various embodiments, first metal to second metal atom ratio in metal particles at the surface of the catalyst support generally increases with increasing particle size. It is currently believed that as particle size increases the portion of the particle constituting the first metal-rich core increases, while the portion (i.e., weight fraction) of the particles constituting the second metal-containing shell decreases. As previously noted, larger metal-containing particles are generally more resistant to leaching from the surface of the catalyst support. However, a significant fraction of larger particles is generally undesired in conventional noble metal-containing catalysts because as particle size increases the proportion of noble metal distributed within the particle that does not contribute to effective catalytic surface area increases. Thus, a relatively high proportion of large particles comprising a second metal-rich shell in accordance with the present invention provides improved stability, without the sacrifice in exposed noble (second) metal catalytic surface area associated with relatively large particles in conventional noble metal-containing catalysts.

For example, in various embodiments, the catalyst includes metal-containing particles characterized by a particle size, as determined using electron microscopy, such that a significant fraction (e.g., at least about 80%, at least about 90%, or at least about 95%, number basis) of the particles are from about 5 to about 60 nm, or from about 5 to about 40 nm in their largest dimension. In addition, the thickness of the second metal-containing shells of the particles within these size distributions nm is typically less than about 3 nm, more typically less than about 2 nm, and preferably less than about 1 nm (e.g., less than about 0.8 nm or less than about 0.6 nm).

Improvements in metal utilization may be characterized by an increase in the proportion of exposed noble (second) metal of the catalyst. More particularly, improvements in metal utilization may be indicated by an increase in the surface area of exposed noble metal per unit weight catalyst per unit weight noble metal. The total exposed noble metal surface area of catalysts of the present invention may be determined using static carbon monoxide chemisorption analysis, including Protocol A described in Example 67. The carbon monoxide chemisorption analysis described in Example 67 includes first and second cycles. Catalysts of the present invention subjected to such analysis are generally characterized as chemisorbing at least about 500 μmoles of carbon monoxide per gram catalyst per gram noble metal and, more generally, at least about 600 μmoles of carbon monoxide per gram catalyst per gram noble metal. Typically, catalysts of the present invention are characterized as chemisorbing at least about 700, at least about 800, at least about 900, at least about 975, at least about 1000, or at least about 1100 μmoles of carbon monoxide per gram catalyst per gram noble metal.

An alternative or additional indicator of efficient metal utilization is the proportion of the noble (second) metal of the catalyst that may be found within a shell at least partially surrounding a first metal-rich core. Generally, at least about 10%, at least about 20%, at least about 30%, at least about 40%, or at least about 50% of the noble metal is present within the shell of the metal particles. Typically, at least about 60% and, more typically, at least about 70% (e.g., at least about 80% or at least about 90%) of the noble metal is present within the shell of the metal particles.

Additionally or alternatively, efficient metal utilization may be indicated by the proportion of noble (second) metal at the surface of metal particles. That is, efficient metal utilization may be indicated by the proportion of noble metal at the surface of first metal-rich particles, e.g., second metal present in an alloy and/or within a second metal-rich shell at least partially surrounding a first metal-rich core. Generally, the atom percent of noble metal at the surface of first and noble (second) metal-containing particles is at least about 2%, or at least about 5%. Typically, the atom percent of noble metal at the surface of first and noble metal-containing particles is at least about 10%, more typically at least about 20%, even more typically at least about 30%, and preferably at least about 40% (e.g., at least about 50%).

Energy dispersive x-ray spectroscopy (EDX) line scan analysis results for catalysts of the present invention (e.g., as described in Protocol B in Example 68) also indicate efficient metal utilization. More particularly, line scan analysis results for metal particles of catalysts of the present invention indicate a distribution of noble (second) metal in which a significant fraction of the noble (second) metal is present within a shell at least partially surrounding a first metal-rich core. Additionally or alternatively, line scan analysis results for metal particles of catalysts of the present invention indicate a noble metal distribution in which a significant fraction of the noble metal is disposed at or near the surface of a metal particle(s).

Efficient metal utilization in particles of catalysts of the present invention is indicated by a second metal distribution that produces an EDX line scan signal that does not vary significantly over a scanning region. As used herein, the term scanning region refers to the portion of the largest dimension of the particle analyzed over which a relatively low degree of variation in second metal signal indicates improved metal utilization. A relatively constant second metal line scan signal over a scanning region corresponding to a significant portion of the largest dimension of the particle indicates that a significant fraction of the second metal is distributed near the surface of the particle rather than throughout the metal particle. By contrast, the latter type of distribution would cause the second metal signal to increase (decrease) significantly in that portion of the scanning region where the probe is directed to a thicker (thinner) dimension of the particle. For example, in various embodiments, the second metal signal generated during EDX line scan analysis of a particle at the surface of a catalyst in accordance with the present invention varies by no more than about 25%, no more than about 20%, no more than about 15%, no more than about 10%, or no more than about 5% across a scanning region that is a least about 70% of the largest dimension of at least one particle. In further embodiments, the second metal signal varies by no more than about 20%, no more than about 15%, no more than about 10%, or no more than about 5% across a scanning region that is at least about 60% of the largest dimension of at least one particle. In still further embodiments, the second metal signal varies by no more than about 15%, no more than about 10%, or no more than about 5% across a scanning region that is at least about 50% of the largest dimension of at least one particle.

The particles having metal distributions characterized by EDX line scan analysis as detailed above are typically first metal-rich and, more particularly, typically include the second metal and first metal at an atomic ratio of second metal to first metal in a particle(s) analyzed of less than 1:1. Typically, the second metal to first metal atomic ratio of the particle(s) is less than about 0.8:1 and, more typically, less than about 0.6:1 (e.g., less than about 0.5:1).

Generally, the first and second metal particle(s) of catalysts of the present invention having a second metal distribution characterized by EDX line scan analysis indicating efficient metal utilization have a largest dimension of at least about 6 nm, typically at least about 8 nm, more typically at least about 10 nm and, still more typically, at least about 12 nm.

The relative magnitudes of first and second metal signals across the scanning region may also indicate first and second metal distributions in a form that indicates efficient metal utilization. More particularly, generally in accordance with various embodiments, the ratio of the maximum first metal signal to the maximum second metal signal across the scanning region is at least about 1.5:1, at least about 2:1, or at least about 2.5:1. Typically, the ratio of the maximum first metal signal to the maximum second metal signal across the scanning region is at least about 3:1, at least about 4:1, or at least about 5:1.

It is to be understood that efficient metal utilization may be indicated by identification of at least one particle at the surface of the catalyst support having a noble (second) metal distribution characterized as described above. That is, the population of metal particles at the surface of the catalyst support may include both particles satisfying one or more of the noble metal distribution characteristics and those that do not. However, metal utilization is enhanced as the proportion of metal particles exhibiting these preferred noble metal distribution characteristics increases and typically a plurality of metal particles will possess these characteristics. More typically, the second metal distribution of each of a portion (number basis) of the particles at the surface of the support indicates efficient metal utilization. Generally, at least about 1%, at least about 5%, at least about 10%, at least about 15%, at least about 20%, or at least about 25% of the metal particles satisfy the second metal distribution characteristics. Typically, at least about 30%, at least about 35%, at least about 40%, at least about 45%, at least about 50%, at least about 55%, at least about 60%, or at least about 65% of the metal particles satisfy the second metal distribution characteristics. The proportion of metal particles satisfying one or more of the noble metal distribution characteristics is somewhat dependent upon the particular first metal and second metal combination. For example, catalysts prepared with copper and platinum as the first and second metals, respectively, have been observed to produce catalysts in which a large portion of metal particles at the surface thereof possess these preferred noble metal distribution characteristics. Accordingly, in these and other preferred embodiments, at least about 70%, at least about 75%, at least about 85%, or at least about 90% of the metal particles at the surface of the support satisfy one or more of the second metal distribution characteristics determined by EDX line scan analysis.

As previously noted, in various embodiments of the present invention (e.g., in which copper is the first metal and platinum is the second metal) the second metal-rich shell may provide relatively low coverage of the first metal-rich core and, during subsequent use of the catalyst, the structure of the particles may shift toward increased coverage of the first metal-rich core by the second metal-containing shell. This shift generally comprises leaching of the first metal from the metal particles at the support surface. Second metal may be removed or leached from the particles, but to a lesser degree than first metal is removed from the particles. This behavior has been observed to provide a shift toward preferred first metal to second metal atomic ratios.

Platinum-iron catalysts of the present invention have been observed to behave as described. That is, during use, iron and platinum may be leached from the metal particles at the surface of the catalyst and, more particularly, iron is leached from the particles to a greater degree than platinum. Leaching in this manner may proceed in accordance with the "self-correcting" mechanism described above in connection with platinum-copper catalysts. However, leaching may also proceed to form platinum-iron particles of advantageous structures. Rather than compensating for a relatively low excess of first metal to second metal to provide a structure in which the atomic ratio of first metal to second metal is at a suitable excess, leaching of first metal predominates over any leaching of second metal to such a degree that one or more particles are provided that exhibit minimal, if any, excess of first metal to second metal. In fact, in various embodiments, a catalyst structure exhibiting an excess of second metal to first metal is achieved. Although these particles may not include a first metal-rich alloy or a first metal-rich core at least partially surrounded by a second metal-rich shell, they do nonetheless provide improved metal utilization.

In various such embodiments, the metal particles at the surface of the catalyst are in the form of a structure comprising a discontinuous shell comprising a layer of first metal atoms and a layer (e.g., monolayer) of second metal atoms at the surface of the first metal atoms. Reference to a shell in connection with these embodiments does not indicate the presence of a continuous or discontinuous shell surrounding a relatively continuous core. Rather, shell refers to the overall structure of the resulting particle. The shell structure may surround an inner region including first metal, but the inner regions of the shell structure are not in the form of a relatively continuous first metal-rich core surrounded by the outer regions of the shell structure. The discontinuous porous shell generally comprises pores and, more particularly, nanopores (i.e., pores having a size in their largest dimension of from about 1 to about 6 nanometers (nm), or from about 2 to about 5 nm). In this manner, the shell structure may be referred to as a discontinuous nanoporous shell. In accordance with such embodiments, the atomic ratio of iron (first metal) to platinum (second metal) is generally less than 1:1, typically from about 0.25:1 to about 0.9:1, more typically from about 0.4:1 to about 0.75:1 and, more typically, from about 0.4:1 to about 0.6:1 (e.g., about 0.5:1). Further in accordance with these embodiments, the layer or regions of first metal generally have a thickness of no more than about 5 first metal atoms, typically no more than about 3 first metal atoms and, still more typically, no more than about 2 first metal atoms. Additionally or alternatively, the layer or regions of second metal atoms generally have a thickness of no more than about 5 second metal atoms, typically no more than about 4 second metal atoms, more typically no more than about 3 second metal atoms and, more typically, no more than about 2 second metal atoms.

Extensive leaching of metal from catalyst particles to form platinum-iron "shell" particles has been observed to occur during use under certain conditions (e.g., acidic conditions prevailing during oxidation of PMIDA). Experimental evidence indicates that catalysts including platinum-iron shell particles are effective for use in, for example, the liquid phase oxidation of PMIDA. Thus, rather than simply relying on formation of the shell structure during use, catalysts including platinum-iron shell particles may be prepared by a process generally as described above for preparation of platinum-iron catalysts further including treatment for leaching of metals from one or more particles of the catalyst prior to or during use of the catalyst. Generally, treatment for metal leaching to form platinum-iron shell particles comprises contacting a platinum-iron catalyst with a suitable liquid medium. Typically, the liquid medium is acidic and the catalyst is contacted with the liquid medium at a temperature of at least about 5° C., or at least about 15° C.

III. Use of Oxidation Catalysts

Oxidation catalysts of the present invention may be used for liquid phase oxidation reactions. Examples of such reactions include the oxidation of alcohols and polyols to form aldehydes, ketones, and acids (e.g., the oxidation of 2-propanol to form acetone, and the oxidation of glycerol to form glyceraldehyde, dihydroxyacetone, or glyceric acid); the oxidation of aldehydes to form acids (e.g., the oxidation of formaldehyde to form formic acid, and the oxidation of furfural to form 2-furan carboxylic acid); the oxidation of tertiary amines to form secondary amines (e.g., the oxidation of nitrilotriacetic acid (NTA) to form iminodiacetic acid (IDA)); the oxidation of secondary amines to form primary amines (e.g., the oxidation of IDA to form glycine); and the oxidation of various acids (e.g., formic acid or acetic acid) to form carbon dioxide and water.

The above-described catalysts are especially useful in liquid phase oxidation reactions at pH levels less than 7, and in particular, at pH levels less than 3. One such reaction is the oxidation of PMIDA or a salt thereof to form an N-(phosphonomethyl)glycine product in an environment having pH levels in the range of from about 1 to about 2. This reaction is often carried out in the presence of solvents which solubilize noble metals and, in addition, the reactants, intermediates, or products often solubilize noble metals.

The oxidation catalyst disclosed herein is particularly suited for catalyzing the liquid phase oxidation of a tertiary amine to a secondary amine, for example in the preparation of glyphosate and related compounds and derivatives. For example, the tertiary amine substrate may correspond to a compound of Formula I having the structure

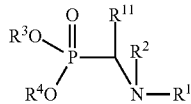

(Formula I)

wherein $R^1$ is selected from the group consisting of $R^5OC(O)CH_2$— and $R^5OCH_2CH_2$—, $R^2$ is selected from the group consisting of $R^5OC(O)CH_2$—, $R^5OCH_2CH_2$—, hydrocarbyl, substituted hydrocarbyl, acyl, —$CHR^6PO_3R^7R^8$, and —$CHR^9SO_3R^{13}$, $R^6$, $R^9$ and $R^{11}$ are selected from the group consisting of hydrogen, alkyl, halogen and —$NO_2$, and $R^3$, $R^4$, $R^5$, $R^7$, $R^8$ and are independently selected from the group consisting of hydrogen, hydrocarbyl, substituted hydrocarbyl and a metal ion. Preferably, $R^8$ comprises $R^5OC(O)CH_2$—, $R^{11}$ is hydrogen, $R^5$ is selected from hydrogen and an agronomically acceptable cation and $R^2$ is selected from the group consisting of $R^5OC(O)CH_2$—, acyl, hydrocarbyl and substituted hydrocarbyl.

As noted above, the oxidation catalyst of the present invention is particularly suited for catalyzing the oxidative cleavage of a PMIDA substrate to form N-(phosphonomethyl)glycine product. In such an embodiment, the catalyst is effective for oxidation of by-product formaldehyde to formic acid, carbon dioxide and/or water. More particularly, it is currently believed that catalysts of the present invention may provide improvements in activity for PMIDA, formaldehyde, and/or formic acid oxidation as compared to conventional noble metal-containing catalysts, either generally or on a per unit metal weight basis.

As is recognized in the art, the liquid phase oxidation of N-(phosphonomethyl)iminodiacetic acid substrates may be carried out in a batch, semi-batch or continuous reactor system containing one or more oxidation reaction zones. The oxidation reaction zone(s) may be suitably provided by various reactor configurations, including those that have back-mixed characteristics, in the liquid phase and optionally in the gas phase as well, and those that have plug flow characteristics. Suitable reactor configurations having back-mixed characteristics include, for example, stirred tank reactors, ejector nozzle loop reactors (also known as venturi-loop reactors) and fluidized bed reactors. Suitable reactor configurations having plug flow characteristics include those having a packed or fixed catalyst bed (e.g., trickle bed reactors and packed bubble column reactors) and bubble slurry column reactors. Fluidized bed reactors may also be operated in a manner exhibiting plug flow characteristics. The configuration of the oxidation reactor system, including the number of oxidation reaction zones and the oxidation reaction conditions are not critical to the practice of the present invention. Suitable oxidation reactor systems and oxidation reaction conditions for liquid phase catalytic oxidation of an N-(phosphonomethyl)iminodiacetic acid substrate are well-known in the art and described, for example, by Ebner et al., U.S. Pat. No. 6,417,133, by Leiber et al., U.S. Pat. No. 6,586,621, and by Haupfear et al., U.S. Pat. No. 7,015,351, the entire disclosures of which are incorporated herein by reference.

The description below discloses with particularity the use of catalysts described above acting as the catalyst to effect the oxidative cleavage of a PMIDA substrate to form an N-(phosphonomethyl)glycine product. It should be recognized, however, that the principles disclosed below are generally applicable to other liquid phase oxidative reactions, especially those at pH levels less than 7 and those involving solvents, reactants, intermediates, or products which solubilize noble metals.

To begin the PMIDA oxidation reaction, it is preferable to charge the reactor with the PMIDA substrate, catalyst, and a solvent in the presence of oxygen. The solvent is most preferably water, although other solvents (e.g., glacial acetic acid) are suitable as well.

The reaction may be carried out in a wide variety of batch, semi-batch, and continuous reactor systems. The configuration of the reactor is not critical. Suitable conventional reactor configurations include, for example, stirred tank reactors, fixed bed reactors, trickle bed reactors, fluidized bed reactors, bubble flow reactors, plug flow reactors, and parallel flow reactors.

When conducted in a continuous reactor system, the residence time in the reaction zone can vary widely depending on the specific catalyst and conditions employed. Typically, the residence time can vary over the range of from about 3 to about 120 minutes. Preferably, the residence time is from about 5 to about 90 minutes, and more preferably from about 5 to about 60 minutes. When conducted in a batch reactor, the reaction time typically varies over the range of from about 15 to about 120 minutes. Preferably, the reaction time is from about 20 to about 90 minutes, and more preferably from about 30 to about 60 minutes.

In a broad sense, the oxidation reaction may be practiced in accordance with the present invention at a wide range of temperatures, and at pressures ranging from sub-atmospheric to super-atmospheric. Use of mild conditions (e.g., room temperature and atmospheric pressure) have obvious commercial advantages in that less expensive equipment may be used. However, operating at higher temperatures and super-atmospheric pressures, while increasing capital requirements, tends to improve phase transfer between the liquid and gas phase and increase the PMIDA oxidation reaction rate.

Preferably, the PMIDA oxidation reaction is conducted at a temperature of from about 20 to about 180° C., more preferably from about 50 to about 140° C., and most preferably from about 80 to about 110° C. At temperatures greater than about 180° C., the raw materials tend to begin to slowly decompose.

The pressure used during the PMIDA oxidation generally depends on the temperature used. Preferably, the pressure is sufficient to prevent the reaction mixture from boiling. If an oxygen-containing gas is used as the oxygen source, the pressure also preferably is adequate to cause the oxygen to dissolve into the reaction mixture at a rate sufficient such that the PMIDA oxidation is not limited due to an inadequate oxygen supply. The pressure preferably is at least equal to atmospheric pressure. More preferably, the pressure is from about 30 to about 500 psig, and most preferably from about 30 to about 130 psig.

The concentration of the catalyst prepared in accordance with the present invention in the reaction mixture is preferably is from about 0.1 to about 10% by weight ([mass of catalyst÷total reaction mass]×100%). More preferably, the catalyst concentration preferably is from about 0.1 to about 5% by weight, still more preferably from about 0.2 to about 5% by weight and, most preferably, from about 0.3 to about 1.5% by weight. Concentrations greater than about 10% by weight are difficult to filter. On the other hand, concentrations less than about 0.1% by weight tend to produce unacceptably low reaction rates.

As noted, catalysts prepared in accordance with the methods of the present invention provide for efficient metal utilization. Thus, catalysts of the present invention may provide sufficient activity at lower catalyst loadings as compared to loadings associated with conventional noble metal-containing catalysts. Accordingly, catalysts loadings in accordance with the present invention may suitably be at or near the lower limits of the above-noted ranges. However, it is to be understood that utilizing a lower catalyst loading is not a critical aspect of the present invention. In fact, a further aspect of the present invention involves utilizing the catalysts of the present invention at loadings similar to those associated with conventional noble metal-containing catalysts while providing improved catalytic activity based on the improvements in metal utilization.

The concentration of PMIDA substrate in the feed stream is not critical. Use of a saturated solution of PMIDA substrate in water is preferred, although for ease of operation, the process is also operable at lesser or greater PMIDA substrate concentrations in the feed stream. If the catalyst is present in the reaction mixture in a finely divided form, it is preferred to use a concentration of reactants such that all reactants and the N-(phosphonomethyl)glycine product remain in solution so that the catalyst can be recovered for re-use, for example, by filtration. On the other hand, greater concentrations tend to increase reactor through-put. Alternatively, if the catalyst is present as a stationary phase through which the reaction medium and oxygen source are passed, it may be possible to use greater concentrations of reactants such that a portion of the N-(phosphonomethyl)glycine product precipitates.

Normally, a PMIDA substrate concentration of up to about 50% by weight ([mass of PMIDA substrate total reaction mass]×100%) may be used (especially at a reaction temperature of from about 20 to about 180° C.). Preferably, a PMIDA substrate concentration of up to about 25% by weight is used (particularly at a reaction temperature of from about 60 to about 150° C.) More preferably, a PMIDA substrate concentration of from about 12 to about 18% by weight is used (particularly at a reaction temperature of from about 100 to about 130° C.). PMIDA substrate concentrations below 12% by weight may be used, but are less economical because a relatively low payload of N-(phosphonomethyl)glycine product is produced in each reactor cycle and more water must be removed and energy used per unit of N-(phosphonomethyl) glycine product produced. Relatively low reaction temperatures (i.e., temperatures less than 100° C.) often tend to be less advantageous because the solubility of the PMIDA substrate and N-(phosphonomethyl)glycine product are both relatively low at such temperatures.

The oxygen source for the PMIDA oxidation reaction may be any oxygen-containing gas or a liquid comprising dissolved oxygen. Preferably, the oxygen source is an oxygen-containing gas. As used herein, an oxygen-containing gas is any gaseous mixture comprising molecular oxygen which optionally may comprise one or more diluents which are non-reactive with the oxygen or with the reactant or product under the reaction conditions.

Examples of such gases are air, pure molecular oxygen, or molecular oxygen diluted with helium, argon, nitrogen, or other non-oxidizing gases. For economic reasons, the oxygen source most preferably is air, oxygen-enriched air, or pure molecular oxygen.

Oxygen may be introduced by any conventional means into the reaction medium in a manner which maintains the dissolved oxygen concentration in the reaction mixture at a desired level. If an oxygen-containing gas is used, it preferably is introduced into the reaction medium in a manner which maximizes the contact of the gas with the reaction solution. Such contact may be obtained, for example, by dispersing the gas through a diffuser such as a porous frit or by stirring, shaking, or other methods known to those skilled in the art.

The oxygen feed rate preferably is such that the PMIDA oxidation reaction rate is not limited by oxygen supply. If the dissolved oxygen concentration is too high, however, the catalyst surface tends to become detrimentally oxidized, which, in turn, tends to lead to more leaching of noble metal present in the catalyst and decreased formaldehyde activity (which, in turn, leads to more NMG being produced). Generally, it is preferred to use an oxygen feed rate such that at least about 40% of the oxygen is utilized. More preferably, the oxygen feed rate is such that at least about 60% of the oxygen is utilized. Even more preferably, the oxygen feed rate is such that at least about 80% of the oxygen is utilized. Most preferably, the rate is such that at least about 90% of the oxygen is utilized. As used herein, the percentage of oxygen utilized equals: (the total oxygen consumption rate÷oxygen feed rate)×100%. The term "total oxygen consumption rate" means the sum of: (i) the oxygen consumption rate ("$R_i$") of the oxidation reaction of the PMIDA substrate to form the N-(phosphonomethyl)glycine product and formaldehyde, (ii) the oxygen consumption rate ("$R_{ii}$") of the oxidation reaction of formaldehyde to form formic acid, and (iii) the oxygen consumption rate ("$R_{iii}$") of the oxidation reaction of formic acid to form carbon dioxide and water.

In various embodiments of this invention, oxygen is fed into the reactor as described above until the bulk of PMIDA substrate has been oxidized, and then a reduced oxygen feed rate is used. This reduced feed rate preferably is used after about 75% of the PMIDA substrate has been consumed. More preferably, the reduced feed rate is used after about 80% of the PMIDA substrate has been consumed. Where oxygen is supplied as pure oxygen or oxygen-enriched air, a reduced feed rate may be achieved by purging the reactor with (non-enriched) air, preferably at a volumetric feed rate which is no greater than the volumetric rate at which the pure molecular oxygen or oxygen-enriched air was fed before the air purge. The reduced oxygen feed rate preferably is maintained for from about 2 to about 40 minutes, more preferably from about 5 to about 20 minutes, and most preferably from about 5 to about 15 minutes. While the oxygen is being fed at the reduced rate, the temperature preferably is maintained at the same temperature or at a temperature less than the temperature at which the reaction was conducted before the air purge. Likewise, the pressure is maintained at the same or at a pressure less than the pressure at which the reaction was conducted before the air purge. Use of a reduced oxygen feed rate near the end of the PMIDA reaction allows the amount of residual formaldehyde present in the reaction solution to be reduced without producing detrimental amounts of AMPA by oxidizing the N-(phosphonomethyl)glycine product.

Reduced losses of noble metal may be observed with this invention if a sacrificial reducing agent is maintained or introduced into the reaction solution. Suitable reducing agents include formaldehyde, formic acid, and acetaldehyde. Most preferably, formic acid, formaldehyde, or mixtures thereof are used. Experiments conducted in accordance with this invention indicate that if small amounts of formic acid, formaldehyde, or a combination thereof are added to the reaction solution, the catalyst will preferentially effect the oxidation of the formic acid or formaldehyde before it effects the oxidation of the PMIDA substrate, and subsequently will be more active in effecting the oxidation of formic acid and formaldehyde during the PMIDA oxidation. Preferably from about 0.01 to about 5% by weight ([mass of formic acid, formaldehyde, or a combination thereof total reaction mass]×100%) of sacrificial reducing agent is added, more preferably from about 0.01 to about 3% by weight of sacrificial reducing agent is added, and most preferably from about 0.01 to about 1% by weight of sacrificial reducing agent is added.

In certain embodiments, unreacted formaldehyde and formic acid are recycled back into the reaction mixture for use in subsequent cycles. In this instance, an aqueous recycle stream comprising formaldehyde and/or formic acid also may be used to solubilize the PMIDA substrate in the subsequent cycles. Such a recycle stream may be generated by evaporation of water, formaldehyde, and formic acid from the oxidation reaction mixture in order to concentrate and/or crystallize product N-(phosphonomethyl)glycine. Overheads condensate containing formaldehyde and formic acid may be suitable for recycle.

Typically, the concentration of N-(phosphonomethyl)glycine in the product mixture may be as great as 40% by weight, or greater. Preferably, the N-(phosphonomethyl)glycine concentration is from about 5 to about 40%, more preferably from about 8 to about 30%, and still more preferably from about 9 to about 15%. Concentrations of formaldehyde in the product mixture are typically less than about 0.5% by weight, more preferably less than about 0.3%, and still more preferably less than about 0.15%.

Following the oxidation, the catalyst preferably is subsequently separated by filtration. The N-(phosphonomethyl) glycine product may then be isolated by precipitation, for example, by evaporation of a portion of the water and cooling.

In certain embodiments, it should be recognized that the catalyst of this invention has the ability to be reused over several cycles, depending on how oxidized its surface becomes with use. Even after the catalyst becomes heavily oxidized, it may be reused by being reactivated. To reactivate a catalyst having a heavily oxidized surface, the surface preferably is first washed to remove the organics from the surface. It then preferably is reduced in the same manner that a catalyst is reduced after the noble metal is deposited onto the surface of the support, as described above.

Noble metal-containing catalysts including a treated porous substrate prepared by the present method may also be used in combination with a supplemental promoter as described, for example, in U.S. Pat. No. 6,586,621, U.S. Pat. No. 6,963,009, the entire contents of which are incorporated herein by reference for all relevant purposes.

N-(phosphonomethyl)glycine product prepared in accordance with the present invention may be further processed in accordance with many well-known methods in the art to produce agronomically acceptable salts of N-(phosphonomethyl)glycine commonly used in herbicidal glyphosate compositions. As used herein, an "agronomically acceptable salt" is defined as a salt which contains a cation(s) that allows agriculturally and economically useful herbicidal activity of an N-(phosphonomethyl)glycine anion. Such a cation may be, for example, an alkali metal cation (e.g., a sodium or potassium ion), an ammonium ion, an isopropyl ammonium ion, a tetra-alkylammonium ion, a trialkyl sulfonium ion, a protonated primary amine, a protonated secondary amine, or a protonated tertiary amine.

IV. Additional Embodiments

A. Pore Blocking

With regard to disposing or depositing a pore blocking compound within substrate pores as detailed elsewhere herein, it is to be noted that the present invention is not limited to disposing or depositing a pore blocking compound within the smallest substrate pores (e.g., micropores). That is, various embodiments of the present invention are directed to disposing or depositing a pore blocker within pores of an intermediate or larger size range. In this manner, various embodiments of the present invention provide further opportunities for controlling the sizes of pores that are blocked (i.e., further opportunities for controlling, or tuning blocking of pores). For example, in addition to micropores, porous carbon supports that may be treated by the present method have pores of larger dimensions (e.g., pores having a largest dimension of from about 20 Å to about 3000 Å).

Disposing or depositing a pore blocking agent within pores of a size above the micropore size range proceeds generally in accordance with the above-described method. For example, the substrate may be contacted with the pore blocking compound and/or one or more precursors. Further in accordance with the above-described method, the pore blocker may be retained within the targeted pores by virtue of exhibiting at least one dimension larger than the openings of the targeted pores. And regardless of whether the pore blocking agent is introduced into the targeted pores or formed in situ, the pore blocker may be retained within the targeted pores by virtue of a conformational arrangement of the pore blocker.

As noted above, when relatively small pores are targeted by the pore blocker, the pore blocker may enter the non-targeted pores and subsequently exit therefrom (e.g., by virtue of contacting with a liquid washing medium). It is to be noted that a pore blocker targeting intermediate and/or larger size may not enter the pores smaller than the targeted pores. However, this does not impact the goal of blocking of intermediate and/or larger sized pores.

It is currently believed that a variety of compounds are suitable as pore blocking compounds for the purpose of blocking pores above the micropore size range. For example, the pore blocker may be selected from the group consisting of various hydrophilic polymers (e.g., various polyethylene glycols), and combinations thereof.

In various embodiments, the intermediate and/or larger size pore blocker may comprise the product of a reaction between one or more pore blocking compound precursors. For example, it has been observed that the coupling product of a ketone and a dihydric alcohol may be utilized as a pore blocker.

As with micropores as noted above, it is believed that the presence of the pore blocking compound within targeted pores outside the micropore domain will cause at least a portion of the "blocked" pores to appear as a non-porous portion of the substrate during surface area measurements, thereby reducing the proportion of surface area that would otherwise be provided by the targeted pores if they were not blocked. This blocking of the targeted pores is currently believed to provide a reduction in the surface area of the treated substrate provided by the targeted pores. For example, in various embodiments, the surface area of the treated substrate provided by the pores outside (i.e., above) the micropore size range is generally no more than about 80% or no more than about 70% of the surface area of the substrate provided by these pores prior to treatment. Typically, the surface area of the treated substrate provided by the targeted pores is no more than about 60% and more typically no more than about 50% of the surface area of the substrate provided by these pores prior to treatment.

B. Pore Blocking of Catalyst Pores

As noted, persistence of the pore blocker in treated substrates of the present invention is not critical to provide the advantages described above (e.g., a reduced proportion of metal crystallites at the surface of a porous carbon support among relatively small pores of the substrate surface). And it is currently believed that the pore blocker is most likely decomposed and/or otherwise removed from the substrate surface before calcining. In various alternative embodiments, the methods for treating porous substrates may be applied to treatment of finished catalysts. For example, catalysts comprising a noble metal deposited onto a carbon support may be treated by depositing a pore blocker at the surface of the catalyst within its relatively small pores. It is currently believed that the presence of the pore blocker within the relatively small pores may promote preferential contact of reactants with the deposited metal among the intermediate and larger-sized porous regions within which the deposited metal is more accessible to the reactants. In this manner, conversion of reactants to products may be promoted by reducing the proportion of reactants that contact deposited metal among the relatively small porous regions in which the deposited metal may be relatively inaccessible to the reactants. By way of further example, treating carbon-supported catalysts suitable for in preparation of DSIDA from DEA in accordance with the methods detailed are currently believed to provide catalysts including a reduced proportion of exposed noble metal and, accordingly, reduced by-product (e.g., glycine and/or oxalate). However, it is to be understood that treatment of finished catalyst (i.e., carbon or metal-containing having one or more metals deposited thereon) is not a critical aspect of the invention and that catalysts prepared using substrates treated by the present methods have proven to be effective catalysts.

C. Non-Carbon Supports

In addition to treatment of porous carbon supports as detailed herein, the method of the present invention for blocking certain pores of a substrate may be used to treat non-carbonaceous supports. More particularly, the methods detailed herein may be used for treatment of porous metal alloys often referred to as metal sponges. Metal sponge alloys that may be treated by the present method are described, for example, in U.S. Pat. No. 5,627,125, U.S. Pat. No. 5,916,840, U.S. Pat. No. 6,376,708, and U.S. Pat. No. 6,706,662, the entire contents of which are incorporated herein by reference for all relevant purposes. It is currently believed that treated metal-containing substrates may exhibit one or more of the above-noted properties concerning treated porous carbon substrates.

D. Preparation of Carboxylic Acids

In addition to PMIDA oxidation as detailed elsewhere herein, catalysts including treated substrates prepared by the present method are currently believed to be suitable for use in other reactions. For example, catalysts including treated substrates prepared by the present method may be used in the preparation of carboxylic acids including, for example, the preparation of disodiumiminodiacetic acid (DSIDA) by dehydrogenation of diethanolamine (DEA). More particularly, catalysts including treated substrates of the present invention may address one or more issues that may be observed with conventional catalysts utilized in preparation of carboxylic acids such as DSIDA. For example, suitable catalysts often include copper deposited over the surface of a carbon support having a noble metal (e.g., platinum or palladium) at its surface. It is currently believed that at least a portion, and possibly a significant fraction of the noble metal may remain exposed after deposition of the copper. Excessive exposed noble metal is undesired since it is believed to promote formation of various undesired by-products (e.g., glycine and oxalate). A substantial portion, if not nearly all the exposed noble metal is believed to be at the surface of the support within relatively small pores that are inaccessible to copper during its deposition. Other catalysts suitable for preparation of carboxylic acids include copper deposited at the surface of metal-containing (e.g., nickel-containing) sponges. As with exposed noble metal at the surface of carbon-supported catalysts, metal support surface that is not coated by the copper within relatively small pores of the metal sponge support are believed to contribute to formation of undesired by-products. It is currently believed that selective blocking of relatively small pores of substrates in accordance with the methods detailed herein may be used to prepare effective carbon- and metal-supported catalysts that may address one or more of the above-noted issues.

Preparation of DSIDA from DEA using a catalyst comprising a substrate treated as detailed herein generally proceeds in accordance with methods known in the art including, for example, U.S. Pat. No. 5,627,125, U.S. Pat. No. 5,916,840, U.S. Pat. No. 6,376,708, and U.S. Pat. No. 6,706,662, the entire contents of which are incorporated herein by reference for all relevant purposes.

The present invention is illustrated by the following examples which are merely for the purpose of illustration and not to be regarded as limiting the scope of the invention or the manner in which it may be practiced.

EXAMPLES

The following non-limiting examples are provided to further illustrate the present invention.

I. Pore Plugging

Example 1

Three carbon supports were treated to determine the effectiveness of candidate pore blocking compounds. Support A had a total Langmuir surface area of approximately 1500 $m^2/g$ (including total micropore surface area of approximately 1279 $m^2/g$ and total macropore surface area of approximately 231 $m^2/g$). Support B had a total Langmuir surface area of approximately 2700 $m^2/g$ (including total micropore surface area of approximately 1987 $m^2/g$ and total macropore surface area of approximately 723 $m^2/g$). Support C had a total Langmuir surface area of approximately 1100 m²/g (including total micropore surface area of approximately 876 m²/g and total macropore surface area of approximately 332 m²/g).

The candidate pore blocking compounds were 1,4-cyclohexanedione, ethylene glycol, and the diketal product of a coupling reaction between 1,4-cyclohexanedione and ethylene glycol (i.e., 1,4-cyclohexanedione bis(ethylene ketal)).

Support samples (30 g) were contacted with a solution of 1,4-cyclohexanedione in ethylene glycol (6 g/40 g) at approximately 25° C. for approximately 60 minutes. The pH of the slurry was adjusted to approximately 1 by addition of concentrated hydrochloric acid and agitated by stirring for approximately 60 minutes. The pH of the slurry was then adjusted to approximately 8.5 by addition of 50 wt. % sodium hydroxide solution. The slurry was then filtered to isolate the treated support, which was washed using deionized water at a temperature of approximately 90° C. (mechanism one)

Support samples (2 g) were also contacted with a solution of 1,4-cyclohexanedione bis(ethylene ketal) in water (0.6 g/40 g) at approximately 25° C. for approximately 60 minutes. (mechanism two)

As controls, samples of carbon A were separately treated by contact with (1) ethylene glycol and (2) 1,4-cyclohexanedione.

The treated supports were analyzed by the well-known Langmuir method to determine their surface area (SA) profiles (e.g., total surface area, surface area attributed to micropores, and surface area attributed to macropores). The results are shown in Table 1.

TABLE 1

| Support | Mechanism | % of original micropore SA | % of original macropore SA |
|---|---|---|---|
| Carbon A | One | 24.2 | 74.9 |
| Carbon A | Two | 34.4 | 70.9 |
| Carbon A | Control One | 93.7 | 98.7 |
| Carbon A | Control Two | 68.9 | 94.4 |
| Carbon B | One | 55.6 | 78.7 |
| Carbon B | Two | 65.4 | 81.5 |
| Carbon C | One | 17.9 | 76.8 |
| Carbon C | Two | 22 | 72.3 |

As shown, both mechanism one and mechanism two provided a reduction in micropore and macropore surface areas for each of supports A-C, and more particularly a greater reduction in micropore surface area as compared to the reduction in macropore surface area (e.g., a three times greater reduction in micropore surface area). The percentage reduction in surface area for carbon B is believed to be lower than that observed for the other two carbons because of its higher surface area. However, it should be noted that the percentage of micropore surface area reduction for carbon B nonetheless corresponds to an absolute reduction of approximately 900 m²/g.

The control testing of carbon A with ethylene glycol provided minimal reduction in micropore and macropore surface areas, while the control testing with 1,4-cyclohexanedione provided a greater reduction in micropore and macropore surface areas, but to a much lesser degree than associated with both mechanism one and mechanism two. Thus, it is believed that the components combine to form the pore blocking compound that provides greater reduction in surface area than either component alone or the cumulative reduction provided by each.

Example 2

Carbons A, B, and C (30 g) described in Example 1 were each treated by contacting with solutions of 1,4-cyclohexanedione in ethylene glycol (6 g/40 g) at approximately 25° C. for approximately 60 minutes. Each carbon was also treated by contacting with solutions of 1,3-cyclohexanedione in ethylene glycol (1 g/50 g) at approximately 25° C. for approximately 120 minutes. Carbon C was also treated by contacting with a solution of 1,4-cyclohexanedione in 1,2-propanediol (1 g/50 g) at approximately 25° C. for approximately 60 minutes. Surface area analysis results are shown in Table 2. As shown, each combination of dione and diol provided reduction of micropore and macropore surface areas, and more particularly preferential reduction in micropore surface area.

TABLE 2

| Sample | Dione | Diol | % of original micropore SA | % of original macropore SA |
|---|---|---|---|---|
| Carbon A | 1,4-disubstituted | Ethylene Glycol | 22.6 | 75.8 |
| Carbon A | 1,3-disubstituted | Ethylene Glycol | 58.4 | 84 |
| Carbon B | 1,4-disubstituted | Ethylene Glycol | 55.6 | 78.7 |
| Carbon B | 1,3-disubstituted | Ethylene Glycol | 32.2 | 39.8 |
| Carbon C | 1,4-disubstituted | Ethylene Glycol | 17.9 | 76.8 |
| Carbon C | 1,3-disubstituted | Ethylene Glycol | 45 | 75.6 |
| Carbon C | 1,4-disubstituted | 1,2-Propanediol | 14.4 | 67.5 |
| Carbon C | 1,3-disubstituted | 1,2-Propanediol | 56.1 | 80.7 |

Example 3

This example provides transmission electron microscopy results (TEM) for a platinum on carbon catalyst prepared using Carbon B treated as described in Example 1 (mechanism one). The catalyst contained approximately 5 wt. % platinum and was prepared generally as detailed herein (e.g., by liquid phase deposition of platinum onto the treated carbon support), followed by treatment at elevated temperatures in a non-oxidizing environment. For comparison purposes, a catalyst including 5 wt. % platinum on Carbon B that was not treated was also analyzed. The TEM analysis was conducted generally as described by Wan et al. in International Publication No. WO 2006/031198.

Figure 3A:
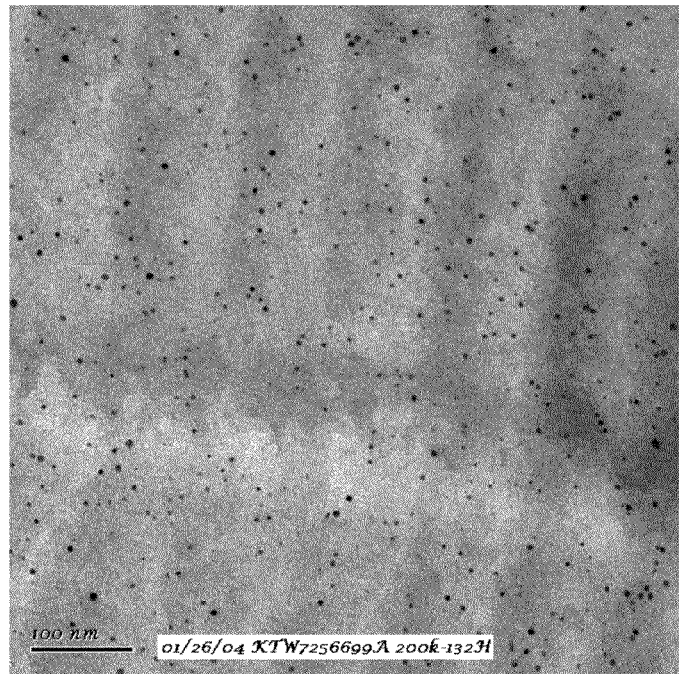
FIGS. 3A/5A and 3B/5B transmission electron microscopy (TEM) results as described in Example 3.
Figure 3B:
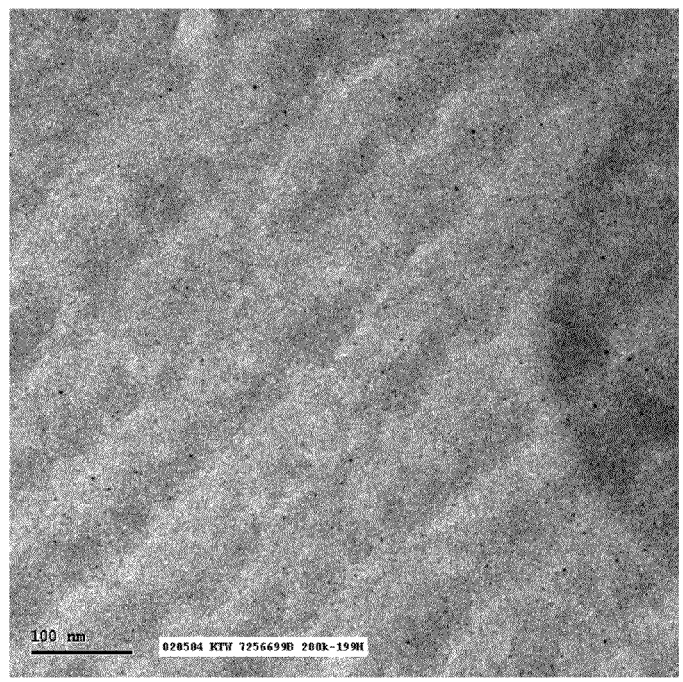

The results for the catalyst including the untreated and treated carbons are shown in FIGS. 3A/5A and 3B/5B, respectively. These results suggest a reduction in relatively small platinum-containing particles (e.g., having a particle size less than 4 nm) for the catalyst prepared using the treated support.

The TEM results generally correspond to high density regions of the substrates including primarily micropores and these results indicate higher platinum density among these regions for the catalyst including the untreated support.

Example 4

This example provides surface area analysis results for a carbon support of the type described in U.S. Pat. Nos. 4,624,937 and 4,696,771 to Chou et al. (designated MC-10) treated in accordance with the present invention. Support samples were treated in accordance with both mechanism one and mechanism two described above in Example 1. The support had an initial micropore Langmuir surface area of approximately 1987 m²/g and an initial macropore Langmuir surface area of approximately 723 m²/g. Micropore and macropore surface area retention results for the treated supports are shown in Table 3.

TABLE 3

| Support | Plugging Mechanism | % of original micropore SA | % of original macropore SA |
|---|---|---|---|
| MC-10 | One | 55.6 | 78.7 |
| MC-10 | Two | 65.4 | 81.5 |

Figure 4A:
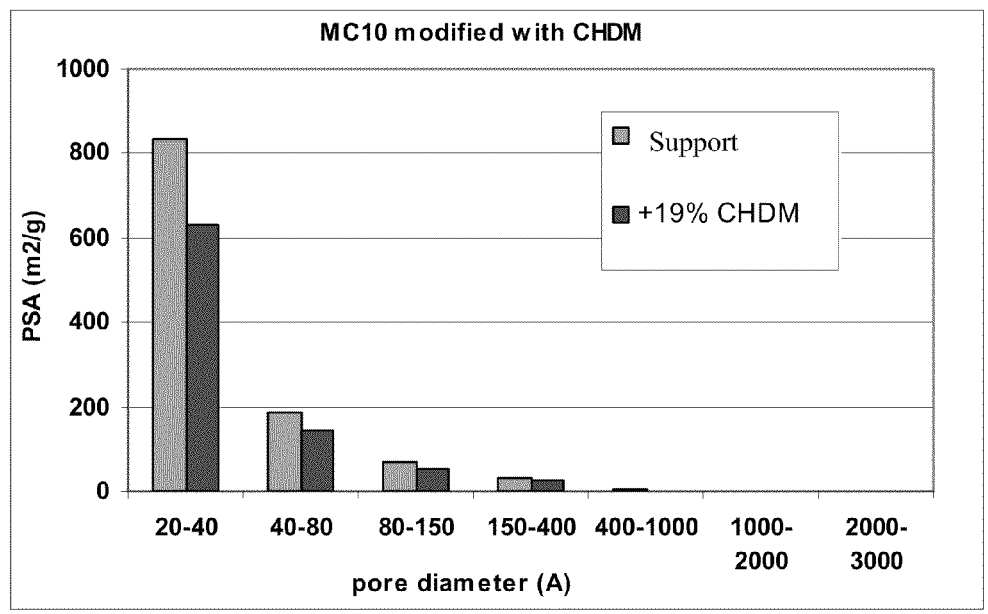
FIGS. 4A and 4B provide pore volume and surface area for treated and untreated substrates as described in Example 4.
Figure 4B:
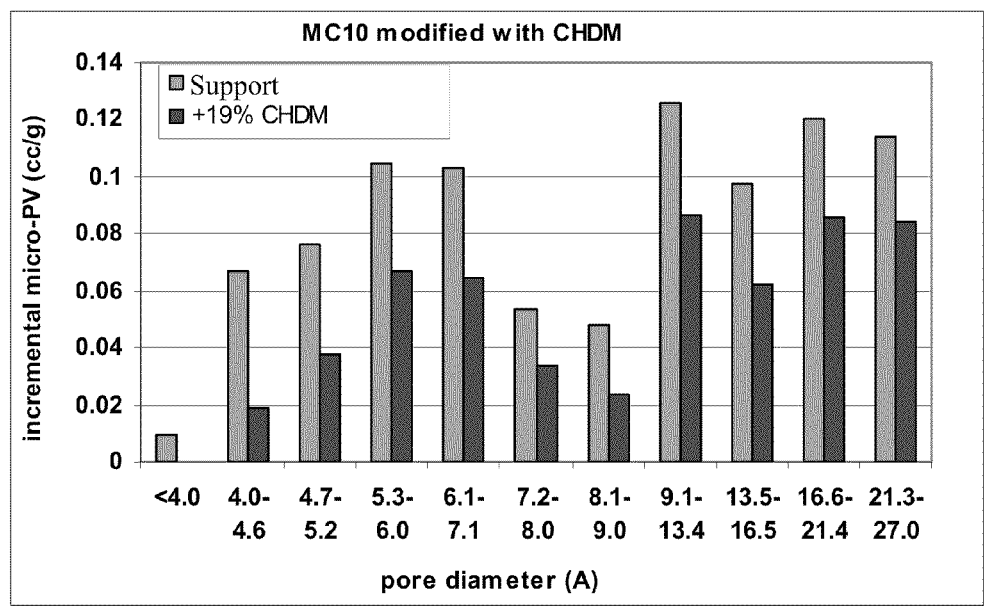

FIGS. 4A and 4B provide pore volume data for untreated and treated MC-10 supports.

Example 5

This example provides results of carbon monoxide (CO) chemisorption analysis for the platinum-containing catalysts of Example 4. CO chemisorption is an analysis method suitable for estimating the proportion of exposed metal, and the analysis was conducted generally in accordance with "Protocol A" described in Example 67 herein and Example 23 of WO 2006/031938, incorporated herein by reference.

The results are shown in Table 4. The lower CO chemisorption for the catalyst including a treated carbon support (38.6 and 43.3 μmol CO/gram versus 54.7 μmol CO/gram catalyst) indicate a reduced proportion of exposed noble metal for the platinum-containing catalyst prepared using the treated carbon support.

TABLE 4

| Catalyst | Cycle 2 CO μmol/g catalyst |
|---|---|
| Pt on regular MC-10 | 54.7 |
| Pt on modified MC-10 | 38.6/43.3 |

Example 6

Catalysts containing approximately 5 wt. % Pt and approximately 0.5 wt. % Fe were prepared generally as detailed herein using untreated MC-10 carbon supports, and MC-10 carbon supports treated in accordance with both mechanism one and mechanism two described in Example 1. These catalysts were tested in PMIDA oxidation generally under the conditions set forth in Example 7; the results are shown in Table 5. The Catalyst (1) included an untreated support. Catalysts (2) and (3) each included supports treated in accordance with mechanism two detailed above in Example 1. Catalyst (2) was prepared by a method that included filtration of the copper-impregnated support prior to platinum deposition. Catalyst (3) was prepared by a method that did not include filtration of the copper-impregnated support prior to platinum deposition (i.e., a one-pot method as described in Example 16).

TABLE 5

| Run Number | 1 | 2 | 3 | 4 | 5 | 6 |
|---|---|---|---|---|---|---|
| Catalyst (1) | | | | | | |
| Run Time, min | 43.0 | 46.2 | 47.8 | 50.6 | 50.8 | 52.0 |
| GLY wt. % | 5.413 | 5.600 | 5.620 | 5.678 | 5.556 | 5.748 |
| PMIDA wt. % | 0.034 | 0.034 | 0.094 | 0.134 | 0.075 | 0.149 |
| CH₂O wt. % | 0.150 | 0.182 | 0.199 | 0.211 | 0.190 | 0.209 |
| FORMIC wt. % | 0.384 | 0.455 | 0.521 | 0.516 | 0.505 | 0.512 |
| IDA wt. % | 0.074 | 0.046 | 0.031 | 0.030 | 0.030 | 0.027 |
| Pt in soln. (ppm) | 0.03 | 0.07 | 0.07 | 0.09 | 0.08 | 0.12 |
| Fe in soln. (ppm) | 5.4 | 1.9 | 2.3 | 2.3 | 2.0 | 1.6 |
| Catalyst (2) | | | | | | |
| Run Time, min | 43.0 | 45.1 | 48.8 | 47.2 | 47.6 | 48.3 |
| GLY wt. % | 5.363 | 5.543 | 5.541 | 5.592 | 5.557 | 5.604 |
| PMIDA wt. % | 0.036 | 0.097 | 0.022 | 0.129 | 0.154 | 0.177 |
| CH₂O wt. % | 0.125 | 0.143 | 0.105 | 0.139 | 0.144 | 0.169 |
| FORMIC wt. % | 0.389 | 0.456 | 0.435 | 0.479 | 0.484 | 0.508 |
| IDA wt. % | 0.086 | 0.052 | 0.041 | 0.033 | 0.031 | 0.028 |
| Pt in soln. (ppm) | 0.05 | 0.14 | | | | |
| Fe in soln. (ppm) | 6.3 | 1.9 | | | | |
| Catalyst (3) | | | | | | |
| Run Time, min | 43.0 | 46.3 | 46.7 | 48.5 | 48.5 | 49.8 |
| GLY wt. % | 5.475 | 5.596 | 5.543 | 5.649 | 5.790 | 5.980 |
| PMIDA wt. % | 0.058 | 0.141 | 0.167 | 0.136 | | |
| CH₂O wt. % | 0.175 | 0.171 | 0.192 | 0.191 | 0.208 | 0.222 |
| FORMIC wt. % | 0.466 | 0.505 | 0.547 | 0.565 | | |
| IDA wt. % | 0.073 | 0.044 | 0.030 | 0.026 | 0.025 | 0.022 |
| Pt in soln. (ppm) | | | | | | |
| Fe in soln. (ppm) | | | | | | |

GLY = Glyphosate
FORMIC = Formic Acid
IDA = Iminodiacetic Acid
ppm = Parts Per Million II. Catalyst Precursors; First and Second Metal-Containing Catalysts; Catalyst Precursor Structures The following Examples describe preparation of catalysts as detailed herein, their testing by various characterization methods, and their testing in PMIDA oxidation. The following Examples also provide comparisons of catalysts prepared as detailed herein, and various other metal-containing carbon-supported catalysts. For example, the following Examples provide comparisons to carbon-supported catalysts including 5 wt. % Pt, 0.1 wt. % Fe, and 0.4 wt. % Co, and carbon-supported catalysts including 5 wt. % Pt and 0.5 wt. % Fe. These catalysts were prepared generally as described by Wan et al. in International Publication No. WO 2006/031938.

Example 7

Catalysts prepared as described herein and comparison samples were tested in PMIDA oxidation conditions also generally described by Wan et al. in International Publication No. WO 2006/031938. For example, PMIDA oxidation cycles were conducted in a glass reactor (200 ml commercially available from Ace Glass Inc.) containing a reaction mass (approx. 140 g) which included water (approx. 128 g), approximately 8.2 wt. % PMIDA (approx. 11.48 g), and a catalyst loading of approximately 0.18 wt. % (0.25 g). The oxidations were generally conducted at a temperature of approximately 100° C., under a pressure of approximately 60 psig, and an oxygen flow rate of approximately 100 cc/min.

Unless noted otherwise, reaction cycles were conducted to an endpoint determined by generation of approximately 1600 cm$^3$ of carbon dioxide.

As described in the following Examples and accompanying figures, various data were collected, including cycle time, metal leaching, residual formaldehyde (HCHO) content, residual formic acid (HCOOH) content, iminodiacetic acid (IDA) formation, N-methyl-N-(phosphonomethyl)glycine (NMG) formation, total carbon dioxide ($CO_2$) generation, etc.

Example 8

This example details preparation of a catalyst containing a nominal Pt content of approximately 2.5 wt. % and a nominal Cu content of approximately 5 wt. % Cu on an activated carbon support having a Langmuir surface area of approximately 1500 m$^2$/g.

Activated carbon (approx. 10 g), $CuSO_4.5H_2O$ solution (approx. 2.07 g), sucrose (approx. 5.67 g), degassed deionized water (approx. 30 g), and degassed 1M NaOH (70 g) were mixed in a baffled beaker. The mixture was agitated at ambient conditions (approx. 25° C.) for approx. 20 minutes. Formaldehyde (approx. 2.25 g of 37 wt. % solution) was added to the mixture and the resulting slurry was heated to approx. 30° C. and agitated for approx. 60 minutes.

The resulting slurry was filtered, washed with degassed deionized water, re-slurried in deionized water, and 1M HCl was added to provide a pH of approx. 1.5.

A solution of $K_2PtCl_4$ (approx. 0.557 g) in degassed water (15 g) was added to the slurry, followed by continued stirring for 60 minutes at ambient conditions. The slurry was filtered, and the recovered metal-impregnated support was washed with water, and dried under vacuum at approx. 110° C. A total of 12.12 g of dried metal-impregnated support was recovered. Elemental analysis indicated a composition of approx. 2.04 wt. %. Pt and approx. 1.93 wt. % Cu on carbon.

The catalyst precursor was then heated at elevated temperatures up to approximately 815° C. in the presence of a hydrogen/argon stream (2%/98%; v/v) for approximately 60 minutes. Elemental analysis indicated final metal contents of approx. 2.34% wt. Pt and approx. 2.22 wt. % Cu.

As detailed below, catalysts prepared by heating the metal-impregnated support at varying temperatures were also tested. In addition, various metal-impregnated supports were also tested for their catalytic activity.

Example 9

Copper Plating at Ambient Temperature

Preparation of nominal 2% Pt/3.45% Cu on activated carbon catalyst: The following were added to a baffled beaker including approx. 10 g of activated carbon: $CuSO_4.5H_2O$ solution (1.410 g), 3.866 g of sucrose, 90 g of degassed deionized water, and 5.974 g of 50 wt. % NaOH. The mixture was stirred at approx. 22° C. for approx. 10 minutes using a mechanical agitator. Following stirring, approx. 1.468 g of 37 wt. % formaldehyde solution was added and the resulting slurry was stirred at approx. 22° C. for 60 minutes. The slurry was then filtered and washed twice in the filter, and then re-slurried in water to pH of approx. 2.0 by addition of 1.5M degassed HCl. To this slurry was added a solution of $K_2PtCl_4$ (0.444 g) in 15 g of degassed water, followed by stirring for approximately 60 minutes under ambient conditions. The slurry was then heated to approx. 65° C., followed by stirring for an additional 30 minutes. The resulting slurry was then filtered and washed with water and dried under vacuum at approx. 110° C. A total of 11.389 g of dried material was recovered.

Example 10

Preparation of nominal 2.5% Pt/5% Cu on activated carbon: The following was added to approx. 10 g of activated carbon in a baffled beaker: 2.072 g of a $CuSO_4.5H_2O$ solution, 5.694 g of sucrose, 30 g of degassed deionized water, and 70 g of degassed 1M NaOH was added. The mixture was heated to approx. 35° C. using a mechanical agitator. To this mixture was added 2.249 g of 37 wt. % formaldehyde solution and the resulting slurry was heated to approx. 33-35° C., followed by continued stirring for 60 minutes. The slurry was filtered and washed with degassed deionized water in the filter, and then re-slurried in water at pH of approx. 1.5 by adding 0.5M HCl. A solution of 0.557 g of $K_2PtCl_4$ in 15 g of degassed water was then added to the slurry, followed by continued stirring for 60 minutes under ambient conditions. Then the slurry was heated to approx. 60° C. and stirred for an additional 30 minutes. The resulting slurry was filtered and washed with water, and dried under vacuum at approx. 110° C. A total of 11.701 g of dried material was recovered. Upon heat treatment to a maximum temperature of approx. 950° C. in the presence of an argon/hydrogen atmosphere (2%/98%) (v/v) for 120 minutes, a final catalyst composition indicating a weight loss of approximately 12.1 wt. % during heating was recovered.

Example 11

No Washing after Copper Deposition

Preparation of nominal 2% Pt/4% Cu on activated carbon: The following was added to a baffled beaker including approx. 10 g of activated carbon: 1.643 g of $CuSO_4.5H_2O$ solution, 4.509 g of sucrose, 90 g of degassed deionized water, and 4.625 g of 50 wt. % NaOH. The mixture was heated to approx. 30° C. for approx. 10 minutes with a mechanical agitator. To this slurry was added 1.706 g of 37 wt. % formaldehyde solution and the resulting slurry was heated to approx. 30-35° C., followed by continued stirring for approx. 90 minutes. Then the slurry was filtered, and then without washing re-slurried in water to pH 2.02 by adding 1M degassed HCl. A solution of 0.454 g of $K_2PtCl_4$ in 10 g of degassed water was then added to the slurry, followed by continued stirring for 60 minutes at ambient conditions. The resulting slurry was then heated to approx. 60° C. and stirred for an additional 30 minutes. This slurry was then filtered and washed with water, and dried under vacuum at approx. 110° C. A total of 11.720 g of dried material was recovered. During heat treatment to a maximum temperature of approximately 950° C. in the presence of an argon/hydrogen atmosphere (2%/98%) (v/v) for approximately 120 minutes, the sample lost approximately 13.5% weight.

Example 12

Preparation of nominal 2% Pt/3.75% Cu on activated carbon: The following was added to a baffled beaker including approx. 10 g of activated carbon 1.533 g of $CuSO_4.5H_2O$ solution, 4.210 g of sucrose, 90 g of degassed deionized water, and 4.300 g of 50 wt. % NaOH was added. This mixture was heated to approx. 30° C. and stirred for approx. 10 minutes using a mechanical agitator. To this mixture was added 1.507 g of 37 wt. % formaldehyde and the slurry was heated to approx. 30-35° C., followed by continued stirring for 60 minutes. The slurry was filtered and the recovered solids washed once in the filter, and then re-slurried in water to a pH of 1.97 by adding 1M degassed HCl. A solution of 0.452 g of $K_2PtCl_4$ in 10 g of degassed water was then added to the slurry, followed by continued stirring for 60 minutes under ambient conditions. Then the slurry was heated to approx. 60° C. and stirred for 30 more minutes. The slurry was filtered and washed with water, dried under vacuum at approx. 110° C. A total of 11.413 g of dried material was recovered. Upon heat treatment to a maximum temperature of approximately 950° C. in the presence of a 2%/98% (v/v) $H_2$/Ar atmosphere for 120 minutes, the sample lost approximately 12.5% weight.

Example 13

Platinum Deposition at Higher Temperature

Preparation of nominal 2% Pt/4% Cu on activated carbon: The following were added to a baffled beaker including 10 g of activated carbon: 1.645 g of $CuSO_4.5H_2O$ solution, 4.502 g of sucrose, 90 g of degassed deionized water, and 4.636 g of 50 wt. % NaOH. The mixture was stirred under ambient conditions for approx. 20 minutes with a mechanical agitator. Then 1.721 g of 37% formaldehyde was added and the slurry was heated to approx. 30-35° C., followed by continued stirring for 70 minutes. Then the slurry was filtered and washed once in the filter, and then re-slurried in water to pH 2.95 by adding 1M degassed HCl. A solution of 0.455 g of $K_2PtCl_4$ in 10 g of degassed water was then added to the slurry, followed by continued stirring for 45 minutes at 40-45° C. Then the slurry was heated to 60° C. and stirred for 30 more minutes. The slurry was filtered and the recovered solids washed with water, and dried under vacuum at approx. 110° C. A total of 12.008 g of dried material was recovered. Upon heat treatment at a maximum temperature of approx. 950° C. in the presence of a (2%/98%) (v/v) $H_2$/Ar atmosphere for approx. 120 minutes, the sample lost approximately 12.6% weight.

Example 14

Preparation of nominal 3% Pt/6% Cu on activated carbon: The following were added to a baffled beaker including 10 g of activated carbon: 2.507 g of $CuSO_4.5H_2O$ solution, 6.878 g of sucrose, 90 g of degassed deionized water, and 6.974 g of 50 wt. % NaOH. The mixture was heated to 30° C. and stirred for approx. 10 minutes with a mechanical agitator. Then 2.444 g of 37% formaldehyde was added and the slurry was heated to approx. 35-37° C., followed by continued stirring for 45 minutes. Then the slurry was filtered and washed twice in the filter, and then re-slurried in water to pH 1.97 by adding 1M degassed HCl. A solution of 0.700 g of $K_2PtCl_4$ in 20 g of degassed water was then added to the slurry, followed by continued stirring for 60 minutes under ambient conditions. Then the slurry was heated to 60° C. and stirred for an additional 30 minutes. The slurry was then filtered and washed with water, and dried under vacuum at approx. 110° C. A total of 11.868 g of dried material was recovered. Upon heat treatment at a maximum temperature of approx. 950° C. in the presence of (2%/98%) (v/v) $H_2$/Ar atmosphere for 120 minutes, the sample lost approximately 12.5% weight.

Example 15

Higher Platinum Content and Platinum Deposition Temperature

Preparation of nominal 4% Pt/8% Cu on activated carbon: The following were added to a baffled beaker including approx. 10 g of activated carbon: 3.420 g of $CuSO_4.5H_2O$ solution, 9.375 g of sucrose, 100 g of degassed deionized water, and 9.675 g of 50 wt. % NaOH. The mixture was heated to 30° C. and stirred for 10 minutes with a mechanical agitator. Then 3.331 g of 37% formaldehyde was added and the resulting slurry was heated to approx. 30-35° C., followed by continued stirring for 90 minutes. Then the slurry was filtered and washed once in the filter, and then re-slurried in water to pH 1.97 by adding 1M degassed HCl. A solution of 0.964 g of $K_2PtCl_4$ in 20 g of degassed water was then added to the slurry, followed by continued stirring for 45 minutes at 45° C. Then the slurry was heated to 60° C. and stirred for an additional 45 minutes. The slurry was then filtered and washed with water, and dried under a vacuum at approx. 110° C. A total of 12.283 g of dried material was recovered. Upon heat treatment to a maximum temperature of approx. 950° C. in the presence of a 2%/98% (v/v) $H_2$/Ar atmosphere for 120 minutes, the sample lost approximately 12.6% weight.

Example 16

One-Pot Recipe

Preparation of nominal 2% Pt/4% Cu on activated carbon: The following were added to baffled beaker including 10 g of activated carbon: 1.644 g of $CuSO_4.5H_2O$ solution, 4.509 g of sucrose, 90 g of degassed deionized water, and 4.715 g of 50 wt. % NaOH. The mixture was heated to 30° C. and stirred for 10 minutes with a mechanical agitator. Then 1.736 g of 37% formaldehyde was added and the slurry was heated to approx. 30-35° C., followed by continued stirring for 90 minutes. Then the slurry was acidified to pH 2.98 by adding 1M degassed HCl. A solution of 0.454 g of $K_2PtCl_4$ in 10 g of degassed water was then added to the slurry, followed by continued stirring for 60 minutes at ambient conditions. Then the slurry was heated to 60° C. and stirred for 30 more minutes. The slurry was then filtered and washed with water, and dried under vacuum at approx. 110° C. A total of 11.864 g of dried material was recovered. Upon heat treatment at approx. 950° C. in the presence of a (2%/98%) (v/v) $H_2$/Ar for 120 minutes, the sample lost approximately 12.2% weight.

Example 17

Preparation of nominal 2% Pt/4% Cu on activated carbon: The following were added to a baffled beaker including 10 g of activated carbon: 1.645 g of $CuSO_4.5H_2O$ solution, 4.509 g of sucrose, 90 g of degassed deionized water, and 4.630 g of 50 wt. % NaOH. The mixture was heated to 30° C. and stirred for 10 minutes with a mechanical agitator. Then 1.710 g of 37% formaldehyde was added and the slurry was heated to approx. 30-35° C., followed by continued stirring for 90 minutes. Then the slurry was filtered and washed once in the filter, and then re-slurried in water to pH 2.01 by adding 1M degassed HCl. A solution of 0.570 g of $H_2PtCl_6$ in 15 g of degassed water was then added to the slurry, followed by continued stirring for 60 minutes at ambient conditions. Then the slurry was heated to 60° C. and stirred for an additional 30 minutes. The slurry was then filtered and washed with water, and dried under vacuum at approx. 110° C.

Example 18

Preparation of nominal 2% Pt/4% Cu on activated carbon: The following were added to a baffled beaker including approx. 10 g of activated carbon: 1.644 g of $CuSO_4.5H_2O$ solution, 4.517 g of sucrose, 70 g of degassed deionized water, and 4.701 g of 50 wt. % NaOH. The mixture was heated to 30° C. and stirred for approx. 10 minutes with a mechanical agitator. Then 1.705 g of 37% formaldehyde diluted to 17.10 g with degassed water was added, and the slurry was heated at approx. 30-35° C., followed by continued stirring for 60 minutes. Then the slurry was filtered and washed once in the filter, and then re-slurried in water to pH 1.99 by adding 1M degassed HCl. A solution of 0.460 g of $K_2PtCl_4$ in 10 g of degassed water was then added to the slurry, followed by continued stirring for 60 minutes at ambient conditions. Then the slurry was heated to 60° C. and stirred for 30 more minutes. It was then filtered and washed with water, and dried under vacuum at approx. 110° C. A total of 11.203 g of dried material was recovered.

Example 19

This Example details surface area (SA) and CO chemisorption analysis for catalysts of varying platinum and copper contents prepared generally in accordance with the conditions detailed herein in Example 7, and tested in PMIDA oxidation for 10 cycles generally under the conditions set forth in Example 7.

TABLE 6

| Description | Average C | 10 cycle 955° C.-120 (temp/time) 2%Pt/ 3.45% Cu/C | 10 cycle 955° C.-120 3%Pt/ 6% Cu/C | 10 cycle 955° C.-120 2%Pt/ 3.45% Cu/C | 10 cycle 815° C.-60 2%Pt/ 7.5% Cu/C | 10 cycle 955° C.-120 2.5%Pt/ 4% Cu/C | 10 cycle spent 955° C.-120 treated 2%Pt/ 4% Cu/C | 10 cycle spent 955° C.-120 treated 2%Pt/ 3.75% Cu/C |
|---|---|---|---|---|---|---|---|---|
| Langmuir SA ($m^2/g$) | 1499 | 1307 | 1208 | 1230 | 970 | 1236 | 1240 | 1254 |
| t-plot micro SA ($m^2/g$) | 1193 | 1065 | 984 | 1002 | 776 | 1019 | 1017 | 1034 |
| Pore diameter (Å) | 15.6 | 19.9 | 20.0 | 19.9 | 20.1 | 19.7 | 19.8 | 19.7 |
| Meso-macro pore SA ($m^2/g$) | 293.184 | 235.358 | 220.629 | 223.477 | 189.809 | 214.329 | 219.437 | 216.215 |
| 20-40 | 175.666 | 147.013 | 137.710 | 139.592 | 119.950 | 133.968 | 136.617 | 134.627 |
| 40-80 | 77.937 | 60.166 | 56.648 | 57.408 | 48.620 | 54.628 | 56.582 | 55.397 |
| 80-150 | 25.781 | 18.164 | 16.873 | 16.961 | 13.806 | 16.522 | 16.811 | 16.678 |
| 150-400 | 11.205 | 7.963 | 7.469 | 7.518 | 5.954 | 7.177 | 7.463 | 7.468 |
| 400-1000 | 2.159 | 1.736 | 1.630 | 1.685 | 1.251 | 1.672 | 1.666 | 1.680 |
| 1000-2000 | 0.396 | 0.315 | 0.297 | 0.313 | 0.228 | 0.331 | 0.298 | 0.315 |
| 2000-3000 | 0.04 | 0.001 | 0.002 | 0.000 | 0.000 | 0.031 | 0.000 | 0.050 |
| Total meso-macro pore SA ($m^2/g$) | 293.184 | 235.358 | 220.629 | 223.477 | 189.809 | 214.329 | 219.437 | 216.215 |
| Pt(0)[μmol CO/g] | NA | 17.2 | 27.5 | 14.6 | 19.3 | 13.9 | 14.2 | 17.8 |
| Total Pt [μmol CO/g] | NA | 21.9 | 34.9 | 20 | 30.1 | 19.5 | 19.2 | 20.6 |

TABLE 7

| Pore diameter (Å) | Average C (3 lots) | 10 cycle 955° C.-120 (temp/time) 2%Pt/ 3.45% Cu/C | 10 cycle 955° C.-120 3%Pt/ 6% Cu/C | 10 cycle 955° C.-120 2%Pt/ 3.45% Cu/C | 10 cycle 815° C.-60 2%Pt/ 7.5% Cu/C | 10 cycle 955° C.-120 2.5%Pt/ 4% Cu/C | 10 cycle spent 955° C.-120 treated 2%Pt/ 4% Cu/C | 10 cycle spent 955° C.-120 treated 2%Pt/ 3.75% Cu/C |
|---|---|---|---|---|---|---|---|---|
| <4.0 | 0.0541 | 0.0475 | 0.0475 | 0.0474 | 0 | 0.0478 | 0.0379 | 0.0476 |
| 4.0-4.6 | 0.1072 | 0.0853 | 0.0758 | 0.0759 | 0.0952 | 0.0765 | 0.0851 | 0.0856 |
| 4.7-5.2 | 0.063 | 0.0568 | 0.0473 | 0.0567 | 0.0471 | 0.0572 | 0.0565 | 0.0569 |
| 5.3-6.0 | 0.063 | 0.0568 | 0.0566 | 0.0473 | 0.0356 | 0.0476 | 0.0472 | 0.0474 |
| 6.1-7.1 | 0.0465 | 0.0369 | 0.0454 | 0.0459 | 0.0329 | 0.0462 | 0.0459 | 0.0458 |
| 7.2-8.0 | 0.0346 | 0.0254 | 0.0241 | 0.0254 | 0.0239 | 0.0254 | 0.0331 | 0.025 |
| 8.1-9.0 | 0.0235 | 0.0224 | 0.0142 | 0.0221 | 0.0133 | 0.0226 | 0.0207 | 0.022 |
| 9.1-13.4 | 0.0589 | 0.0567 | 0.0538 | 0.0513 | 0.0424 | 0.0533 | 0.0498 | 0.0517 |
| 13.5-16.5 | 0.0216 | 0.017 | 0.016 | 0.0164 | 0.0129 | 0.0159 | 0.0196 | 0.0191 |
| 16.6-21.4 | 0.0274 | 0.0241 | 0.0248 | 0.023 | 0.0211 | 0.024 | 0.0214 | 0.0212 |
| 21.5-27.0 | 0.0254 | 0.021 | 0.018 | 0.02 | 0.0156 | 0.0174 | 0.0179 | 0.0176 |
| total micropore volume (cc/g) | 0.5252 | 0.4499 | 0.4235 | 0.4314 | 0.34 | 0.4339 | 0.4351 | 0.4399 |

Figure 5A:
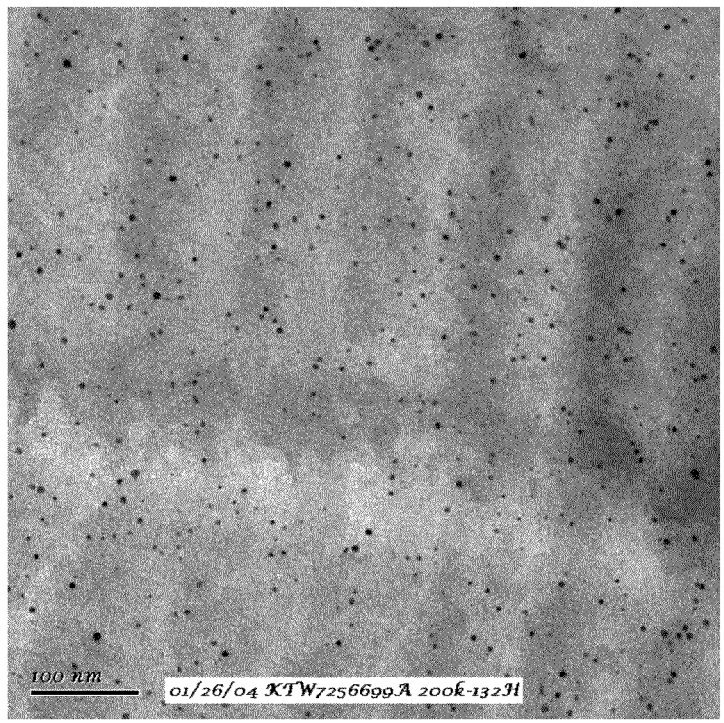
FIG. 5C provides porosity data for catalysts analyzed as described in Example 19.
FIG. 5D provides pore volume results for catalysts analyzed as described in Example 20.
Figure 5B:
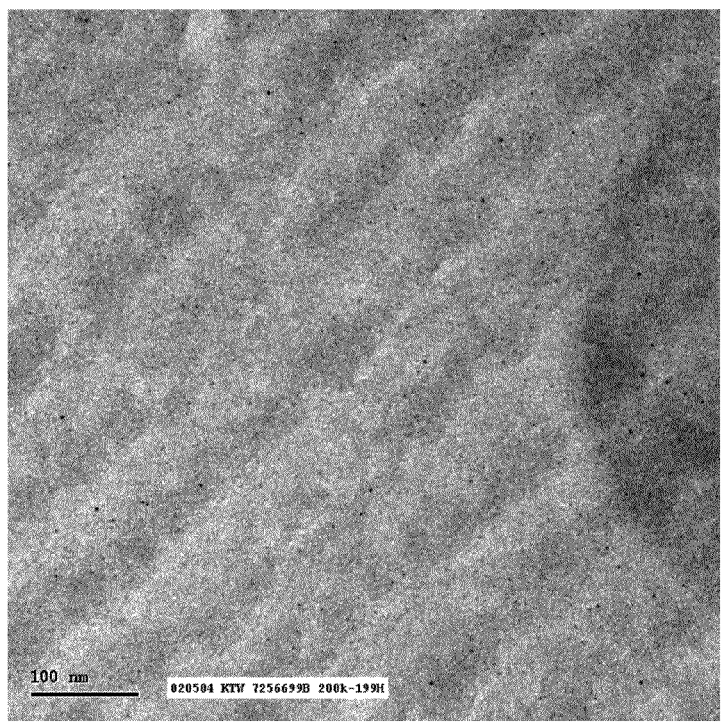
Figure 5C:
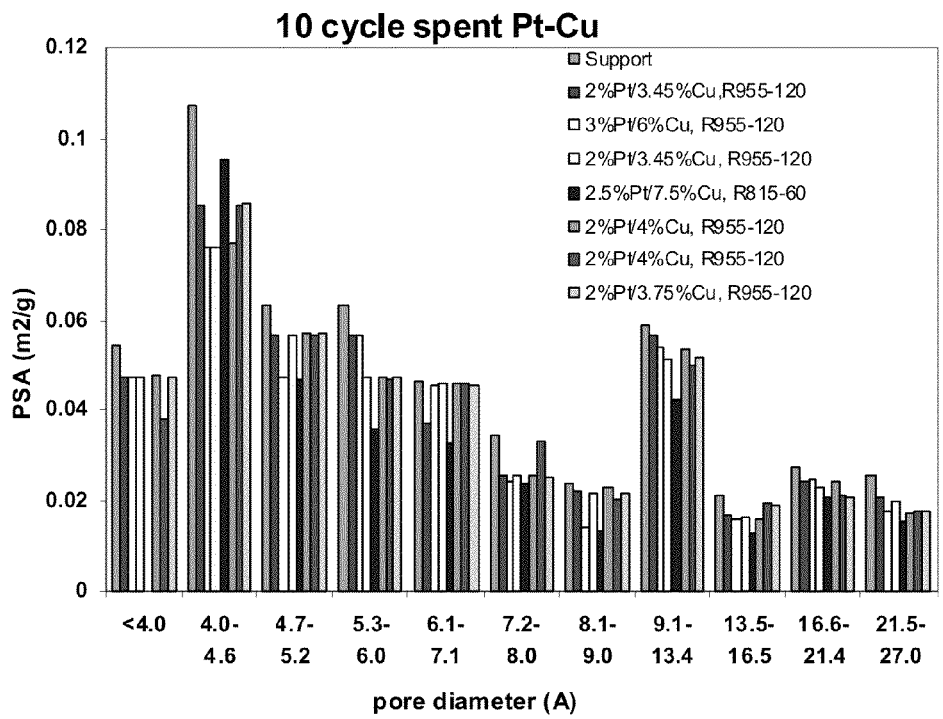

FIG. 5C provides porosity data for each of the catalysts tested.

Example 20

This example provides surface area (SA) and pore volume (PV) analysis data for a carbon support treated by contact with sucrose generally in accordance with the method described below. Also provided are results for a nominal 2% Pt/3.45% Cu/C catalyst prepared using a carbon support treated by contact with sucrose generally as described below, along with copper and platinum deposition generally as described in Example 12. The metal impregnated support was not subjected to elevated temperatures.

Carbon support (10 g) was added to a mixture including degassed $H_2O$ (approx. 100 g), sucrose (approx. 3.8 g), 1M NaOH (approx. 6.15 g). To prepare the sucrose mixture, the sucrose was first added to the water followed by addition of NaOH, which was followed by addition of approx. 1.9 g of 37 wt. % formaldehyde solution. After approximately 60 minutes at approximately 25° C., the mixture was acidified to pH of approximately 4.8 by addition of 2M HCl. The mixture was then stirred for approximately 45 minutes at approximately 25° C., then filtered to isolate the support and the support was dried for approx. 10 hours in a vacuum oven at a temperature of approx. 110° C. in the presence of nitrogen. Approx. 11.5 g of treated support was recovered.

Figure 5D:
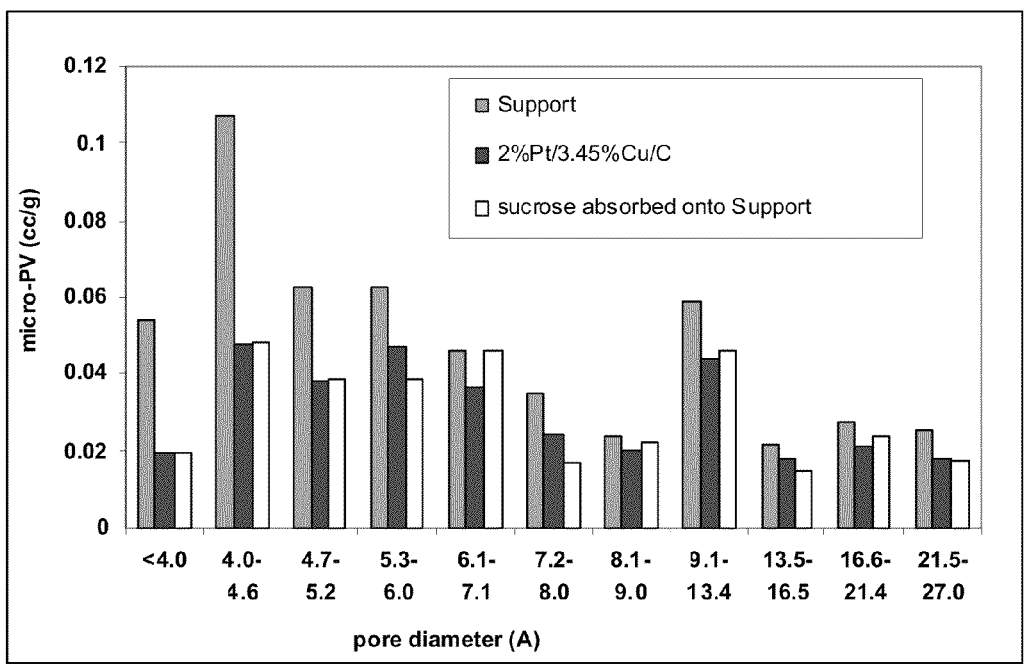

Both the catalyst and treated support were analyzed by surface area and pore volume analyses generally as described by Wan et al. in International Publication No. WO 2006/031938. The surface area and pore volume analysis results are shown in Tables 8 and 9, respectively. FIG. 5D also provides the pore volume results.

TABLE 8

| Description | Average Carbon | Precursor, 2% Pt/3.45% Cu/C | Sucrose adsorbed onto Carbon |
|---|---|---|---|
| Langmuir SA ($m^2/g$) | 1499 | 957 | 954 |
| t-plot micro pore SA ($m^2/g$) | 1193 | 727 | 726 |
| meso-macro pore SA ($m^2/g$) | 293.184 | 222.314 | 219.061 |
| 20-40 | 175.666 | 136.964 | 133.600 |
| 40-80 | 77.937 | 58.165 | 58.144 |
| 80-150 | 25.781 | 17.608 | 17.651 |
| 150-400 | 11.205 | 7.676 | 7.743 |
| 400-1000 | 2.159 | 1.625 | 1.672 |
| 1000-2000 | 0.396 | 0.276 | 0.251 |
| 2000-3000 | 0.04 | 0.000 | 0.000 |
| total meso-macro pore SA ($m^2/g$) | 293.184 | 222.314 | 219.061 |

TABLE 9

| Pore diameter (Å) | Average carbon (3 lots) | Precursor, 2% Pt/3.45% Cu/C | Sucrose adsorbed onto carbon |
|---|---|---|---|
| <4.0 | 0.0541 | 0.0191 | 0.0193 |
| 4.0-4.6 | 0.1072 | 0.0478 | 0.0483 |
| 4.7-5.2 | 0.063 | 0.0381 | 0.0385 |
| 5.3-6.0 | 0.063 | 0.0475 | 0.0385 |
| 6.1-7.1 | 0.0465 | 0.0366 | 0.0464 |
| 7.2-8.0 | 0.0346 | 0.0243 | 0.0171 |
| 8.1-9.0 | 0.0235 | 0.0197 | 0.0222 |
| 9.1-13.4 | 0.0589 | 0.0443 | 0.0465 |

TABLE 9-continued

| Pore diameter (Å) | Average carbon (3 lots) | Precursor, 2% Pt/3.45% Cu/C | Sucrose adsorbed onto carbon |
|---|---|---|---|
| 13.5-16.5 | 0.0216 | 0.0182 | 0.0149 |
| 16.6-21.4 | 0.0274 | 0.0207 | 0.0238 |
| 21.5-27.0 | 0.0254 | 0.018 | 0.0177 |
| total micro PV (cc/g) | 0.5252 | 0.3343 | 0.3332 |

As shown in these results, reductions in total surface area, micropore surface area, and meso-/macropopre surface were approx. equivalent for the catalyst in which sucrose was present in the copper deposition bath, and for the carbon support treated by contact with sucrose alone. Based on these results, it is believed that a significant portion, if not substantially all, of the surface area reduction for the finished catalyst as compared to the starting support is based on the presence of sucrose in the copper deposition bath.

Example 21

This example details microscopy results for the following samples:
(1) a carbon support having a total Langmuir surface of approx. 1500 $m^2/g$ (including micropore surface area of approx. 1200 $m^2/g$ and meso-/macropore surface area of approx. 300 $m^2/g$);
(2) the carbon support of (1) containing a nominal copper content of approx. 3.45 wt. % deposited generally in accordance with Example 12;
(3) a nominal 2% Pt/3.45% Cu/C catalyst including support (1) and prepared generally as described in Example 12, but prior to heating at elevated temperatures;
(4) the nominal 2% Pt/3.45% Cu/C catalyst of (3) after heating at temperatures of approximately 950° C.

Microscopy analysis was generally conducted as described in Example 46.

Carbon Support

Figure 6:
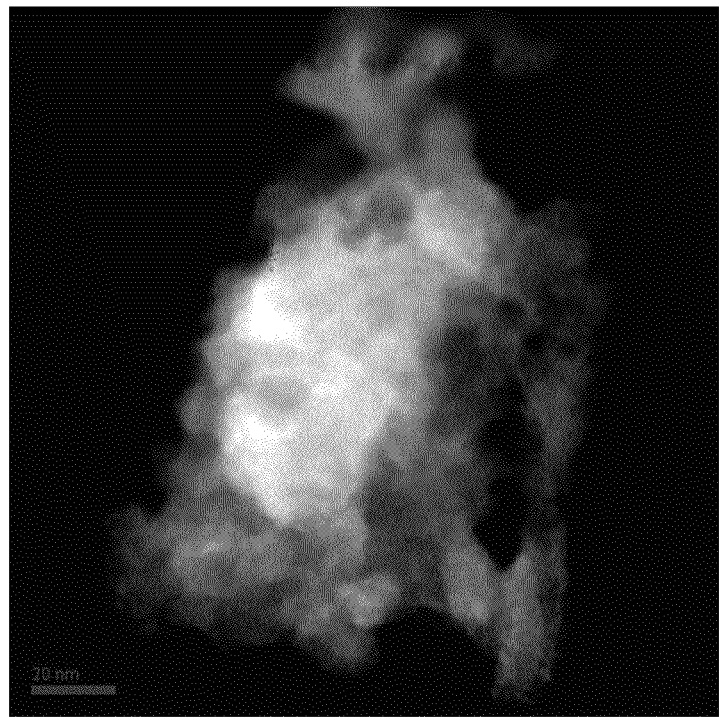
FIGS. 6-13 are micrographs generated by scanning transmission electron microscopy (STEM) analysis for a carbon support and metal-impregnated supports as described in Example 21.

FIG. 6 is a STEM micrograph of the surface of the carbon support.

Cu-Impregnated Support

Figure 7:
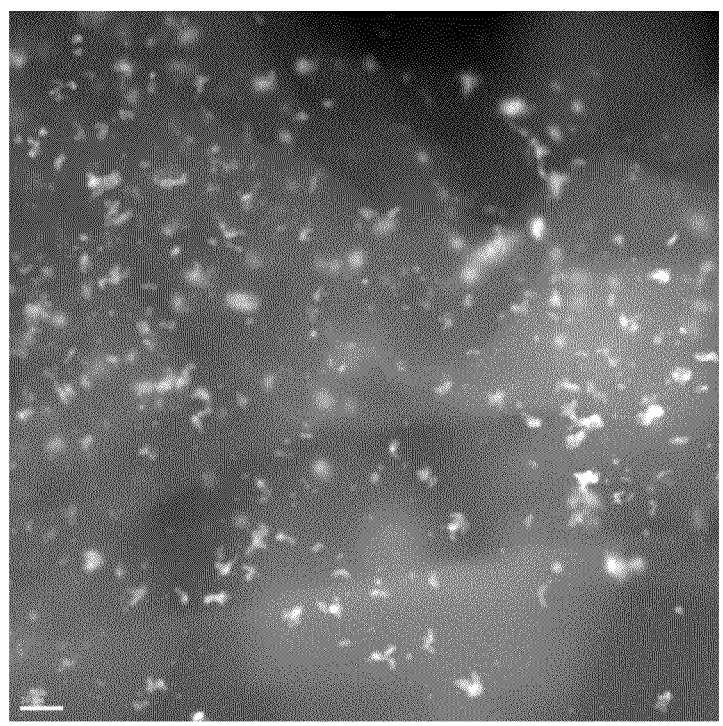
Figure 8:
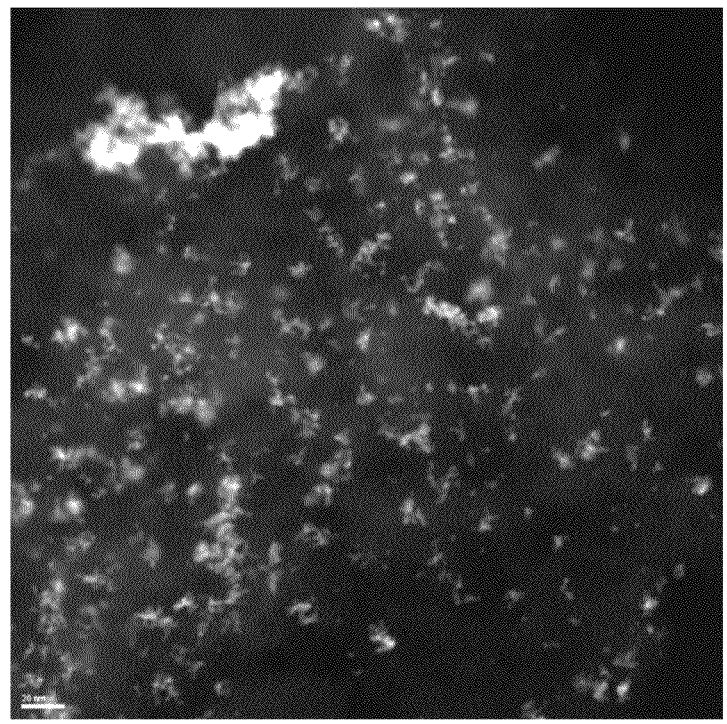
Figure 9:
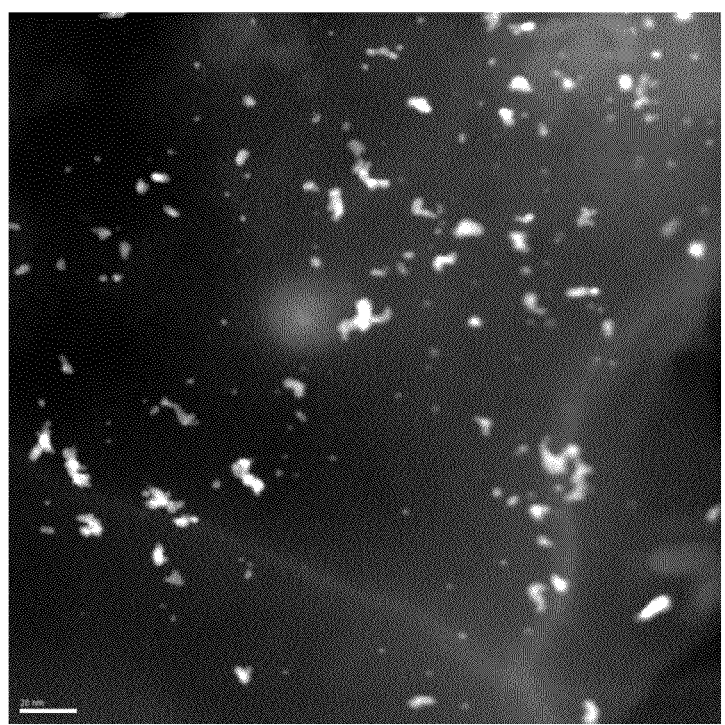
Figure 10:
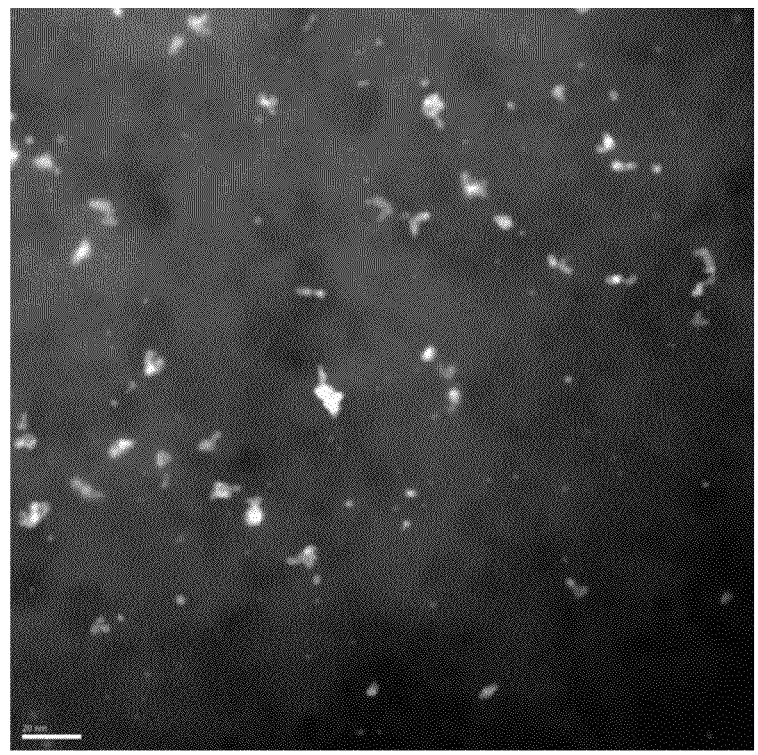
Figure 11:
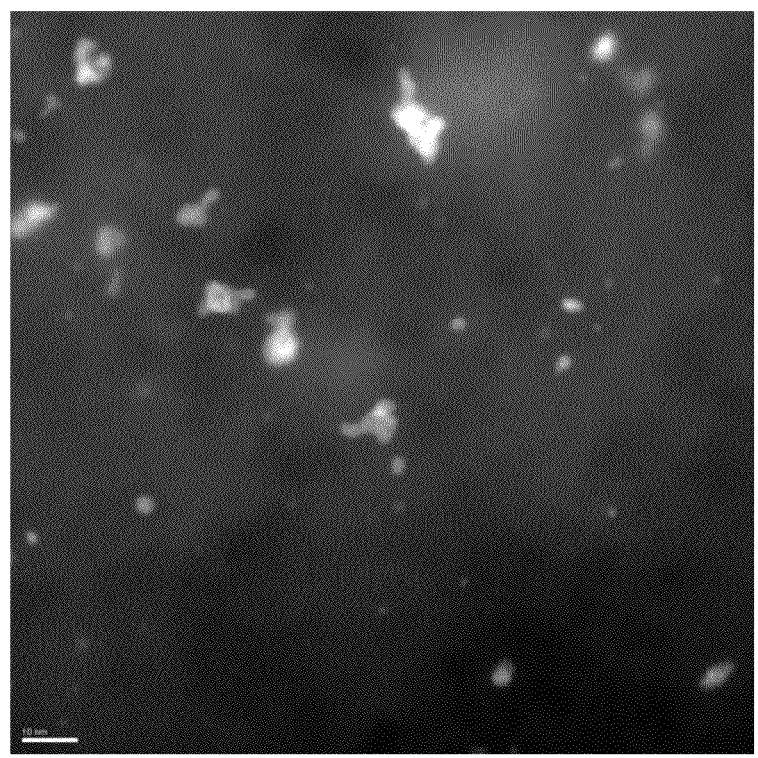
Figure 12:
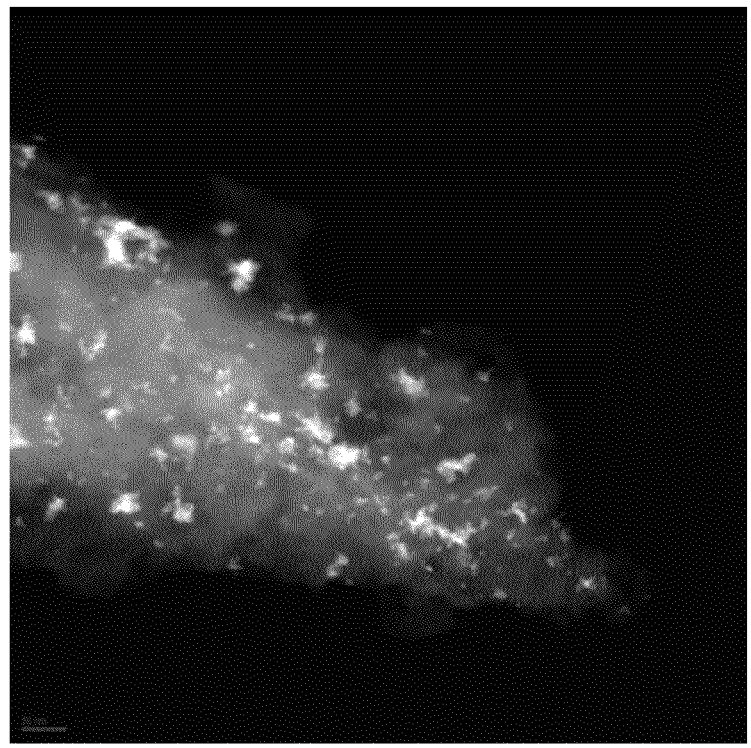

FIGS. 7 and 8 are STEM micrographs of the surface of the Cu-impregnated support. These results indicate Cu regions of irregular morphology and size deposited at the surface of the carbon support.

Pt/Cu-Impregnated Support (Prior to Heat Treatment)

FIGS. 9-12 are micrographs of the surface of the Pt/Cu impregnated support prior to treatment at elevated temperatures. These results indicate regions of Cu deposited at the surface of the carbon support having Pt deposited thereon that have generally retained the irregular morphology and size of the deposited Cu regions.

Figure 13:
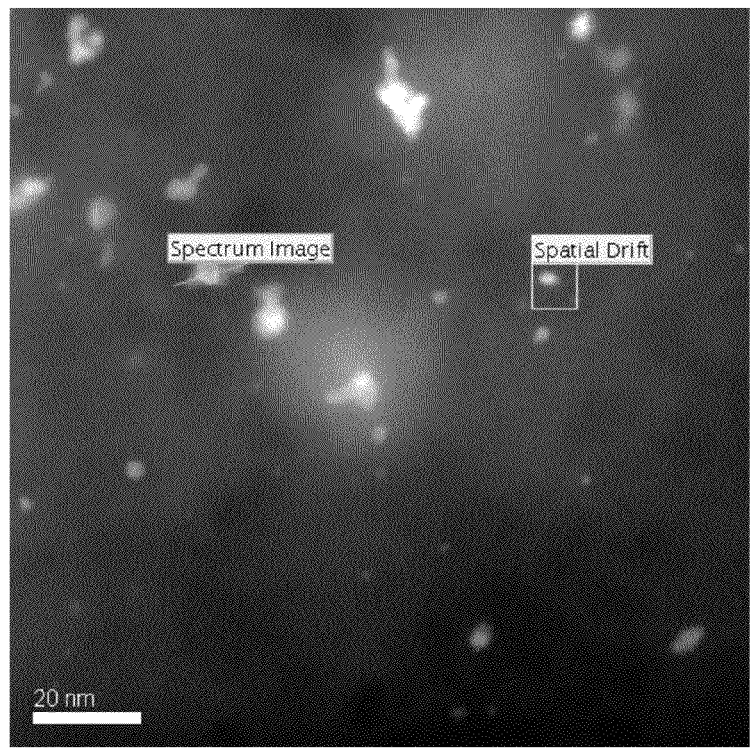
Figure 14:
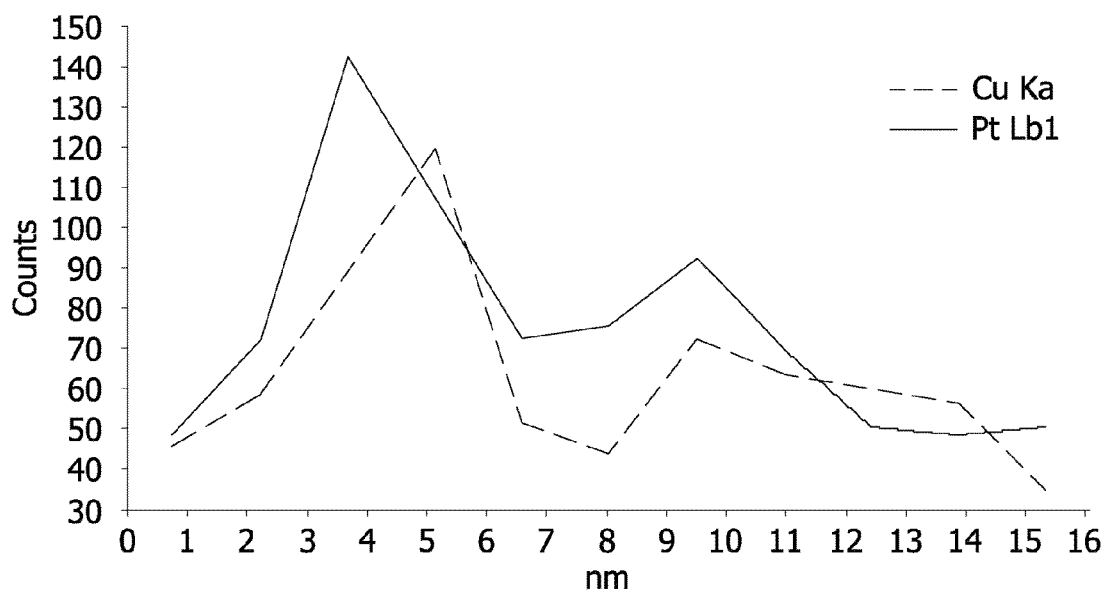
FIG. 14 provides results of line scan analysis for a metal-impregnated support as described in Example 21.

FIG. 13 provides a STEM micrograph for a portion of the impregnated support. The portion marked "Spectrum Image" was subjected to line scan analysis, the results of which are shown in FIG. 14. As shown, the line scan analysis indicates the presence of copper and platinum throughout the Spectrum Image portion.

Pt/Cu/C Catalyst (after Heating)

Figure 15:
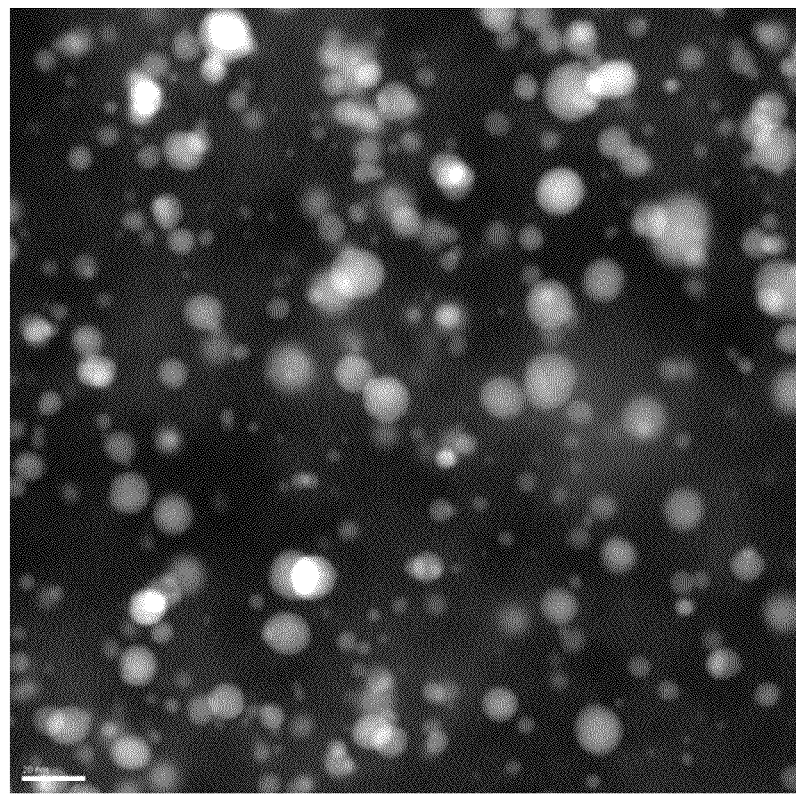
FIGS. 15 and 16 are STEM micrographs for catalysts as described in Example 21.
Figure 16:
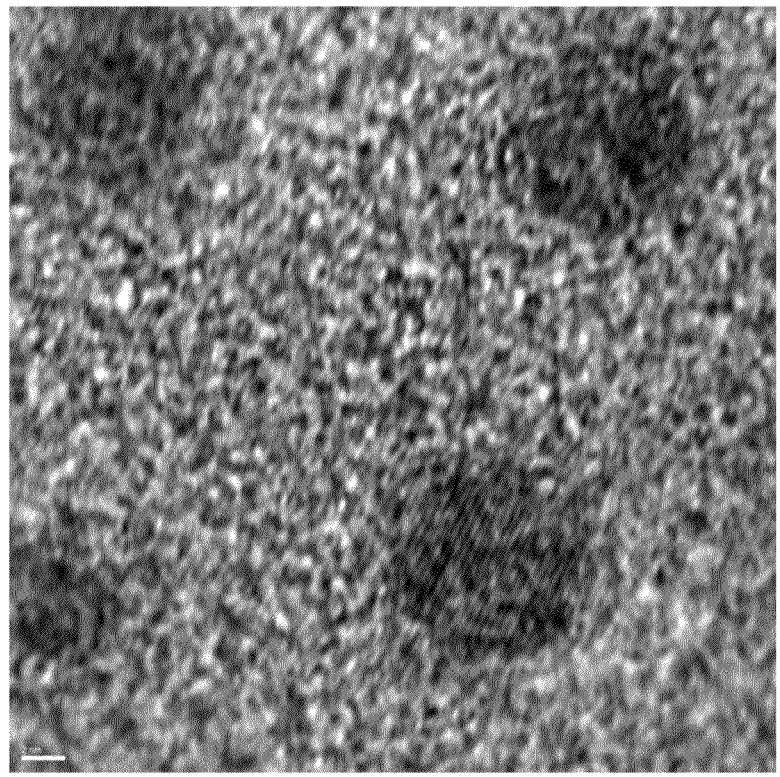

FIG. 15 is an STEM photomicrograph and FIG. 16 is a high resolution TEM (HRTEM) photomicrograph of a portion of the Pt/Cu/C catalyst after heating at elevated temperatures. These Figs. indicate a change in the morphology of the Pt/Cu regions. These results indicate formation of spherical particles of sizes ranging from approx. 1 nm to approx. 15 nm.

Figure 17:
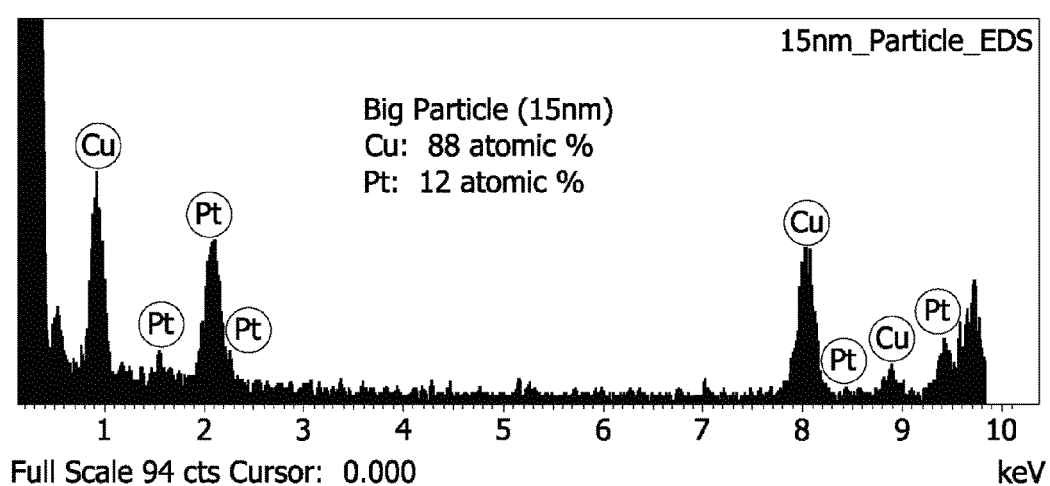
FIGS. 17 and 18 are results of energy dispersive spectroscopy (EDS) analysis of catalysts as described in Example 21.
Figure 18:
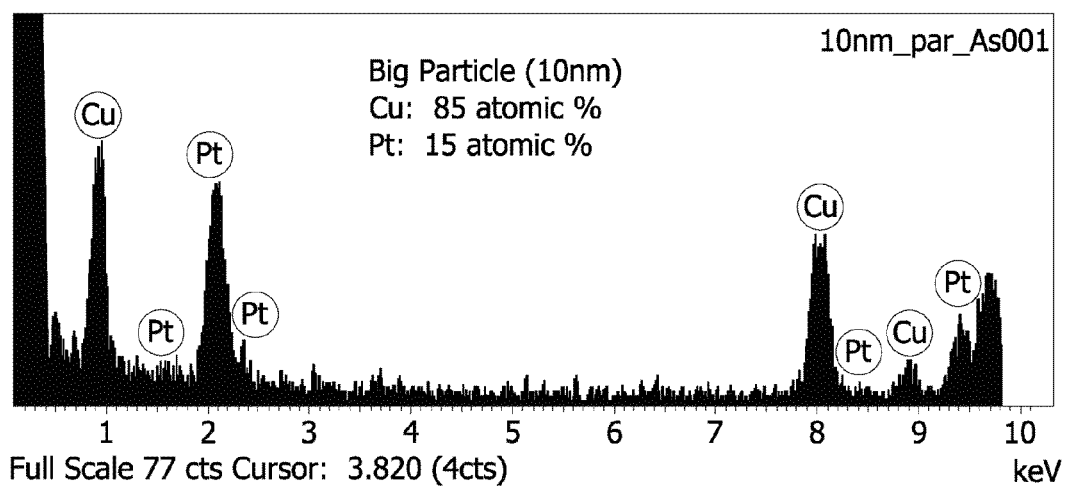

FIGS. 17 and 18 are EDS spectra for particles of varying sizes. As particle size increases, the atom ratio of copper to platinum increases, indicating relatively constant amount of platinum among of the particles. It is currently believed that thickness of the platinum layer is relatively constant over a range of particle size.

Pt/Cu/C Catalyst Used in 3 PMIDA Reaction Cycles

Figure 19:
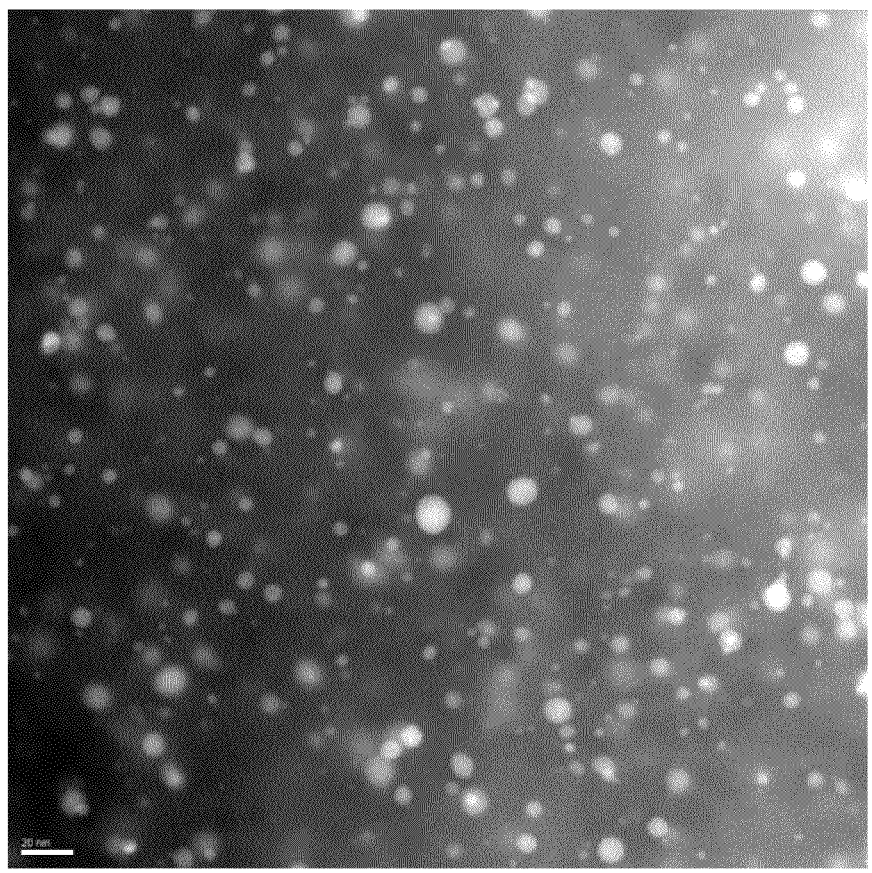
FIGS. 19-21 are STEM micrographs for reaction-tested catalysts as described in Example 21.
Figure 20:
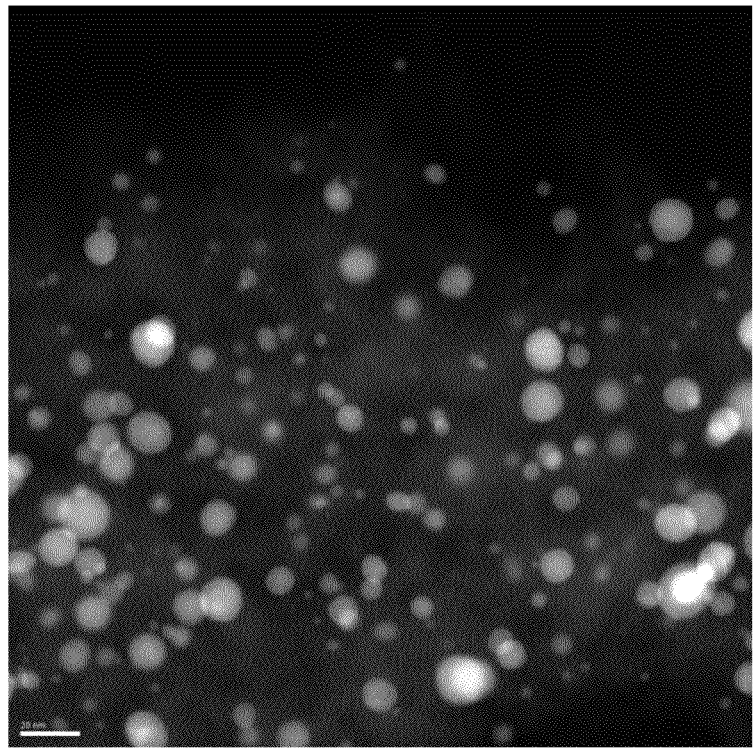
Figure 21:
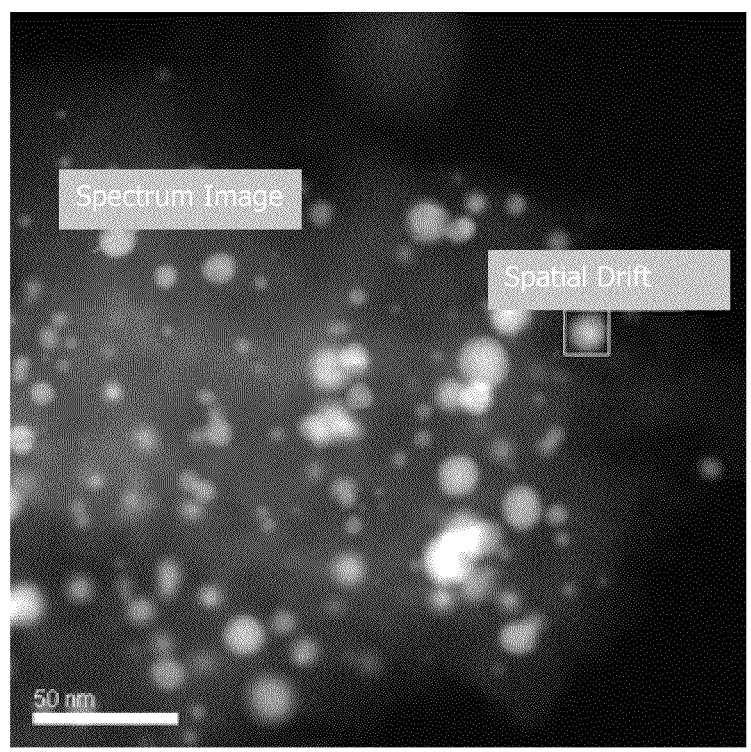

FIGS. 19-21 are STEM photomicrographs for a portion of a catalyst used in 3 PMIDA reaction cycles under the above-noted conditions. These results indicate the presence of stable particles of varying sizes, including those in the range of from approx. 1-1.5 nm.

Figure 22:
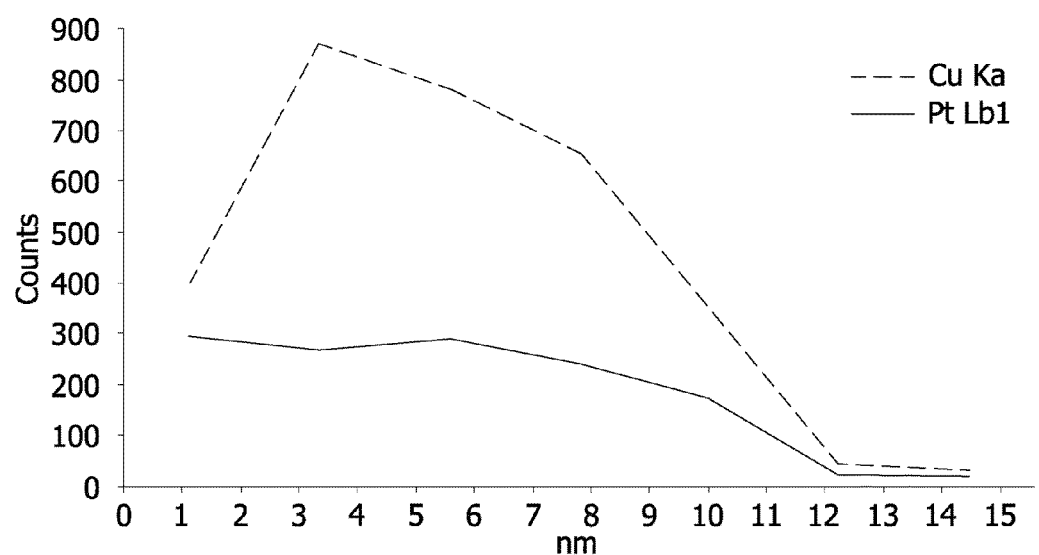
FIG. 22 provides results of line scan analysis for a reaction-tested catalyst as described in Example 21.

FIG. 22 provides line scan data for the portion of the catalyst surface marked "Spectrum Image" in FIG. 21. Based on detection of Cu over the entire Spectrum Image, with the highest copper content at the center of the particle while the platinum signal remained relatively flat, these results suggest the presence of a relatively thin outer platinum-containing shell (i.e., no more than 3 atoms thick). That is, since the line scan analysis utilized an X-ray beam of approx. 1 nm (10 Å) in size this suggests the presence of a platinum-containing shell having a thickness of no more than 3 platinum atoms (atomic size of platinum is 3 Å).

Pt/Cu/C Catalyst Used in 30 PMIDA Reaction Cycles

Figure 23:
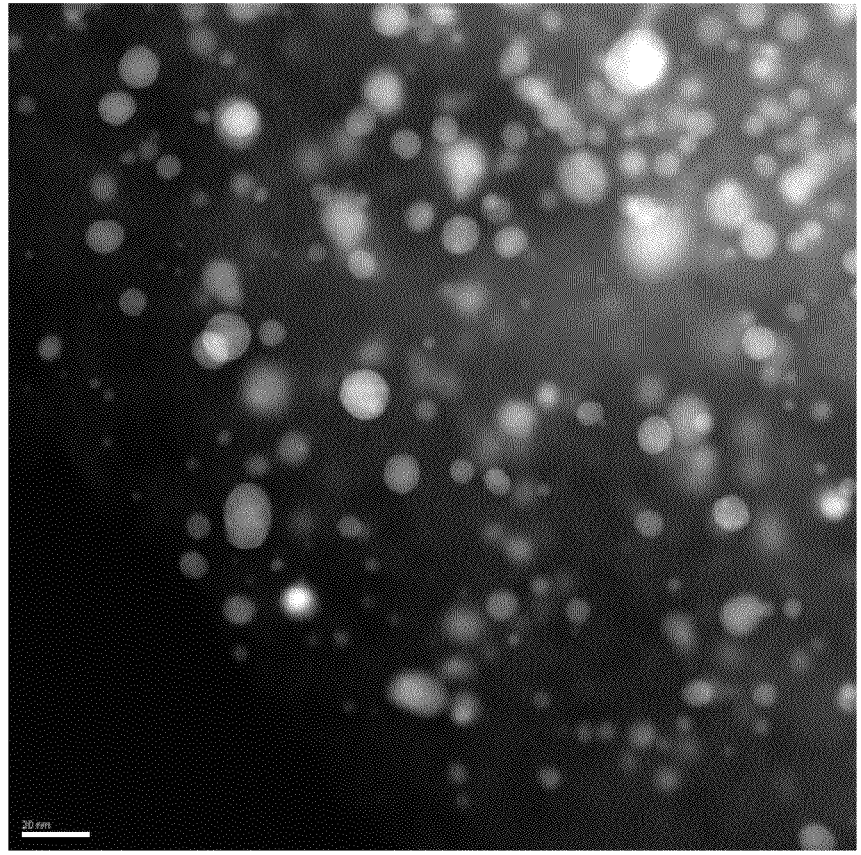
FIGS. 23 and 24 are STEM micrographs for reaction-tested catalysts as described in Example 21.
Figure 24:
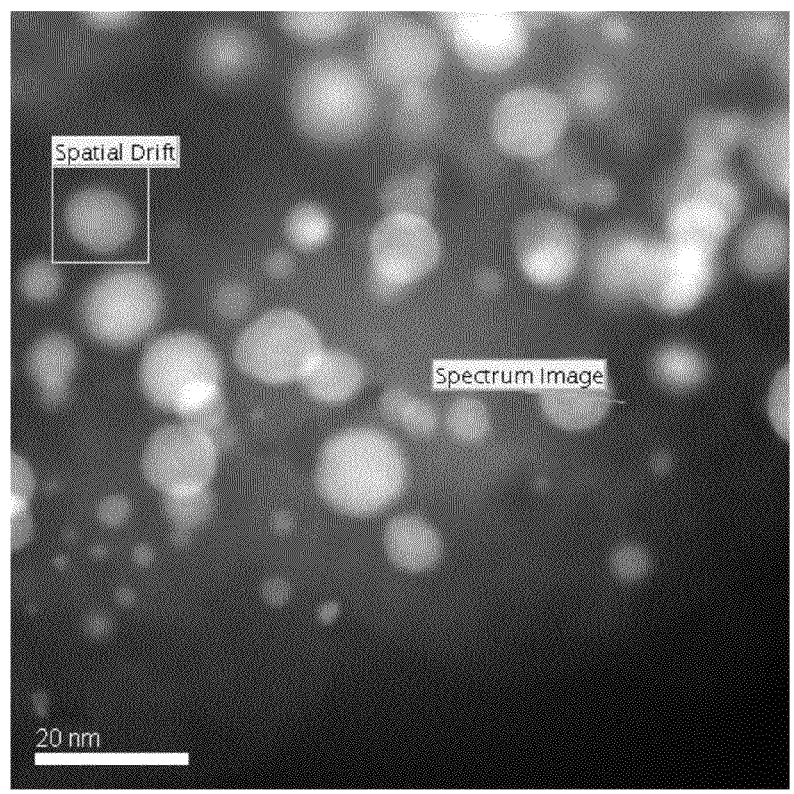
Figure 25:
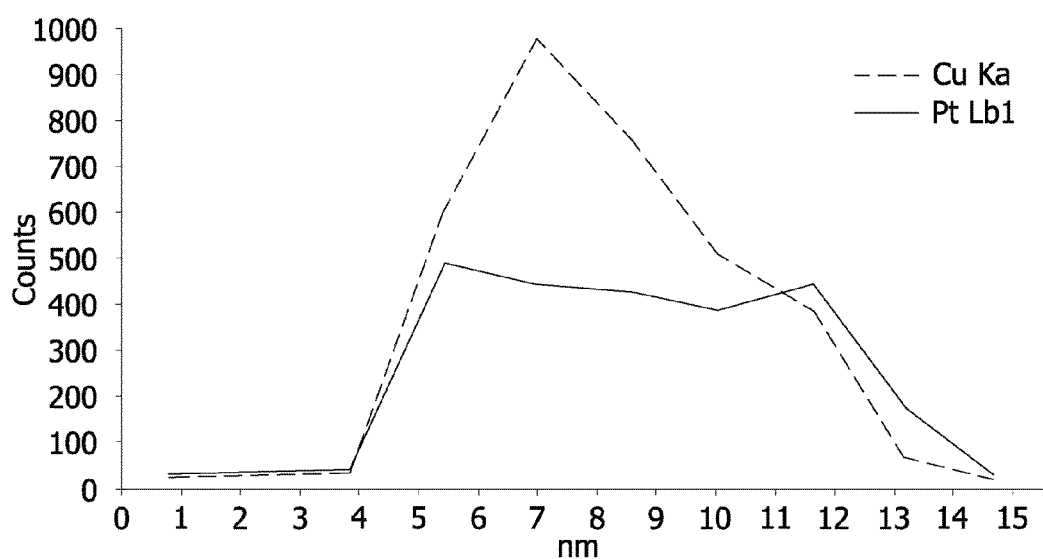
FIG. 25 provides results of line scan analysis for a reaction tested catalyst as described in Example 21.

These results are for catalysts tested for 30 reaction cycles. The STEM photomicrographs of FIGS. 23 and 24 indicate the presence of stable particles of varying sizes, including approx. 1-1.5 nm. FIG. 25 provides line scan data for the portion marked "Spectrum Image" in FIG. 24. These results also indicate a relatively thin layer of platinum as both the platinum and copper signals began to be detected at the same point by the X-ray beam having a size of approx. 1 nm, again indicating the presence of a platinum-containing shell less than 1 nm (i.e., less than 3 platinum atoms) thick.

Figure 26:
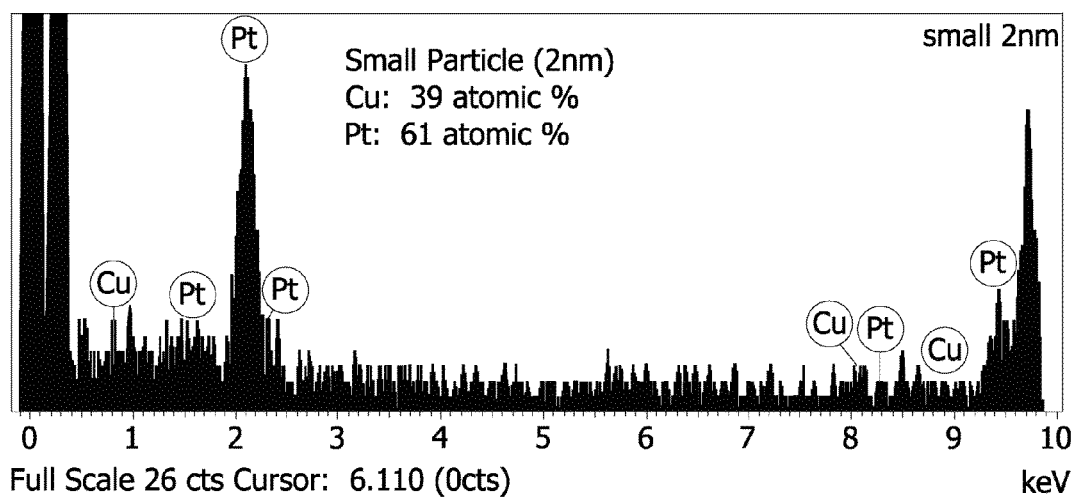
FIGS. 26 and 27 are EDS spectra for reaction-tested catalysts as described in Example 21.
Figure 27:
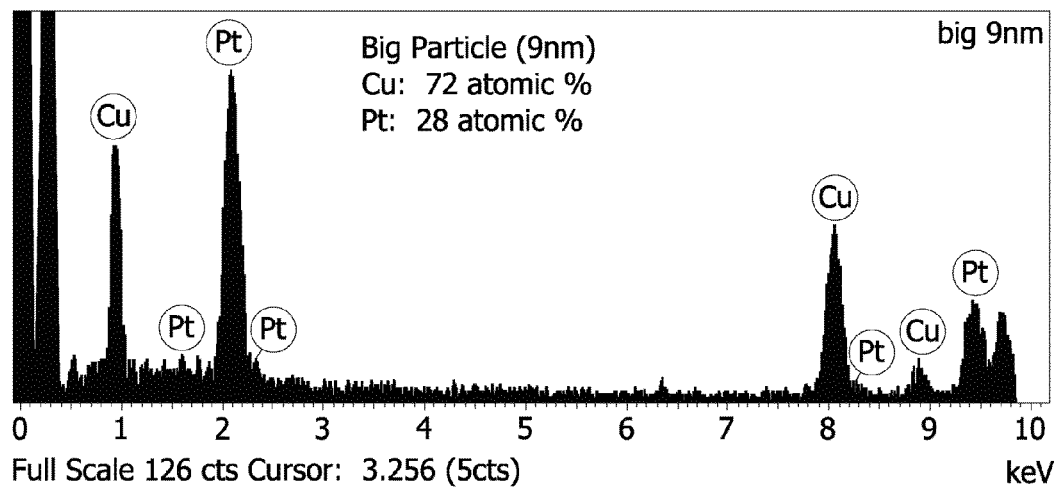

FIGS. 26 and 27 provide EDS spectra for particles of approx. 2 nm and 9 nm in size. As shown, the atom percent of copper increased significantly with particle size, including the presence of a copper-rich core.

Example 22

This example details results of microscopy analysis conducted generally as described in Example 46 for: (1) a nominal 2% Pt/3.45% Cu/C catalyst precursor prepared as described in Example 9, and (2) a nominal 2% Pt/3.45% Cu/C catalyst prepared from the precursor (1) (e.g., heating of the precursor to a maximum temperature of approximately 950° C.).

Figure 28:
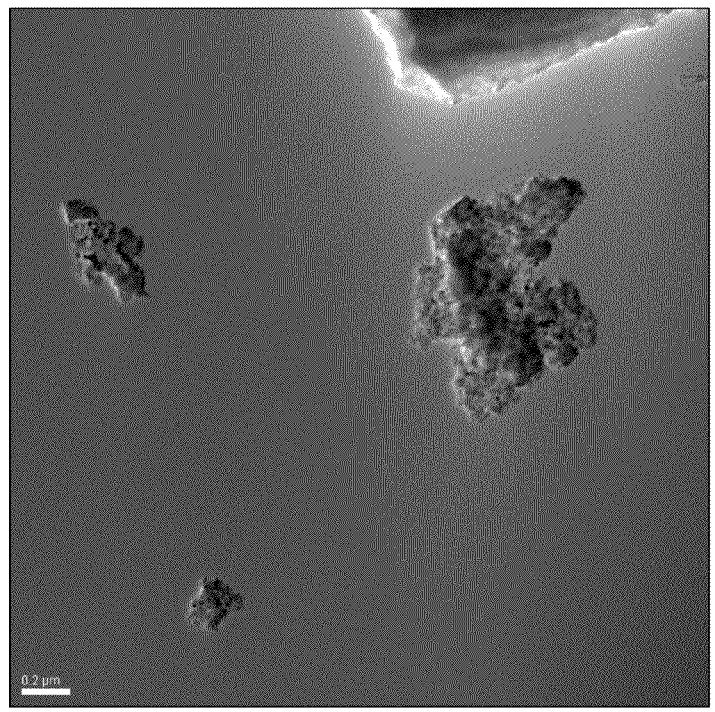
FIGS. 28 and 29 are TEM and STEM images for metal-impregnated supports as described in Example 22.
Figure 29:
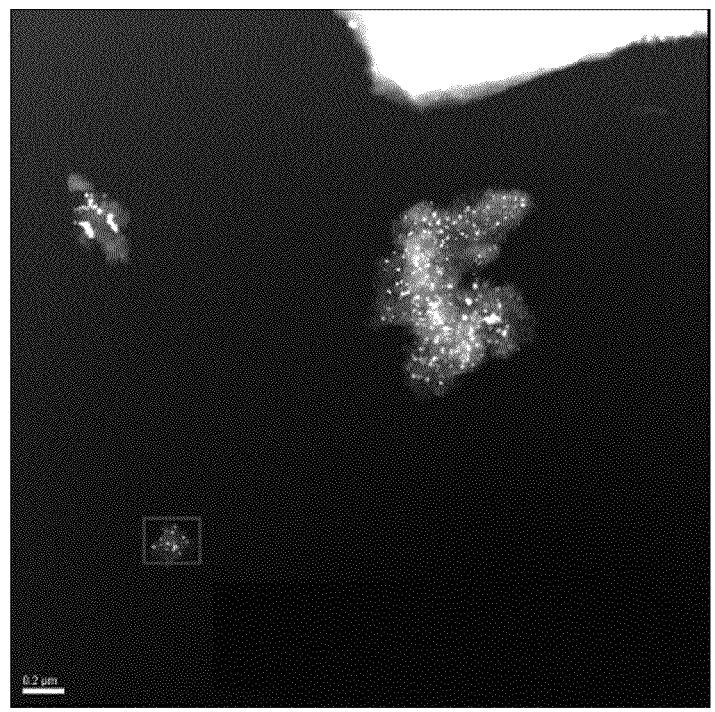
Figure 30:
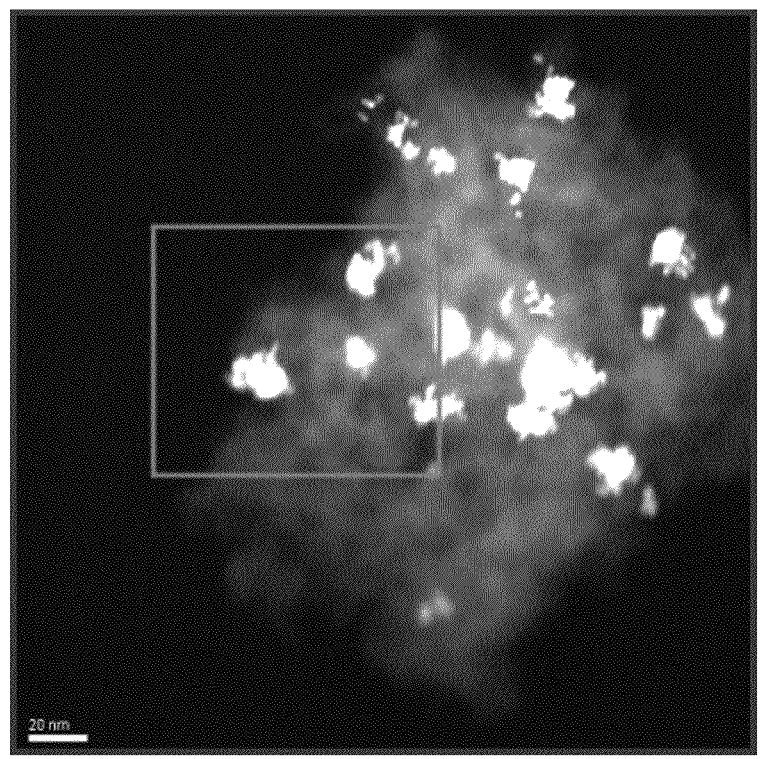
FIGS. 30-31, 32-33, 34-35, and 36-37 are TEM images and corresponding line scan analysis results for metal-impregnated supports as described in Example 22.
Figure 31:
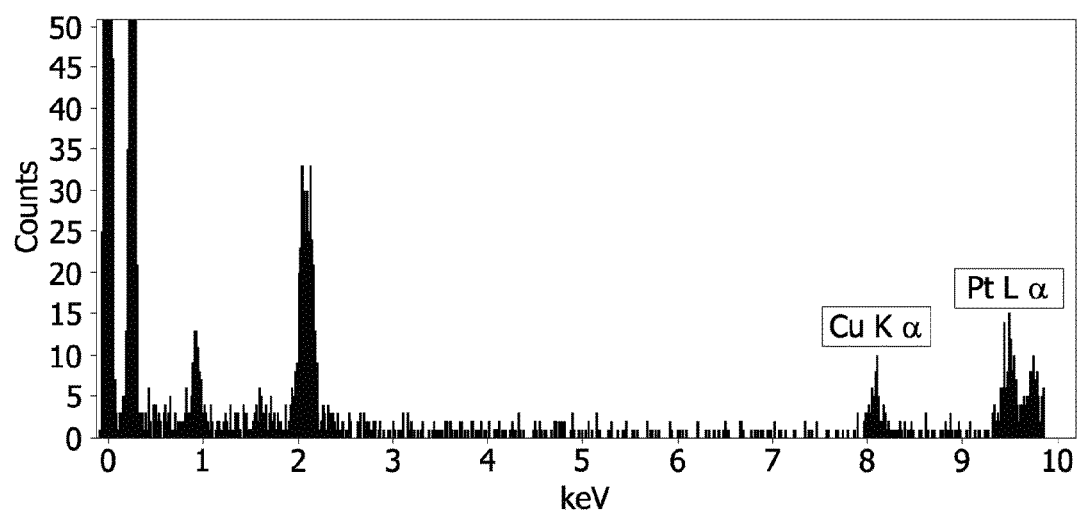
Figure 32:
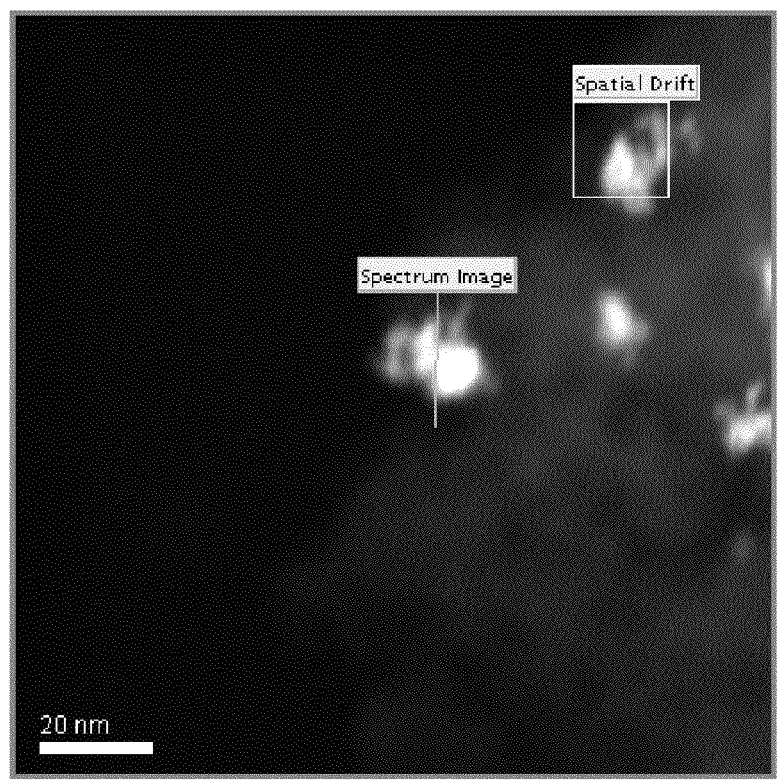
Figure 33:
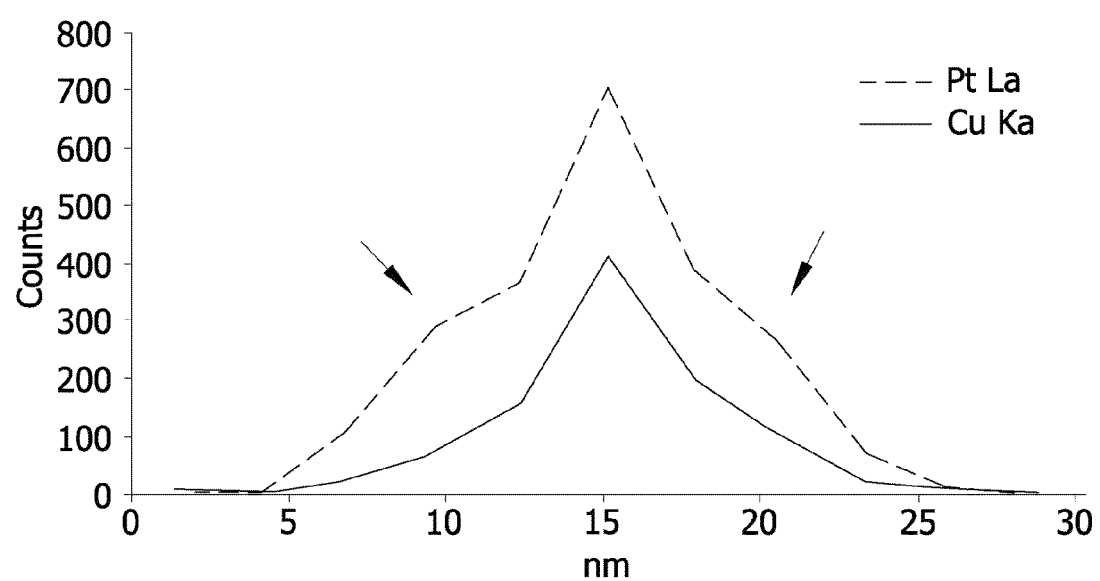
Figure 34:
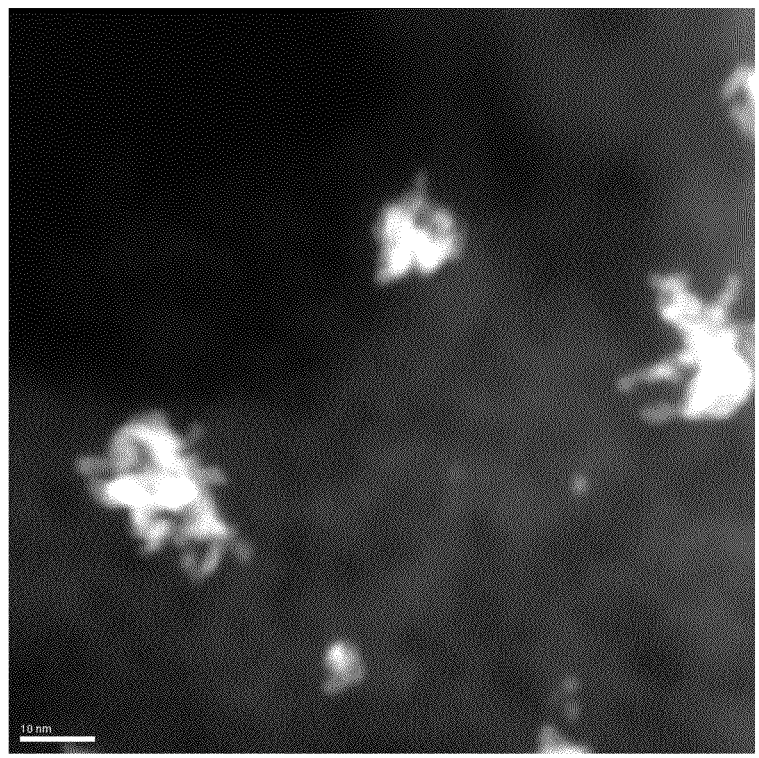
Figure 35:
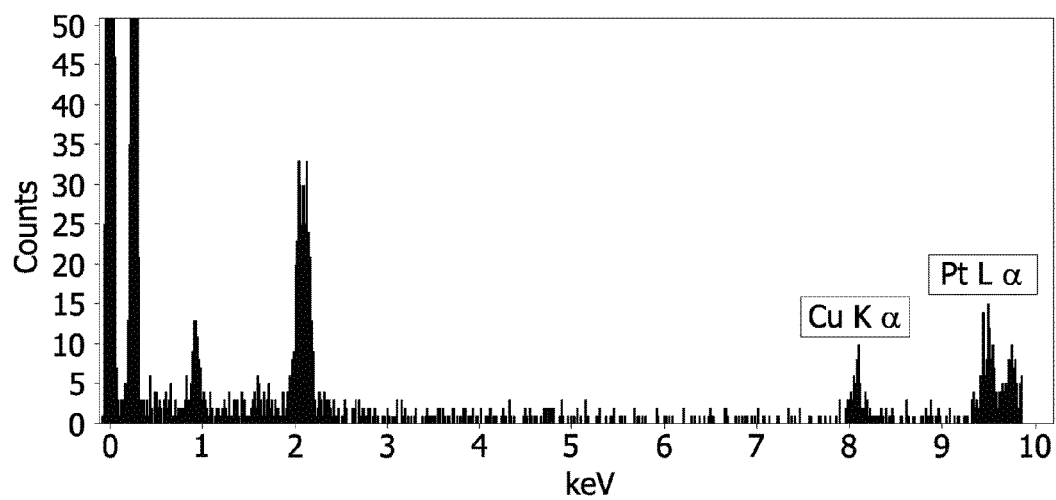
Figure 36:
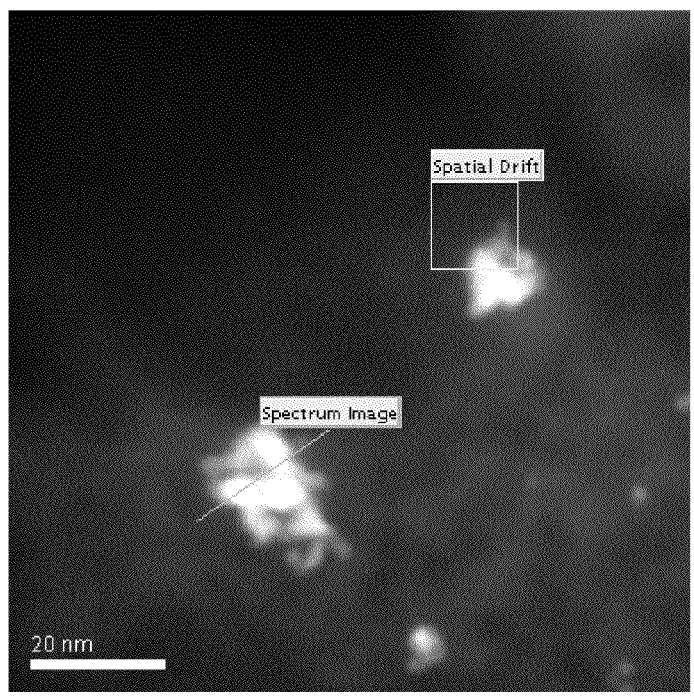
Figure 37:
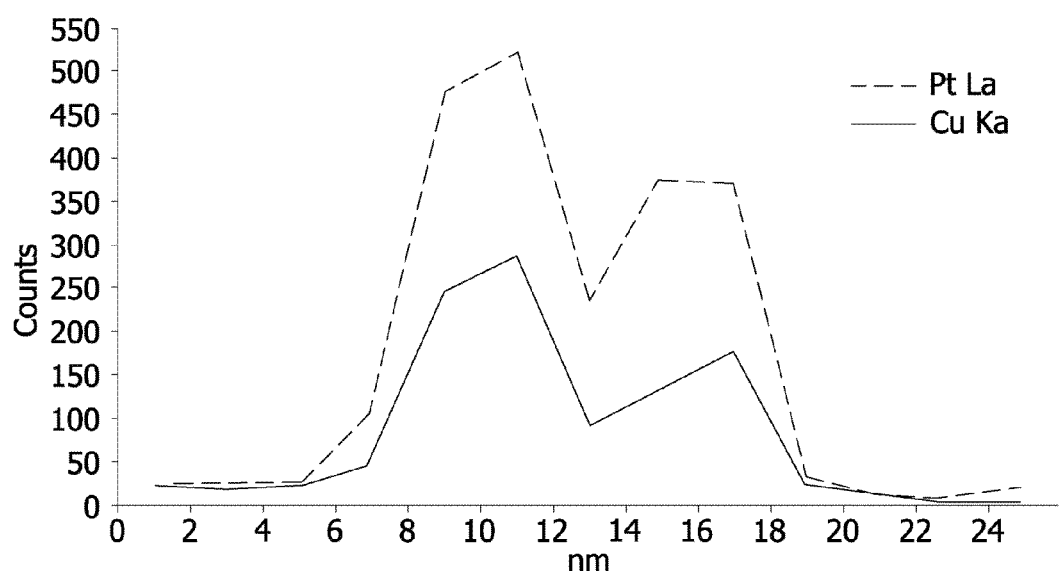

FIGS. 28 and 29 are TEM and STEM images for precursor (1). FIGS. 30-37 provide TEM images and corresponding line scan data for portions of the precursor surface. As shown by the line scans, platinum and copper were detected throughout the particle.

Figure 38:
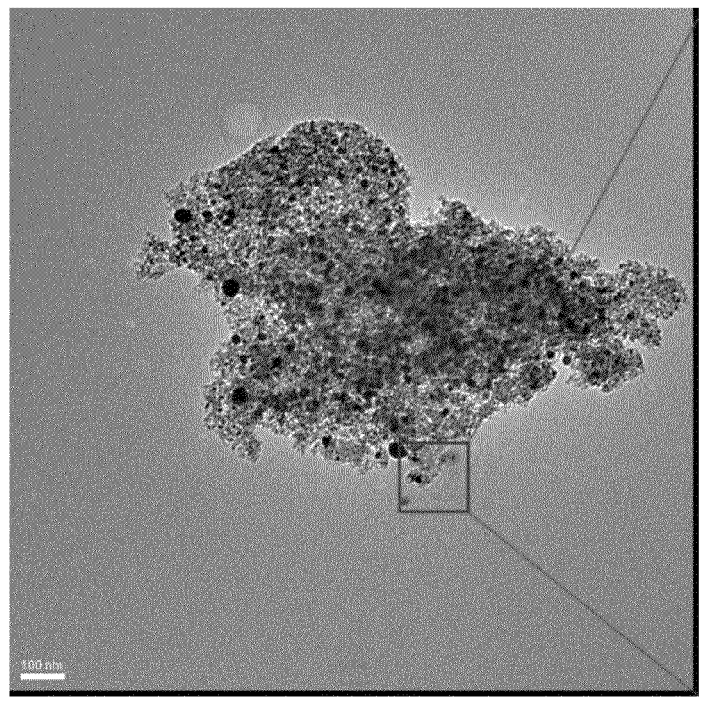
FIGS. 38 and 39 are TEM and STEM images for catalysts as described in Example 22.
Figure 39:
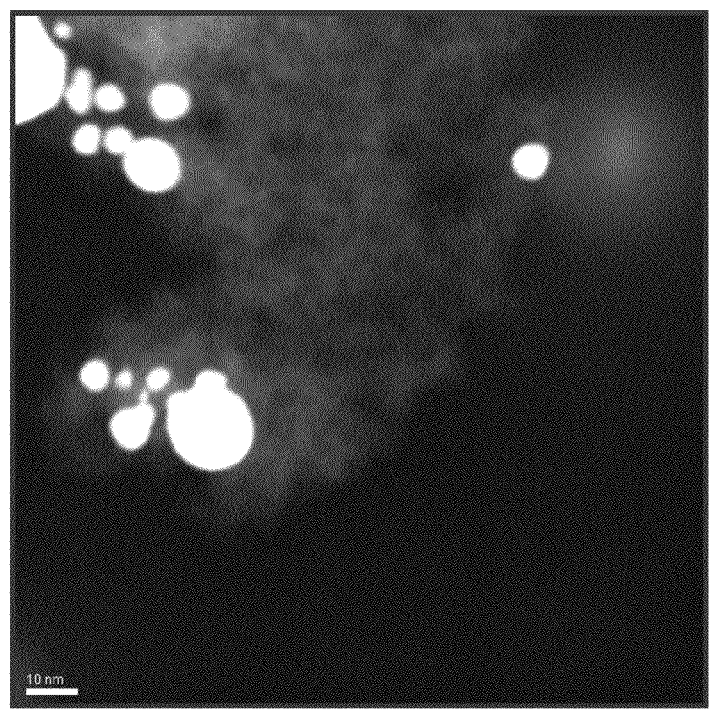
Figure 40:
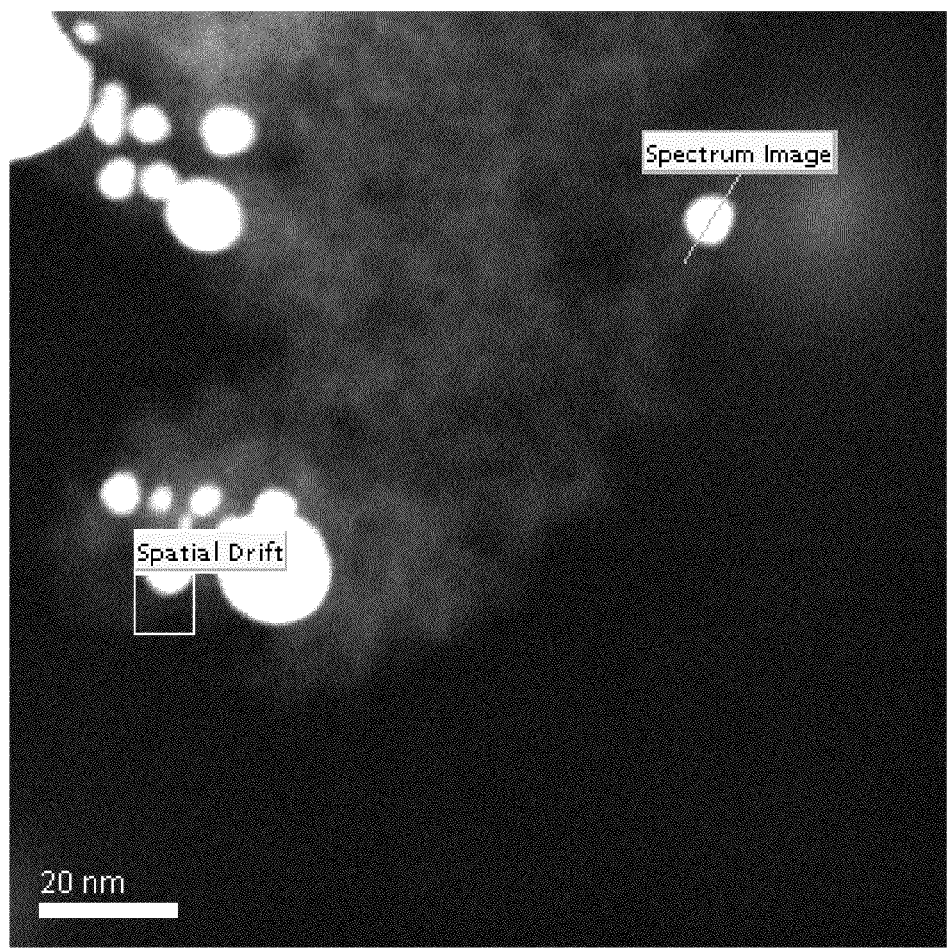
FIG. 40 indicates the portion of catalyst analyzed by line scan analysis as described in Example 22.
Figure 41:
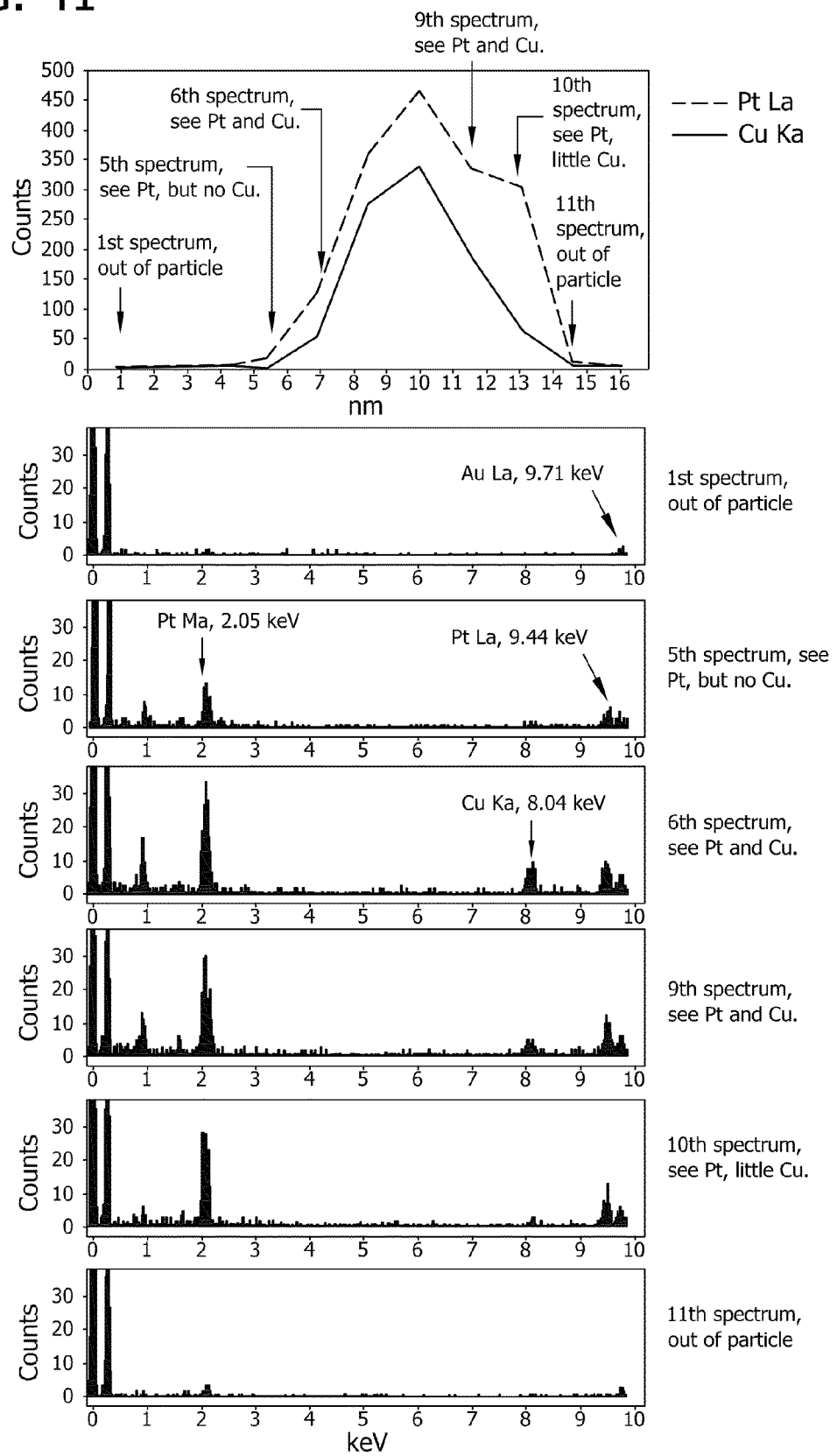
FIG. 41 provides line scan analysis for the portion of the support identified in FIG. 40.
Figure 42:
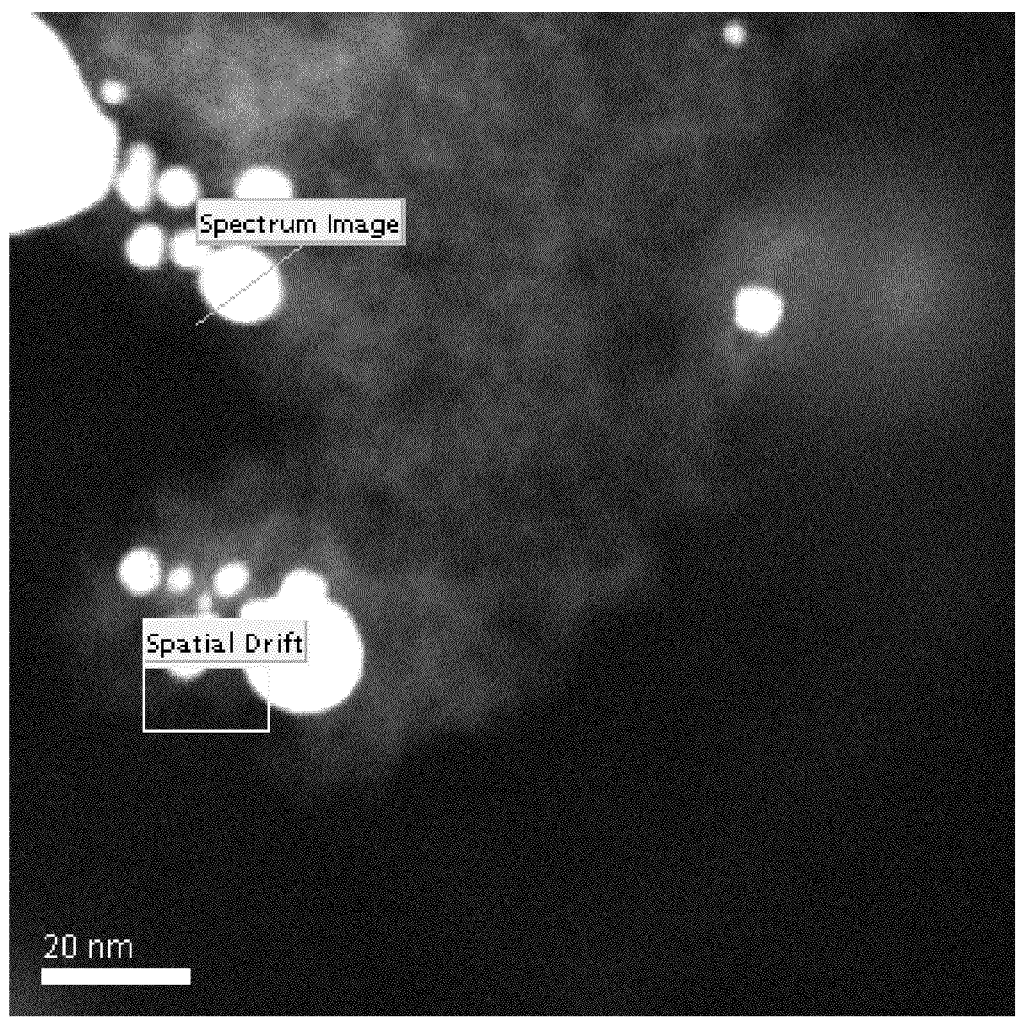
FIG. 42 indicates the portion of catalyst analyzed by line scan analysis as described in Example 22.
Figure 43:
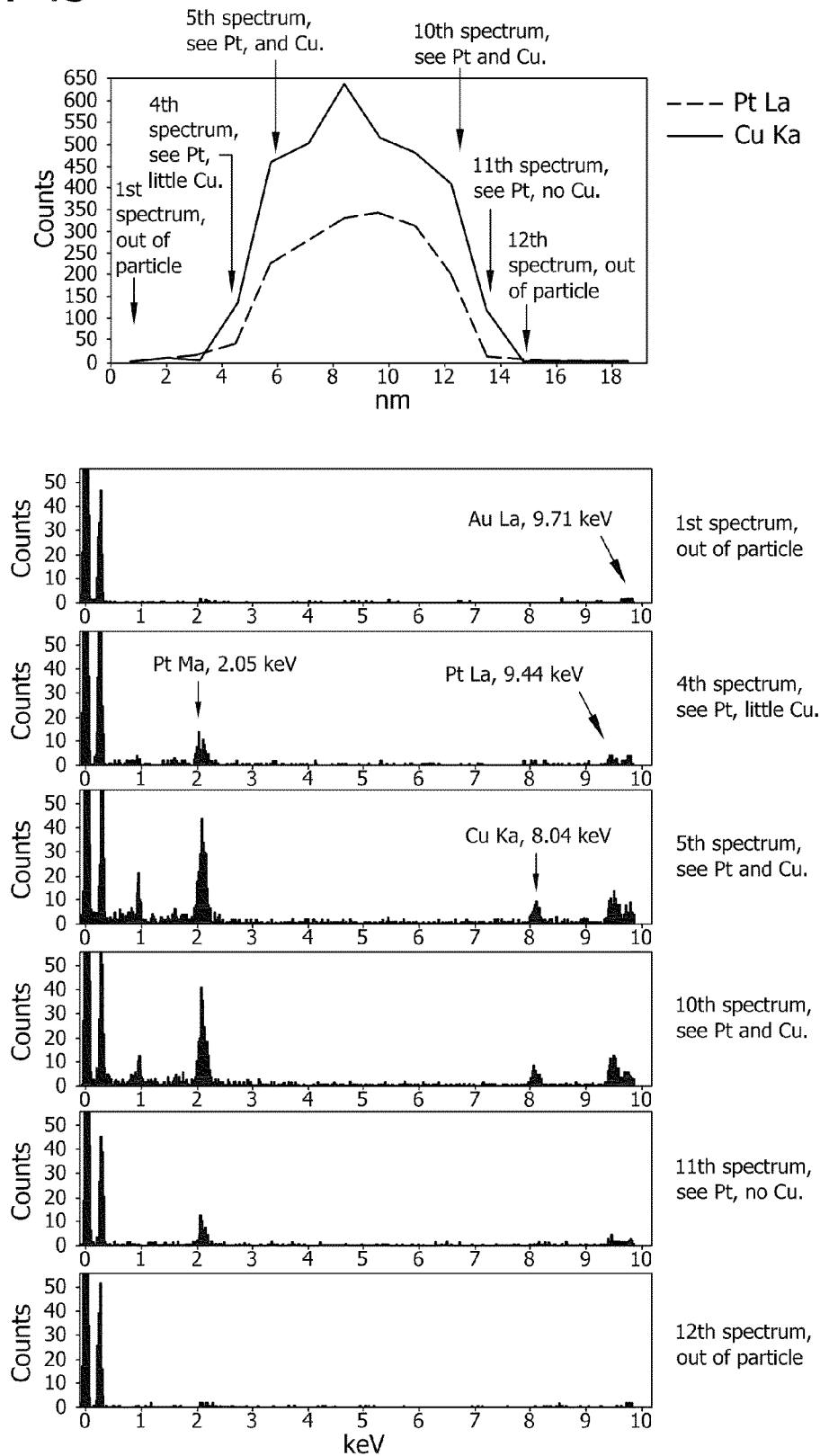
FIG. 43 provides line scan analysis for the portion of the support identified in FIG. 40.

FIGS. 38 and 39 are TEM and STEM images for catalyst (2). FIGS. 40 and 42 indicate the portion of the catalyst surface analyzed by line scans, the results of which are shown in FIGS. 41 and 43, respectively. The line scan results indicate the presence of platinum throughout the particles.

Example 23

Figure 44:
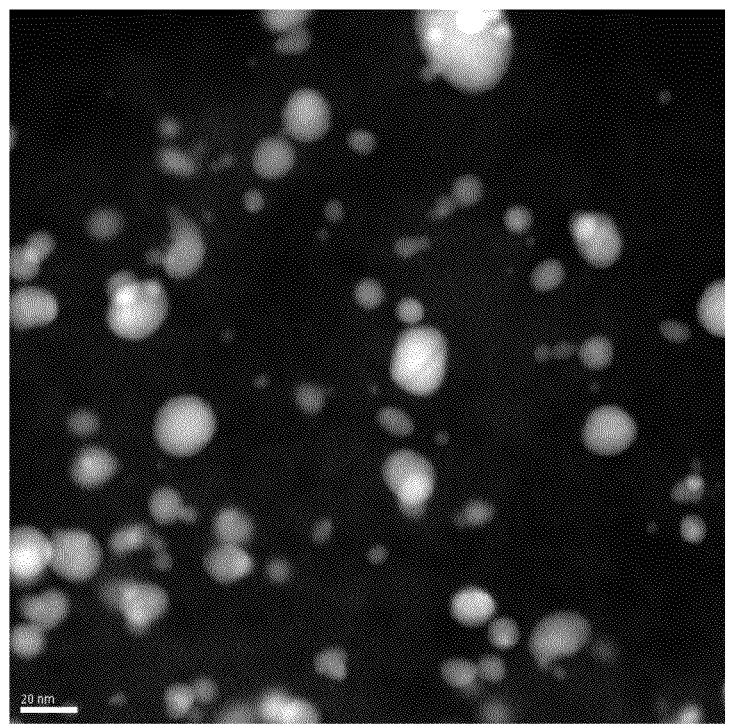
FIGS. 44 and 45 are TEM images utilized in particle size analysis as described in Example 23.
Figure 45:
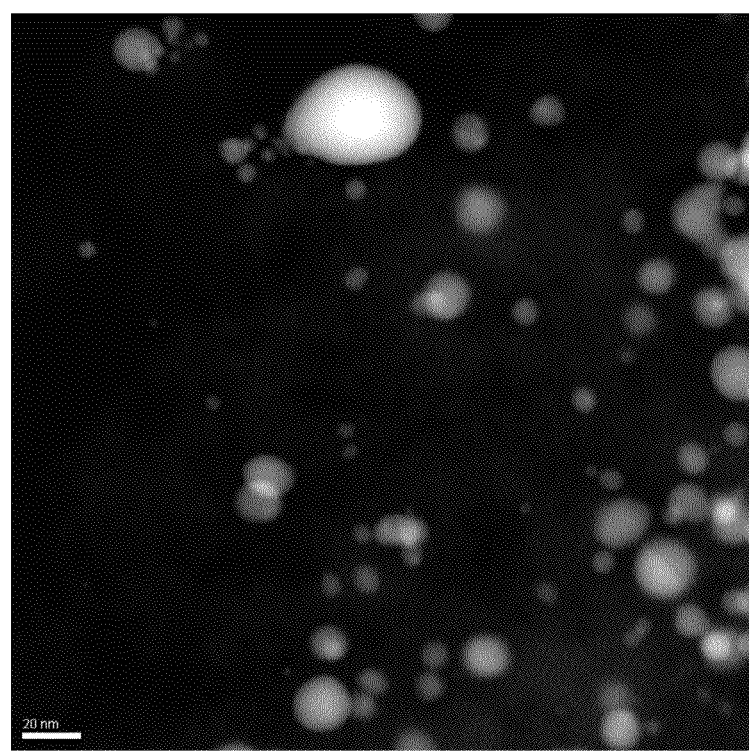
Figure 46:
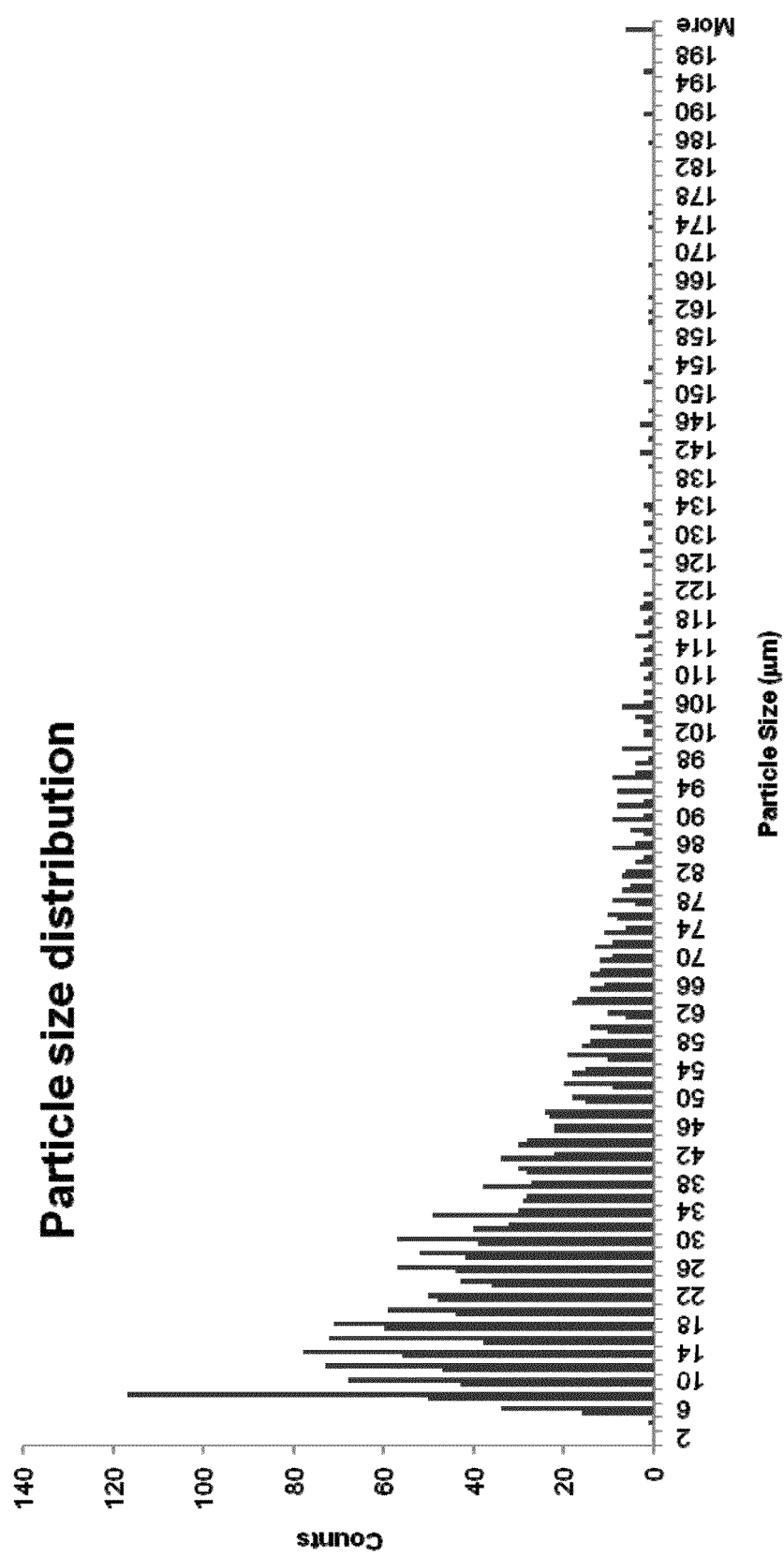
FIG. 46 provides particle size distribution data for catalyst analyzed as described in Example 23.
Figure 47:
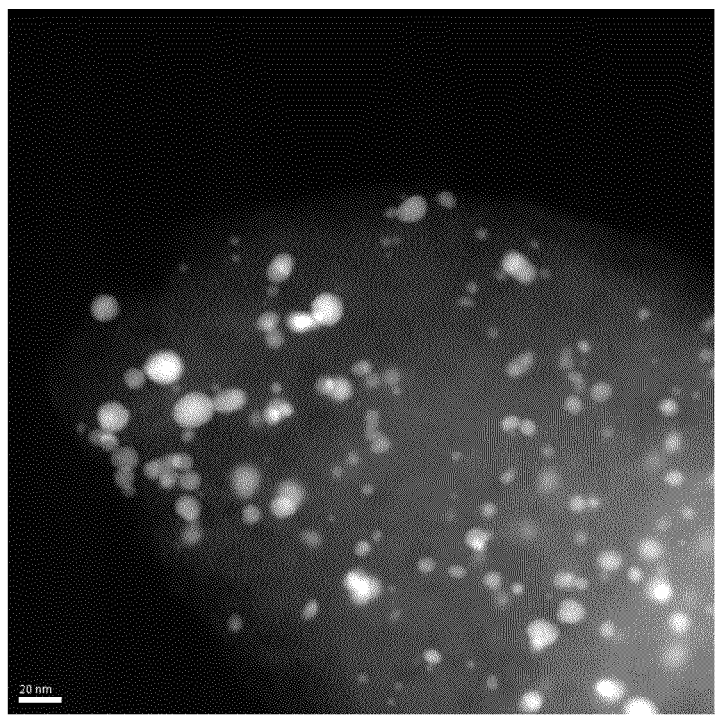
FIGS. 47 and 48 are TEM images utilized in particle size analysis as described in Example 23.
Figure 48:
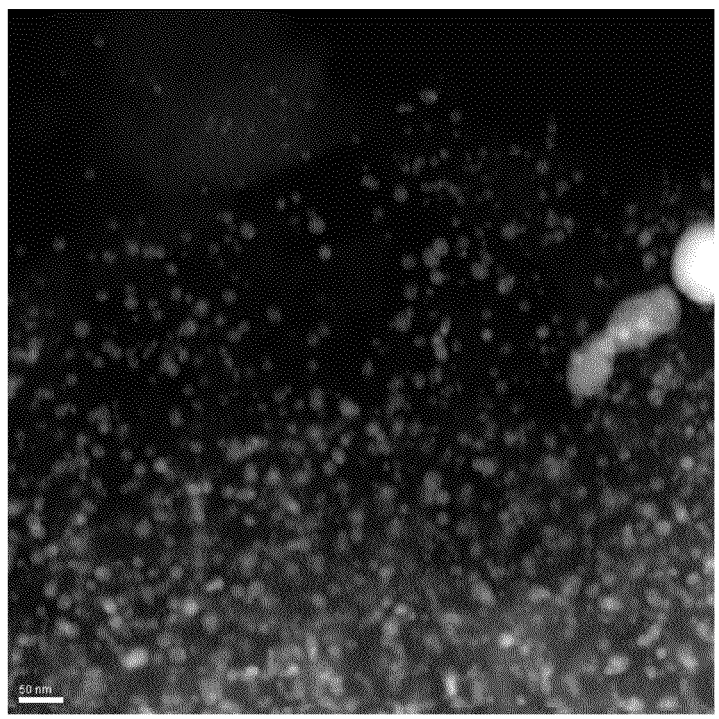
Figure 49:
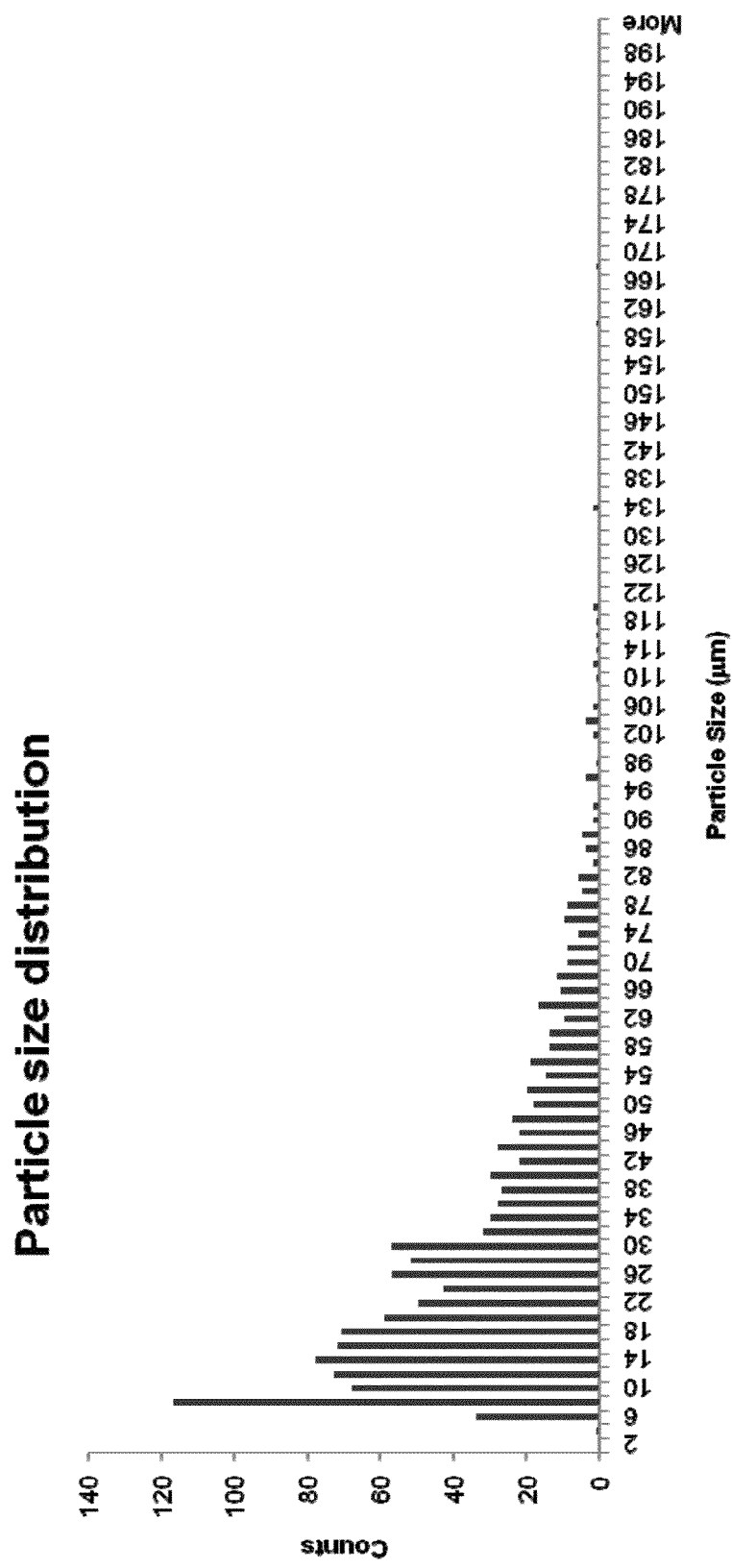
FIG. 49 provides particle size distribution data for catalyst analyzed as described in Example 23.

This example provides particle size distribution analysis for a nominal 2% Pt/3.45% Cu/C catalyst prepared as described in Example 9. Fifteen images of the type shown in FIGS. 44 and 45 were used for determining the size of a total of 1177 particles. The size distribution of the measured particles is shown in FIG. 46. This example also provides particle size distribution analysis for the catalyst after use in PMIDA oxidation for 4 reaction cycles under the conditions described in Example 7. Fourteen images of the type shown in FIGS. 47 and 48 were used to determine the size of 1319 particles. The size distribution of the measured particles is shown in FIG. 49.

Example 24

This example provides X-ray diffraction results for a nominal 2% Pt/3.45% Cu/C catalyst prepared as described in Example 12.

Figure 50:
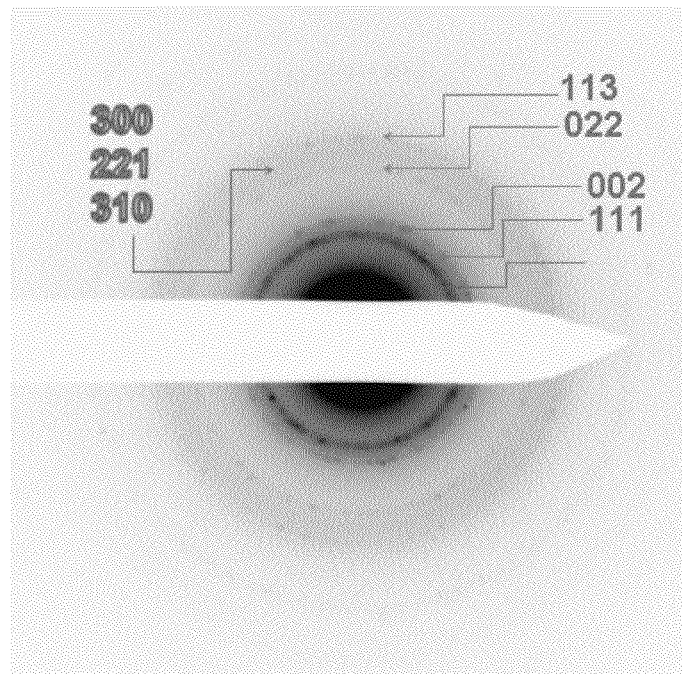
FIGS. 50 and 51 are X-ray diffraction results for a catalyst analyzed as described in Example 24.
Figure 51:
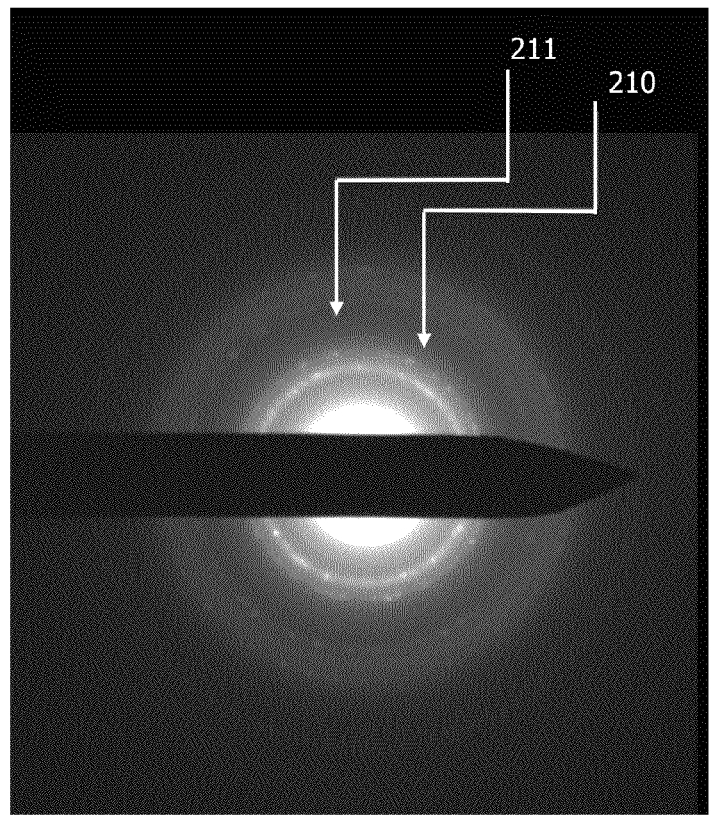

FIGS. 50 and 51 provide diffraction results for an area of the catalyst surface having a diameter of approximately 1 μm, measured using selected area electron diffraction (SAED). Based on the generation of FCC (face centered cubic) indices (i.e., the results denoted 113, 022, 002, and 111) and primitive cubic indices (i.e., the results denoted 300, 221, 310, and 210), the SAED results indicate the presence of a CuPt alloy phase (likely a $Cu_3Pt$) alloy phase. The results may also indicate the presence of a metallic copper phase.

Figure 52:
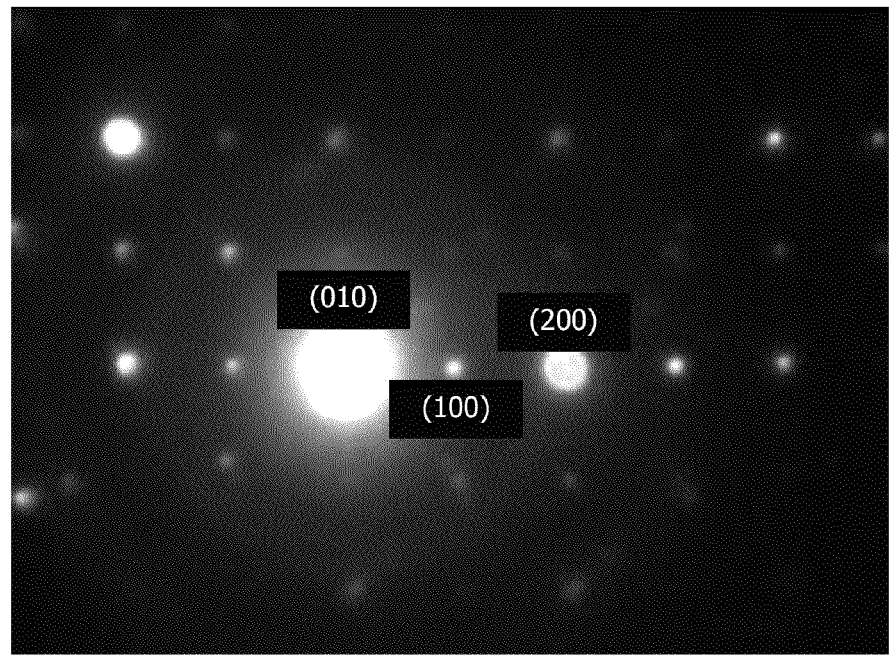
FIGS. 52-55 are nano-diffraction results for a metal particle analyzed as described in Example 24.
Figure 53:
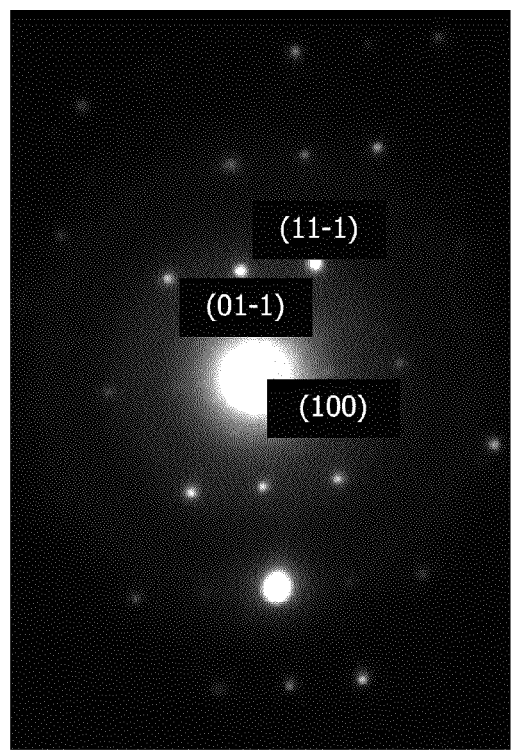
Figure 54:
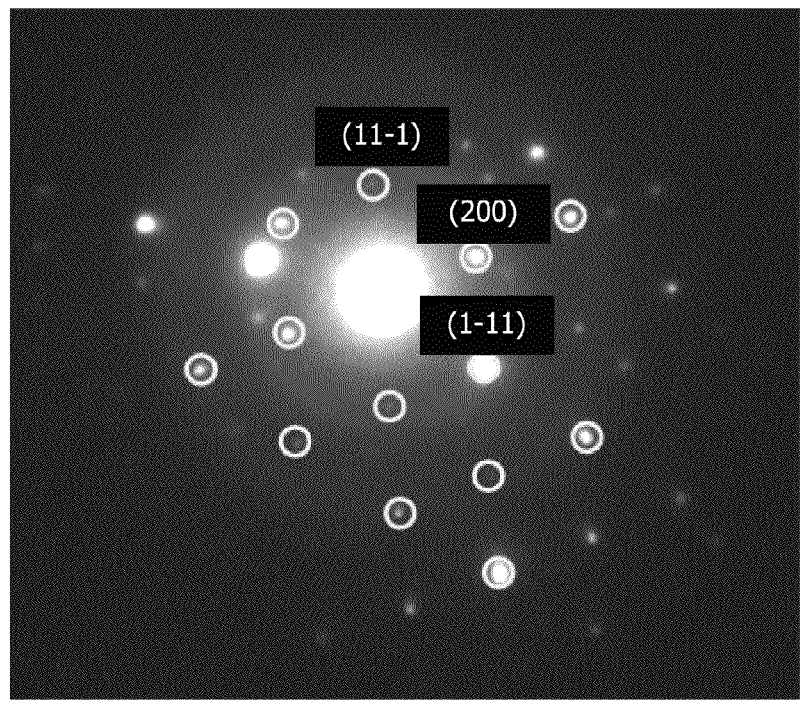
Figure 55:
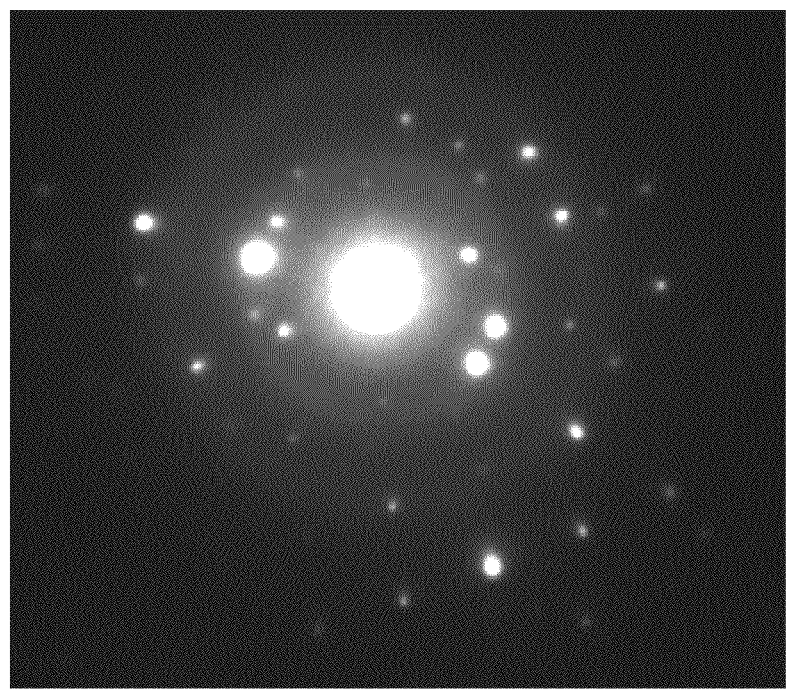

FIGS. 52 and 53 provide nanodiffraction results from a single particle at the surface of the support. The nanodiffraction results are obtained by focusing an X-ray beam having a diameter of approximately 50 nm in diameter on a portion of the catalyst surface. Based on the generation of primitive cubic indices (i.e., 010, 100, and 01-1), these results also indicate the presence of a CuPt alloy phase (likely $Cu_3Pt$). The indices denoted 200 and 11-1 are believed to be evidence of the presence of a Cu phase, Pt phase, or further evidence of a CuPt alloy phase. FIGS. 54 and 55 highlight nanodiffraction results (the circled portions) indicating the presence of a metallic copper phase.

The following Examples 25-42 provide reaction testing data for various catalysts prepared generally as described in Examples 8-18. Various parameters (e.g., metal loading, metal deposition temperature, and heat treatment temperature) were modified to determine the effect, if any, on catalyst performance. Unless specifically noted otherwise, the metal-impregnated support was heated to a maximum temperature of approximately 955° C. in the presence of a hydrogen (2%)/argon atmosphere. The catalysts were generally tested in PMIDA oxidation under the conditions set forth in Example 7.

Example 25

Catalysts: (1) 2.5% Pt/10% Cu; (2) 2.5% Pt/20% Cu; (3) 2.5% Pt/7.5% Cu; and (4) 5% Pt/0.1% Fe/0.4% Co. (nominal compositions)

Figure 56:
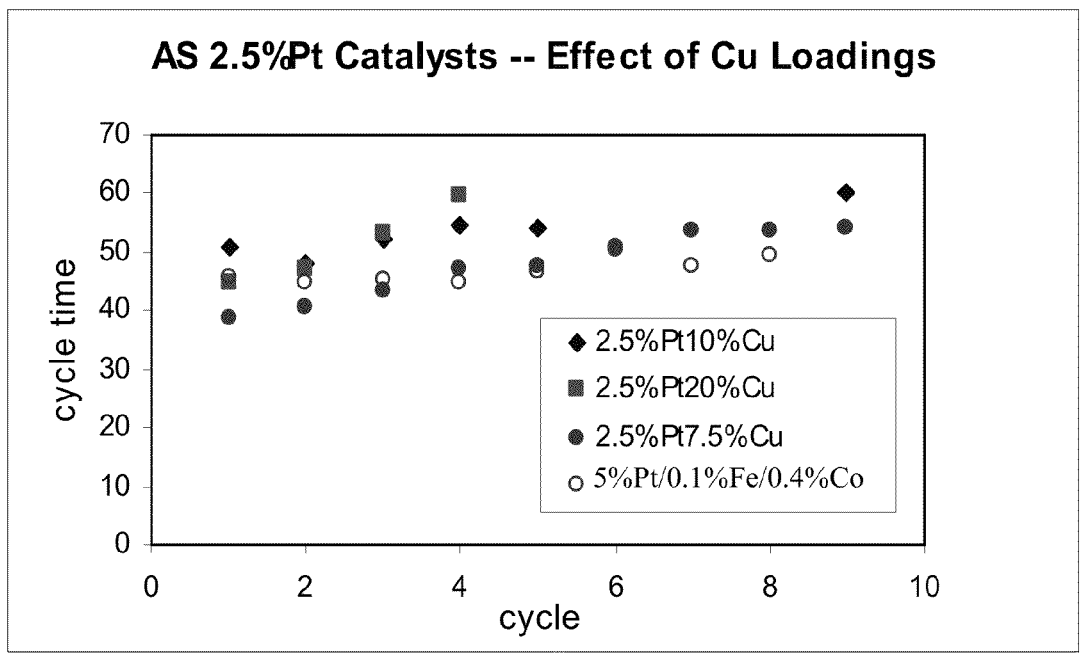
FIGS. 56 and 57 provide reaction testing data as described in Example 25.

FIG. 56 provides cycle time data for each of (1)-(4) for nine reaction cycles.

Figure 57:
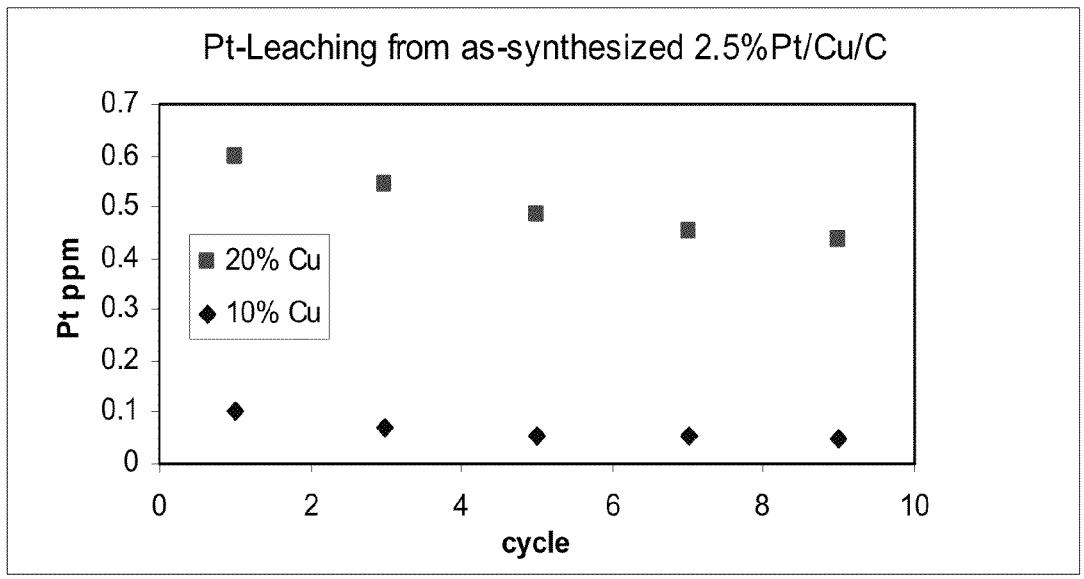

FIG. 57 provides platinum leaching data for (1) and (2) for each of nine reaction cycles.

Example 26

Catalysts: (1) 2.5% Pt/7.5% Cu; (2) 2.5% Pt/5% Cu; (3) 5% Pt/0.1% Fe/0.4% Co; and (4) 720° C./2.5% Pt/10% Cu. (nominal compositions)

Figure 58:
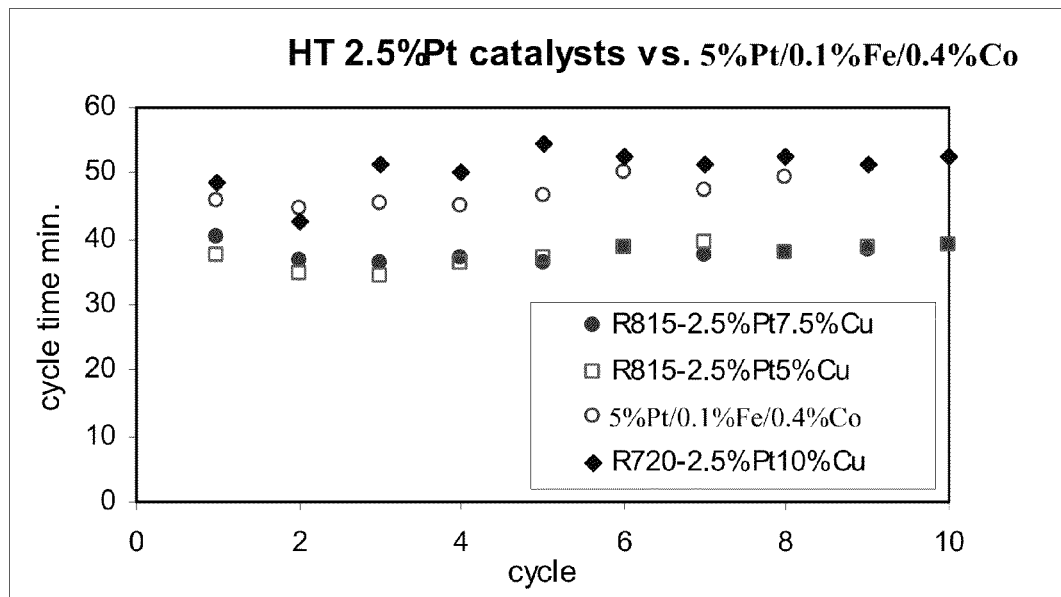
FIG. 58 provides reaction testing data of Example 26.

FIG. 58 provides cycle time data for each of (1)-(4) for nine reaction cycles.

Example 27

Catalysts: (1) 2.5% Pt/10% Cu and (2) 720° C./2.5% Pt/10% Cu. (nominal compositions)

Each catalyst was tested for 10 reaction cycles.

Figure 59:
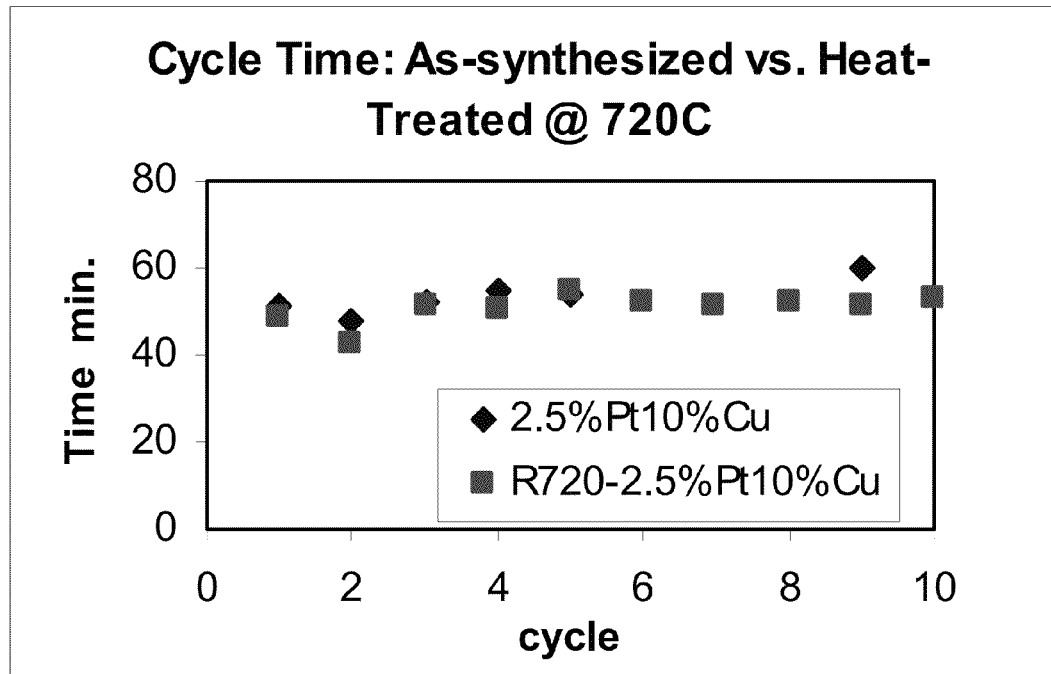
FIGS. 59-62 provide reaction testing data of Example 27.

FIG. 59 provides cycle time data.

Figure 60:
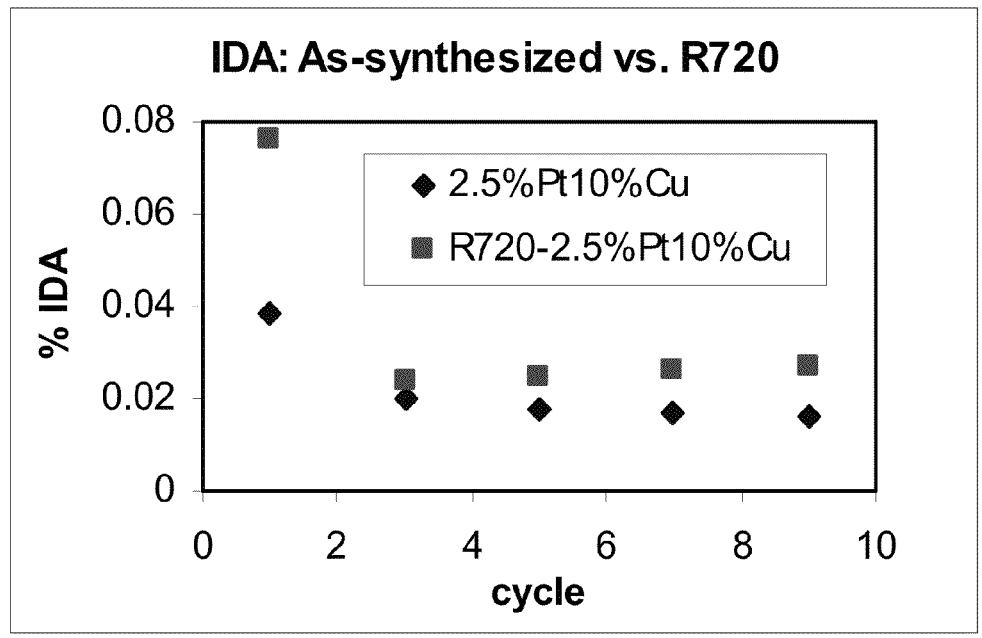

FIG. 60 provides IDA generation data.

Figure 61:
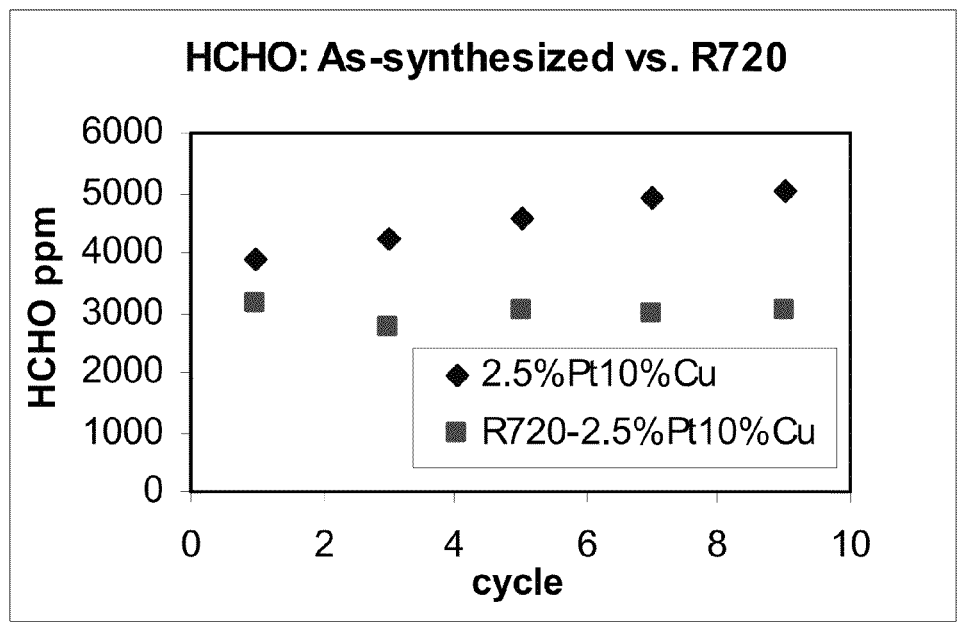
Figure 62:
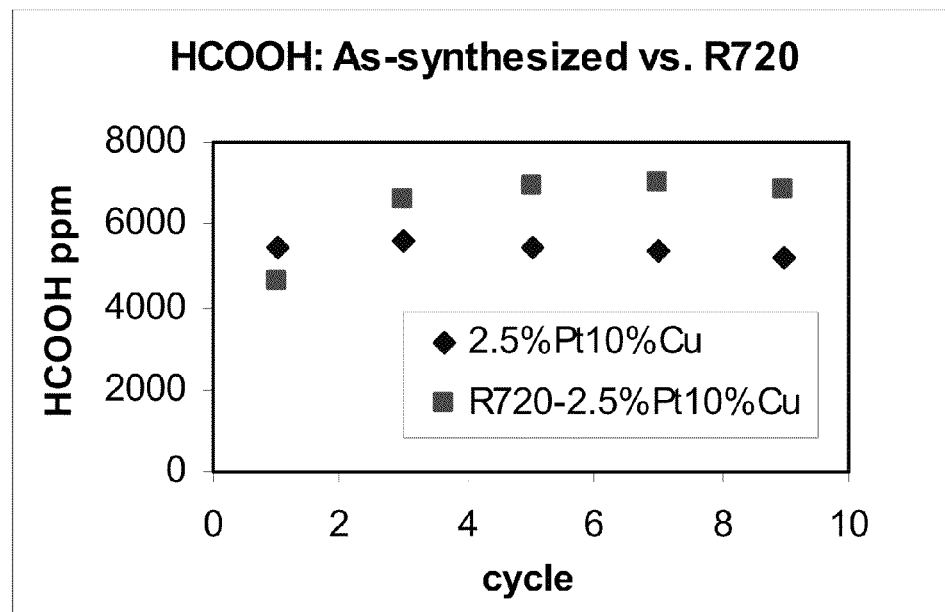

FIGS. 61 and 62 provide residual formaldehyde and formic acid concentration, respectively.

Table 10 provides a comparison of platinum leaching for the two catalysts. As shown, less platinum was leached from the catalyst prepared including heat treatment at 720° C.

TABLE 10

| | Pt/Parts per Million (ppm) | |
| --- | --- | --- |
| Cycle | 2.5% Pt10% Cu | 720° C.-2.5% Pt10% Cu |
| 1 | 0.103 | <0.02 |
| 2 | | |
| 3 | 0.0715 | <0.02 |
| 4 | | |
| 5 | 0.0539 | <0.02 |
| 6 | | |
| 7 | 0.0514 | <0.02 |
| 8 | | |
| 9 | 0.0507 | 0.0202 |
| 10 | | |

Example 28

Catalysts: (1) 2.5% Pt/7.5% Cu; (2) 815° C./2.5% Pt/7.5% Cu; and (3) 5% Pt/0.1% Fe/0.4% Co. (nominal compositions) Each catalyst was tested for nine reaction cycles.

Figure 63:
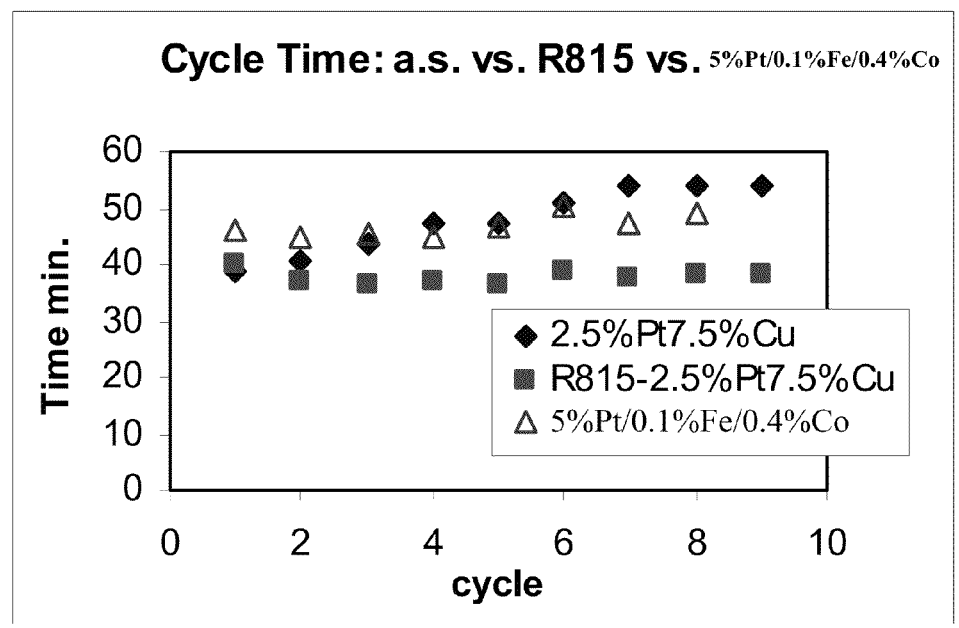
FIGS. 63-65 provide reaction testing data of Example 28.

FIG. 63 provides cycle time data for each of (1)-(3).

Figure 64:
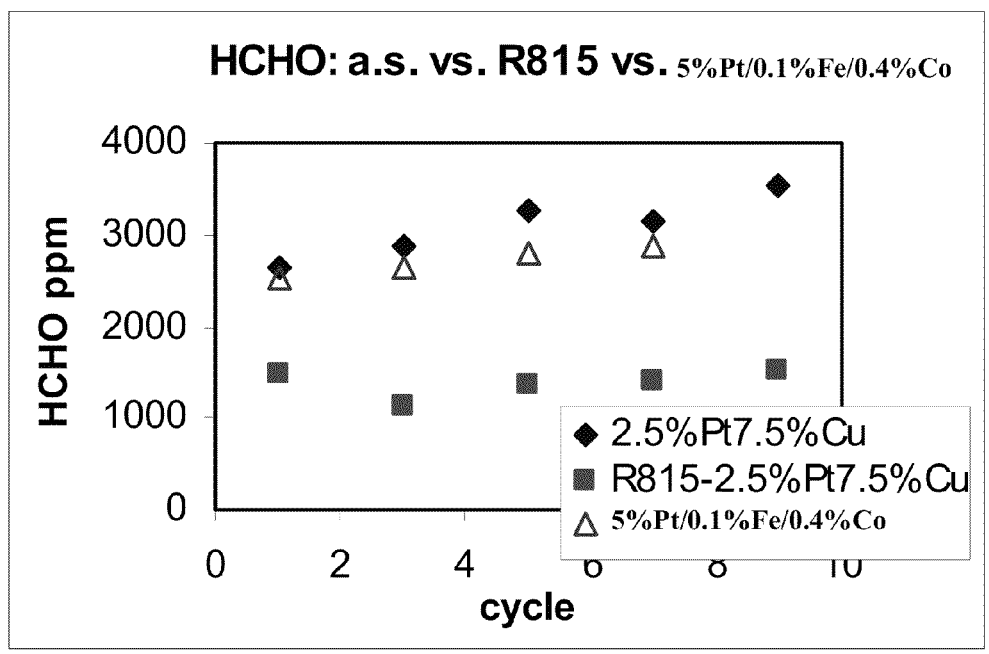
Figure 65:
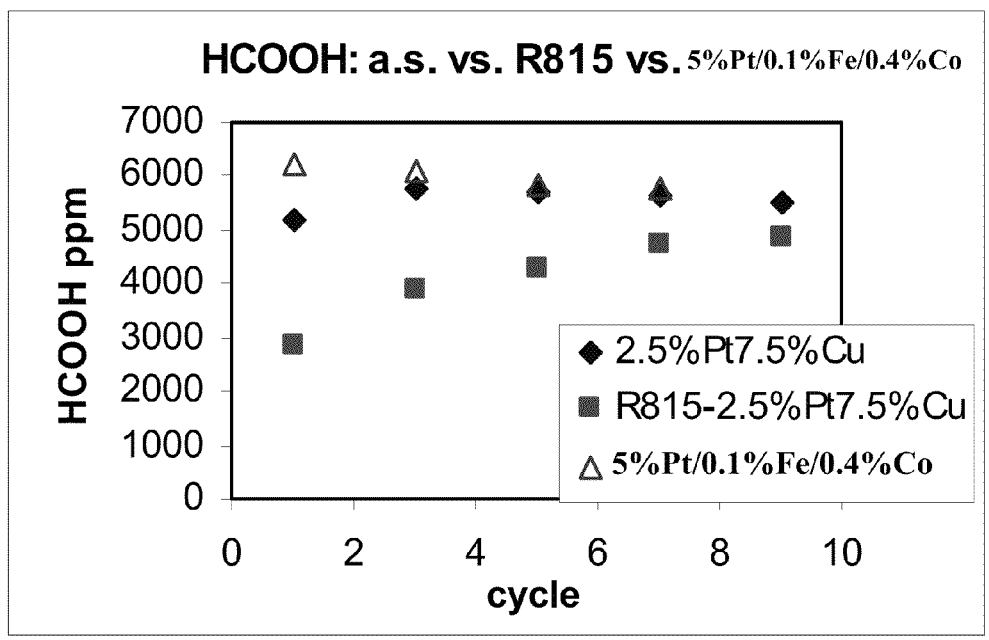

FIGS. 64 and 65 provide residual formaldehyde and formic acid concentration, respectively for each of (1)-(3).

Example 29

Catalysts: (1) 815° C./2.5% Pt/7.5% Cu; (2) 815° C./2.5% Pt/7.5% Cu; and (3) 5% Pt/0.1% Fe/0.4% Co. (nominal compositions) Each catalyst was tested for nine reaction cycles.

Figure 66:
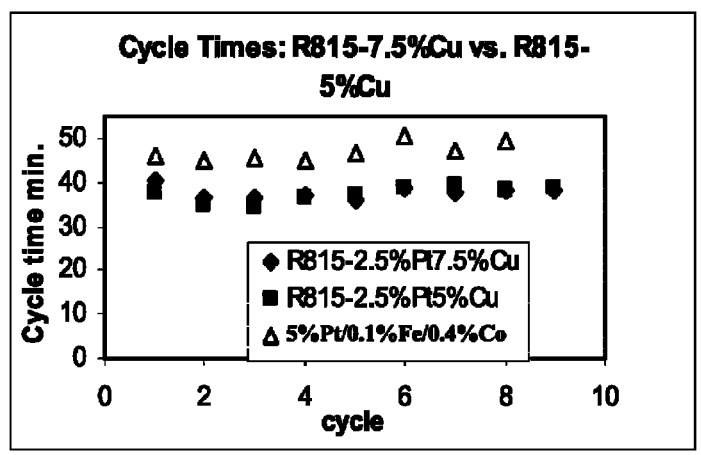
FIGS. 66-68 provide reaction testing data of Example 29.

FIG. 66 provides cycle time data for each of (1)-(3).

Figure 67:
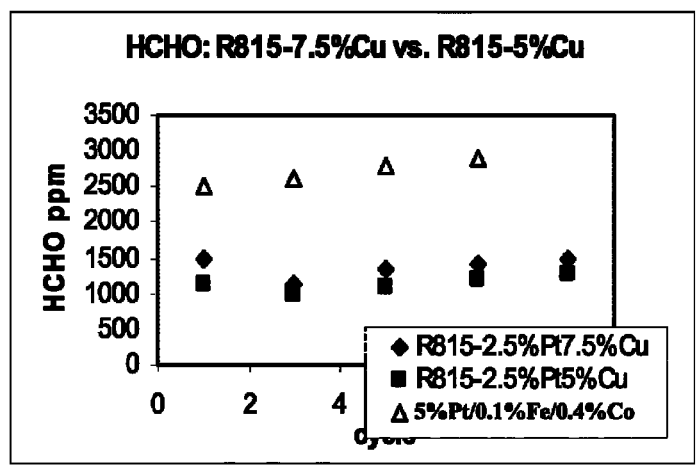
Figure 68:
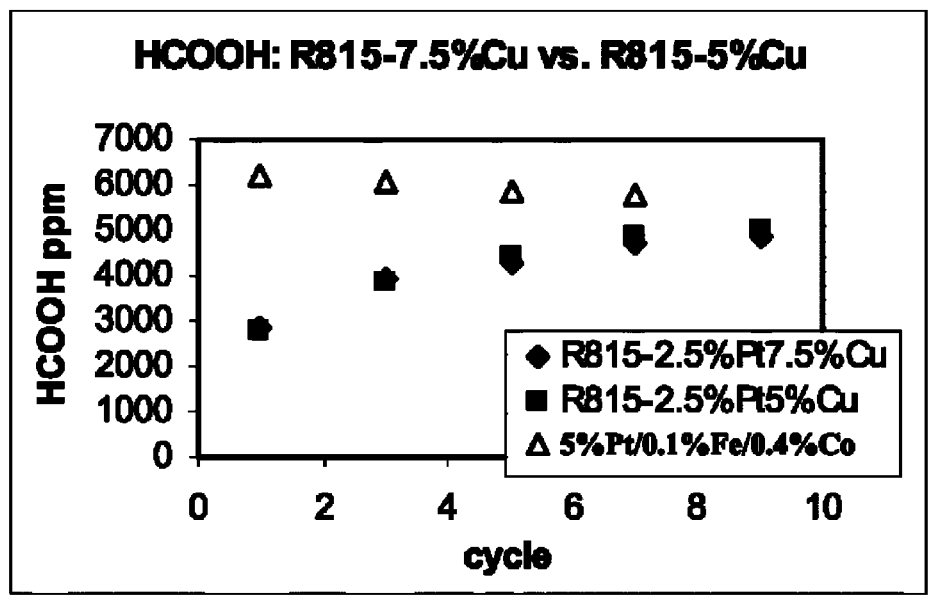

FIGS. 67 and 68 provide residual formaldehyde and formic acid concentration, respectively, for each of (1)-(3).

Example 30

Catalysts: (1) 815° C./2.5% Pt/7.5% Cu; (2) 815° C./2.5% Pt/5% Cu; (3) 5% Pt/0.1% Fe/0.4% Co; (4) 815° C./2.5% Pt/3% Cu. (nominal compositions) Each catalyst was tested for ten reaction cycles.

Figure 69:
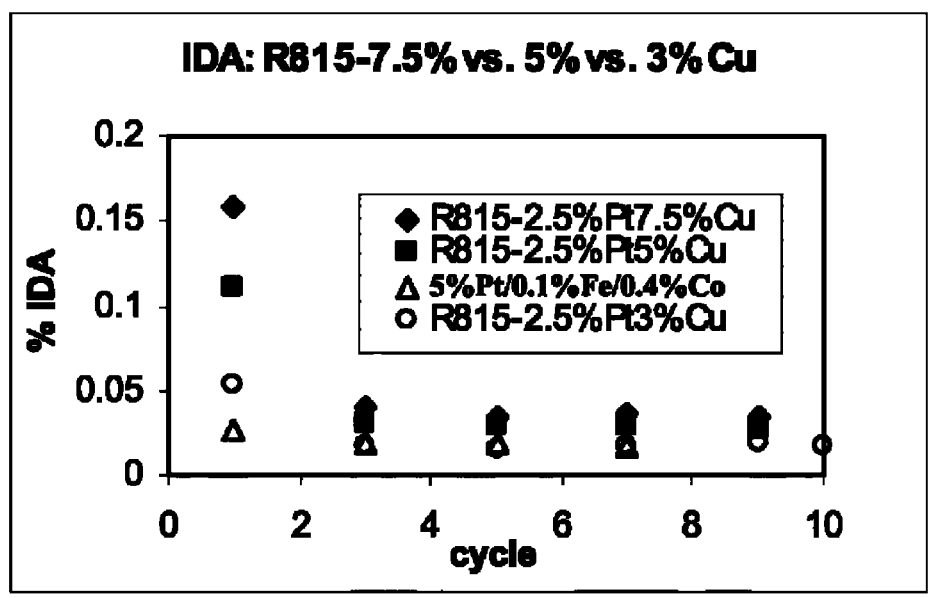
FIGS. 69-71 provide reaction testing data of Example 30.

FIG. 69 provides IDA generation results for each of (1)-(4).

Figure 70:
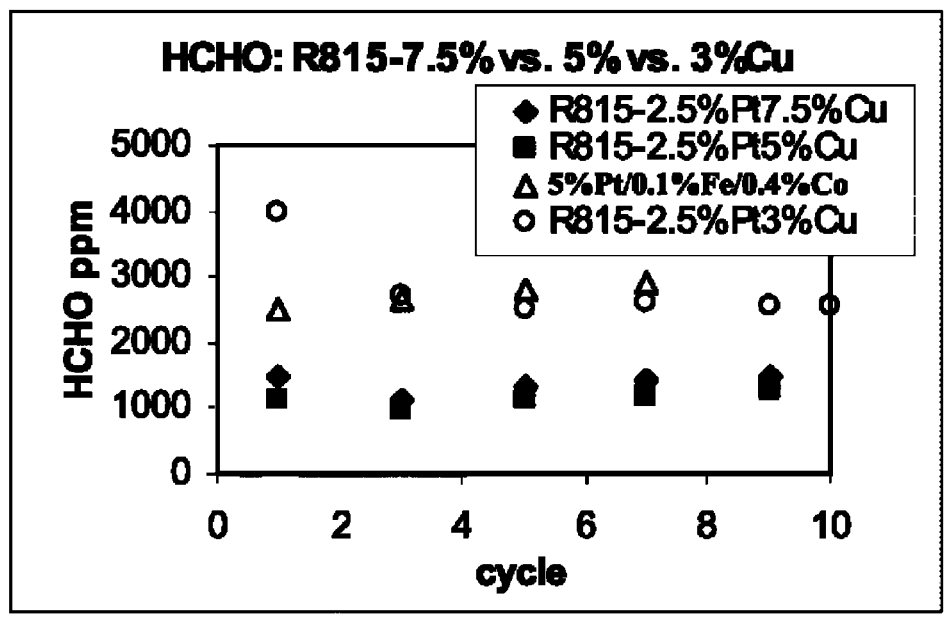
Figure 71:
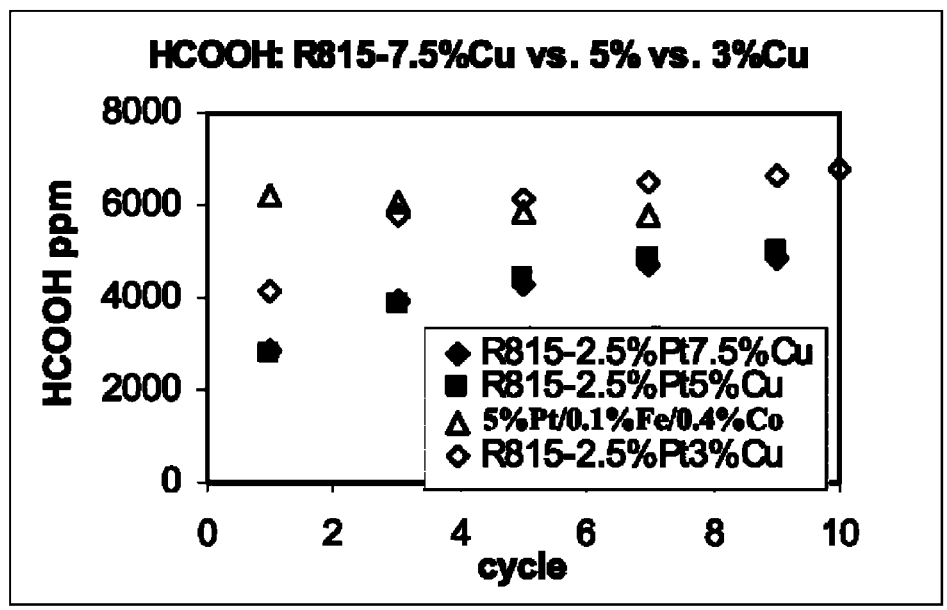

FIGS. 70 and 71 provide residual formaldehyde and formic acid concentration, respectively, for each of (1)-(4).

Example 31

Catalysts: (1) 815° C./2.5% Pt/5% Cu; (2) 715° C./2.5% Pt/5% Cu; (3) 615° C./2.5% Pt/5% Cu; and (4) 5% Pt/0.1% Fe/0.4% Co. (nominal compositions) Each catalyst was tested for ten reaction cycles and various parameters were compiled for nine or each of the ten reaction cycles.

Figure 72:
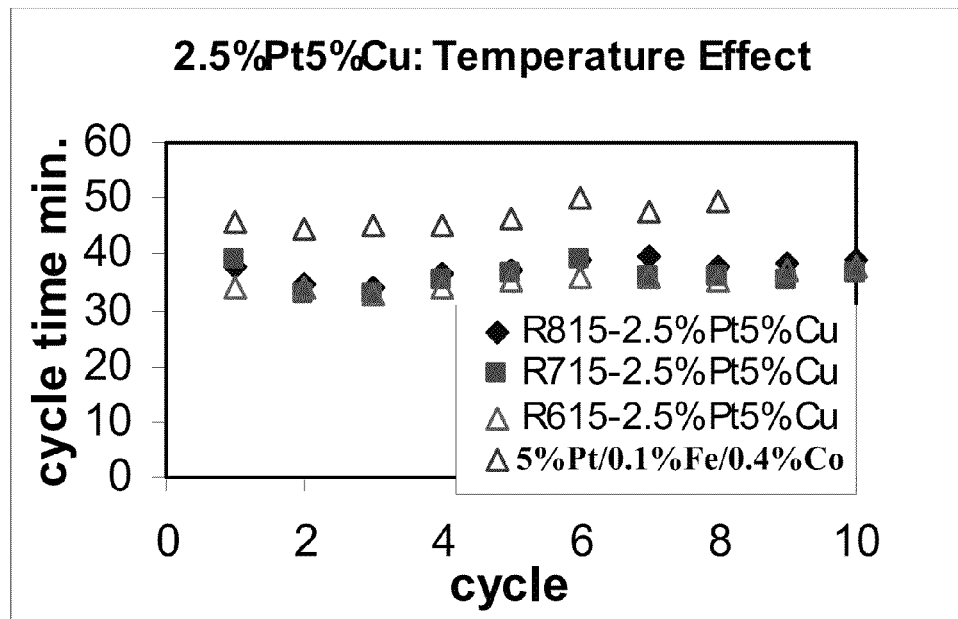
FIGS. 72-78 provide reaction testing data of Example 31.

FIG. 72 provides cycle time results.

Figure 73:
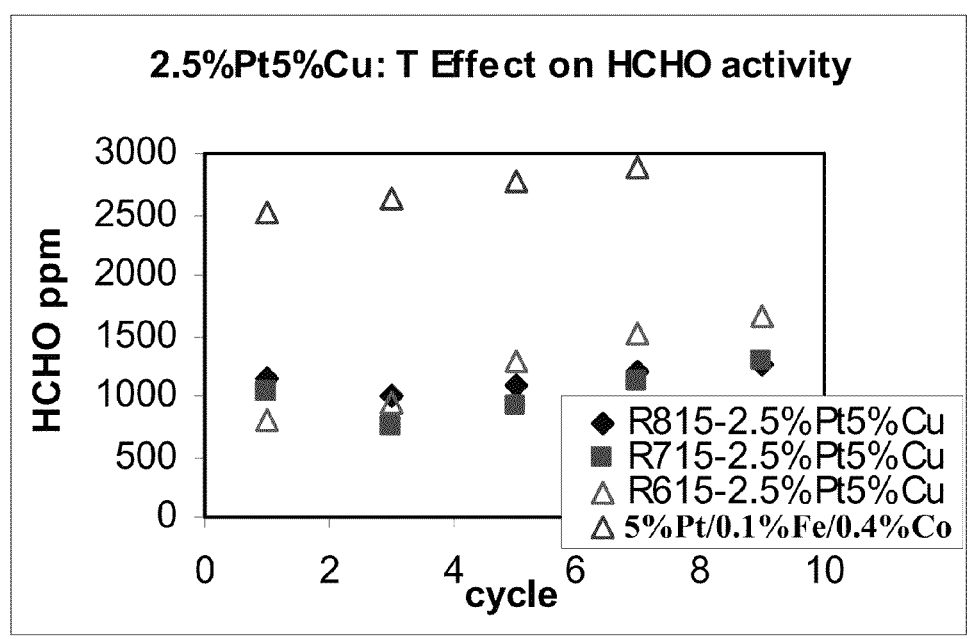
Figure 74:
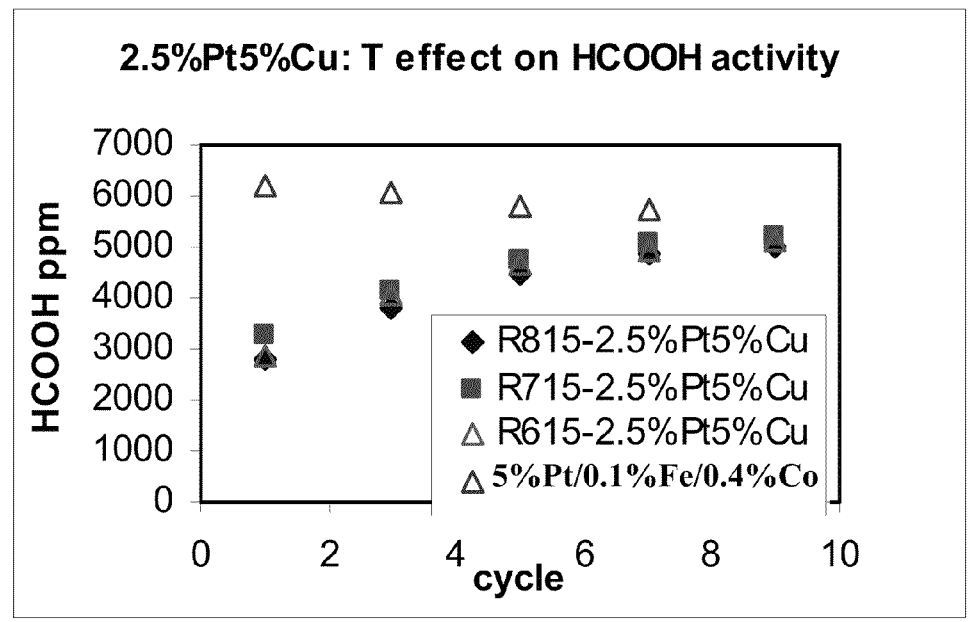

FIGS. 73 and 74 provide residual formaldehyde and formic acid concentrations, respectively.

Figure 75:
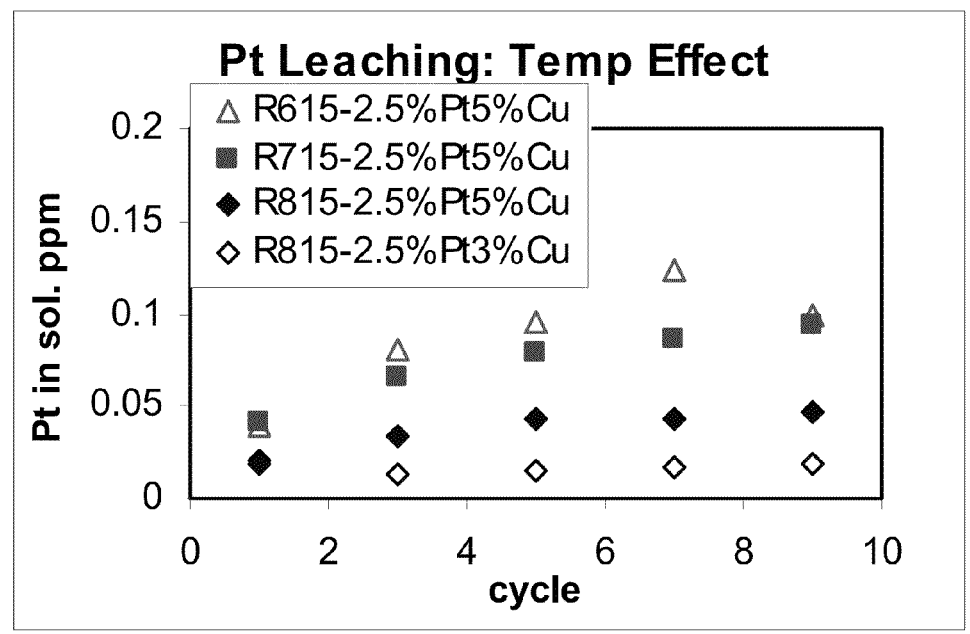

FIG. 75 provides platinum leaching results.

Figure 76:
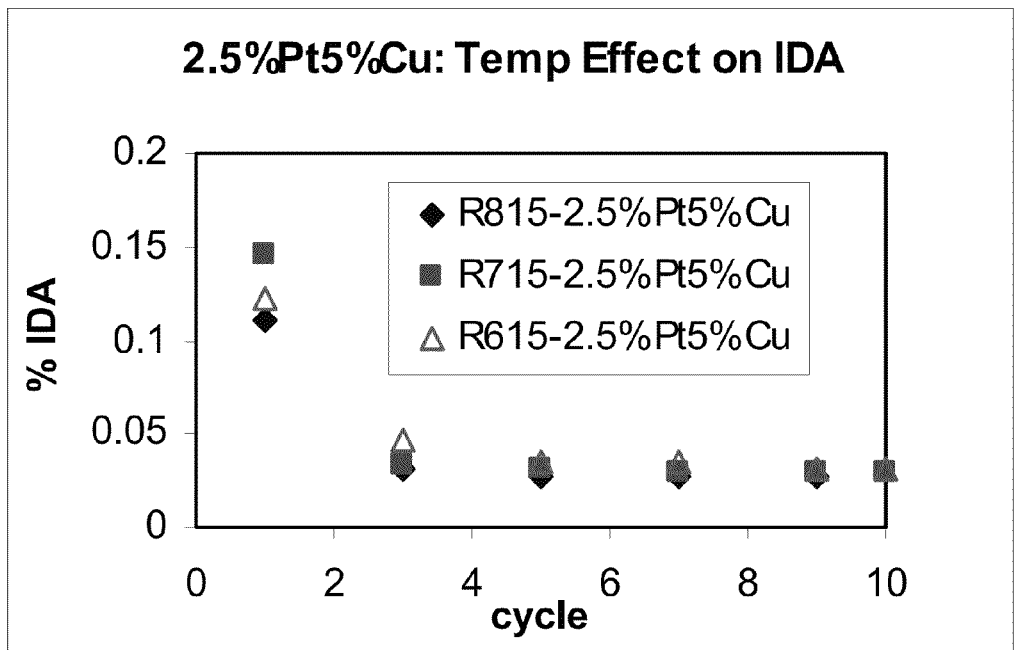

FIG. 76 provides IDA generation results.

Figure 77:
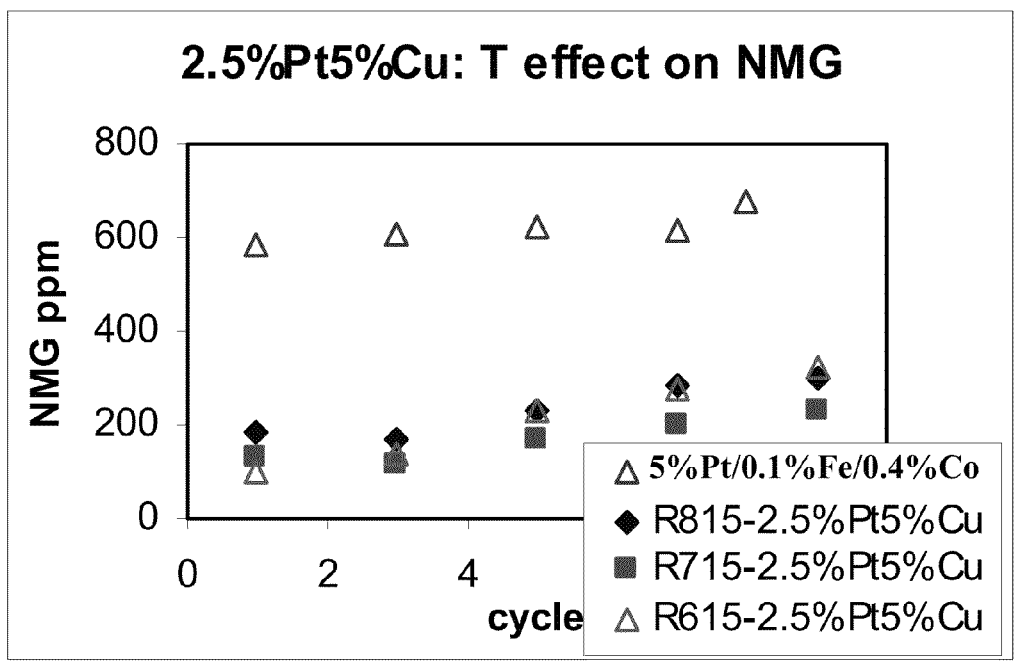

FIG. 77 provides NMG generation results.

Figure 78:
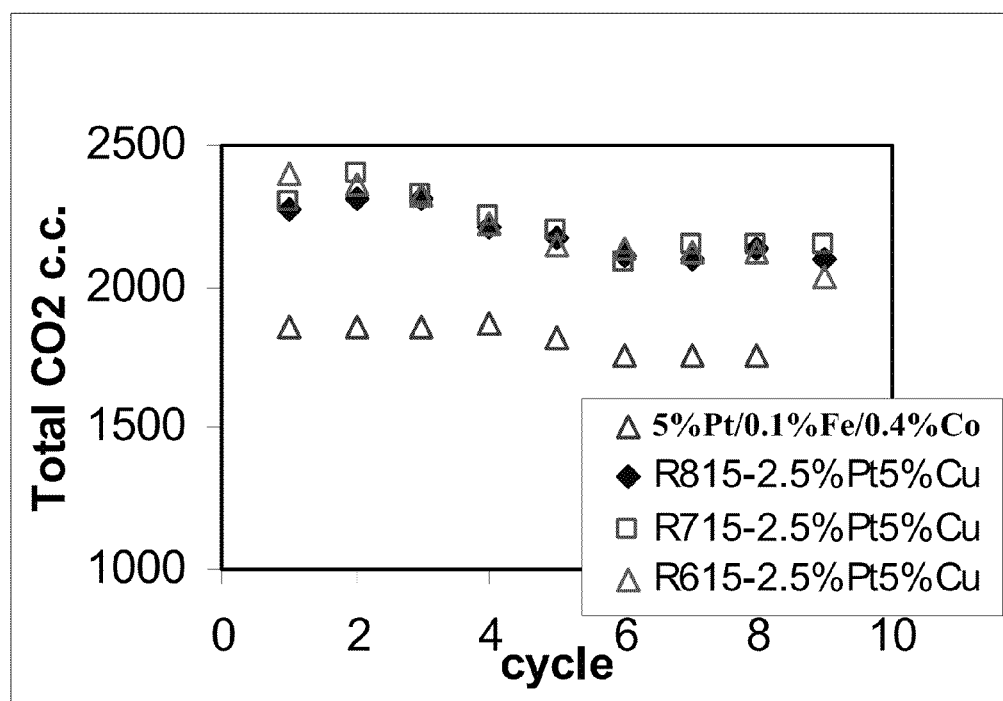

FIG. 78 provides total $CO_2$ generation results.

Example 32

Catalysts: (1) 915° C./2% Pt/4% Cu (heated in a hydrogen containing atmosphere, i.e., reduced); (2) 910° C./2% Pt/4% Cu (heated in an inert atmosphere, i.e., calcined); and (3) 5% Pt/0.1% Fe/0.4% Co. (nominal compositions) Each catalyst was tested for nine reaction cycles.

Figure 79:
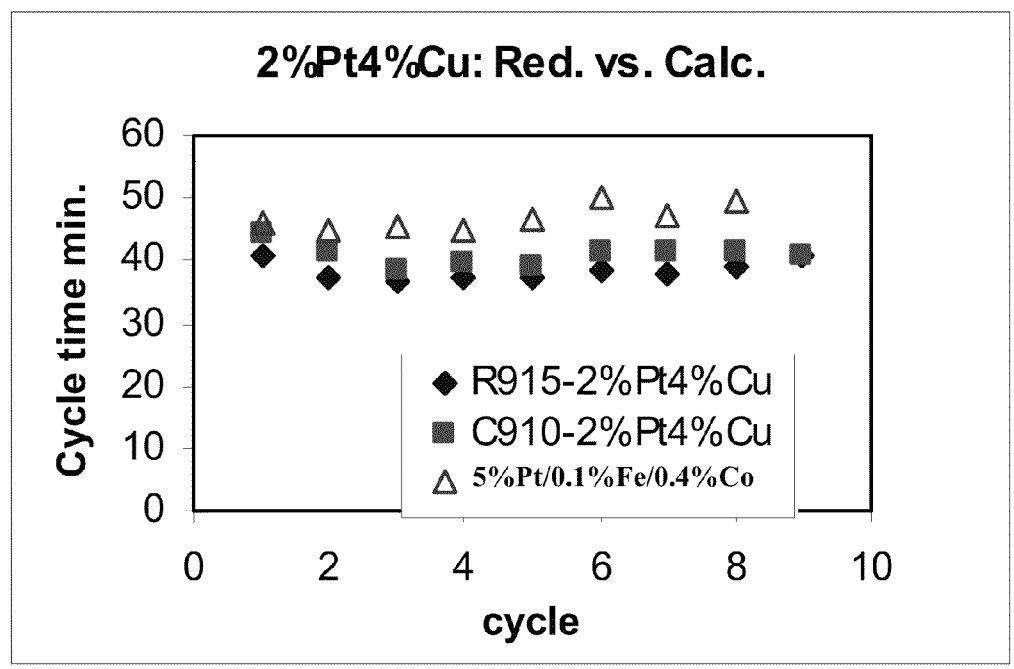
FIGS. 79-84 provide reaction testing data of Example 32.

As shown in FIG. 79, cycle time was similar for each of (1)-(3), but cycle time for catalyst (3) was slightly higher for cycles 3 through 8.

Figure 80:
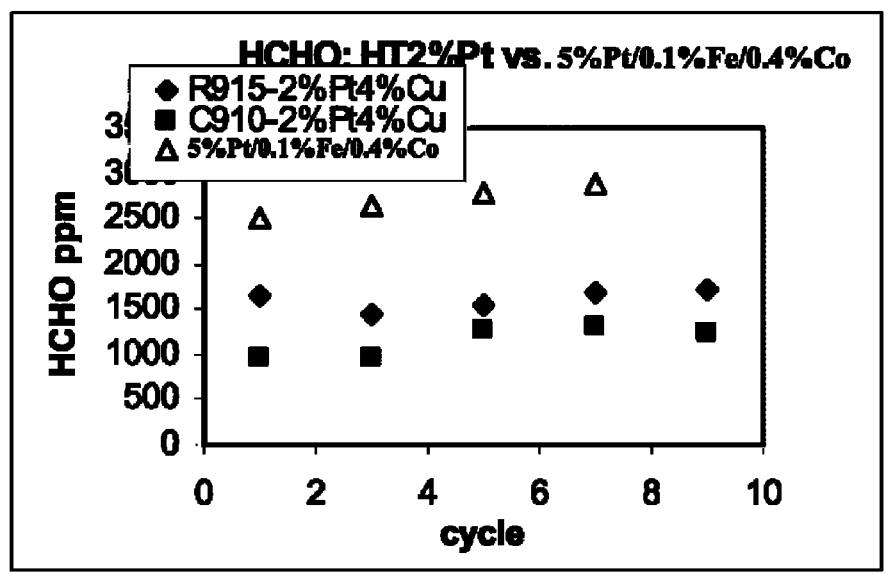

FIG. 80 provides formaldehyde generation results.

Figure 81:
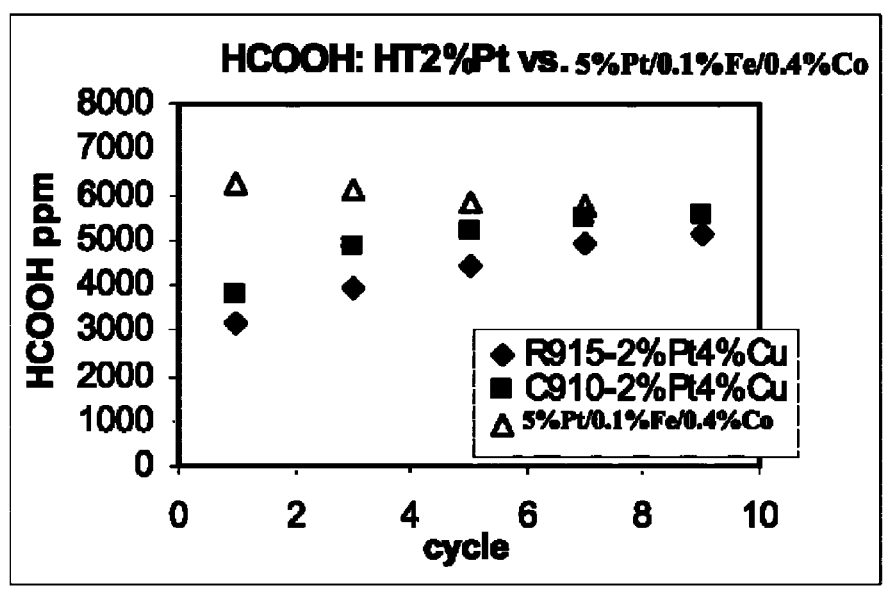

FIG. 81 provides formic acid generation results.

Figure 82:
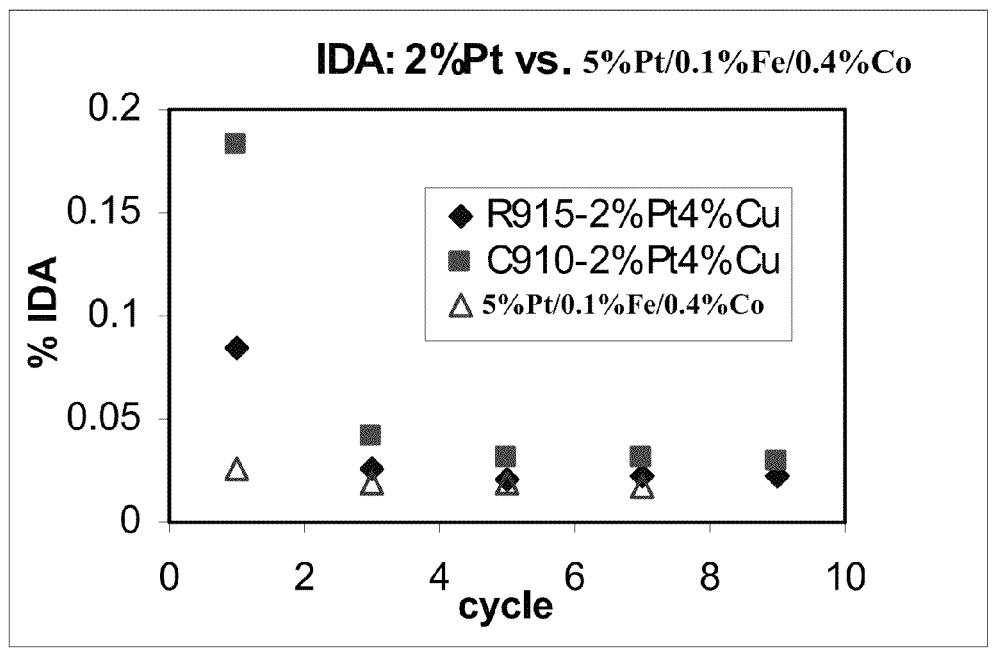

As shown in FIG. 82, IDA generation was substantially equivalent for each catalyst during cycles 3 through 9.

Figure 83:
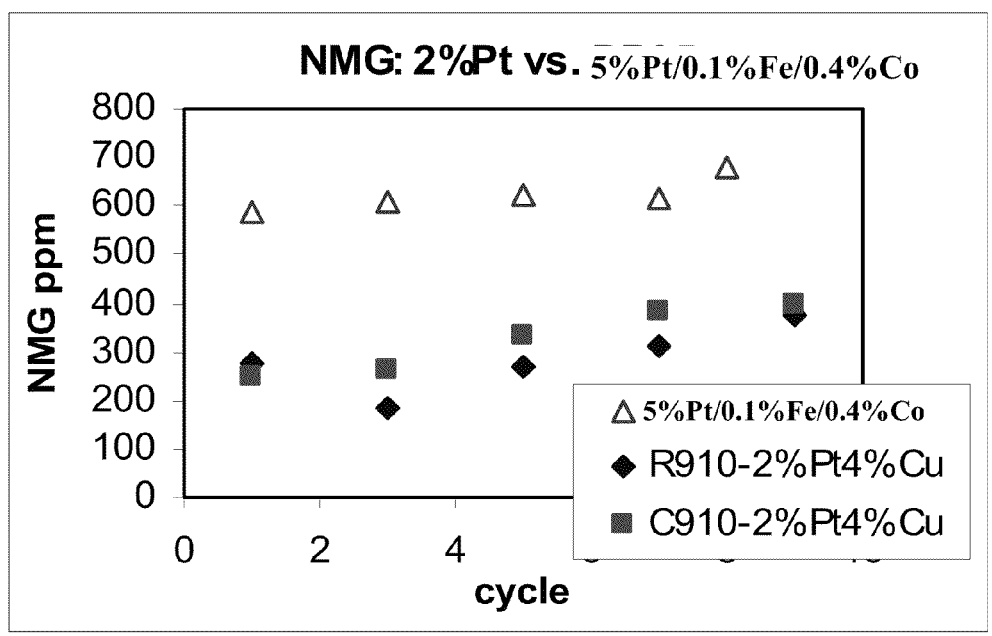

The results shown in FIG. 83 indicate reduced NMG generation for each of the 2% Pt catalysts as compared to the 5% Pt catalyst.

Figure 84:
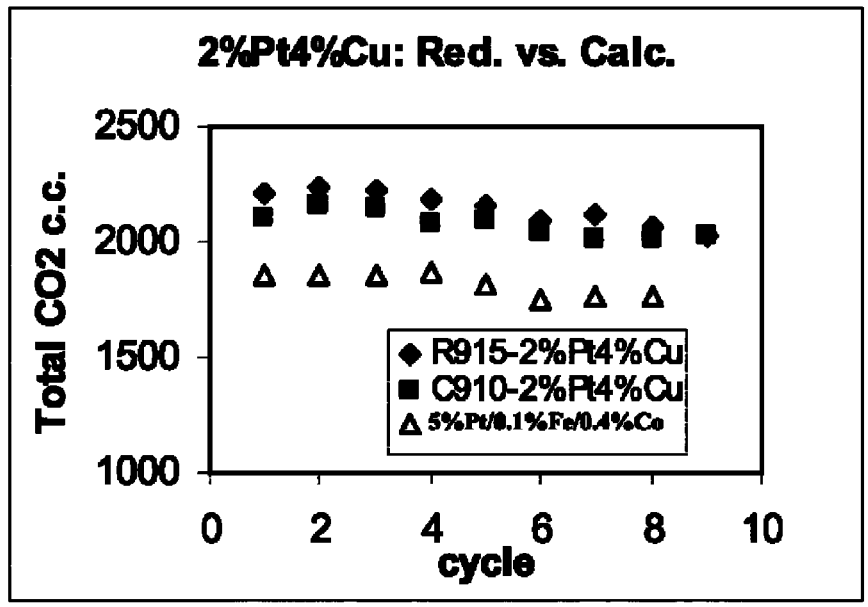

FIG. 84 provides total $CO_2$ generation results.

Example 33

Figure 85:
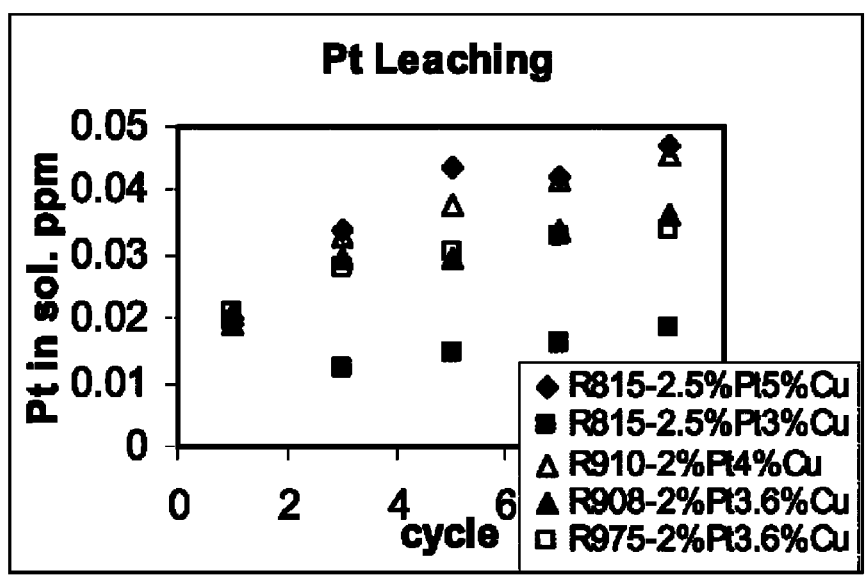
FIG. 85 provides reaction testing data of Example 33.

This example provides platinum leaching results for the following catalysts: (1) 815° C./2.5% Pt/5% Cu; (2) 815° C./2.5% Pt/3% Cu; (3) 910° C./2% Pt/4% Cu; (4) 908° C./2% Pt/3.6% Cu; and (5) 975° C./2% Pt/3.6% Cu. (nominal compositions). The results are shown in FIG. 85.

Example 34

This example provides testing results for catalysts in which the temperature of copper deposition varied by approx. 10° C. (approx. 25° C. and approx. 35° C.) while the heat treatment temperature after platinum deposition was substantially similar.

Catalysts: (1) 970° C./2% Pt/3.45% Cu/35° C. and (2) 965° C./2% Pt/3.45% Cu/25° C. (nominal compositions)

Figure 86:
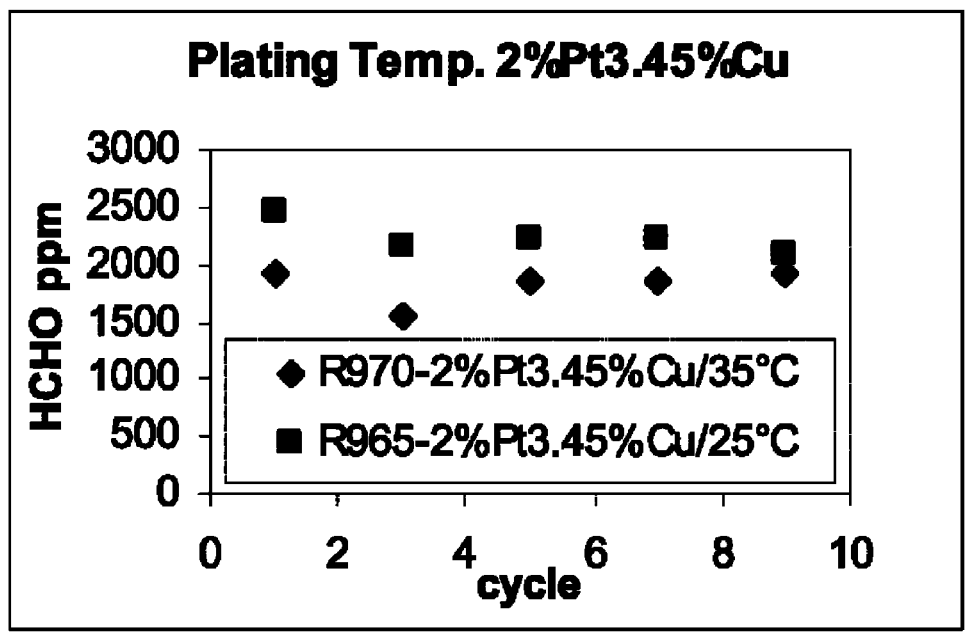
FIGS. 86-90 provide reaction testing data of Example 34.
Figure 87:
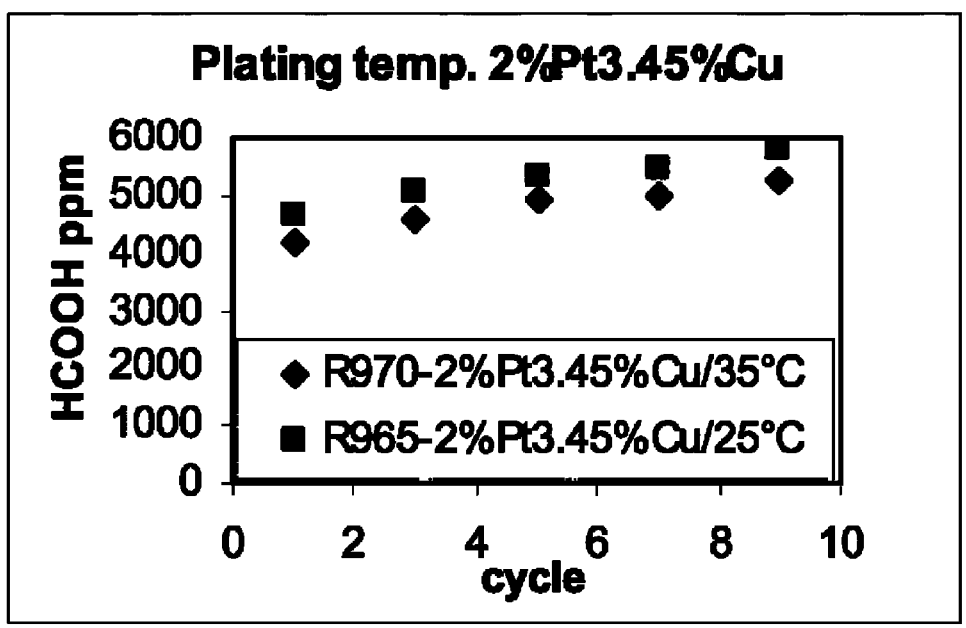

As shown in FIGS. 86 and 87, formaldehyde and formic acid generation were slightly lower for the catalyst prepared at the higher copper plating temperature.

Figure 88:
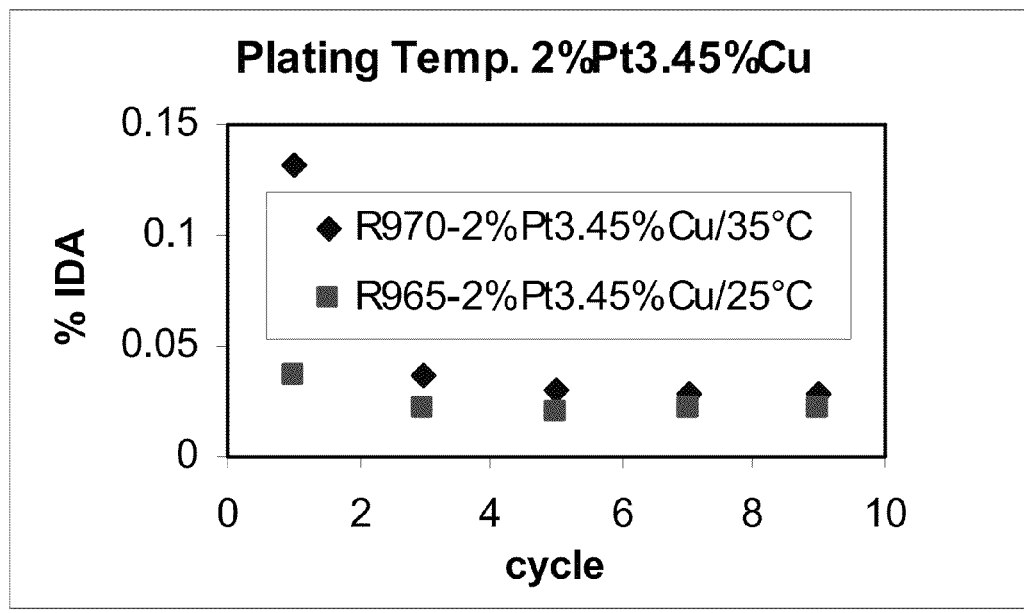

The results shown in FIG. 88 indicate higher initial IDA generation for the catalyst prepared at the higher copper plating temperature, but similar results for each catalyst beginning with the third cycle.

Figure 89:
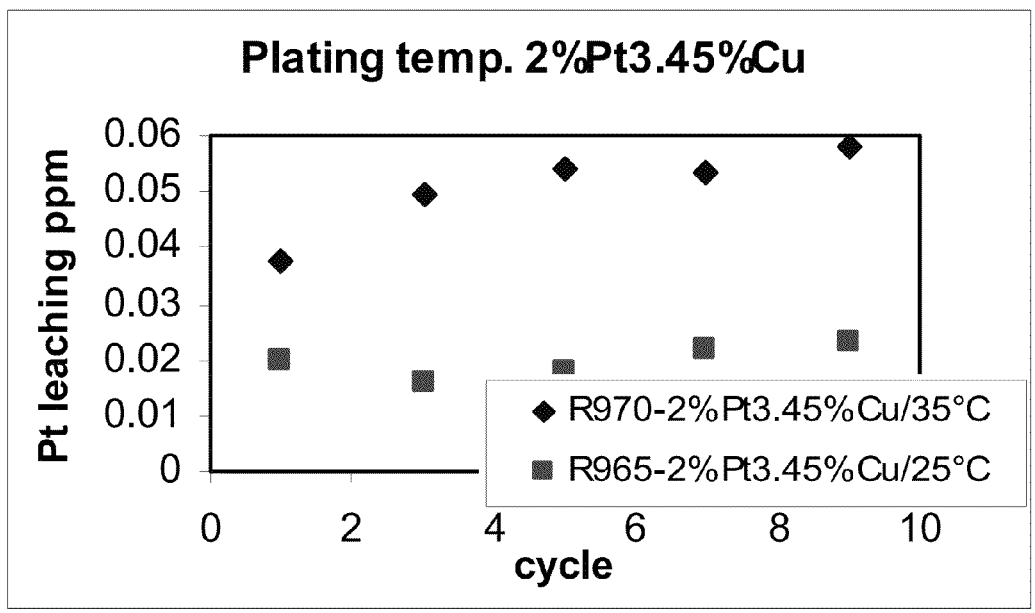
Figure 90:
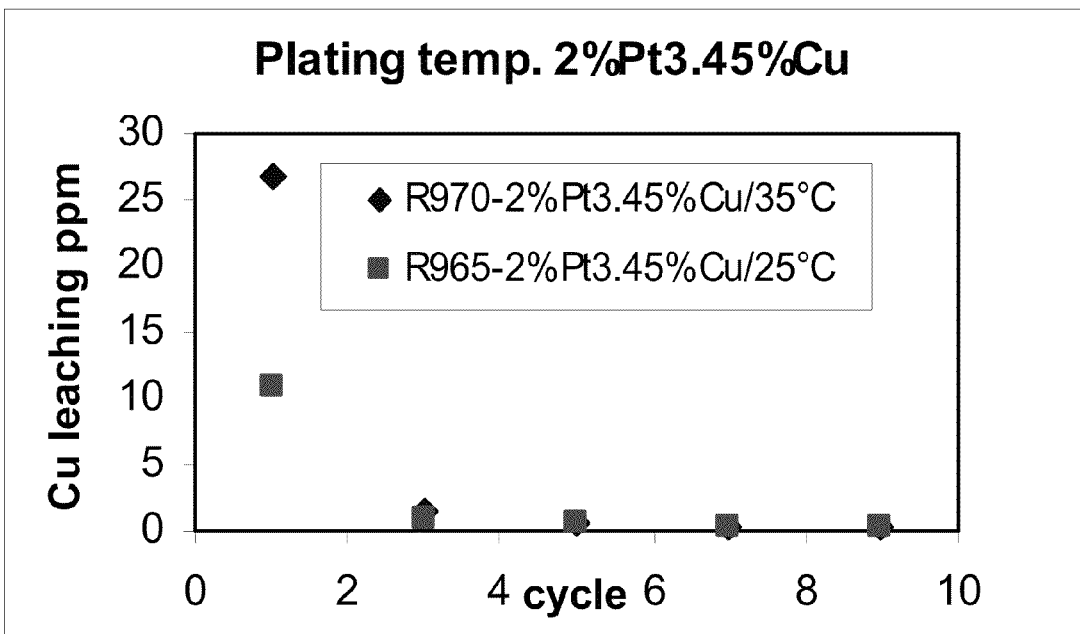
Figure 91:
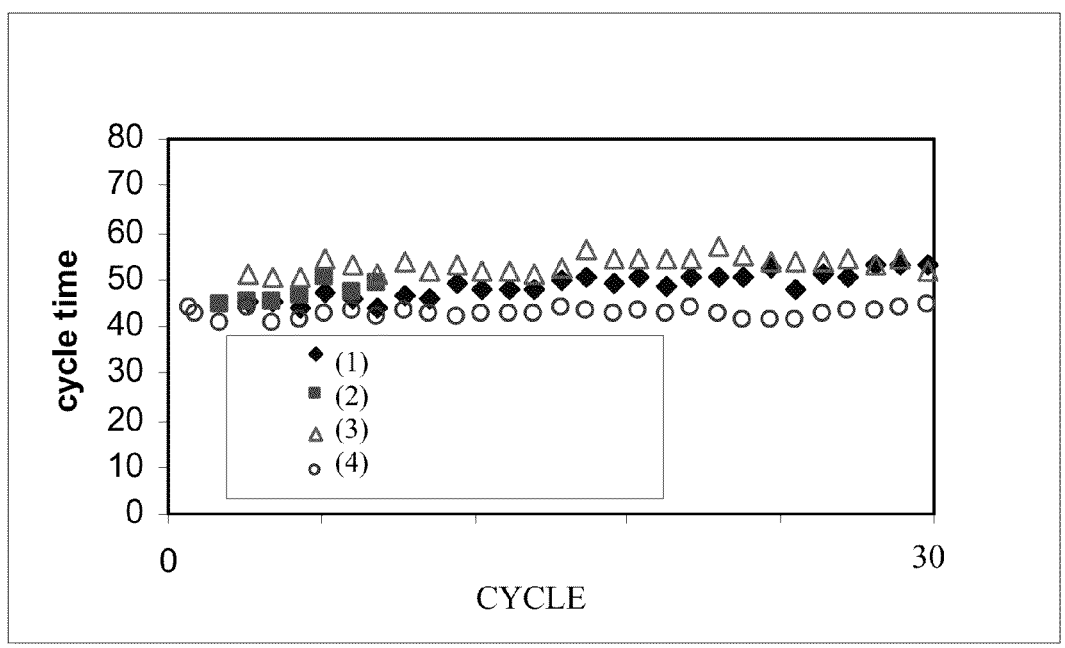
FIGS. 91-95 provide reaction testing data of Example 35.
Figure 92:
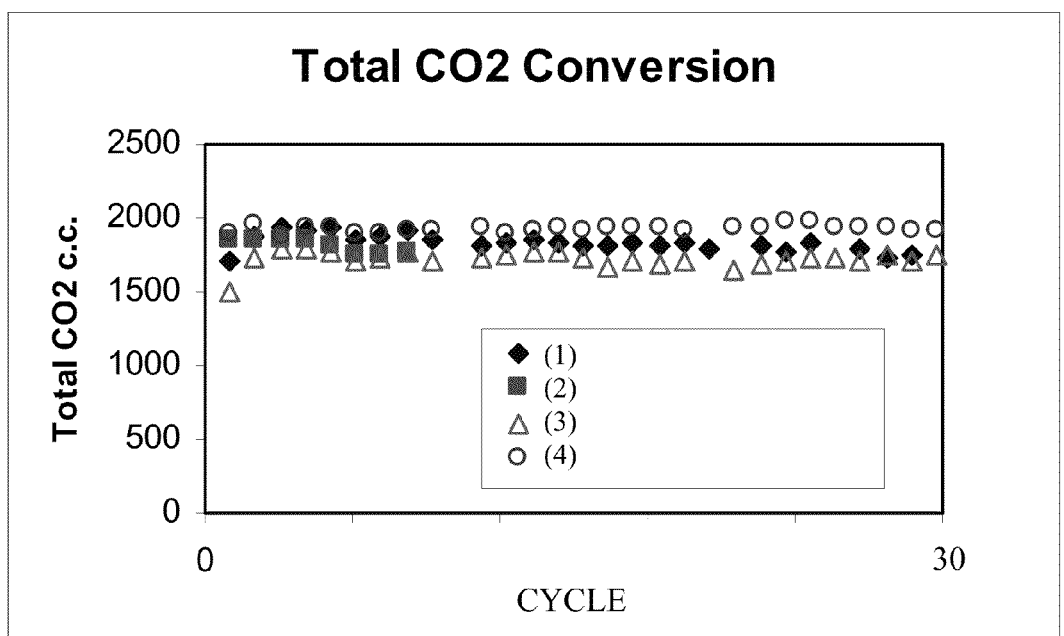
Figure 93:
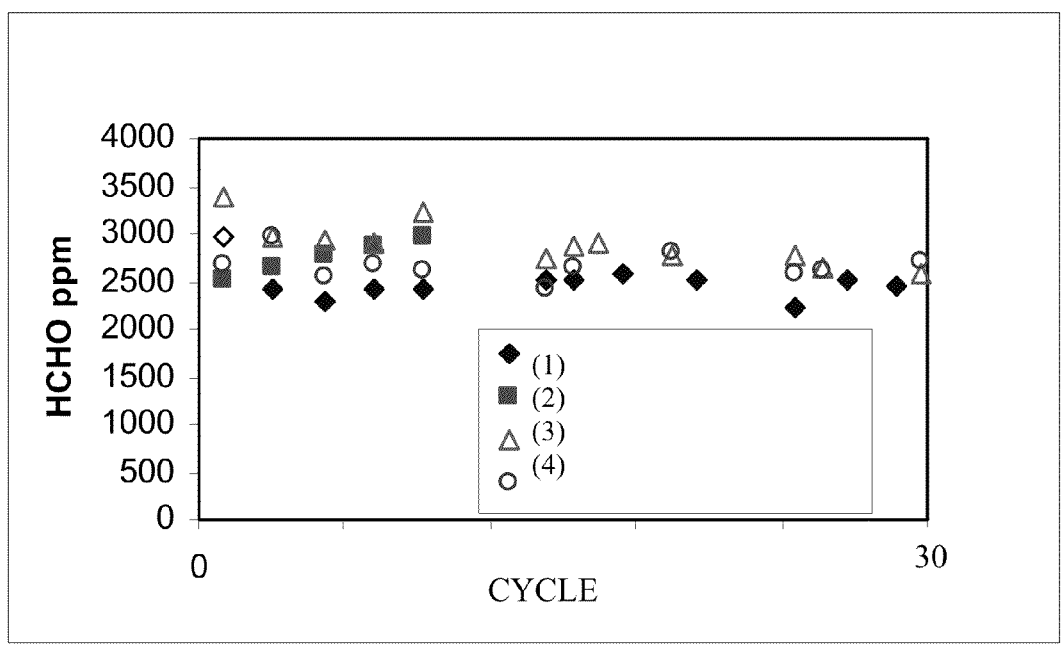
Figure 94:
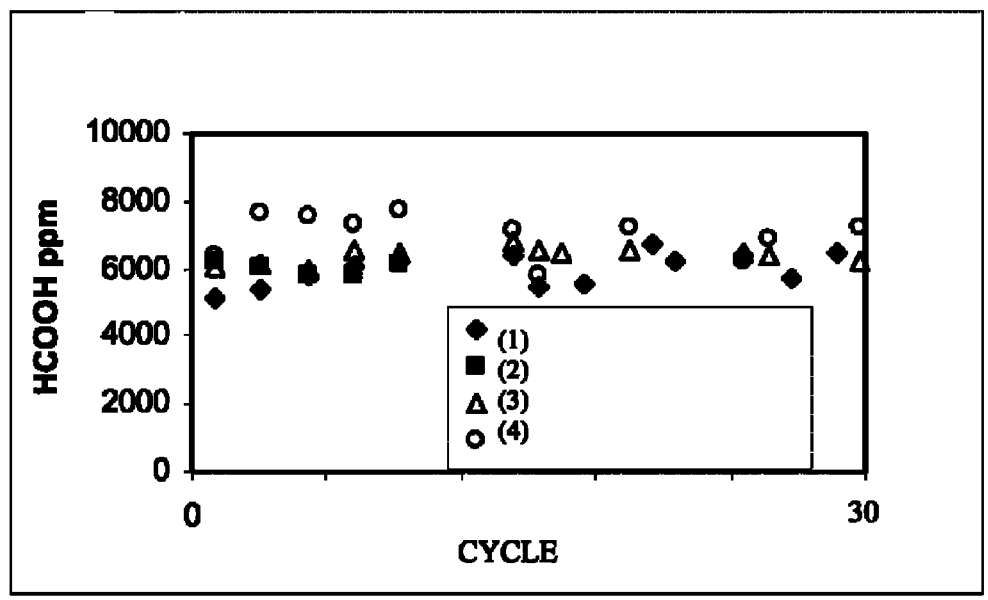

As shown in FIG. 89, platinum leaching was lower for the catalyst prepared at the lower copper plating temperature. And FIG. 90 indicates reduced initial copper leaching for the catalyst prepared at the lower copper plating temperature.

Example 35

This example provides results for extended PMIDA oxidation testing over 30 reaction cycles.

The catalysts tested included:

(1) nominal 2% Pt/3.45% Cu/C prepared as described in Example 12; (2) 5% Pt/0.1% Fe/0.4% Co; (3) nominal 2% Pt/3.45% Cu/C prepared as described in Example 16; and (4) 5% Pt/0.5% Fe catalyst.

As shown in FIGS. 91-94, the cycle time, total $CO_2$ generation, formaldehyde generation, and formic acid generation were substantially similar for each of (1)-(4). The catalyst loading was constant for each catalyst; thus, catalysts (1) and (3) provided similar results at reduced platinum loadings as compared to catalysts (2) and (4).

Figure 95:
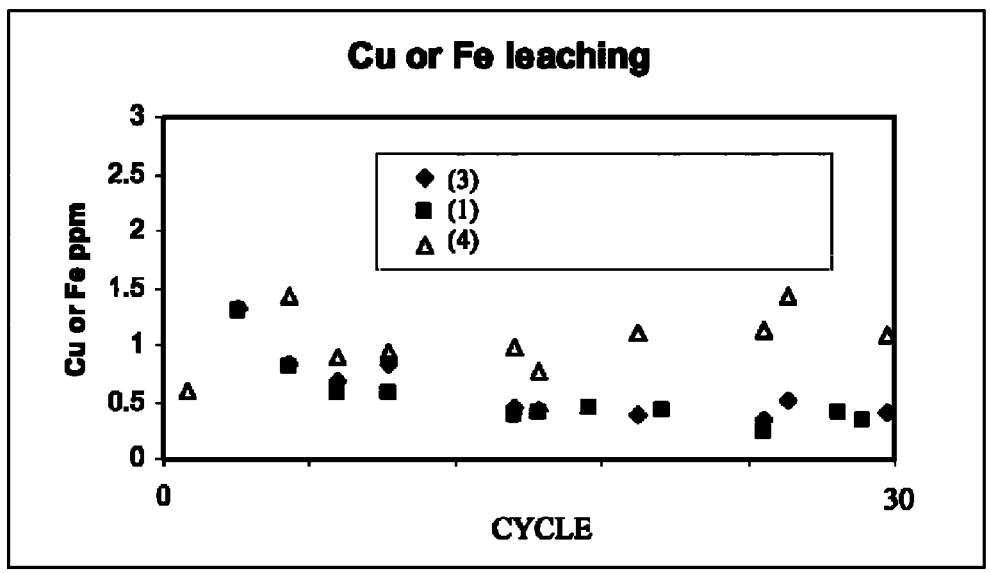

FIG. 95 provides Cu and Fe leaching data for catalysts (1), (3), and (4).

Example 36

This example provides PMIDA oxidation testing results for catalysts prepared at varying calcining temperatures and having varying copper contents.

Catalysts: (1) 908° C./2% Pt/3.6% Cu; (2) 975° C./2% Pt/3.6% Cu; (3) 910° C./2% Pt/4% Cu; and (4) 970° C./2% Pt/3.45% Cu. (nominal compositions)

Figure 96:
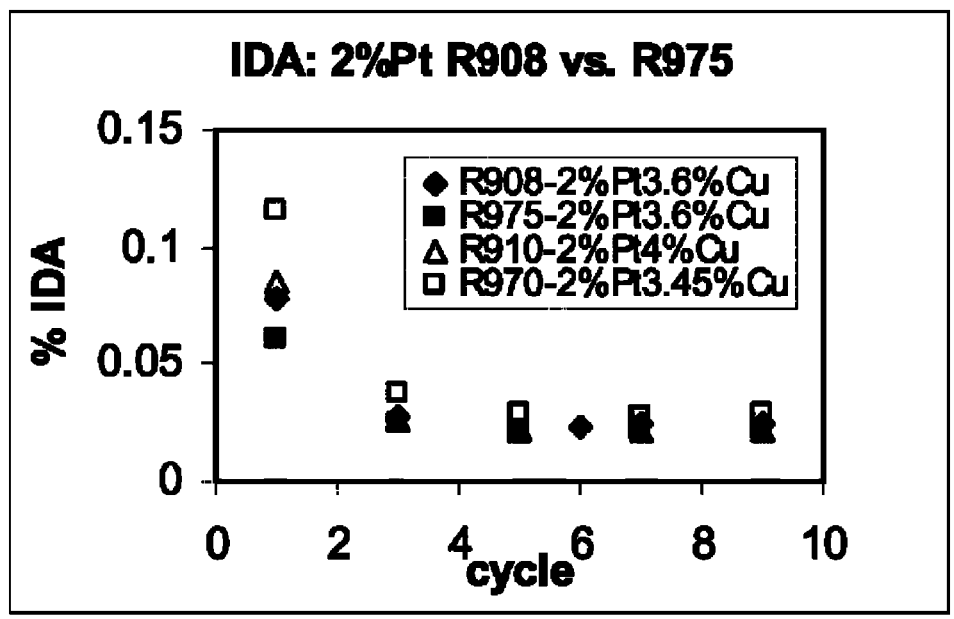
FIGS. 96-98 provide reaction testing data of Example 36.

FIG. 96 provides IDA generation results.

Figure 97:
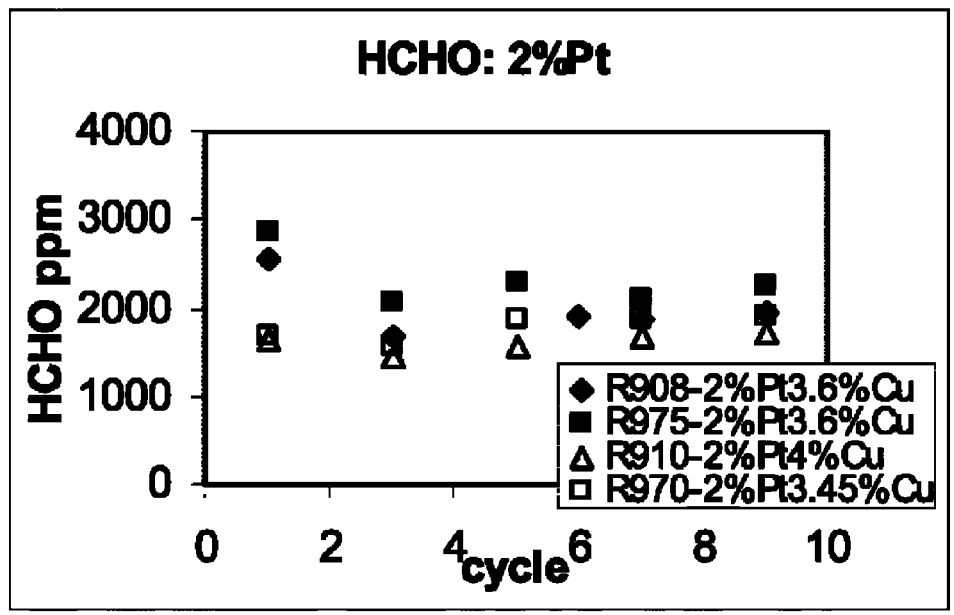
Figure 98:
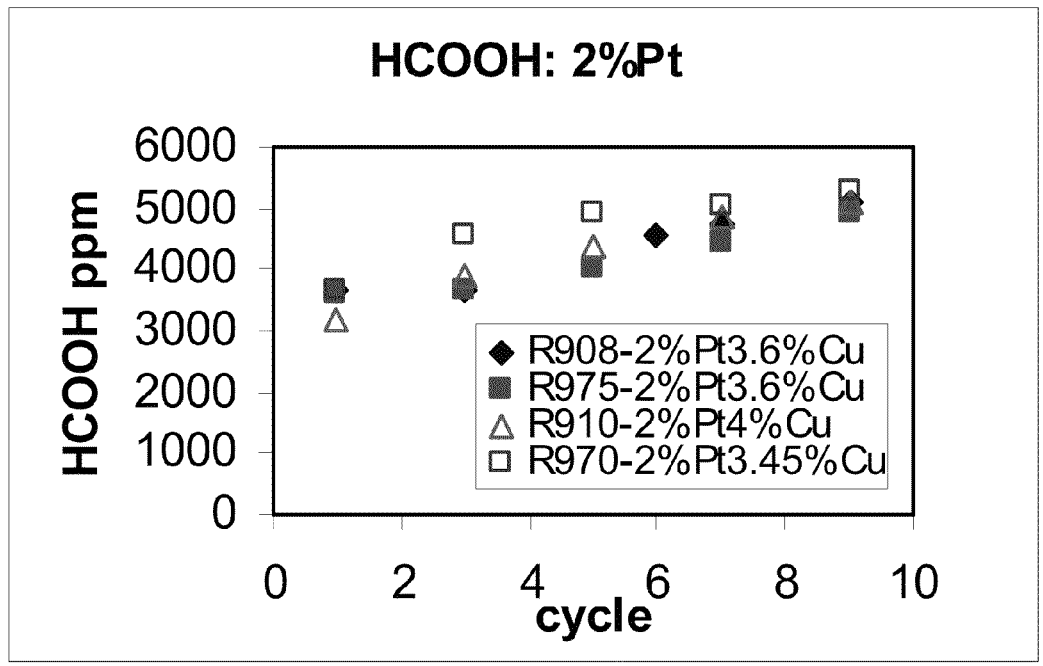

FIGS. 97 and 98 indicate substantially similar results for formaldehyde and formic acid generation.

Example 37

This example provides reactor testing data for 2% Pt/4% Cu/C catalysts prepared generally as described in Example 11. Each catalyst was tested over 9 PMIDA reaction cycles.

One catalyst was prepared by heating the metal-impregnated support to a maximum temperature of approximately 950° C. in the presence of an inert argon atmosphere. A second catalyst was prepared by contacting the metal-impregnated support to a maximum temperature of approximately 950° C. in the presence of a hydrogen/argon (2%/98%) (v/v) atmosphere.

Figure 99:
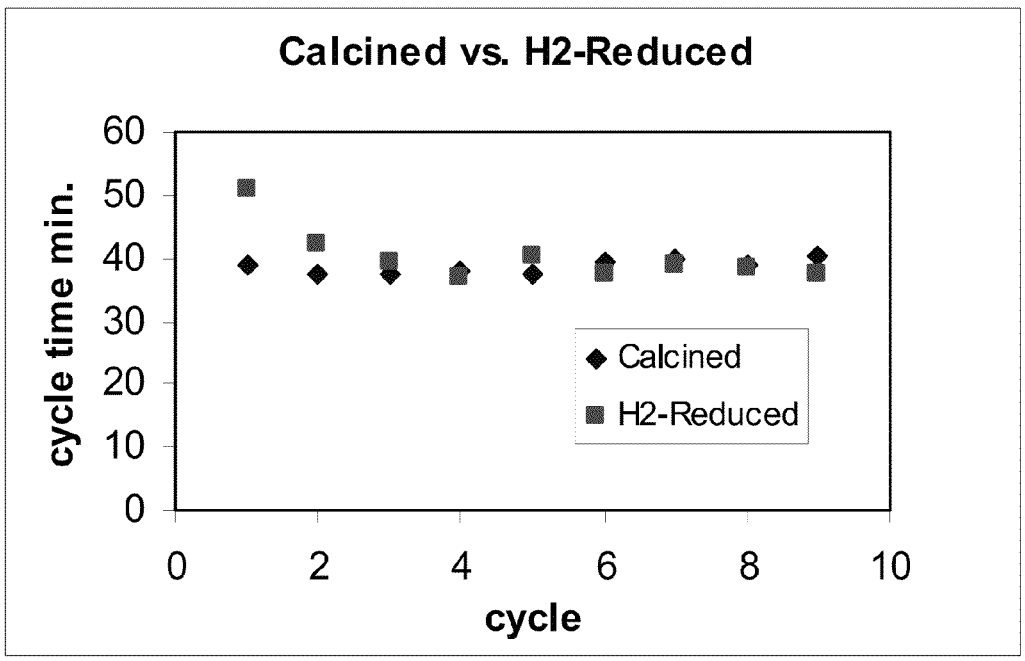
FIG. 99 provides reaction testing data of Example 37.

Cycle time and $CO_2$ generation data are provided for the two catalysts in Table 11. FIG. 99 shows cycle time for each catalyst.

TABLE 11

| Cycle | Calcined | Calcined | $H_2$-Reduced | $H_2$-Reduced |
|---|---|---|---|---|
| 1 | 2220 | 38.75 | 1867 | 50.92 |
| 2 | 2226 | 37.67 | 2077 | 42.33 |
| 3 | 2181 | 37.58 | 2109 | 39.42 |
| 4 | 2181 | 38 | 2155 | 37.08 |
| 5 | 2179 | 37.25 | 2095 | 40.42 |
| 6 | 2094 | 39.25 | 2136 | 37.42 |
| 7 | 2078 | 39.75 | 2089 | 39 |
| 8 | 2075 | 39 | 2067 | 38.5 |
| 9 | 2034 | 40.33 | 2060 | 37.42 |

Example 38

This example provides reactor testing data for a 2% Pt/4% Cu/C catalyst and a 2% Pt/4% Cu/C metal-impregnated support (precursor) prepared generally as described in Example 11. The catalyst and metal-impregnated support were tested over 4 PMIDA reaction cycles. The catalyst was prepared by contacting a metal-impregnated support to a maximum temperature of approximately 950° C. in the presence of a hydrogen/argon (2%/98%) (v/v) atmosphere.

Figure 100:
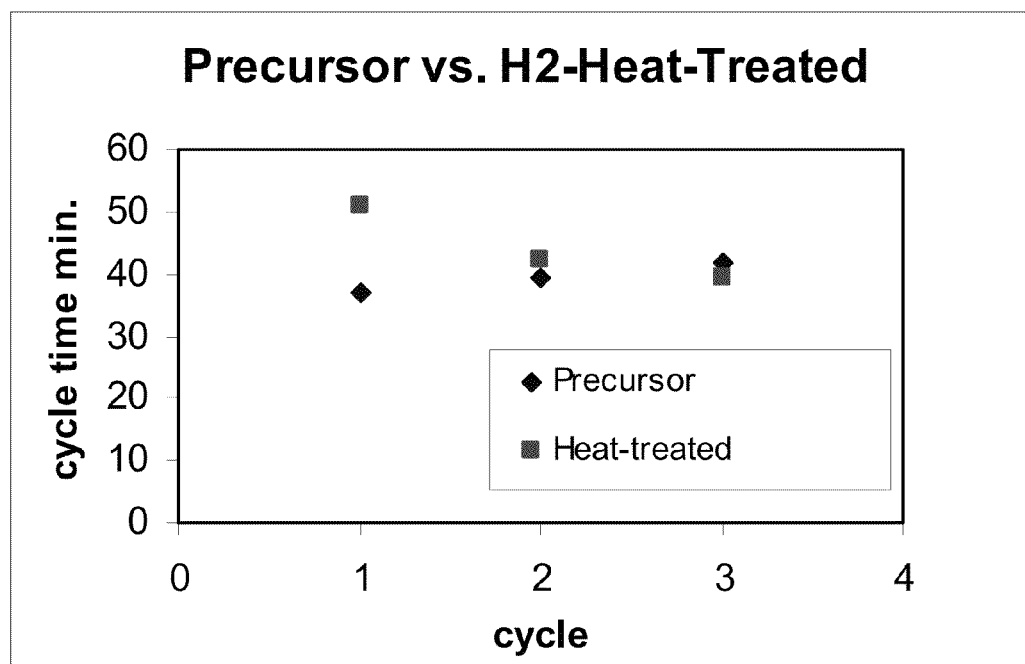
FIG. 100 provides reaction testing data of Example 38.

Cycle time and $CO_2$ generation data are provided for the catalyst and metal-impregnated support in Table 12. FIG. 100 shows cycle time for each catalyst.

TABLE 12

| Cycle | Precursor | Precursor | Catalyst | Catalyst |
|---|---|---|---|---|
| 1 | 2003.4 | 36.92 | 1866.6 | 50.92 |
| 2 | 1912.5 | 39.17 | 2076.8 | 42.33 |
| 3 | 1841 | 41.58 | 2109.2 | 39.42 |

Example 39

This example provides a comparison of 2% Pt/4% Cu/C catalysts prepared using different sources of platinum. Each catalyst was prepared generally as described in Example 11, including heating of a metal-impregnated support to a maximum temperature of approximately 950° C. Platinum was deposited by displacement deposition onto copper-impregnated supports using platinum sources of: (1) $K_2PtCl_4$ (i.e., $Pt^{+2}$ ions) and (2) $H_2PtCl_6.H_2O$ (i.e., $Pt^{+4}$ ions).

Figure 101:
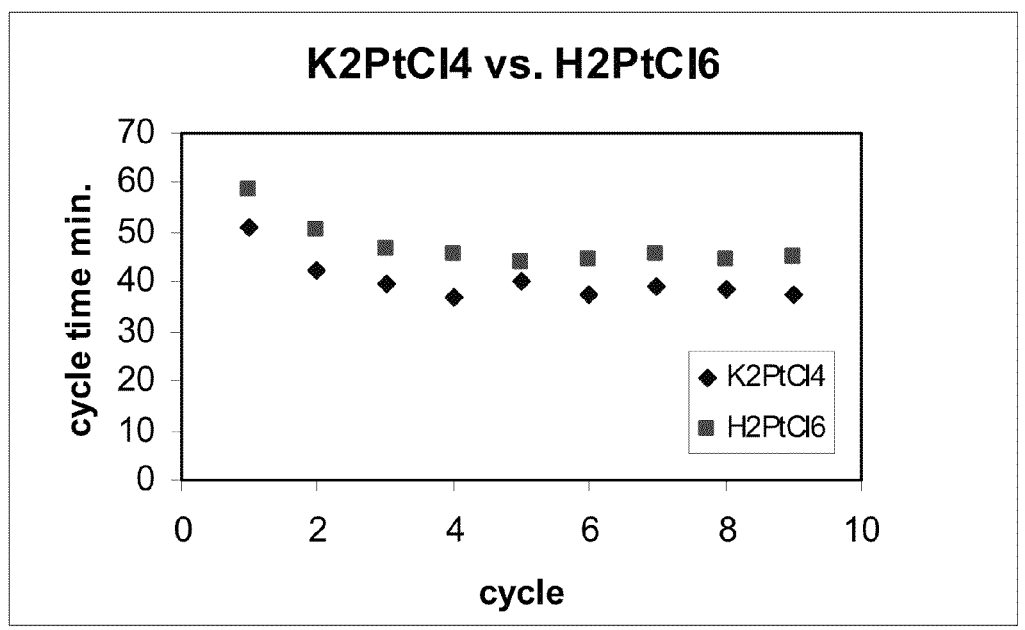
FIGS. 101 and 102 provide reaction testing data of Example 39.
Figure 102:
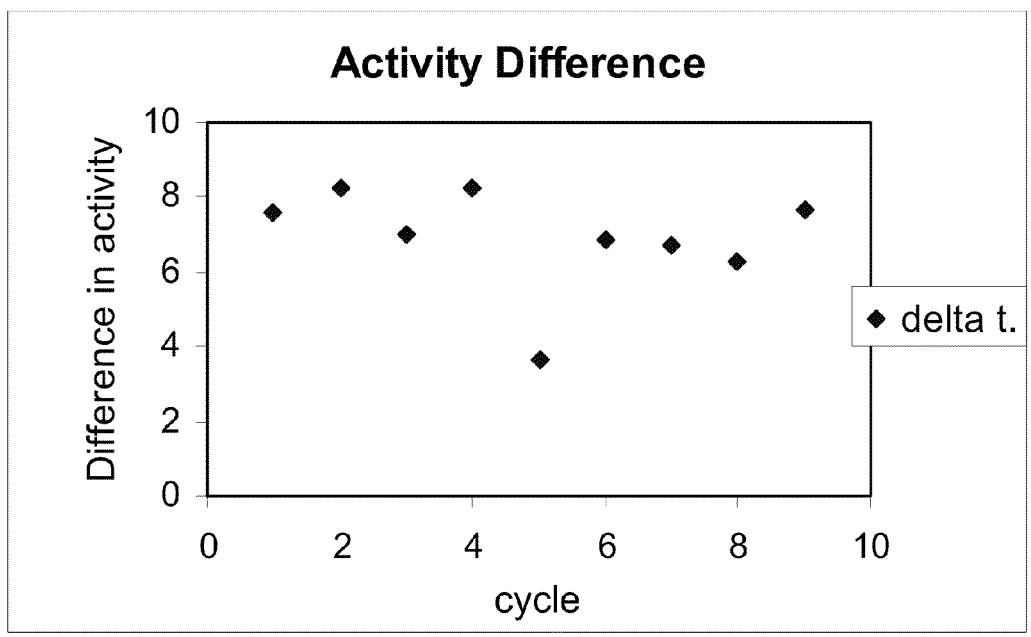

Table 13 provides cycle time, $CO_2$ generation data, and difference in activity (based on cycle time) for each catalyst over 9 reaction cycles. FIGS. 101 and 102 provide cycle time and activity difference data.

TABLE 13

| Cycle | $K_2PtCl_4$ | $K_2PtCl_4$ | $H_2PtCl_6$ | $H_2PtCl_6$ | delta t | % Activity |
|---|---|---|---|---|---|---|
| 1 | 1866.6 | 50.92 | 1640.8 | 58.5 | 7.58 | 0.87 |
| 2 | 2076.8 | 42.33 | 1879.8 | 50.58 | 8.25 | 0.84 |
| 3 | 2109.2 | 39.42 | 1989.6 | 46.42 | 7 | 0.85 |
| 4 | 2155.1 | 37.08 | 1980.4 | 45.33 | 8.25 | 0.82 |
| 5 | 2095.1 | 40.42 | 1982 | 44.08 | 3.66 | 0.92 |
| 6 | 2135.9 | 37.42 | 1994.7 | 44.25 | 6.83 | 0.85 |
| 7 | 2089 | 39 | 1954.2 | 45.75 | 6.75 | 0.85 |
| 8 | 2066.8 | 38.5 | 1973.4 | 44.75 | 6.25 | 0.86 |
| 9 | 2059.6 | 37.42 | 1962.1 | 45.08 | 7.66 | 0.83 |
| | Total $CO_2$ | Cycle time | Total $CO_2$ | Cycle time | | avg. 0.846 excluding the 5th cycle |

Example 40

Figure 103:
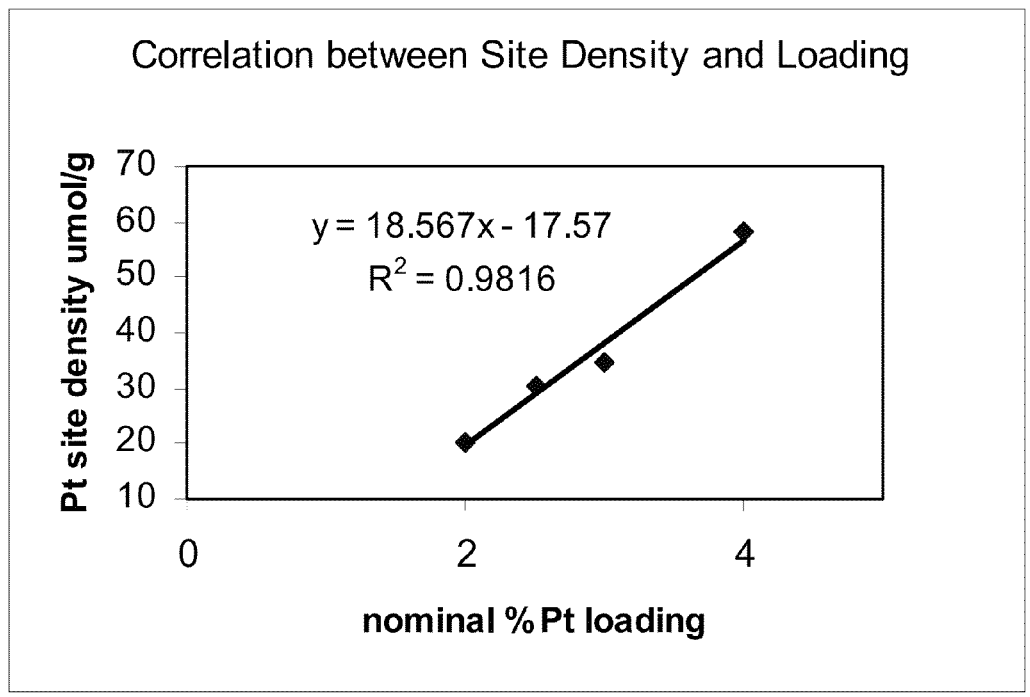
FIG. 103 provides platinum site density data as described in Example 20.

This example provides CO chemisorption data (i.e., platinum site density) for catalysts of varying platinum content prepared generally as described in Examples 8, 11, 14, and 15. Table 14 provides the CO chemisorption (determined generally in accordance with the method described in Example 67) and FIG. 103 provides a plot of platinum loading versus platinum site density. The catalysts were tested in PMIDA oxidation for 10 reaction cycles prior to CO chemisorption analysis.

TABLE 14

| Pt loading | Chemisorption Cycle 2 Pt site density (μmol CO/g catalyst) |
|---|---|
| 2 | 20.24 |
| 2.5 | 30.1 |
| 3 | 34.9 |
| 4 | 58 |

These results show a linear relationship between platinum loading and site density. Based on these results, it is currently believed that a significant portion of the platinum incorporated in the catalyst is present in the form of a relatively thin shell. Conversely, a non-liner relationship between platinum loading and site density has been observed for conventional platinum-containing catalysts. This is currently believed to be due to the fact that a greater portion of the platinum is distributed throughout metal particles. Thus, beyond certain level of platinum, loading platinum site density does not increase since the portion of platinum distributed throughout the particles does not contribute to exposed platinum surface area.

Example 41

Figure 104:
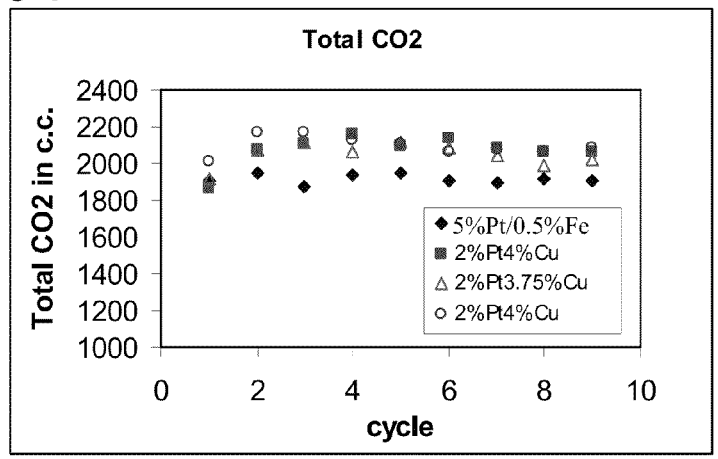
FIG. 104 provides reaction testing data of Example 41.

Catalysts containing nominal metal contents of approximately 2% Pt and 4% Cu were prepared generally as described in Examples 11 and 12. The metal deposition bath was maintained under a nitrogen atmosphere during copper deposition. Reaction testing results comparing the Pt/Cu catalysts to a 5% Pt/0.5% Fe catalyst are shown in FIG. 104. As shown, all catalysts provided comparable activity.

Example 42

Figure 105:
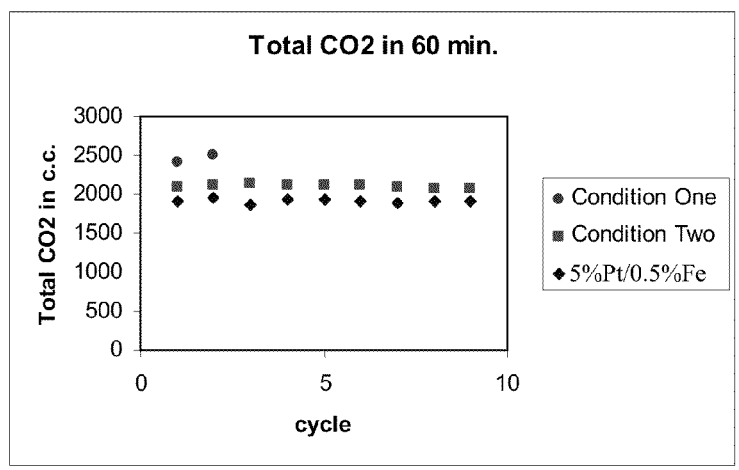
FIGS. 105 and 106 provide reaction testing data of Example 42.
Figure 106:
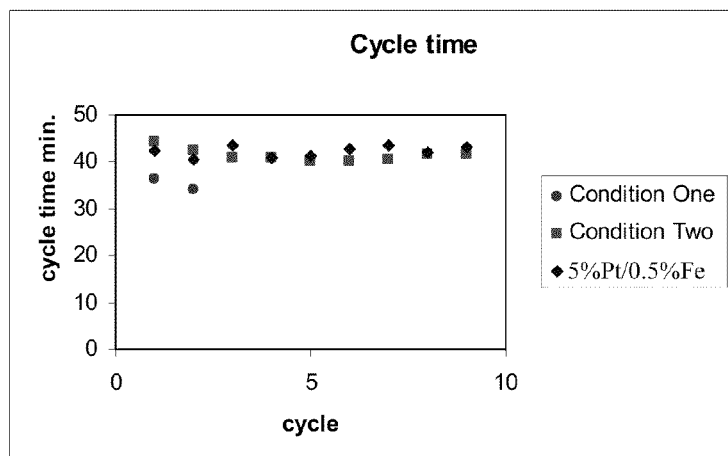

This example details reaction testing of nominal 3% Pt/6% Cu catalysts prepared as described in Example 14 at varying catalyst loadings. One catalyst was tested at a catalyst loading of approximately 0.25 g and another was tested at a loading of approximately 0.17 g. The performance of each catalyst was compared to a 5% Pt/0.5% Fe catalyst prepared generally as described in U.S. Pat. No. 6,417,133 at a loading of 0.25 g. Total catalyst and platinum loadings are summarized in Table 15. Total $CO_2$ generation results and cycle time results are shown in FIGS. 105 and 106, respectively. As compared to the 5% Pt/0.5% Fe catalyst, these results indicate improved activity for the 3% Pt catalyst at equivalent catalyst loading and at least comparable activity at reduced catalyst loading. Accordingly, 3% Pt catalysts of the present invention, or other similar catalysts, may be utilized to provide an improvement in catalyst activity, or a reduction in working metal capital.

TABLE 15

|  | Cat. Loading | Reduction | Pt loading | Reduction in Pt loading |
|---|---|---|---|---|
| Condition One | 0.25 g | 0% | 0.0075 g | 40% |
| Condition Two | 0.167 g | 33% | 0.005 g | 60% |
| Control | 0.25 g | 0% | 0.0125 g | 0% |

III. Additional Embodiments

Disodiumiminodiacetic Acid (DSIDA) Preparation

Example 43

This example details analysis and testing of: (1) a carbon-supported palladium and copper-containing catalyst (CuPdC) of the type described in U.S. Pat. Nos. 5,916,840, 5,689,000, and/or 5,627,125; and (2) a CuPdC catalyst prepared as described in U.S. Pat. Nos. 5,916,840, 5,689,000, and/or 5,627,125 that was treated by contact with a mixture containing 1,4-cyclohexane dione and ethylene glycol as described in Example 1 (mechanism 2).

The treated and un-treated catalysts were analyzed to determine their Langmuir surface areas and to provide comparisons of the micropore and macropore surface areas prior to and after treatment.

TABLE 16

| Sample | Dione | Diol | % of original micropore SA | % of original macropore SA |
|---|---|---|---|---|
| Carbon A | 1,4-disubstituted | Ethylene Glycol | 22.6 | 75.8 |
| Carbon A | 1,3-disubstituted | Ethylene Glycol | 58.4 | 84 |
| Carbon B | 1,4-disubstituted | Ethylene Glycol | 55.6 | 78.7 |
| Carbon B | 1,3-disubstituted | Ethylene Glycol | 32.2 | 39.8 |
| Carbon C | 1,4-disubstituted | Ethylene Glycol | 17.9 | 76.8 |
| Carbon C | 1,3-disubstituted | Ethylene Glycol | 45 | 75.6 |
| Carbon C | 1,4-disubstituted | 1,2-Propanediol | 14.4 | 67.5 |
| Carbon C | 1,3-disubstituted | 1,2-Propanediol | 56.1 | 80.7 |

As shown in Table 16, treatment of the catalyst provided a 75% reduction in micropore surface area of the catalyst, while providing a reduction in macropore surface area of less than 20% (i.e., a preferential reduction in micropore surface area approximately 4 times greater than the reduction in macropore surface area).

Figure 107:
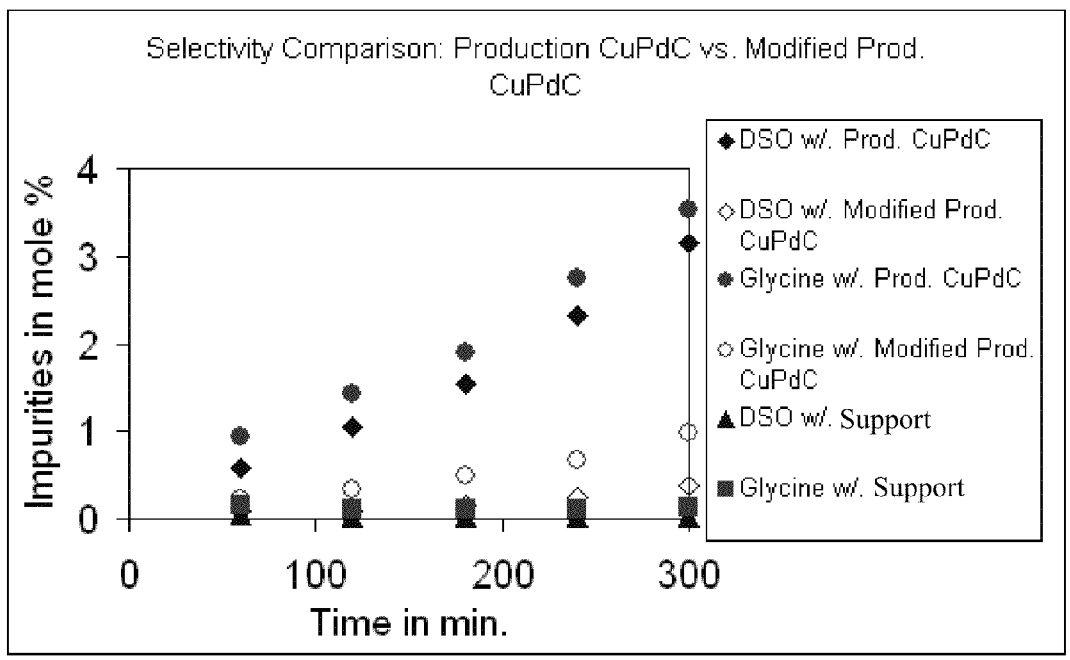
FIG. 107 provides reaction testing data of Example 43.

The treated and untreated catalysts were also tested for the conversion of diethanolamine to disodiumiminodiacetic acid. Mixtures including water, the (original or modified) catalyst (2 wt. %), diethanolamine (1.8 wt. %), sodium hydroxide (2.4 wt. %), and disodiumiminodiacetic acid (DSIDA) (12.5 wt. %) were heated to temperatures ranging from 150-160° C. over the course of 5 hours and under a pressure of approximately 135 psig. These conditions were selected to determine the performance of the modified and unmodified catalysts with regard to oxalate and glycine formation. The results are shown in FIG. 107. The modified catalyst provided an approximately 8-10 fold reduction in oxalate formation and an approximately 4 fold reduction in glycine generation. These results suggest that the modified catalyst provided reduced exposed noble metal believed to contribute to glycine and oxalate formation.

Example 44

This example details testing of palladium and copper-containing carbon-supported (CuPdC) catalysts in preparation of DSIDA by dehydrogenation of DEA. The catalysts were prepared as described in U.S. Pat. Nos. 5,916,840, 5,689,000, and/or 5,627,125 and tested generally under the conditions described therein. Two CuPdC catalysts were prepared generally in accordance with the method described in one or more of these patents. Each catalyst was prepared to include 24 wt. % Cu. One catalyst was prepared using an untreated carbon support; this resulted in a catalyst including 3 wt. % Pd (i.e., 24% Cu/3% Pd/C). The second catalyst was prepared using a carbon support treated by the present method as described in Example 1 by contact with 1,4-CHDM; this resulted in a catalyst including approx. 2.4 wt. % Pd (i.e., 24% Cu/2.4% Pd/C). Thus, it is believed that use of the modified support resulted in reduced palladium deposition.

Each catalyst was tested in conversion of DEA to DSIDA generally in accordance with the conditions set forth in U.S. Pat. Nos. 5,916,840, 5,689,000, and/or 5,627,125. The results are shown in FIG. 108 and Table 17.

Figure 108:
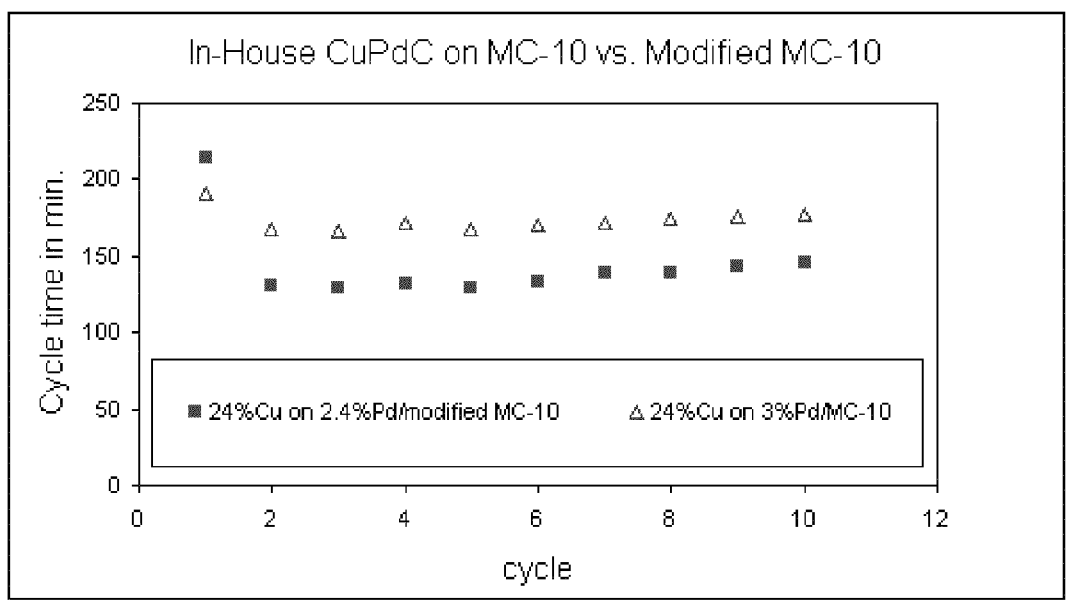
FIG. 108 provides reaction testing data of Example 44.

As shown in FIG. 108, beginning with the second cycle, cycle time was reduced for the catalyst including 2.4% Pd on the treated carbon support. That is, the catalyst prepared using the treated carbon support provided an increase in activity of approx. 15-20% at a lower noble metal content.

TABLE 17

| Cycle | 24%Cu on 2.4%Pd/ modified MC-10 | | | 24%Cu on 3%Pd/ MC-10 | | |
|---|---|---|---|---|---|---|
| mol % | Gly-cine | Oxalic Acid | Hydroxyethyl Glycine | Gly-cine | Oxalic Acid | Hydroxyethyl Glycine |
| 1 | 1.08 | 0.49 | 0.46 | 1.69 | 0.73 | 0.56 |
| 2 | 0.9 | 0.38 | 0.46 | 1.28 | 0.45 | 0.42 |
| 3 | 0.88 | 0.35 | 0.49 | 1.22 | 0.44 | 0.43 |
| 4 | 0.9 | 0.34 | 0.58 | 1.3 | 0.43 | 0.4 |
| 5 | 0.9 | 0.34 | 1.01 | 1.25 | 0.42 | 0.42 |
| 6 | 0.94 | 0.34 | 0.87 | 1.31 | 0.44 | 0.41 |
| 7 | 0.96 | 0.34 | 0.89 | 1.3 | 0.43 | 0.39 |
| 8 | 0.97 | 0.34 | 0.76 | 1.35 | 0.43 | 0.36 |
| 9 | 1.01 | 0.34 | 0.71 | 1.35 | 0.43 | 0.38 |
| 10 | 1.01 | 0.35 | 0.61 | 1.38 | 0.43 | 0.36 |

As shown in Table 17, use of the 2.4% Pd catalyst on the modified carbon support provided reduced oxalic acid generation and glycine generation as compared to the 3% Pd catalyst on the unmodified carbon support (e.g., an improvement in oxalic acid and glycine selectivities of approx. 15% and 25%, respectively).

IV. Platinum-Iron

Example 45

This example details preparation of a catalyst having a nominal platinum content of 2 wt. % and a nominal iron content of 4 wt. % on an activated carbon support having a Langmuir surface area of approximately 1500 m²/g. The following preparation was conducted under nitrogen protection.

Activated carbon (approximately 10.458 g) and degassed water (approximately 90 g) were mixed in a baffled beaker under a nitrogen atmosphere. $FeCl_3 \cdot xH_2O$ (2.007 g) was dissolved in degassed water (40 g) and this solution was pumped into the baffled beaker over a period of one hour. The pH of the slurry within the baffled beaker was maintained at 4 by introduction of 2.5N degassed NaOH, as necessary. After addition of the $FeCl_3$ solution was completed, the pH of the slurry was raised to approximately 4.5 and the slurry was allowed to mix at room temperature for approximately 15 minutes. The slurry was then heated to a temperature of approximately 60° C. over a period of approximately 48 minutes, during which time the pH of the slurry was maintained at approximately 4.5 by addition of 2.5N NaOH.

The pH of the slurry was then raised to approximately 10.5 over a period of approximately 30 minutes at a temperature of approximately 60° C., and at a rate of 0.5 pH units per 5 minutes. After pH adjustment, the slurry was allowed to mix for approximately 10 minutes.

Sodium borohydride ($NaBH_4$) (approximately 0.686 g) was dissolved in degassed water (approximately 20 g); seven drops of 2.5N degassed NaOH were added to stabilize the $NaBH_4$ solution, and the resulting $NaBH_4$ solution was introduced to the baffled beaker at approximately 60° C. over a period of 20 minutes. The slurry was then allowed to mix for ten additional minutes at approximately 60° C. The slurry was then filtered and the wet cake was then re-slurried in the baffled beaker in degassed deionized water (approx. 90 g). The pH of the resulting slurry was then lowered to approximately 5 by introduction of degassed 2M HCl.

$K_2PtCl_4$ (approximately 0.456 g) was dissolved in degassed water (approximately 20 g) and the resulting Pt solution was then added to the baffled beaker over a period of three minutes. The resulting slurry was then allowed to mix at ambient conditions (approximately 22° C.) for approximately 60 minutes, and then heated to a final temperature of 65° C. over a period of 30 minutes, and then allowed to mix at 60° C. The resulting slurry was then filtered and washed twice by contact with degassed water (approximately 100 g) at a temperature of approximately 65° C. The washed sample was then dried in a vacuum oven at approximately 110° C. for approximately 12 hours with a small nitrogen stream to form a Pt/Fe catalyst precursor.

The catalyst precursor was then heated at elevated temperatures up to approximately 900° C. in the presence of a hydrogen/argon stream (2%/98%; v/v) for approximately 120 minutes.

The 2% Pt/4% Fe finished catalyst was tested in PMIDA oxidation under the conditions set forth in Example 7. Inductively Coupled Plasma (ICP) analysis was used to determine platinum and iron leached from the catalyst and present in the reaction mixture. ICP was conducted using a VG PQ ExCell Inductively Coupled Plasma-Mass Spectrometer (ICP-MS) (commercially available from Thermo Jarrell Ash Corp., Thermo Elemental, Franklin, Mass.). The results are set forth in Table 18.

Figure 109:
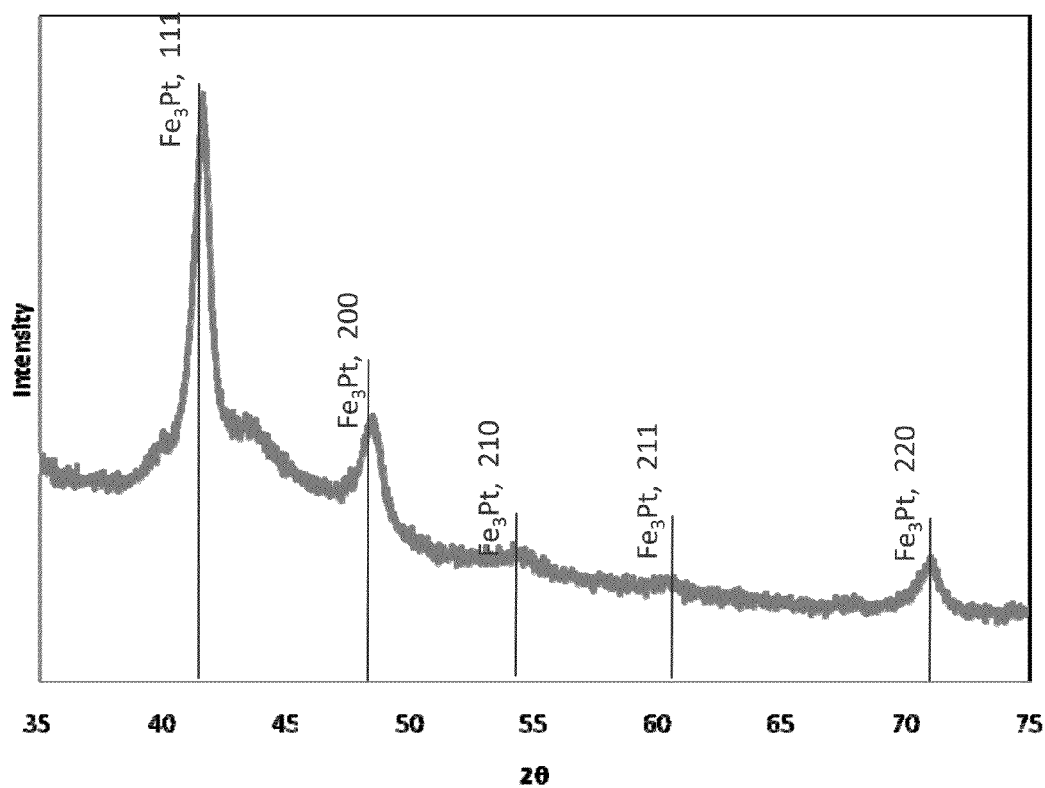
FIG. 109 provides X-Ray Diffraction (XRD) results for the catalyst described in Example 45.

FIG. 109 provides results of XRD analysis (conducted as set forth in Example 69) for the finished catalyst (i.e., before reactor testing).

TABLE 18

| Cycle | 1 | 2 | 3 | 4 | 5 | 6 | 7 | 8 | 9 | 10 |
|---|---|---|---|---|---|---|---|---|---|---|
| Total $CO_2$ (cc) | 1766.6 | 1871.4 | 1966.5 | 1946.8 | 1935.5 | 1957.5 | 1940.7 | 1947.9 | 1932.0 | 1600.6 |
| End point(min) | 45.00 | 39.75 | 38.08 | 39.92 | 40.25 | 38.83 | 39.25 | 40.00 | 39.83 | 40.00 |
| Maximum $CO_2$ Concentration (%) | 35.7 | 37.9 | 38.8 | 36.9 | 36.7 | 37.4 | 37.0 | 36.7 | 36.5 | 36.5 |
| PMIDA (wt. %) | 0.008 | | 0.010 | | 0.010 | | 0.010 | | 0.010 | 0.034 |
| Glyphosate(wt. %) | 5.293 | | 5.378 | | 5.400 | | 5.393 | | 5.392 | 5.563 |
| IDA(wt. %) | 0.099 | | 0.065 | | 0.051 | | 0.045 | | 0.040 | 0.039 |
| $CH_2O$(ppm) | 2421 | | 1990 | | 1838 | | 1660 | | 1737 | 2309 |
| HCOOH(ppm) | 6696 | | 6555 | | 6143 | | 6220 | | 5716 | 6635 |
| Pt(ppm) | <0.01 | | <0.01 | | <0.01 | | <0.01 | | <0.01 | <0.01 |
| Fe(ppm) | 1.484 | | 0.494 | | <0.1 | | <0.1 | | <0.1 | <0.1 |

Example 46

This example details preparation of a catalyst having a nominal platinum content of 2 wt. % and a nominal iron content of 4 wt. % on an activated carbon support having a Langmuir surface area of approximately 1500 m²/g. The following preparation was conducted under nitrogen protection.

Activated carbon (approximately 10.455 g) and degassed water (approximately 90 g) were mixed in a baffled beaker under a nitrogen atmosphere. $Fe_2(SO_4)_3 \cdot xH_2O$ (2.990 g) was dissolved in degassed water (40 g) and this solution was pumped into the baffled beaker over a period of one hour. The pH of the slurry within the baffled beaker was maintained at 4 by introduction of 2.5N degassed NaOH, as necessary.

Mixing of the components of the slurry within the baffled beaker occurred for a total of approximately 20 minutes at a pH of approximately 4. The pH of the slurry was then raised to 4.5 by addition of NaOH. The slurry was then heated to a temperature of approximately 60° C. over a period of 30 minutes. During the heating, the pH was maintained at 4.5 by introduction of 2.5N degassed NaOH (as necessary). At this elevated temperature, the pH of the slurry was raised to approximately 6.5 over a period of 20 minutes, via increases in pH at a rate of approximately 0.5 pH units per 5 minutes.

Sodium borohydride ($NaBH_4$) (approximately 0.681 g) was dissolved in degassed water (approximately 20 g) and then pumped into the baffled beaker at approximately 60° C. over a period of 20 minutes. The slurry was then allowed to mix for ten additional minutes at 60° C. The slurry was then allowed to cool to 45° C., and then filtered. The wet cake was then re-slurried in the baffled beaker in degassed deionized water (90 g). The pH of the resulting slurry was then lowered to approximately 5 by introduction of degassed 2M HCl.

$K_2PtCl_4$ (approximately 0.460 g) was dissolved in degassed water (approximately 20 g) and the resulting Pt solution was then added to the baffled beaker over a period of five minutes. The resulting slurry was then allowed to mix under ambient conditions (approximately 22° C.) for approximately 60 minutes, and then heated to a final temperature of 65° C. over a period of 30 minutes, and then allowed to mix at 65° C. for an additional 10 minutes. The resulting slurry was then filtered and washed twice by contact with degassed water (approximately 100 g) at a temperature of approximately 65° C. The washed sample was then dried in a vacuum oven at approximately 110° C. for approximately 12 hours with a small nitrogen stream to form a Pt/Fe catalyst precursor.

The catalyst precursor was then heated at elevated temperatures up to approximately 900° C. in the presence of a hydrogen/argon stream (2%/98%; v/v) for approximately 120 minutes.

Table 19 sets forth PMIDA reaction testing results, platinum leaching data, and iron leaching data for the 2% Pt/4% Fe finished catalyst.

Example 48

This example details preparation of a catalyst having a nominal Pt content of 2 wt. % and a nominal iron content of 4 wt. % on an activated carbon support having a Langmuir surface area of approximately 1500 $m^2$/g. The following preparation was conducted under nitrogen protection.

Activated carbon (approximately 10.455 g) and degassed water (approximately 90 g) were mixed in a baffled beaker under a nitrogen atmosphere.

$FeCl_3 \cdot 6H_2O$ (approximately 2.009 g) was dissolved in degassed water (40 g) and this solution was pumped into the baffled beaker over a period of one hour. The pH of the slurry within the baffled beaker was maintained at 4 by introduction of 2.5N degassed NaOH, as necessary. After addition of the $FeCl_3 \cdot 6H_2O$ solution to the beaker was completed, the pH of the slurry was raised to approximately 4.5 by addition of NaOH and the slurry was allowed to mix at ambient conditions (approximately 22° C.) for approximately 20 minutes.

The slurry was then heated to a temperature of approximately 60° C. over a period of approximately 50 minutes. During the heating, the pH was maintained at 4.5 with addition of 2.5N degassed NaOH. At this elevated temperature, the pH of the slurry was raised to approximately 10.5 over a period of 30 minutes, via increases in pH at a rate of approximately 0.5 pH units per 5 minutes.

Sodium borohydride ($NaBH_4$) (approximately 0.69 g) was dissolved in degassed water (approximately 20 g); 7 drops of 2.5N NaOH was added to stabilize the $NaBH_4$ solution. The sodium borohydride solution was then pumped into the baffled beaker at approximately 60° C. over a period of 20 minutes. The slurry was then filtered and the wet cake was then re-slurried in the baffled beaker in degassed deionized water (90 g). The pH of the resulting slurry was then lowered to approximately 5 by introduction of degassed 2M HCl.

$K_2PtCl_4$ (approximately 0.460 g) was dissolved in degassed water (approximately 20 g) and the resulting Pt solution was then added to the baffled beaker over a period of three minutes. The resulting slurry was then allowed to mix at ambient conditions (approximately 22° C.) for approximately 60 minutes, and then heated to a final temperature of approximately 65° C.

TABLE 19

| Cycle | 1 | 2 | 3 | 4 | 5 | 6 | 7 | 8 | 9 | 10 |
|---|---|---|---|---|---|---|---|---|---|---|
| Total $CO_2$ (cc) | 1912.0 | 1933.8 | 1951.2 | 1978.7 | 1944.0 | 1943.9 | 1956.3 | 1891.4 | 1864.9 | 1602.2 |
| End point(min) | 38.17 | 37.33 | 36.75 | 35.67 | 37.75 | 37.50 | 37.67 | 39.50 | 40.83 | 40.17 |
| Maximum $CO_2$ Concentration (%) | 40.5 | 39.6 | 39.9 | 41.3 | 38.8 | 39.6 | 39.0 | 37.8 | 36.7 | 37.2 |
| PMIDA (wt. %) | ND | | 0.006 | | 0.006 | | 0.007 | | 0.007 | 0.009 |
| Glyphosate(wt. %) | 5.184 | | 5.249 | | 5.382 | | 5.349 | | 5.393 | 5.497 |
| IDA(wt. %) | 0.139 | | 0.055 | | 0.040 | | 0.038 | | 0.032 | 0.032 |
| $CH_2O$(ppm) | 2586 | | 2212 | | 2203 | | 2149 | | 2300 | 2983 |
| HCOOH(ppm) | 5387 | | 5525 | | 6021 | | 5843 | | 5623 | 5958 |
| Pt(ppm) | 0.019 | | 0.024 | | 0.027 | | 0.025 | | 0.027 | 0.032 |
| Fe(ppm) | 16.420 | | 0.629 | | 0.222 | | 0.077 | | <0.05 | <0.05 |

Example 47

This Example provides the results of X-Ray Diffraction (XRD) analysis for the catalyst prepared as described in Example 46. XRD analysis was conducted as set forth in Example 69.

Figure 110:
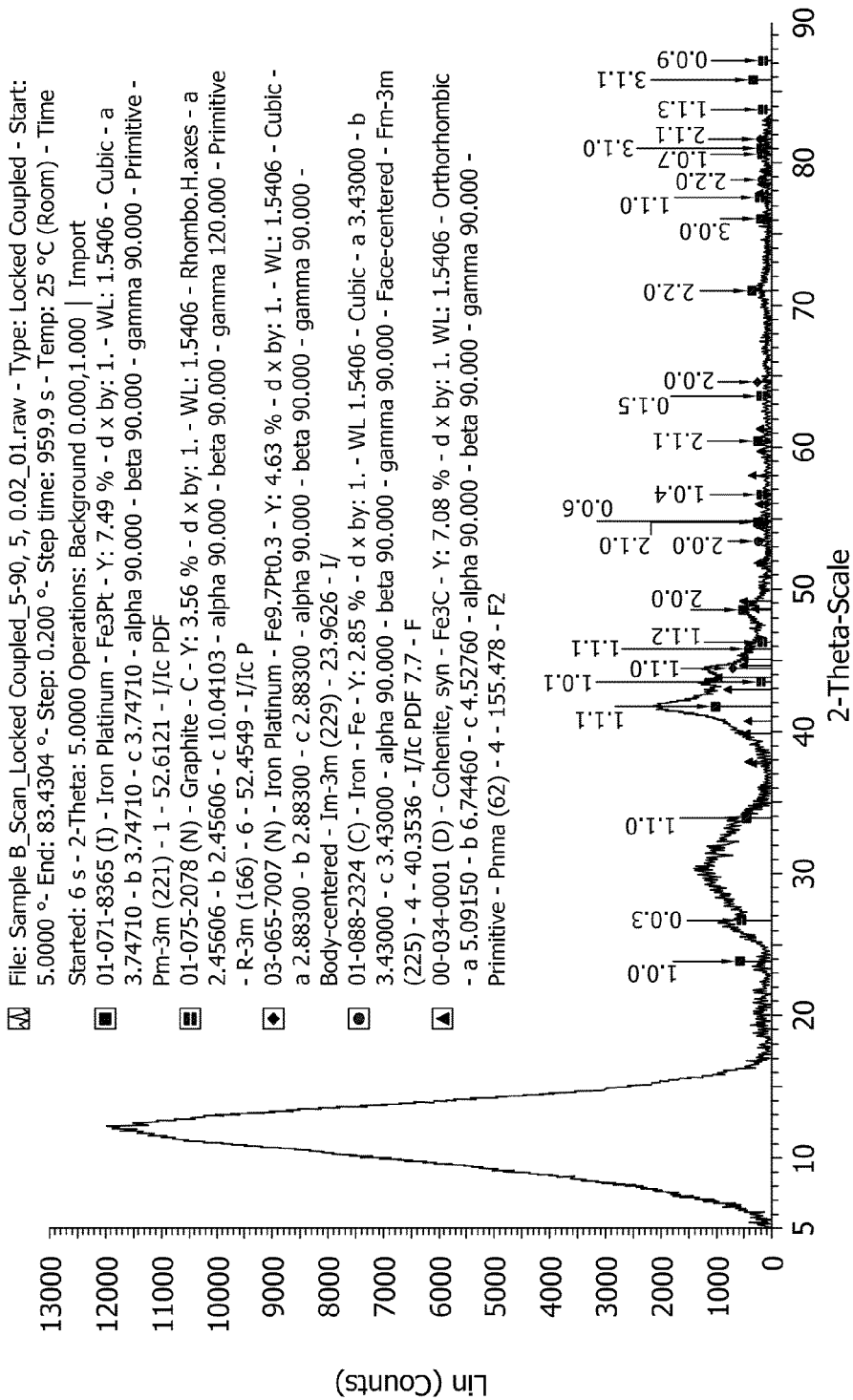
FIGS. 110 and 111 provide XRD results for the catalyst described in Example 46.
Figure 111:
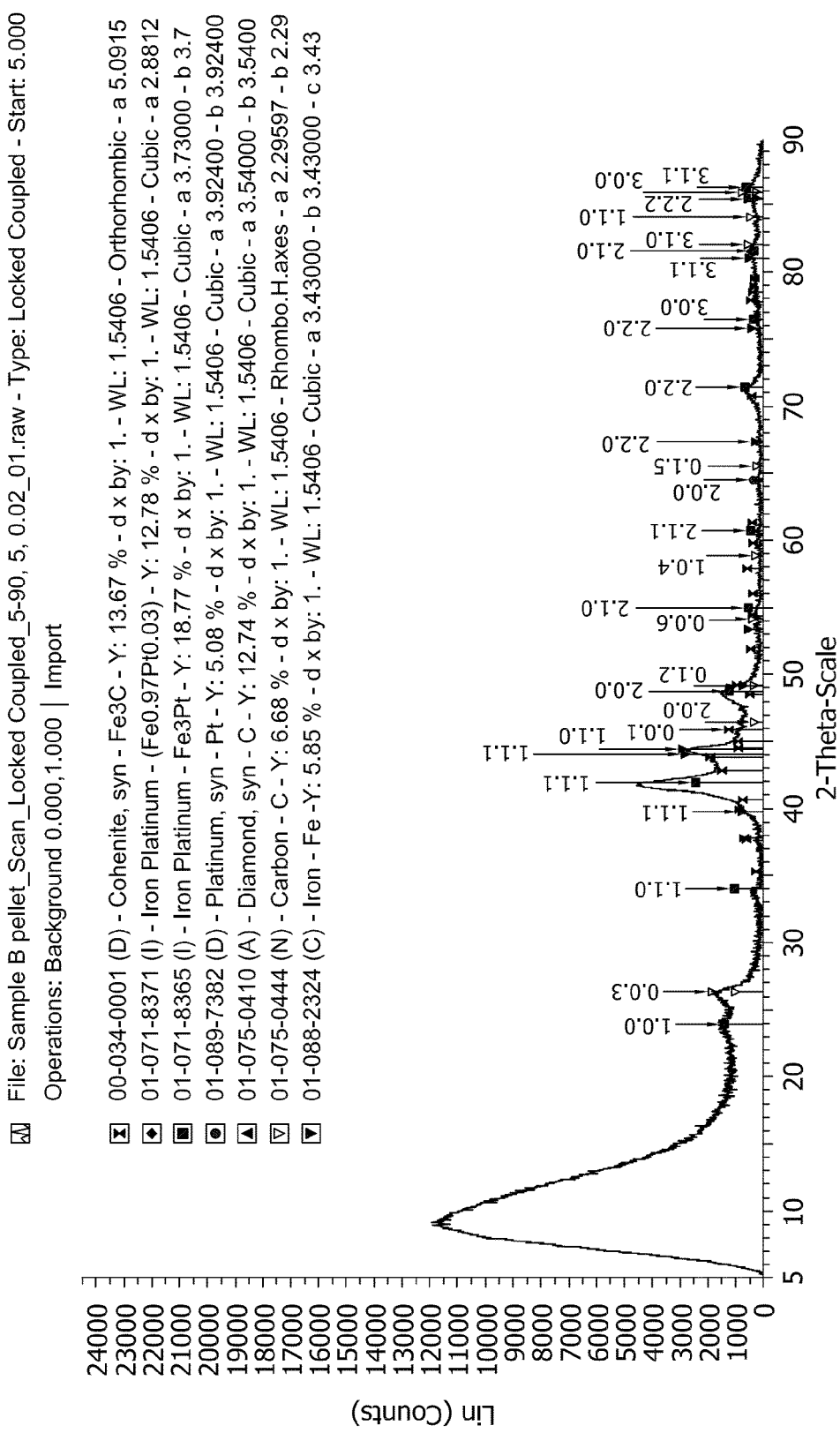

The results are shown in FIGS. 110 and 111. These results indicate the presence of $Fe_3Pt$ bimetallic alloy.

The resulting slurry was then filtered and washed twice by contact with degassed water (approximately 100 g) at a temperature of approximately 65° C. The washed sample was then dried in a vacuum oven at approximately 110° C. for approximately 12 hours with a small nitrogen stream to form a Pt/Fe catalyst precursor.

The catalyst precursor was then heated at elevated temperatures up to approximately 900° C. in the presence of a hydrogen/argon stream (2%/98%; v/v) for approximately 120 minutes.

Table 20 sets forth PMIDA reaction testing results, platinum leaching data, and iron leaching data for the 2% Pt/4% Fe finished catalyst.

then allowed to mix at ambient conditions (approximately 22° C.) room temperature for 30 minutes, and then heated to a temperature of 60° C. over a period of 10 minutes.

TABLE 20

| Cycle | 1 | 2 | 3 | 4 | 5 | 6 | 7 | 8 | 9 | 10 |
|---|---|---|---|---|---|---|---|---|---|---|
| Total $CO_2$ (cc) | 1738.2 | 1826.0 | 1846.2 | 1857.1 | 1866.1 | 1872.0 | 1878.0 | 1862.4 | 1875.6 | 1602.2 |
| End point(min) | 46.75 | 42.50 | 42.08 | 41.67 | 41.50 | 41.58 | 41.50 | 42.25 | 42.00 | 42.58 |
| Maximum $CO_2$ Concentration (%) | 34.4 | 35.3 | 35.6 | 35.7 | 35.7 | 35.6 | 35.9 | 35.3 | 35.4 | 35.0 |
| PMIDA (wt. %) | 0.007 | | 0.010 | | 0.009 | | 0.009 | | 0.009 | 0.060 |
| Glyphosate(wt. %) | 5.339 | | 5.371 | | 5.441 | | 5.389 | | 5.298 | 5.245 |
| IDA(wt. %) | 0.083 | | 0.054 | | 0.046 | | 0.045 | | 0.042 | 0.041 |
| $CH_2O$(ppm) | 2158 | | 1857 | | 1669 | | 1706 | | 1682 | 1831 |
| HCOOH(ppm) | 7454 | | 7161 | | 6919 | | 6648 | | 6487 | 6941 |
| Pt(ppm) | 0.011 | | 0.013 | | 0.015 | | 0.015 | | 0.015 | 0.019 |
| Fe(ppm) | 3.114 | | 0.543 | | 0.178 | | 0.124 | | 0.053 | 0.062 |
| Cycle | 11 | 12 | 13 | 14 | 15 | 16 | 17 | 18 | 19 | 20 | 21 |
| Total $CO_2$ (cc) | 1875.8 | 1868.2 | 1878.2 | 1868.5 | 1855.9 | 1890.5 | 1872.9 | 1837.5 | 1854.1 | 1845.7 | 1830.5 |
| End point(min) | 41.33 | 42.33 | 42.25 | 42.67 | 43.58 | 42.08 | 43.83 | 44.33 | 44.25 | 44.25 | 45.25 |
| Maximum $CO_2$ Concentration (%) | 35.7 | 35.9 | 35.5 | 35.0 | 34.6 | 35.5 | 34.4 | 34.1 | 34.1 | 34.4 | 33.9 |
| PMIDA (wt. %) | 0.009 | | 0.010 | | 0.009 | | 0.010 | | 0.010 | 0.010 | 0.010 |
| Glyphosate(wt. %) | 5.315 | | 5.405 | | 5.406 | | 5.382 | | 5.371 | 5.477 | 5.424 |
| IDA(wt. %) | 0.043 | | 0.041 | | 0.038 | | 0.039 | | 0.037 | 0.036 | 0.037 |
| $CH_2O$(ppm) | 1898 | | 2086 | | 2067 | | 2111 | | 2173 | 2107 | 1853 |
| HCOOH(ppm) | 6159 | | 6287 | | 6199 | | 6302 | | 5805 | 6582 | 6175 |
| Pt(ppm) | 0.023 | | 0.024 | | 0.024 | | 0.023 | | 0.024 | 0.024 | 0.023 |
| Fe(ppm) | <0.05 | | <0.05 | | 0.054 | | <0.05 | | <0.05 | <0.05 | <0.05 |

Figure 111A:
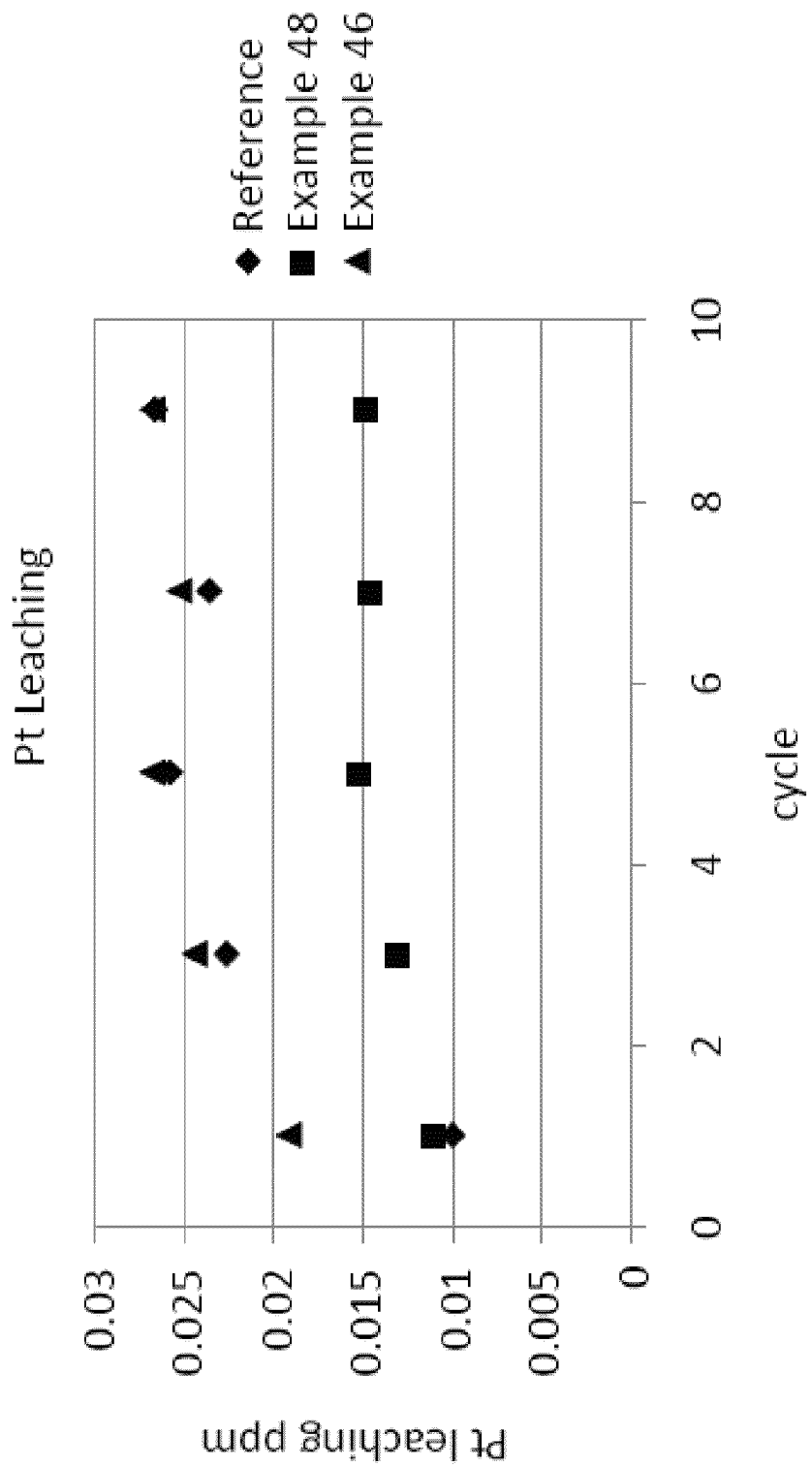
FIG. 111A provides platinum leaching data for catalysts described in Examples 46 and 48.

FIG. 111A includes platinum leaching data for the catalysts of Examples 46 and 48, as compared to a (Reference) 5% Pt/0.5% Fe catalyst prepared as described by Wan et al. in International Publication No. WO 2006/031938.

Example 49

The following preparation was conducted under nitrogen protection.

Activated carbon (approximately 10.456 g) and degassed water (approximately 90 g) were placed in a baffled beaker and allowed to mix for 20 minutes. $FeCl_3.6H_2O$ (2.009 g) was dissolved in degassed water (approx. 40 g) and this solution was pumped into the baffled beaker over a period of 30 minutes while the pH of the slurry was maintained at 4 by addition of 2.5N NaOH. After addition of the $FeCl_3.6H_2O$ solution, the pH was raised to 4.5 and allowed to mix for 10 minutes. The slurry was then heated to approximately 50° C. over a period of 30 minutes, while the pH was maintained at pH 4.5. The pH of the slurry was then raised to 8 over a period of 15 minutes, and allowed to mix for approximately 10 minutes. Ethylene glycol (approx. 1.386 g) was then added to the slurry, and allowed to mix at approximately 60° C. for approximately 20 minutes. After mixing was complete, the slurry was allowed to cool to 30° C.

The pH of the solution was then lowered to 5 by addition of 0.5M degassed HCl. $K_2PtCl_4$ (0.460 g) was dissolved in degassed water (20 g). The Pt solution was then added to the baffled beaker over a period of three minutes. The slurry was The slurry was then filtered, and the wet cake was hot washed twice at 60° C. with approximately 100 mL of degassed water. The resulting sample was then dried in a vacuum oven at 110° C. for 12 hours with a small nitrogen stream.

Example 50

The following preparation was conducted under nitrogen protection.

Activated carbon (10.456 g) and degassed water (approximately 90 g) were placed in a baffled beaker and allowed to mix for 20 minutes. $FeCl_3.6H_2O$ (2.011 g) was dissolved in degassed water (approximately 40 g) and this solution was pumped into the baffled beaker over a period of 34 minutes while the pH of the slurry was maintained at 4 by addition of 2.5N NaOH.

Upon the complete addition of the $FeCl_3.6H_2O$ solution, the pH was raised to 4.5, and allowed to mix for 10 minutes. The slurry was then heated to approximately 60° C. over a period of 34 minutes, while the pH was maintained at 4.5. The pH of the slurry was then raised to 11 over a period of 30 minutes, and then allowed to mix for 10 minutes. Ethylene glycol (1.385 g) was then added to the slurry, and allowed to mix at 60° C. for approximately 10 minutes.

The pH of the solution was then lowered to 5 by addition of 1M degassed HCl. $K_2PtCl_4$ (0.459 g) was dissolved in degassed water (20 g). The Pt solution was then added to the baffled beaker over a period of three minutes. The slurry was then allowed to mix at ambient conditions (approximately 22° C.) for 30 minutes, and then heated to a temperature of approximately 60° C. over a period of 10 minutes.

The slurry was then filtered, and the wet cake was hot washed twice at 60° C. with approximately 100 ml of degassed water. The resulting sample was then dried in a vacuum oven at 110° C. for 12 hours with a small nitrogen stream.

Four 2% Pt/4% Fe catalysts were prepared from a precursor prepared as described that was heated at elevated temperatures in the presence of a hydrogen/argon stream (4%/96%; v/v) for approximately 120 minutes. Maximum heating temperatures were:

(1) 900° C.;
(2) 750° C.;
(3) 650° C.;
(4) 550° C.

Figure 112:
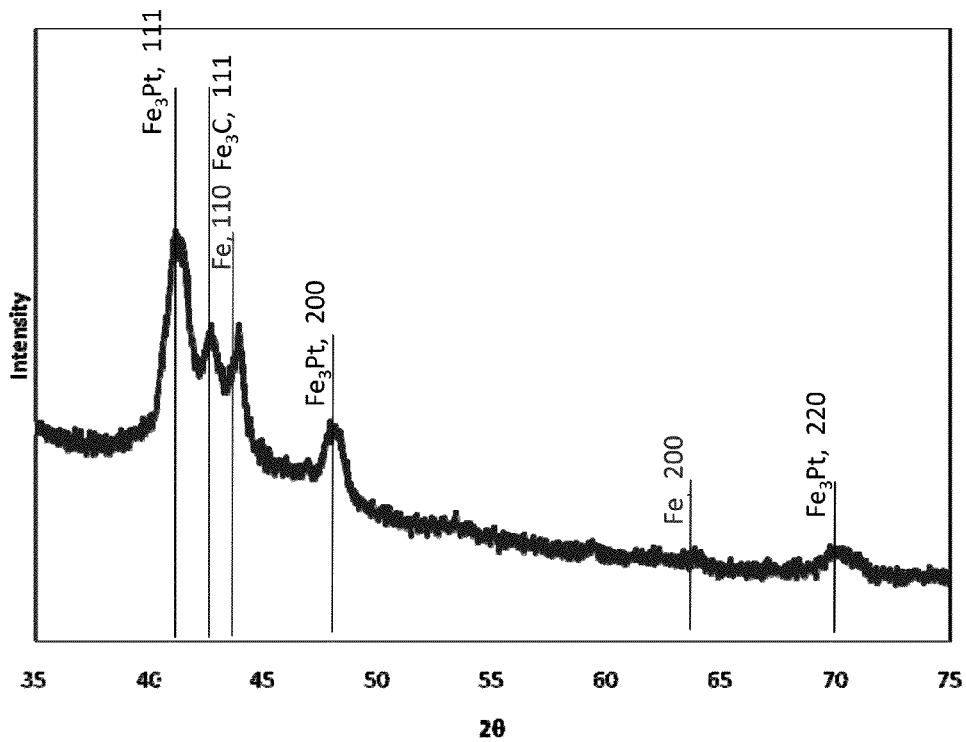
FIGS. 112-115 provide XRD results for the catalysts described in Example 50.

FIG. 112 provides results of XRD analysis of catalyst (1); these results indicate the presence of a $Fe_3Pt$ phase.

Figure 113:
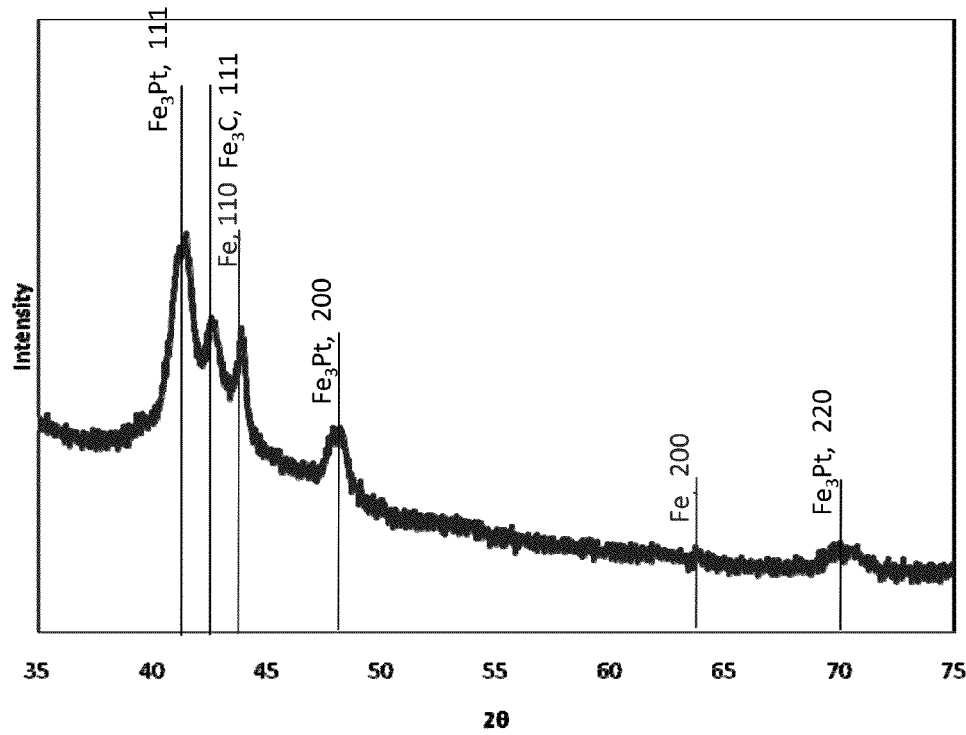

FIG. 113 provides results of XRD analysis of catalyst (2); these results indicate the presence of a $Fe_3Pt$ phase.

Figure 114:
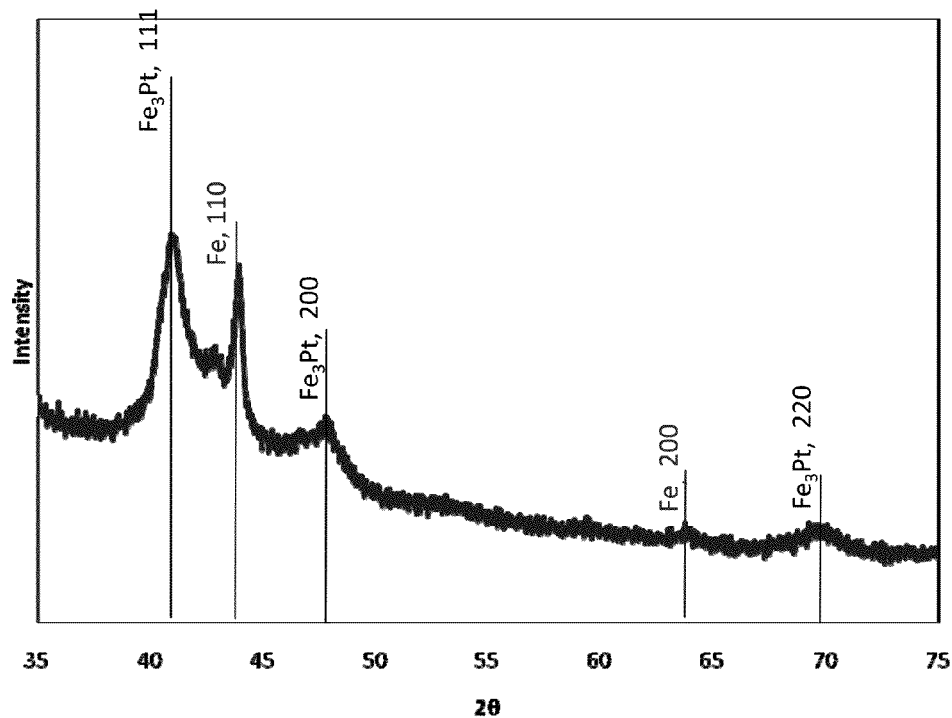

FIG. 114 provides results of XRD analysis of catalyst (3); these results indicate the presence of a $Fe_3Pt$ phase.

Figure 115:
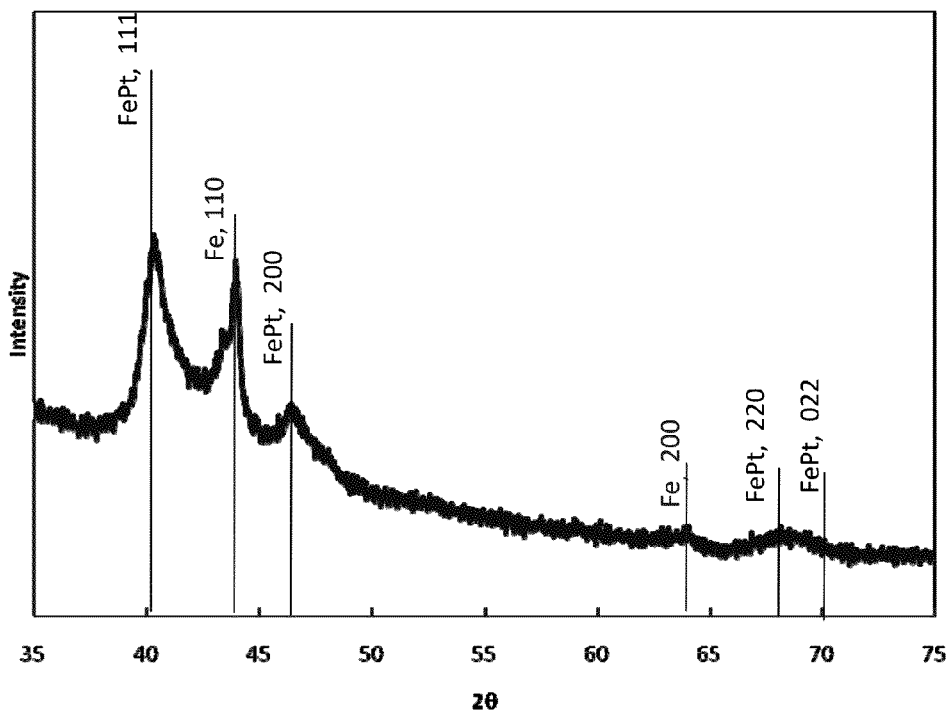

FIG. 115 provides results of XRD analysis of catalyst (4); these results indicate the presence of a FePt phase.

Reaction testing data, platinum leaching data, and iron leaching data for the 900° C./2% Pt/4% Fe catalyst are set forth in Table 21.

TABLE 21

| Cycle | 1 | 2 | 3 | 4 | 5 | 6 | 7 | 8 |
|---|---|---|---|---|---|---|---|---|
| Total $CO_2$ (cc) | 1751.9 | 1793.3 | 1863.9 | 1930.6 | 1931.1 | 1946.4 | 1926.7 | 1602.3 |
| End point(min) | 44.08 | 43.00 | 41.67 | 40.75 | 41.00 | 41.25 | 41.08 | 42.90 |
| Maximum $CO_2$ Concentration (%) | 36.2 | 35.2 | 35.3 | 35.5 | 35.7 | 35.2 | 36.1 | 34.4 |
| PMIDA (wt. %) | 0.003 | | 0.006 | | 0.006 | | 0.006 | 0.104 |
| Glyphosate(wt. %) | 5.243 | | 5.398 | | 5.486 | | 5.376 | 5.539 |
| IDA(wt. %) | 0.079 | | 0.040 | | 0.035 | | 0.034 | 0.032 |
| $CH_2O$(ppm) | 3032 | | 2513 | | 2072 | | 2156 | 2596 |
| HCOOH(ppm) | 6300 | | 6615 | | 6554 | | 6358 | 6488 |
| Pt(ppm) | 0.011 | | 0.014 | | 0.014 | | 0.013 | 0.017 |
| Fe(ppm) | 24.050 | | 3.309 | | 0.494 | | 0.462 | 0.409 |

Reaction testing data, platinum leaching data, and iron leaching data for the 750° C./2% Pt/4% Fe catalyst are set forth in Table 22.

TABLE 22

| Cycle | 1 | 2 | 3 | 4 | 5 | 6 | 7 | 8 | 9 |
|---|---|---|---|---|---|---|---|---|---|
| Total $CO_2$ (cc) | 1812.9 | 1786.8 | 1854.8 | 1901.3 | 1864.6 | 1906.0 | 1921.1 | 1913.3 | 1601.9 |
| End point(min) | 39.92 | 42.58 | 41.42 | 40.25 | 42.58 | 41.83 | 41.50 | 42.00 | 42.55 |
| Maximum $CO_2$ Concentration (%) | 39.2 | 35.8 | 35.7 | 36.3 | 34.5 | 34.9 | 35.6 | 35.0 | 35.2 |
| PMIDA (wt. %) | ND | | 0.009 | | 0.006 | | 0.010 | | 0.064 |
| Glyphosate(wt. %) | 5.275 | | 5.357 | | 5.464 | | 5.471 | | 5.528 |
| IDA(wt. %) | 0.098 | | 0.037 | | 0.033 | | 0.035 | | 0.030 |
| $CH_2O$(ppm) | 2901 | | 2398 | | 2105 | | 2010 | | 2550 |
| HCOOH(ppm) | 6151 | | 6628 | | 6634 | | 6640 | | 6553 |
| Pt(ppm) | 0.013 | | 0.015 | | 0.016 | | 0.016 | | 0.019 |
| Fe(ppm) | 24.870 | | 3.516 | | 0.686 | | 0.476 | | 0.356 |

Reaction testing data, platinum leaching data, and iron leaching data for the 650° C./2% Pt/4% Fe catalyst are set forth in Table 23.

TABLE 23

| Cycle | 1 | 2 | 3 | 4 | 5 | 6 | 7 | 8 | 9 | 10 |
|---|---|---|---|---|---|---|---|---|---|---|
| Total $CO_2$ (cc) | 1782.0 | 1849.5 | 1908.8 | 1897.5 | 1957.4 | 1947.6 | 1878.0 | 1901.6 | 1913.4 | 1602.7 |
| End point(min) | 41.42 | 40.67 | 39.33 | 39.75 | 39.08 | 38.00 | 42.25 | 41.50 | 41.08 | 42.23 |
| Maximum $CO_2$ Concentration (%) | 38.7 | 36.7 | 37.2 | 36.8 | 37.7 | 39.7 | 34.9 | 35.5 | 36.1 | 35.3 |
| PMIDA (wt. %) | ND | | 0.005 | | 0.006 | | 0.005 | | 0.005 | 0.067 |
| Glyphosate(wt. %) | 5.229 | | 5.373 | | 5.394 | | 5.413 | | 5.394 | 5.490 |
| IDA(wt. %) | 0.099 | | 0.045 | | 0.040 | | 0.037 | | 0.036 | 0.036 |
| $CH_2O$(ppm) | 3042 | | 2485 | | 2357 | | 2358 | | 2395 | 2754 |
| HCOOH(ppm) | 6185 | | 6634 | | 6461 | | 6521 | | 6372 | 6512 |
| Pt(ppm) | 0.014 | | 0.016 | | 0.015 | | 0.015 | | 0.015 | 0.019 |
| Fe(ppm) | 25.230 | | 2.754 | | 0.493 | | 0.395 | | 0.422 | 0.332 |

Reaction testing data, platinum leaching data, and iron leaching data for the 550° C./2% Pt/4% Fe catalyst are set forth in Table 24.

TABLE 24

| Cycle | 1 | 2 | 3 | 4 | 5 | 6 | 7 | 8 | 9 |
|---|---|---|---|---|---|---|---|---|---|
| Total $CO_2$ (cc) | 1834.2 | 1842.8 | 1885.9 | 1881.2 | 1876.2 | 1891.8 | 1887.9 | 1842.3 | 1839.5 |
| End point(min) | 38.17 | 39.58 | 38.58 | 39.08 | 40.25 | 39.67 | 40.17 | 42.00 | 42.08 |
| Maximum $CO_2$ Concentration (%) | 41.0 | 38.1 | 38.6 | 38.0 | 36.7 | 37.5 | 37.3 | 35.8 | 35.8 |
| PMIDA (wt. %) | 0.003 | | 0.007 | | 0.006 | | 0.007 | | 0.009 |
| Glyphosate(wt. %) | 5.197 | | 5.376 | | 5.379 | | 5.339 | | 5.341 |
| IDA(wt. %) | 0.095 | | 0.049 | | 0.044 | | 0.041 | | 0.037 |
| $CH_2O$(ppm) | 2670 | | 2306 | | 2018 | | 2236 | | 2425 |
| HCOOH(ppm) | 6221 | | 7076 | | 7141 | | 7100 | | 7033 |
| Pt(ppm) | 0.015 | | 0.015 | | 0.015 | | 0.016 | | 0.016 |
| Fe(ppm) | 27.940 | | 2.972 | | 0.594 | | 0.315 | | 0.406 |

Example 51

The following preparation was conducted under nitrogen protection.

Activated carbon (approximately 10.456 g) and degassed water (approx. 90 g) were placed in a baffled beaker and allowed to mix for approximately 20 minutes.

$FeCl_3.6H_2O$ (2.009 g) was dissolved in degassed water (approx. 40 g) and this solution was then pumped into the baffled beaker over a period of 30 minutes while the pH of the slurry was maintained at 4 by addition of 2.5N NaOH. Upon complete addition of the $FeCl_3.6H_2O$ solution, the pH was raised to 4.5 and the slurry was allowed to mix for 10 minutes. The slurry was then heated to 60° C. over a period of 30 minutes, while the pH was maintained at pH 4.5. The pH of the slurry was then raised to 6.5 over a period of 10 minutes, and allowed to mix for 10 minutes. Ethylene glycol (approx. 1.384 g) was then added to the slurry, and allowed to mix at approximately 60° C. for approximately 10 minutes. The slurry was then filtered, and the wet cake was then re-slurried in degassed deionized water (90 g) and introduced into the baffled beaker.

The pH of the solution was then lowered to 5 by addition of degassed 1M HCl (0.841 g). $K_2PtCl_4$ (0.459 g) was dissolved in degassed water (20 mL). The resulting Pt solution was then added to the baffled beaker over a period of three minutes. The slurry was then allowed to mix at ambient conditions (approximately 22° C.) for 30 minutes, and then heated to a temperature of 60° C. over a period of 10 minutes.

The slurry was filtered, and the wet cake was hot washed twice at 60° C. with approximately 100 mL of degassed water. The resulting sample was then dried in a vacuum oven at 110° C. for 12 hours with a small nitrogen stream.

The catalyst precursor was then heated at elevated temperatures up to approximately 755° C. in the presence of a hydrogen/argon stream (4%/96%; v/v) for approximately 120 minutes.

Example 52

The following preparation was conducted under nitrogen protection.

Activated carbon (approximately 10.456 g) and degassed water (approximately 90 g) were placed in a baffled beaker and allowed to mix for 20 minutes. $FeCl_3.6H_2O$ (2.411 g) was dissolved in degassed water (approximately 41 g) and this solution was then pumped into the baffled beaker over a period of 30 minutes while the pH of the slurry was maintained at 4 by addition of 2.5N NaOH. Upon complete addition of the $FeCl_3.6H_2O$ solution, the pH was raised to 4.5, and allowed to mix for 10 minutes. The slurry was then heated to 60° C. over a period of 25 minutes while the pH was maintained at pH 4.5. The pH of the slurry was then raised to 11 over a period of 30 minutes, and then allowed to mix for 10 minutes.

Ethylene glycol (1.382 g) was then added to the slurry, and allowed to mix at approximately 60° C. for approximately ten minutes. The slurry was then filtered, and the wet cake was then re-slurried in degassed deionized water (90 g) and introduced into the baffled beaker.

The pH of the solution was then lowered to 5 by addition of degassed 1M degassed HCl (3.7 g). $K_2PtCl_4$ (0.552 g) was dissolved in degassed water (20 g) and the Pt solution was then introduced into the baffled beaker over a period of three minutes. The slurry was then allowed to mix at ambient conditions (approximately 22° C.) for 30 minutes and then heated to a temperature of 60° C. over a period of 10 minutes.

The slurry was then filtered, and the wet cake was hot washed twice at 60° C. with approximately 100 mL of degassed water. The sample was then dried in a vacuum oven at 110° C. for 12 hours with a small nitrogen stream.

The catalyst precursor was then heated at elevated temperatures up to approximately 650° C. in the presence of a hydrogen/argon stream (4%/96%; v/v) for approximately 120 minutes.

TABLE 24A

| Cycle | 1 | 2 | 3 | 4 | 5 | 6 | 7 | 8 | 9 | 10 |
|---|---|---|---|---|---|---|---|---|---|---|
| Total $CO_2$ (cc) | 1944.2 | 1977.4 | 2048.3 | 2044.4 | 2055.9 | 2058.7 | 2054.7 | 2065.8 | 2037.7 | 1600.2 |
| End point(min) | 33.58 | 34.92 | 34.08 | 35.58 | 35.50 | 35.58 | 35.42 | 35.25 | 35.83 | 37.67 |
| Maximum $CO_2$ Concentration (%) | 44.5 | 41.3 | 41.8 | 39.8 | 39.5 | 40.0 | 40.2 | 41.0 | 40.6 | 37.8 |
| PMIDA (wt. %) | ND | | 0.005 | | 0.005 | | 0.007 | | 0.007 | 0.106 |
| Glyphosate(wt. %) | 5.121 | | 5.341 | | 5.410 | | 5.378 | | 5.433 | 5.538 |
| IDA(wt. %) | 0.155 | | 0.057 | | 0.048 | | 0.042 | | 0.041 | 0.039 |
| $CH_2O$(ppm) | 2625 | | 2077 | | 1897 | | 1897 | | 1659 | 2602 |

TABLE 24A-continued

| Cycle | 1 | 2 | 3 | 4 | 5 | 6 | 7 | 8 | 9 | 10 |
|---|---|---|---|---|---|---|---|---|---|---|
| HCOOH(ppm) | 5320 | | 5891 | | 5858 | | 5800 | | 5817 | 6283 |
| Pt(ppm) | | 0.019 | | 0.018 | | 0.018 | | 0.018 | 0.018 | 0.022 |
| Fe(ppm) | | 30.170 | | 2.713 | | 0.577 | | 0.372 | 0.331 | 0.541 |

Example 53

The following preparation was conducted under nitrogen protection.

Activated carbon (10.456 g) and degassed water (approximately 90 g) were placed in a baffled beaker and allowed to mix for 20 minutes. $FeCl_3 \cdot 6H_2O$ (2.009 g) was dissolved in degassed water (approximately 41 g) and the resulting solution was pumped into the baffled beaker over a period of 30 minutes while the pH of the slurry was maintained at 4 by addition of 2.5N NaOH. After addition of the $FeCl_3 \cdot 6H_2O$ solution, the pH was raised to 4.5, and allowed to mix for 10 minutes. The slurry was then heated to approximately 50° C. over a period of 32 minutes, while the pH was maintained at pH 4.5. The pH of the slurry was then raised to 8 over a period of 15 minutes, and then allowed to mix for 10 minutes. Ethylene glycol (1.386 g) was then added to the slurry, and allowed to mix at 60° C. for ten minutes. The slurry was then filtered, and the wet cake was then re-slurried in degassed deionized water (90 g) and introduced into the baffled beaker.

The pH of the solution was then lowered to 5 by addition of degassed 0.5M HCl (2.17 g). $K_2PtCl_4$ (0.460 g) was dissolved in degassed water (20 g) and the Pt solution was then introduced into the baffled beaker over a period of three minutes. The slurry was then allowed to mix at room temperature for 30 minutes, and then heated to a temperature of 60° C. over a period of 10 minutes. The slurry was then filtered, and the wet cake hot washed twice at 60° C. with approximately 100 mL of degassed water. The sample was then dried in a vacuum oven at 110° C. for 12 hours with a small nitrogen stream.

The catalyst precursor was then heated at elevated temperatures up to approximately 550° C. in the presence of a hydrogen/argon stream (4%/96%; v/v) for approximately 120 minutes.

Example 54

This example details preparation of a catalyst having a nominal Pt content of 2 wt. % and a nominal iron content of 4 wt. % on an activated carbon support having a Langmuir surface area of approximately 1500 m²/g. The following preparation was conducted under nitrogen protection.

Activated carbon (approximately 10.458 g) and degassed water (approximately 90 g) were mixed in a baffled beaker under a nitrogen atmosphere.

$FeCl_3 \cdot 6H_2O$ (approximately 2.028 g) was dissolved in degassed water (20 g) and this solution was pumped into the baffled beaker over a period of approximately 25 minutes. The pH of the slurry within the baffled beaker was maintained at 4 by introduction of 2.5N degassed NaOH, as necessary. After addition of the $FeCl_3 \cdot 6H_2O$ solution to the beaker was completed, the pH of the slurry was raised to approximately 4.5 by addition of NaOH and the slurry was allowed to mix at ambient conditions (approximately 22° C.) for approximately 10 minutes.

The slurry was then heated to a temperature of approximately 60° C. over a period of approximately 40 minutes. During the heating, the pH was maintained at 4.5 with addition of 2.5N degassed NaOH.

The pH of the slurry was then raised to approximately 7.5 over a period of approximately 15 minutes at a temperature of approximately 60° C., via increases in pH at a rate of approximately 0.5 pH units per 5 minutes. The slurry was then allowed to mix at pH of approximately 7.5 for approximately 10 minutes, and then cooled to ambient conditions (approximately 22° C.)

$K_2PtCl_4$ (approximately 0.460 g) was dissolved in degassed water (approximately 20 g) and the resulting Pt solution was then added to the baffled beaker over a period of approximately 20 minutes. The resulting slurry was allowed to mix for approximately 30 minutes. The thus mixed slurry was then cooled to approximately 60° C. over a period of 45 minutes, and then allowed to mix at 60° C. for 15 minutes.

The resulting slurry was then filtered and then dried in a vacuum oven at approximately 110° C. for approximately 12 hours with a small nitrogen stream to form a Pt/Fe catalyst precursor.

The catalyst precursor was then heated at elevated temperatures up to approximately 950° C. in the presence of a hydrogen/argon stream (2%/98%; v/v) for approximately 120 minutes.

Table 25 sets forth PMIDA reaction testing results, platinum leaching data, and iron leaching data for the 2% Pt/4% Fe finished catalyst.

TABLE 25

| Cycle | 1 | 2 | 3 | 4 | 5 |
|---|---|---|---|---|---|
| Total $CO_2$ (cc) | 2169.6 | 2196.5 | 2147.3 | 2122.5 | 2062.5 |
| End point (min) | 36.42 | 36.08 | 37.83 | 38.42 | 40.00 |
| Maximum $CO_2$ Concentration (%) | 40.5 | 39.7 | 37.8 | 37.5 | 36.4 |
| PMIDA (wt. %) | ND | | 0.008 | | 0.008 |
| Glyphosate (wt. %) | 5.363 | | 5.520 | | 5.461 |
| IDA (wt. %) | 0.087 | 0.030 | 0.021 | | 0.017 |
| $CH_2O$ (ppm) | 1408 | | 1143 | | 1247 |
| HCOOH (ppm) | 5283 | | 5733 | | 5993 |
| Pt (ppm) | 0.122 | | 0.153 | | 0.155 |
| Fe (ppm) | 33.310 | | 0.941 | | 0.491 |

Example 55

This example provides microscopy results (conducted in accordance with Protocol B described in Example 68) for the catalyst precursor prepared as described in Example 54.

Figure 116:
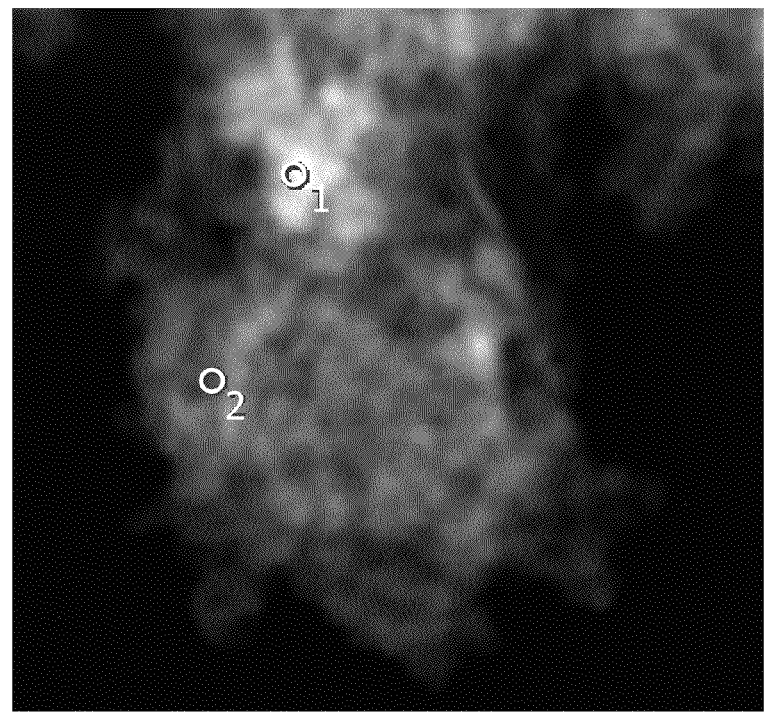
FIG. 116 is a scanning transmission electron microscopy (STEM) micrograph described in Example 55.
Figure 117:
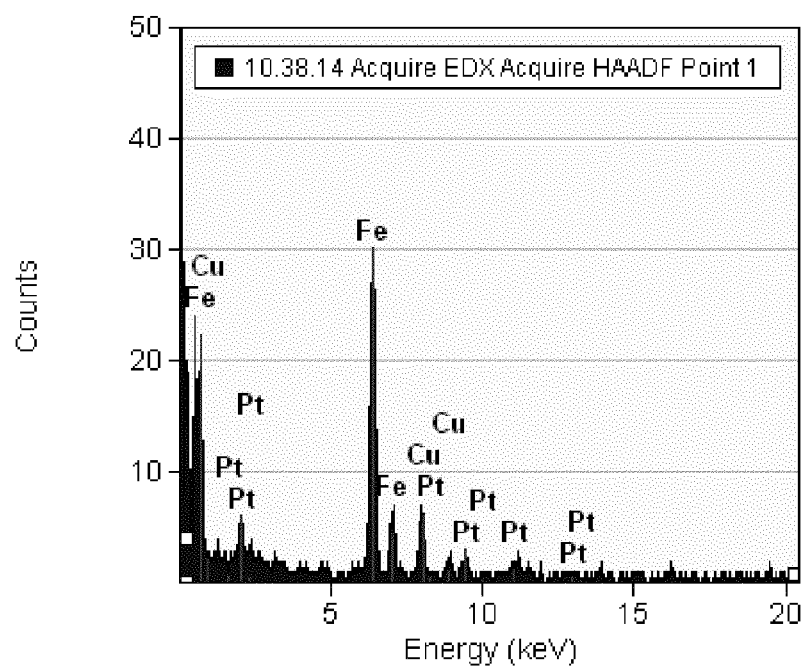
FIGS. 117 and 118 are energy dispersive x-ray (EDX) spectroscopy line scan results described in Example 55.
Figure 118:
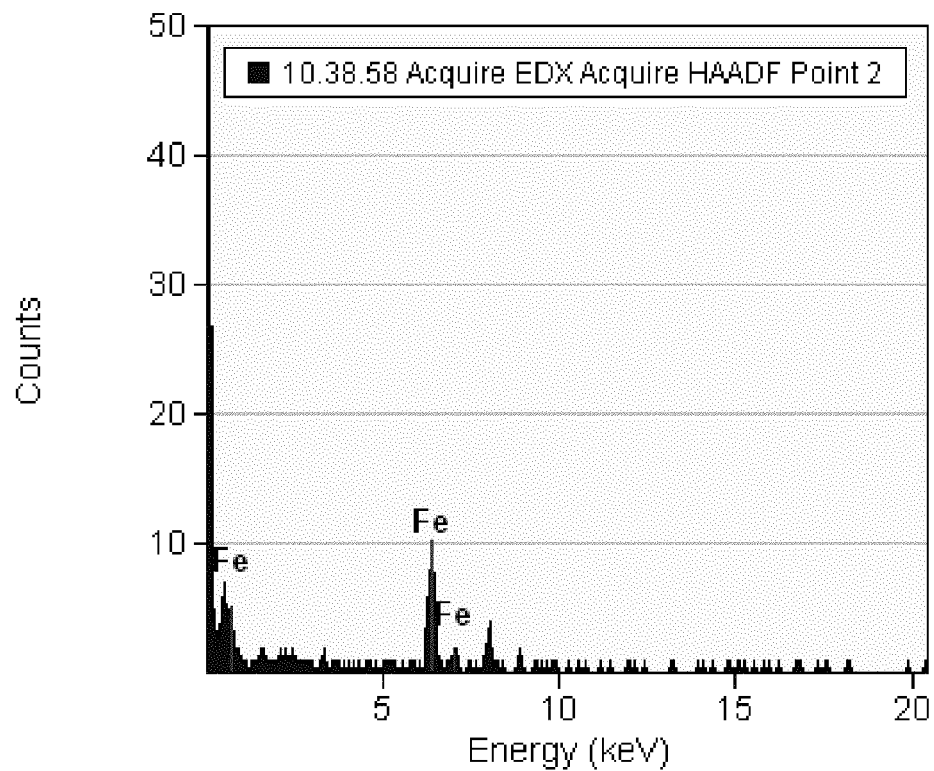

FIG. 116 is a scanning transmission electron microscopy (STEM) micrograph of a portion of the surface of the precursor, including points 1 and 2. FIGS. 117 and 118 are results of energy dispersive x-ray (EDX) spectroscopy analysis for points 1 and 2, respectively. As shown, these portions of the precursor surface included iron well-dispersed throughout, but not all iron had platinum deposited thereon.

Figure 119:
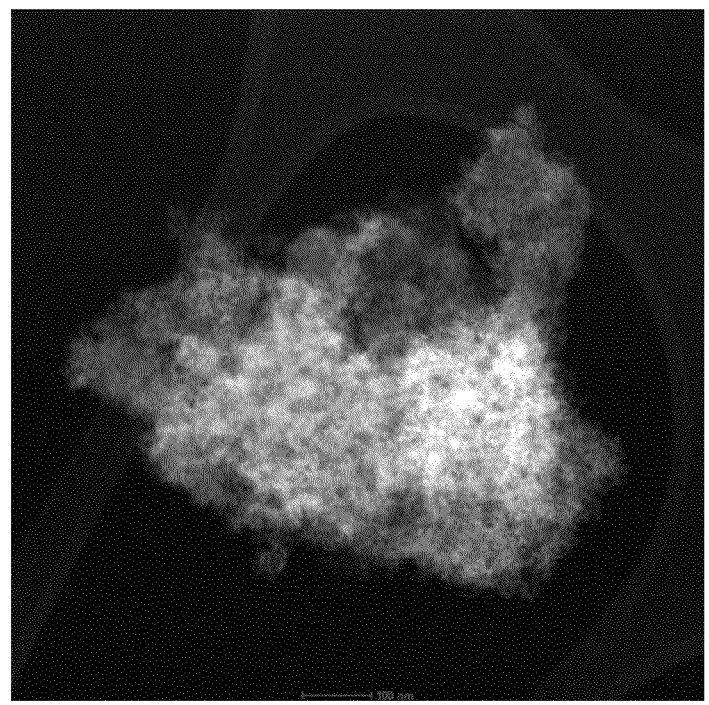
FIGS. 119 and 120 are STEM photomicrographs described in Example 55.
Figure 120:
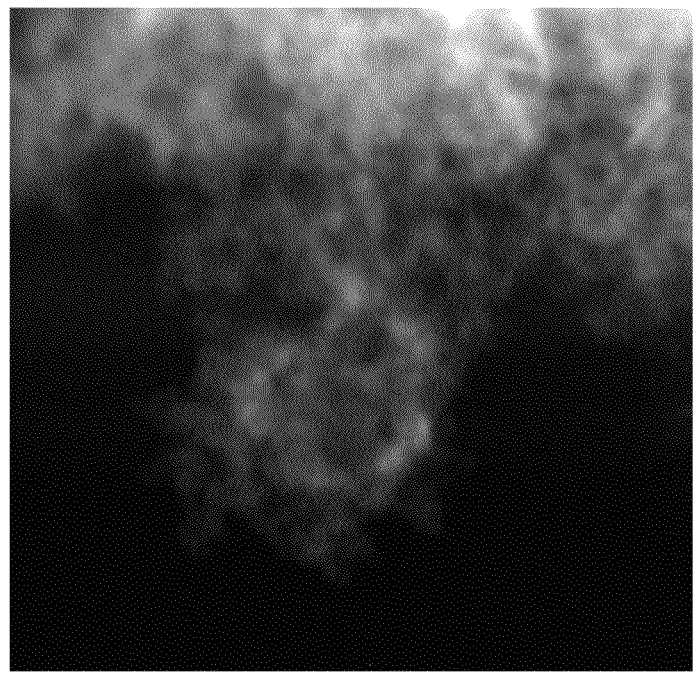

FIGS. 119 and 120 are STEM photomicrographs of a portion of the precursor surface indicating spatial distribution of metal throughout the carbon particle.

Figure 121:
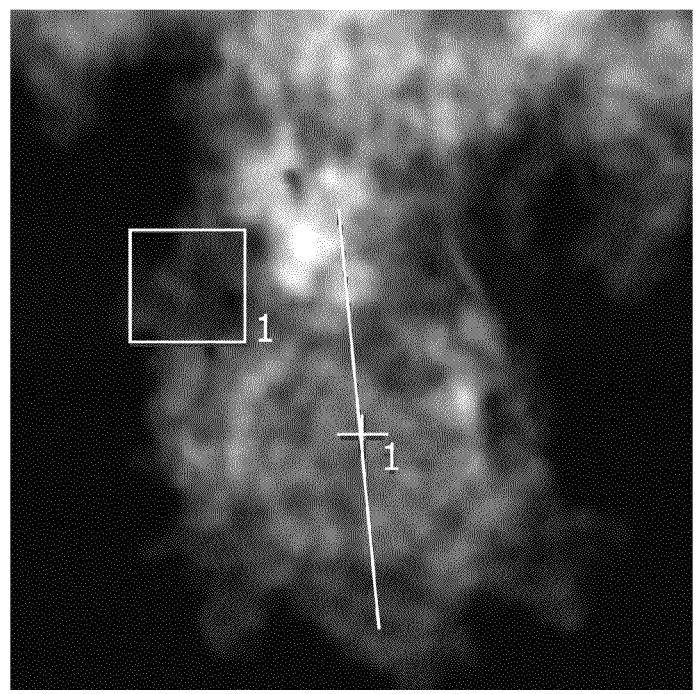
FIG. 121 is an STEM micrograph described in Example 55.
Figure 122:
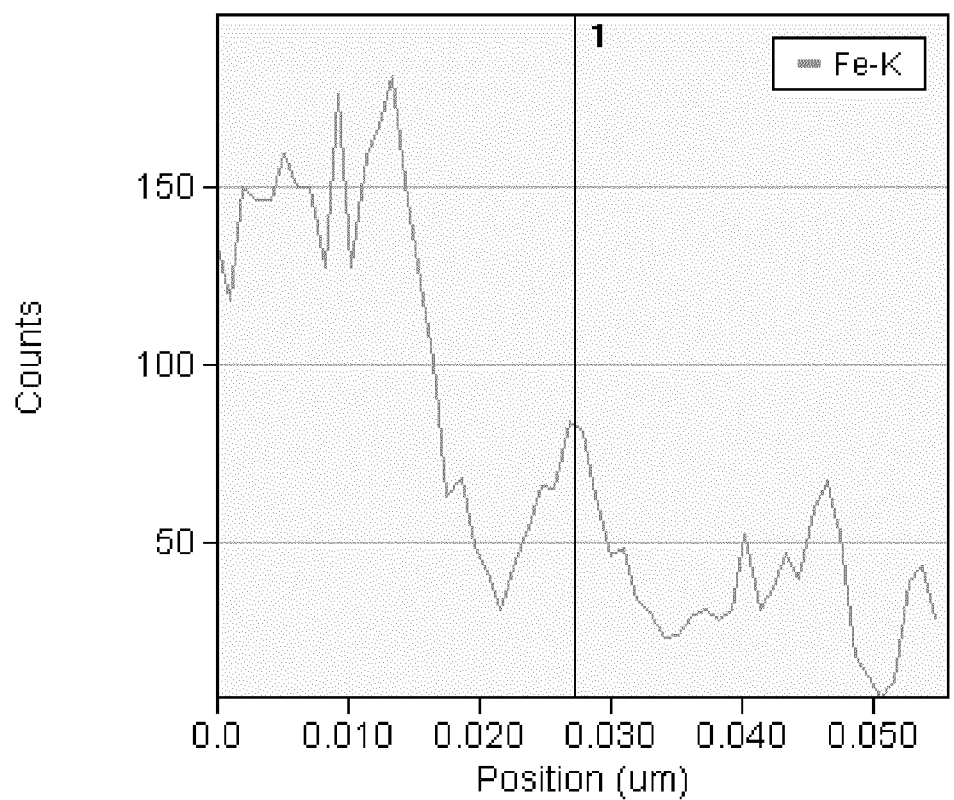
FIG. 122 provides electron energy loss spectroscopy (EELS) line scan results described in Example 55.
Figure 123:
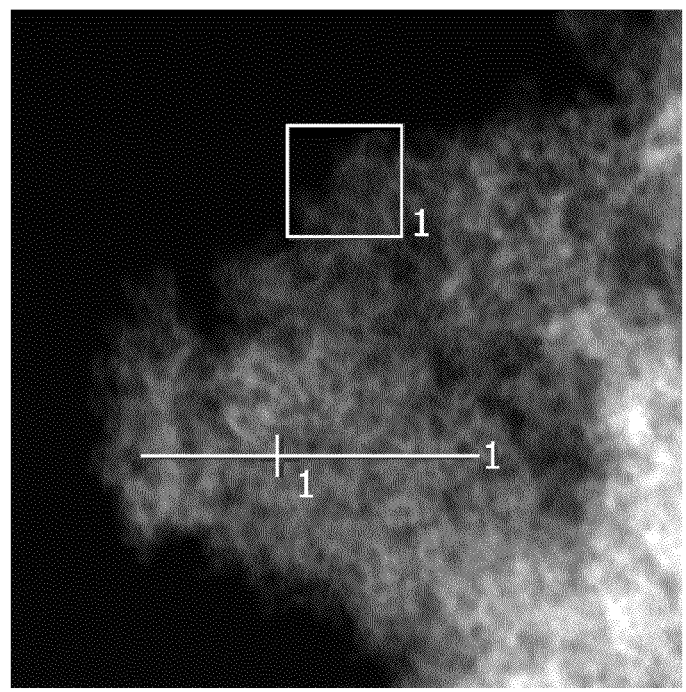
FIG. 123 is an STEM micrograph described in Example 55.
Figure 124:
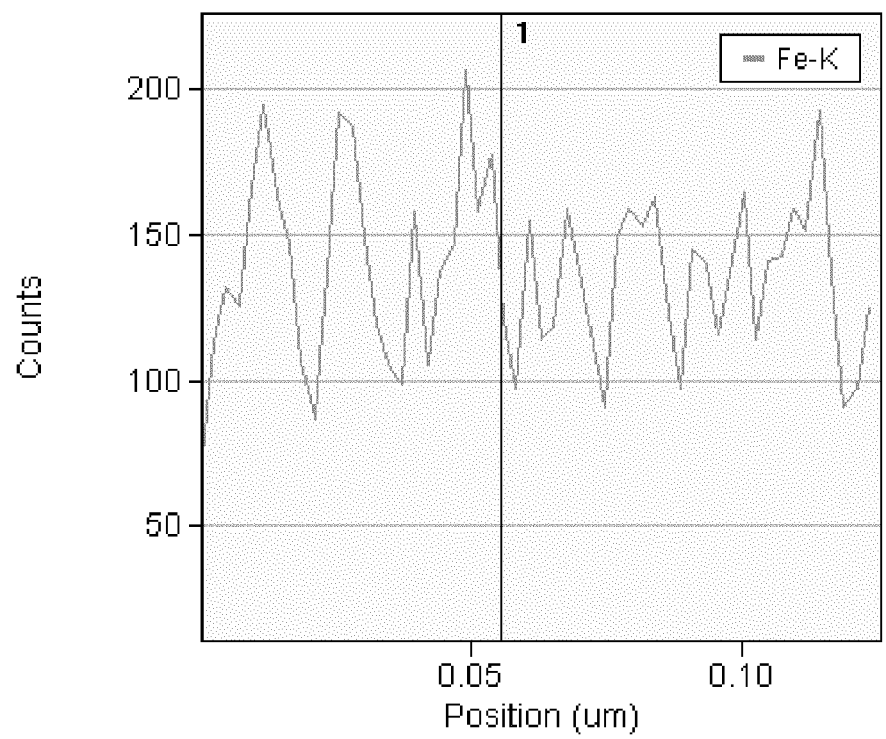
FIG. 124 provides EELS line scan results described in Example 55.
Figure 125:
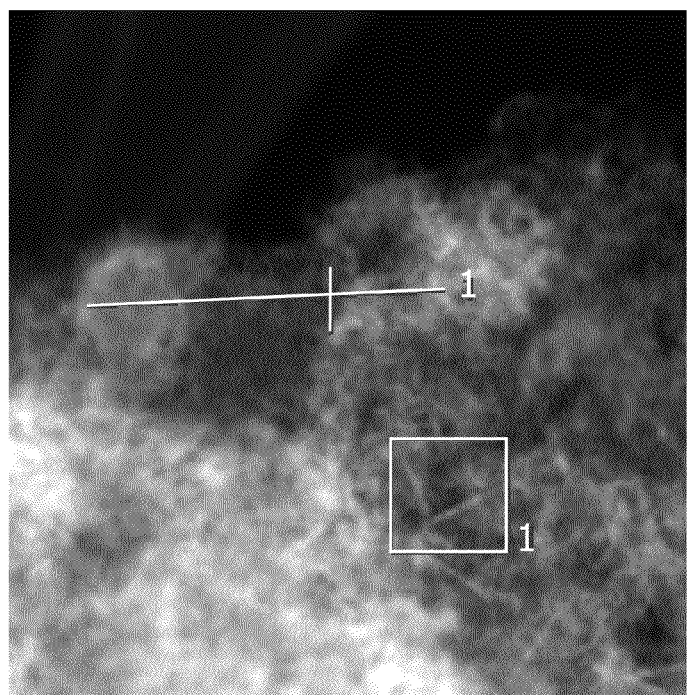
FIG. 125 is an STEM micrograph described in Example 55.
Figure 126:
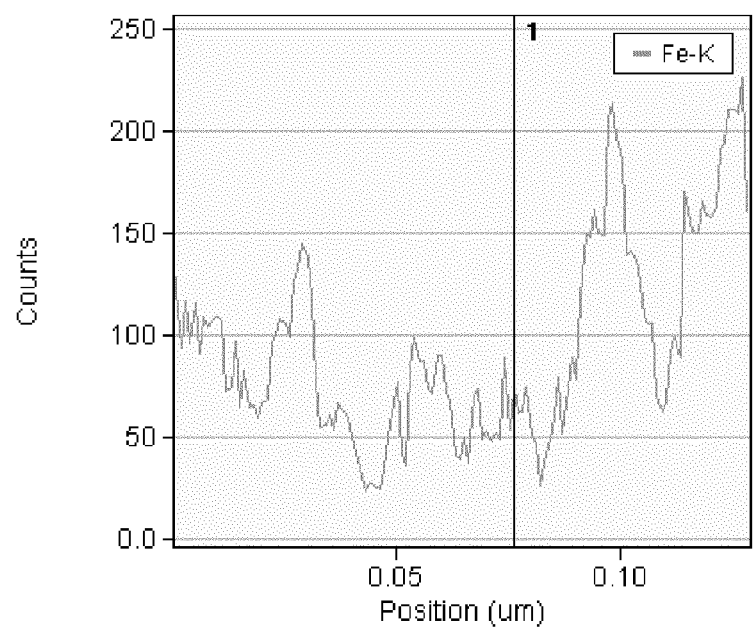
FIG. 126 provides EELS line scan results described in Example 55.

FIGS. 121 and 122 are an STEM micrograph and EELS line scan for a portion of the precursor surface, 1, identified in the micrograph. FIGS. 123 and 124, and 125 and 126 are also pairs of STEM micrographs and EELS line scan analysis. These STEM and EELS results indicate the presence of iron throughout the carbon particle.

Example 56

This example details preparation of a catalyst having a nominal Pt content of 2 wt. % and a nominal iron content of 4 wt. % on an activated carbon support having a Langmuir surface area of approximately 1500 m$^2$/g. The following preparation was conducted under nitrogen protection.

Activated carbon support (approximately 10.457 g) was introduced into a baffled beaker under a nitrogen atmosphere. $FeCl_3.6H_2O$ (approximately 2.013 g) and sucrose (approximately 4.550 g) were dissolved in degassed water (approximately 85 g). 50 wt. % NaOH (approximately 5.225 g) of was added to and mixed with the $FeCl_3.6H_2O$-sucrose solution. The $FeCl_3.6H_2O$-sucrose solution was then poured into the baffled beaker, and allowed to mix. The resulting slurry was then heated to approximately 60° C. over a period of approximately 10 minutes.

Ethylene glycol (approximately 1.263 g) was added to the baffled beaker and allowed to mix with the slurry for approximately ten minutes at approximately 60° C. The slurry was then filtered, and the wet cake was then re-slurried in the baffled beaker in degassed deionized water (approximately 90 g). The pH of the resulting slurry was then lowered to approximately 7 by addition of degassed 2M HCl.

$K_2PtCl_4$ (0.462 g) was dissolved in degassed water (approximately 20 g) to form a platinum solution that was pumped into the baffled beaker over a period of approximately 20 minutes. The resulting slurry was then allowed to mix at ambient conditions (approximately 22° C.) for approximately 30 minutes, and then heated to a temperature of approximately 60° C. over a period of approximately 60 minutes. The final slurry was then filtered and the wet cake was dried in a vacuum oven at approximately 110° C. for approximately 12 hours with a small nitrogen stream to form a Pt/Fe catalyst precursor.

The catalyst precursor was then heated at elevated temperatures up to approximately 900° C. in the presence of a hydrogen/argon stream (2%/98%; v/v) for approximately 120 minutes.

Table 26 sets forth PMIDA reaction testing results, platinum leaching data, and iron leaching data for the 2% Pt/4% Fe catalyst.

Example 57

This Example details the results of microscopy analysis (conducted in accordance with Protocol B described in Example 68) for the finished catalyst prepared as described in Example 56.

FIGS. 127-132 include microscopy results for the catalyst after use in PMIDA oxidation testing as described in Example 56.

Figure 127:
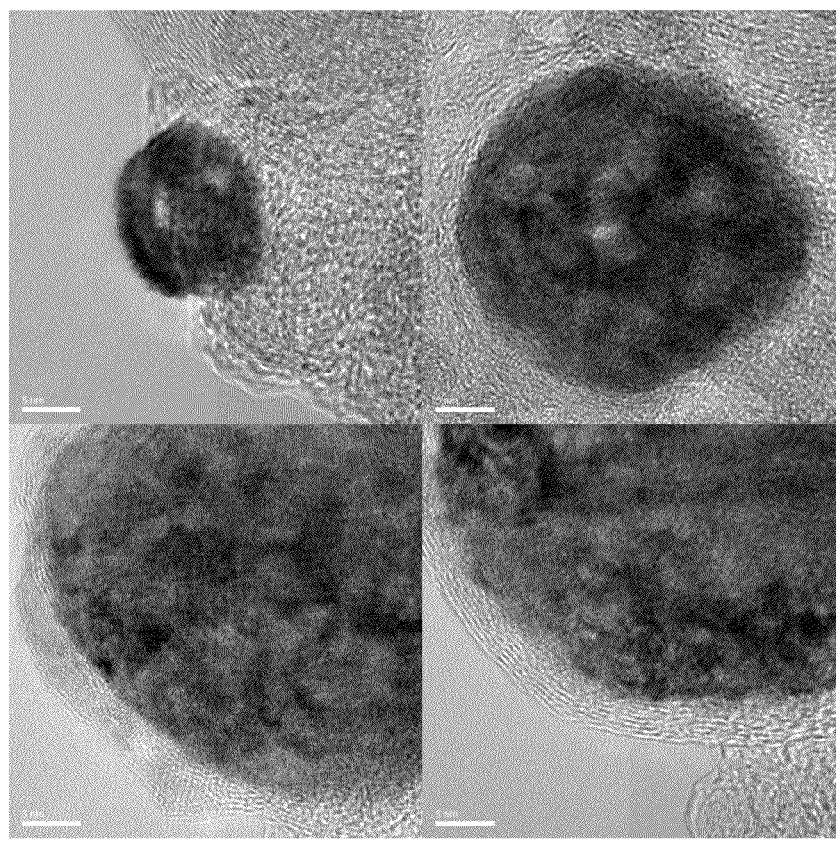
FIG. 127 provides high resolution electron microscopy (HREM) photomicrographs described in Example 57.

FIG. 127 includes four high resolution electron photomicrographs (HREM) for various portions of the spent catalyst surface. These indicate formation of graphite and iron oxide on the outer regions of metal particles. FIG. 128 includes three STEM micrographs, which indicate the presence of nanoporous platinum regions.

Figure 129:
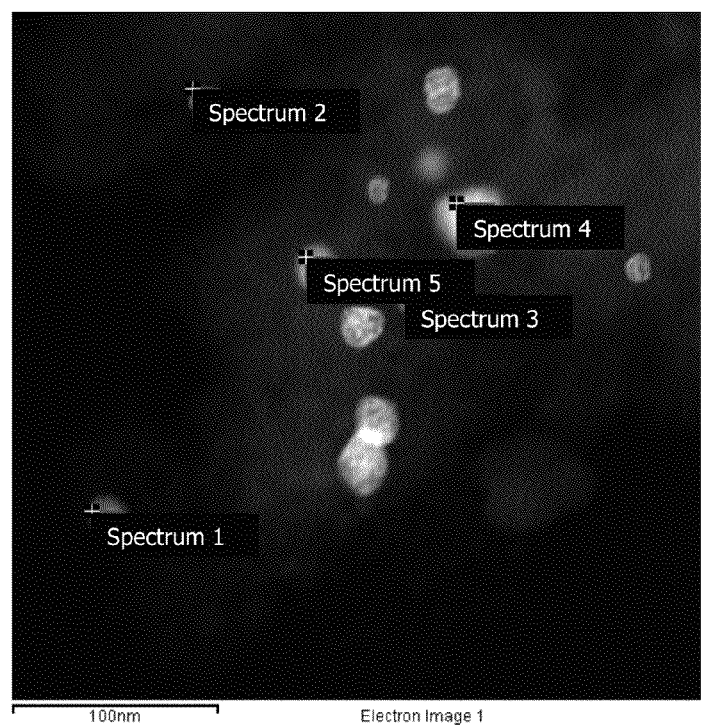
FIG. 129 is an STEM micrograph described in Example 57.
Figure 130:
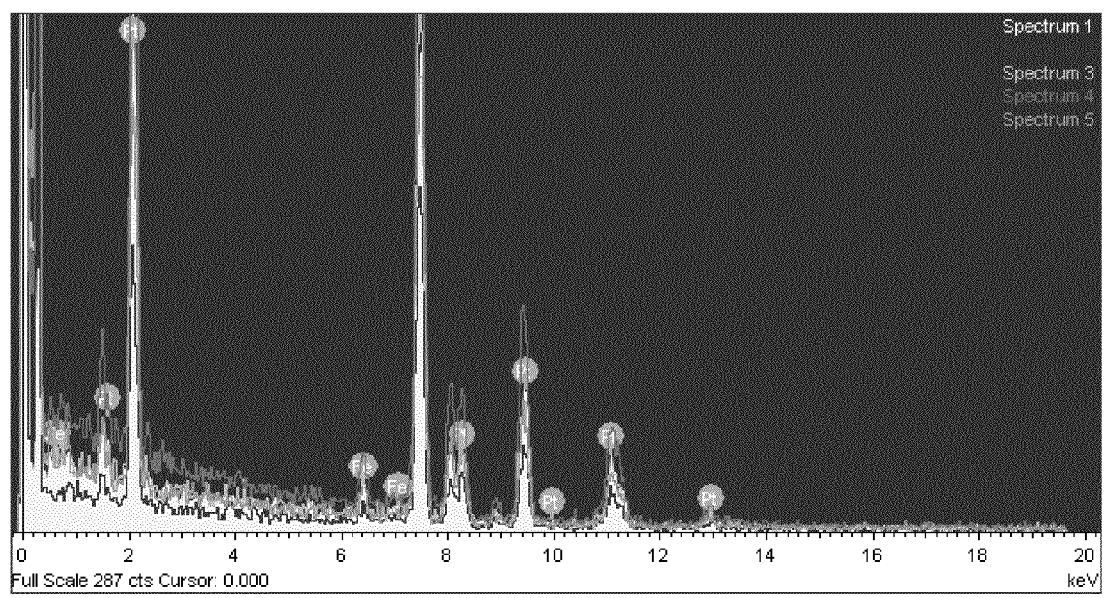
FIG. 130 provides EDX line scan analysis results described in Example 57.

FIG. 129 is an STEM micrograph showing various portions of the spent catalyst surface that were analyzed by EDX analysis. The results of the EDX analysis are shown in FIG. 130, which indicates the presence of a platinum-rich composition.

Figure 131:
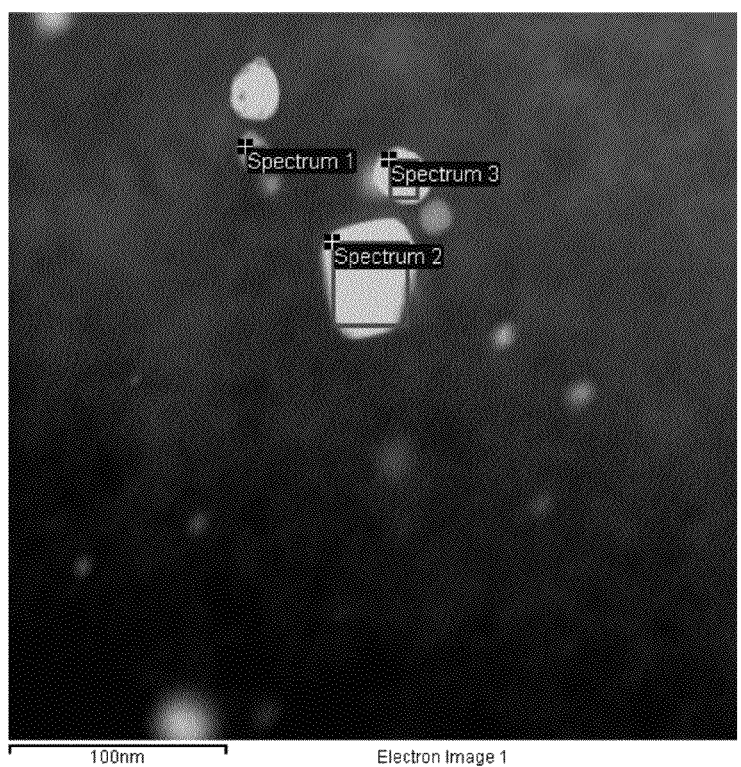
FIG. 131 is an STEM micrograph described in Example 57.
Figure 132:
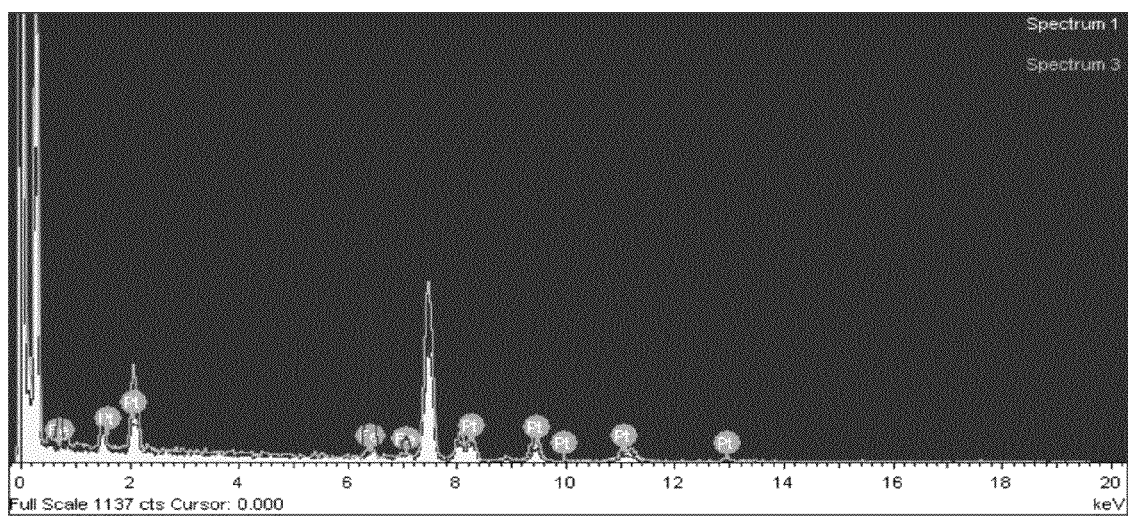
FIG. 132 provides EDX line scan analysis results described in Example 57.

FIG. 131 is also an STEM micrograph and FIG. 132 the results of EDX analysis for the portions of the spent catalyst surface. These results indicate the presence of varying metal compositions.

FIGS. 133-137 include microscopy results for the finished catalyst prepared as described in Example 56, but prior to reaction testing.

Figure 133:
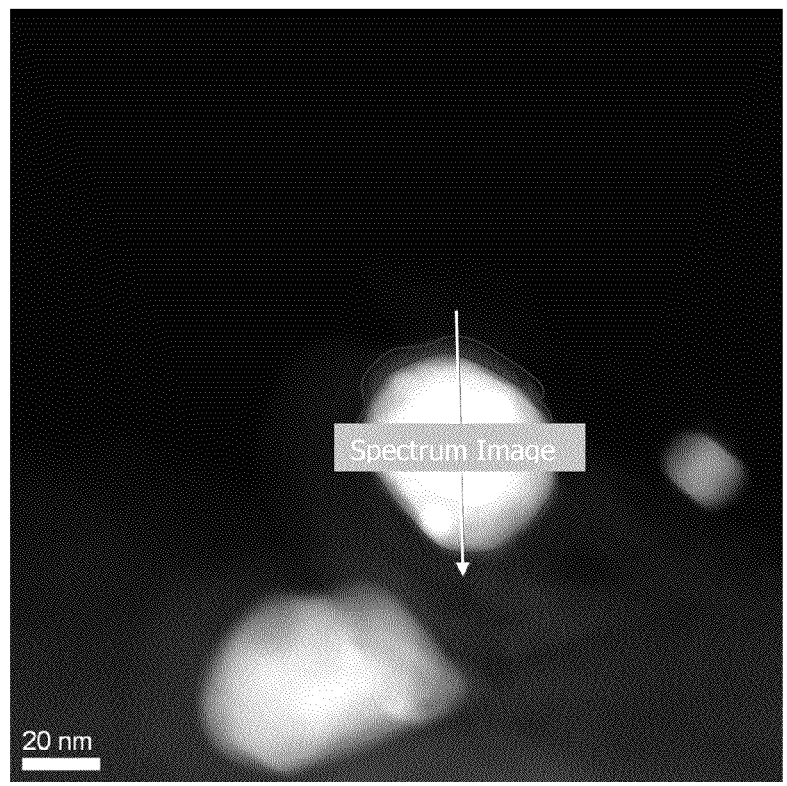
FIG. 133 is an STEM photomicrograph described in Example 57.
Figure 134:
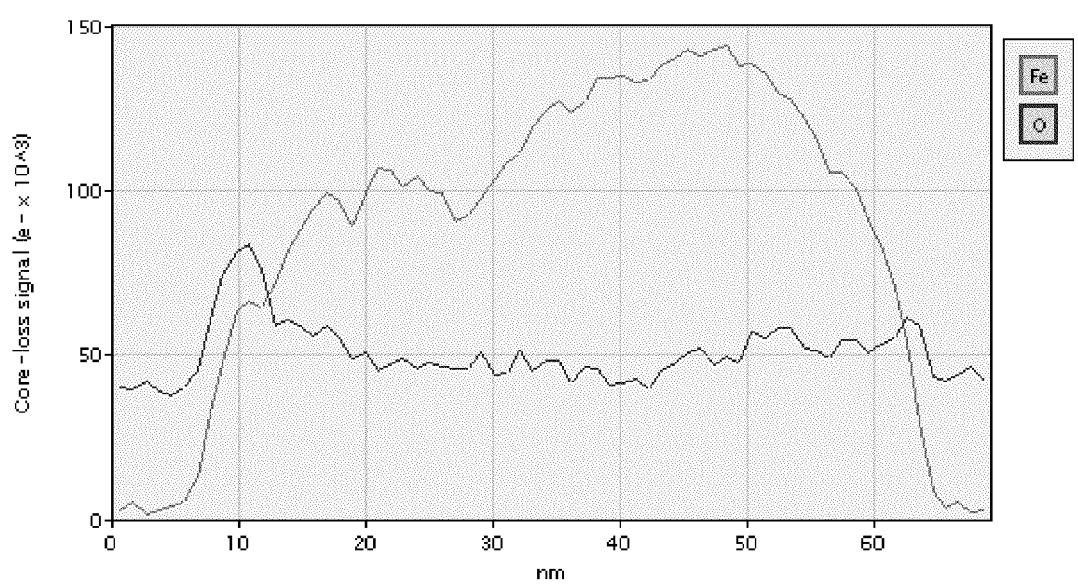
FIG. 134 provides results of EELS line scan analysis described in Example 57.

FIG. 133 is an STEM photomicrograph identifying a particle to be analyzed by EELS line scan analysis, the results of which are shown in FIG. 134. As shown in FIG. 134, a partial shell of iron oxide was detected.

Figure 135:
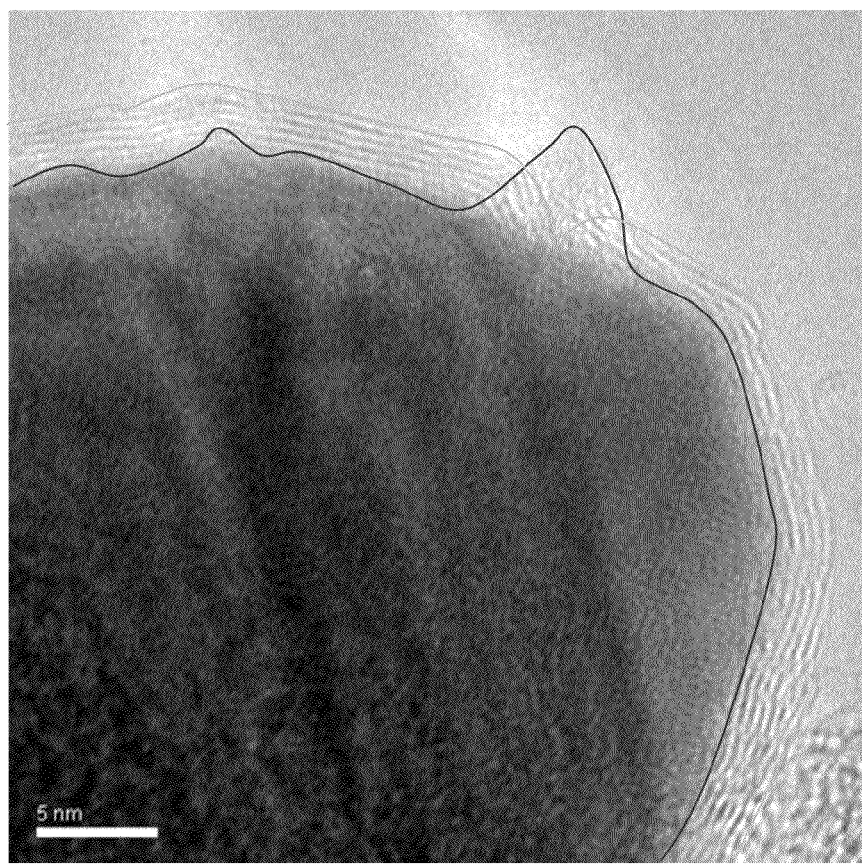
FIGS. 135-137 are HREM photomicrographs described in Example 57.

FIG. 135 is an HREM photomicrograph highlighting Pt lattice regions. As shown in FIG. 135, the particle identified included no more than about 4 Pt lattice fringes. It is currently believed that each lattice fringe corresponds to a layer of platinum atoms. That is, the particle identified included a layer of platinum no more than about 4 platinum atoms thick.

Figure 136:
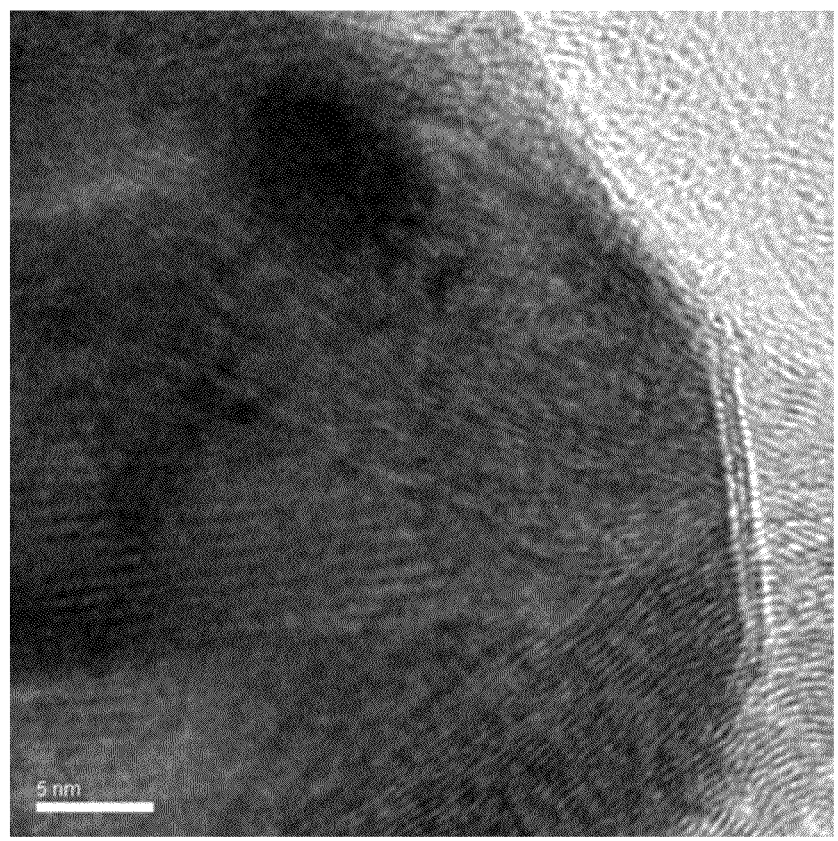
Figure 137:
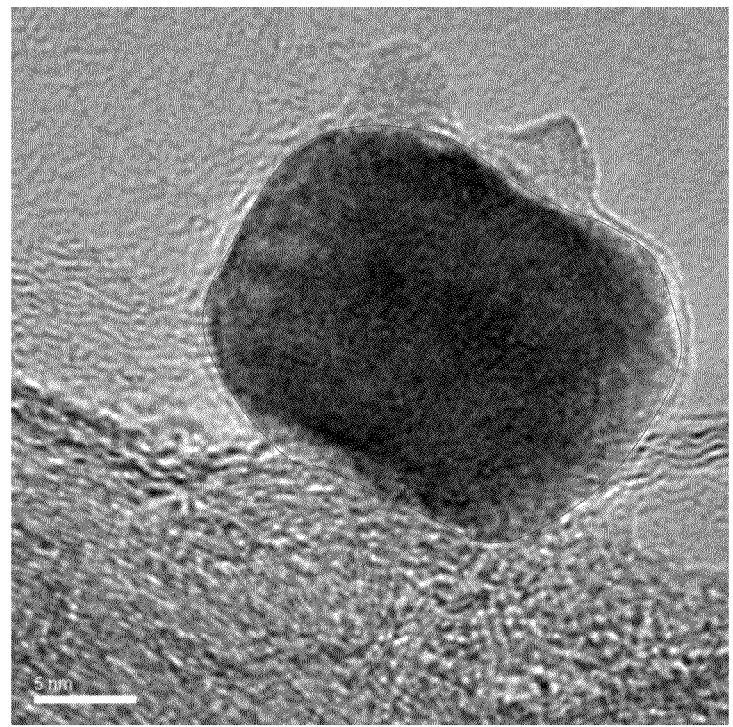

FIGS. 136 and 137 are HREM photomicrographs identifying two layers of platinum atoms.

Figure 138:
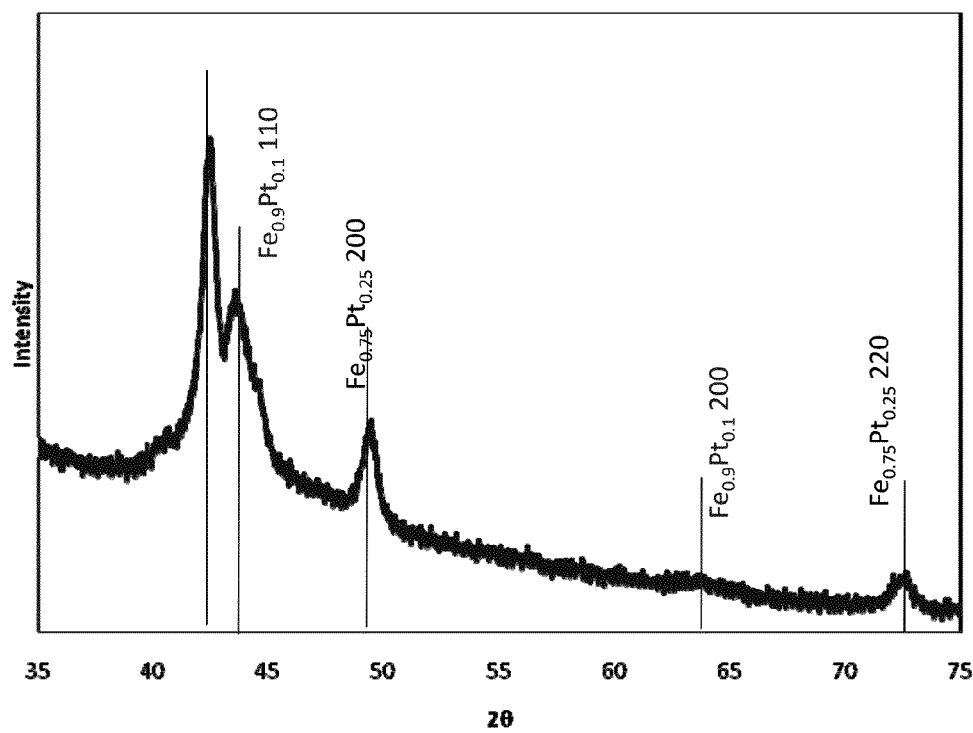
FIG. 138 provides XRD results described in Example 57.

FIG. 138 provides XRD analysis results, which indicate formation of an $Fe_{0.75}Pt_{0.25}$ phase.

Example 58

This example details preparation of a catalyst precursor having a nominal Pt content of 2 wt. % and a nominal iron content of 4 wt. % on an activated carbon support having a Langmuir surface area of approximately 1500 m$^2$/g. The following preparation was conducted under nitrogen protection.

TABLE 26

| Cycle | 1 | 2 | 3 | 4 | 5 | 6 | 7 | 8 | 9 | 10 |
|---|---|---|---|---|---|---|---|---|---|---|
| Total CO$_2$ (cc) | 1765.8 | 1812.5 | 1881.3 | 1908.2 | 1926.6 | 1877.7 | 1891.9 | 1878.2 | 1871.1 | 1603.1 |
| End point(min) | 44.08 | 43.50 | 41.92 | 42.25 | 41.58 | 43.67 | 43.08 | 43.83 | 43.67 | 43.92 |
| Maximum CO$_2$ Concentration (%) | 36.3 | 34.7 | 35.4 | 34.8 | 35.6 | 33.9 | 34.6 | 33.8 | 34.3 | 33.9 |
| PMIDA (wt. %) | 0.005 | | 0.009 | | 0.010 | | 0.009 | | 0.011 | 0.074 |
| Glyphosate(wt. %) | 5.326 | | 5.397 | | 5.348 | | 5.448 | | 5.423 | 5.568 |
| IDA(wt. %) | 0.081 | | 0.038 | | 0.032 | | 0.028 | | 0.028 | 0.027 |
| CH$_2$O(ppm) | 3191 | | 2588 | | 2311 | | 2559 | | 2620 | 2915 |
| HCOOH(ppm) | 6079 | | 6290 | | 6124 | | 6123 | | 6018 | 6223 |
| Pt(ppm) | <0.01 | | 0.014 | | 0.016 | | 0.014 | | 0.015 | 0.018 |
| Fe(ppm) | 55.230 | | 3.238 | | 0.694 | | 0.751 | | 0.457 | 0.454 |

Activated carbon support (approximately 10.456 g) was introduced into a baffled beaker under a nitrogen atmosphere. $FeCl_3.6H_2O$ (approximately 2.011 g) and sucrose (approximately 4.511 g) were dissolved in degassed water (approximately 91.1 g). 50 wt. % NaOH (approximately 5.214 g) was added to and mixed with the $FeCl_3.6H_2O$-sucrose solution. The $FeCl_3.6H_2O$-sucrose solution was then poured into the baffled beaker, and allowed to mix with the activated carbon support. The resulting slurry was then heated to approximately 40° C. over a period of approximately 10 minutes.

Ethylene glycol (approximately 1.309 g) was added to the baffled beaker and allowed to mix with the slurry for approximately ten minutes at approximately 40° C. The slurry was then filtered, and the wet cake was then re-slurried in the baffled beaker in degassed deionized water (90 g). The pH of the resulting slurry was then adjusted/lowered to approximately 7 by addition of degassed 2M HCl (1.52 g).

$K_2PtCl_4$ (approximately 0.461 g) was dissolved in degassed water (20 g) to form a platinum solution that was introduced into the baffled beaker over a period of 3 minutes. The resulting slurry was then allowed to mix at approximately 25° C. for approximately 30 minutes, and then heated to a temperature of approximately 60° C. over a period of approximately 40 minutes.

degassed deionized water (90 g) at a temperature of approximately 12° C. The pH of the resulting solution was then lowered to approximately 7 by addition of degassed 2M HCl (approximately 0.645 g) and 1M HCl (approximately 0.461 g).

$K_2PtCl_4$ (approximately 0.461 g) was dissolved in cold degassed water (approximately 20 g) at a temperature of approximately 12° C. The platinum solution was then pumped into the baffled beaker over a period of approximately 20 minutes.

The final slurry was then filtered and the wet cake was dried in a vacuum oven at approximately 110° C. for approximately 12 hours with a small nitrogen stream to form a Pt/Fe catalyst precursor.

The catalyst precursor was then heated at elevated temperatures up to approximately 755° C. in the presence of a hydrogen/argon stream (4%/96%; v/v) for approximately 120 minutes.

Table 27 sets forth PMIDA reaction testing results, platinum leaching data, and iron leaching data for the 2% Pt/4% Fe finished catalyst.

TABLE 27

| Cycle | 1 | 2 | 3 | 4 | 5 | 6 | 7 | 8 | 9 | 10 |
|---|---|---|---|---|---|---|---|---|---|---|
| Total $CO_2$ (cc) | 1776.6 | 1830.6 | 1877.3 | 1898.8 | 1846.8 | 1868.2 | 1853.1 | 1825.1 | 1827.8 | 1600.2 |
| End point(min) | 44.75 | 44.92 | 43.67 | 44.00 | 46.25 | 45.75 | 46.25 | 47.42 | 47.00 | 48.50 |
| Maximum $CO_2$ Concentration (%) | 35.6 | 33.5 | 33.7 | 33.7 | 32.5 | 32.8 | 32.6 | 32.0 | 32.7 | 31.7 |
| PMIDA (wt. %) | ND | | 0.003 | | 0.005 | | 0.004 | | 0.006 | 0.057 |
| Glyphosate(wt. %) | 5.278 | | 5.463 | | 5.489 | | 5.450 | | 5.508 | 5.516 |
| IDA(wt. %) | 0.079 | | 0.036 | | 0.031 | | 0.029 | | 0.029 | 0.029 |
| $CH_2O$(ppm) | 3702 | | 2914 | | 2366 | | 2434 | | 2422 | 2756 |
| HCOOH(ppm) | 5549 | | 6036 | | 5987 | | 5882 | | 5850 | 5842 |
| Pt(ppm) | 0.016 | 0.016 | 0.018 | | 0.019 | | 0.017 | | 0.017 | 0.022 |
| Fe(ppm) | 36.130 | 11.570 | 2.818 | | 0.552 | | 0.456 | | 0.423 | 0.375 |

The final slurry was then filtered and the wet cake was washed twice by contact with degassed water (approximately 100 g) at a temperature of approximately 60° C. The wet cake was dried in a vacuum oven at approximately 110° C. for approximately 12 hours with a small nitrogen stream to form a Pt/Fe catalyst precursor.

Example 59

This example details preparation of a catalyst having a nominal Pt content of 2 wt. % and a nominal iron content of 4 wt. % on an activated carbon support having a Langmuir surface area of approximately 1500 $m^2$/g. The following preparation was conducted under nitrogen protection.

Activated carbon support (approximately 10.456 g) was introduced into a baffled beaker under a nitrogen atmosphere. $FeCl_3.6H_2O$ (approximately 2.011 g) and sucrose (approximately 4.513 g) were dissolved in degassed water (approximately 91 g). 50 wt. % NaOH (approximately 5.25 g) was added to and mixed with the $FeCl_3.6H_2O$-sucrose solution. The $FeCl_3.6H_2O$-sucrose solution was then poured into the baffled beaker, and allowed to mix with the activated carbon support.

Ethylene glycol (approximately 1.31 g) was added to the baffled beaker and the resulting slurry was heated to a temperature of approximately 30° C. over a period of approximately 15 minutes. The slurry was then filtered, and the wet cake was then re-slurried in the baffled beaker in cold Example 60

FIGS. 139-148 include microscopy results (conducted in accordance with Protocol B described in Example 68) for the finished catalyst prepared as described in Example 59.

Figure 139:
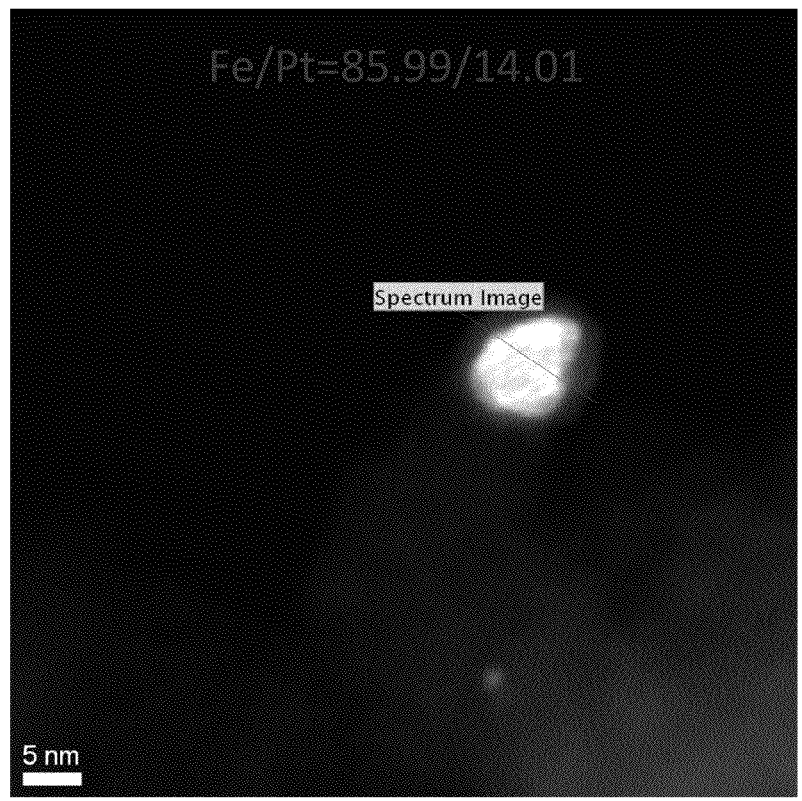
FIG. 139 is an STEM micrograph described in Example 60.
Figure 140:
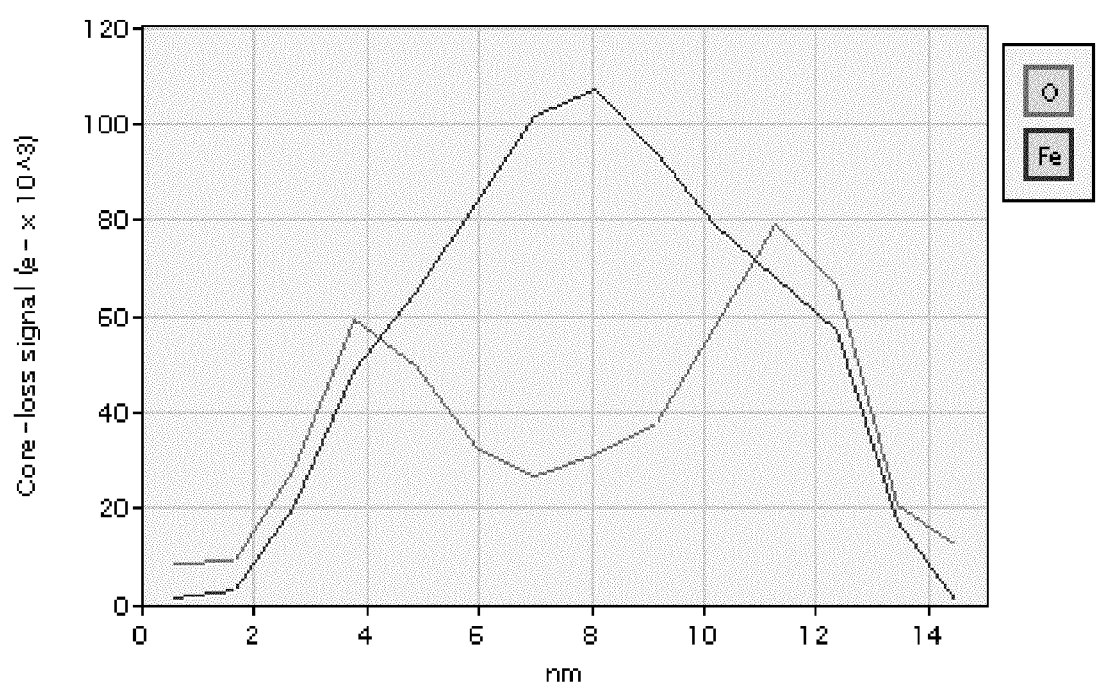
FIG. 140 provides results of EELS line scan analysis described in Example 60.

FIG. 139 is an STEM micrograph identifying the particle analyzed by EELS line scan analysis, the results of which are shown in FIG. 140. As shown in FIG. 139, the Fe:Pt atomic ratio of the particle analyzed was 85.99/14.01. The line scan results of FIG. 140 indicate formation of an iron oxide outer layer.

Figure 141:
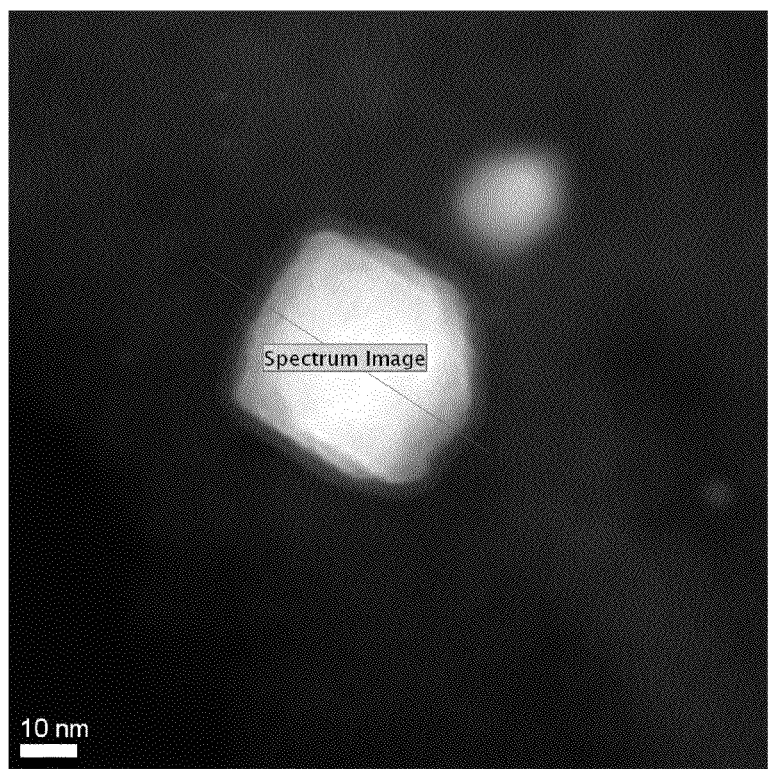
FIG. 141 is an STEM micrograph described in Example 60.
Figure 142:
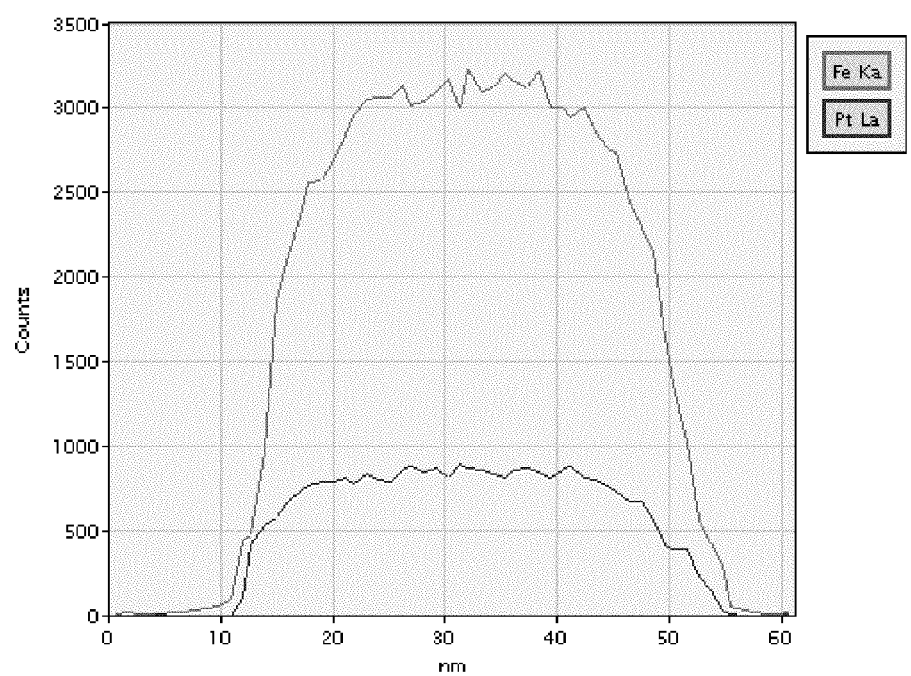
FIG. 142 provides EDX line scan analysis results described in Example 60.

FIG. 141 is an STEM micrograph indicating the particle that was analyzed by EDX line scan analysis, the results of which are shown in FIG. 142. The line scan results indicate a relatively constant platinum signal, suggesting a very thin platinum shell, i.e., varying by no more than about 25% during the scan across the particle (e.g., from about 17.5 nm to about 46 nm along the scanning line. As also shown in FIG. 142, the variation in the magnitude of the iron signal during the scan across the particle is proportionally greater than the variation in the platinum signal during the scan across the particle (i.e., on the order of at least about 1.5:1).

Figure 143:
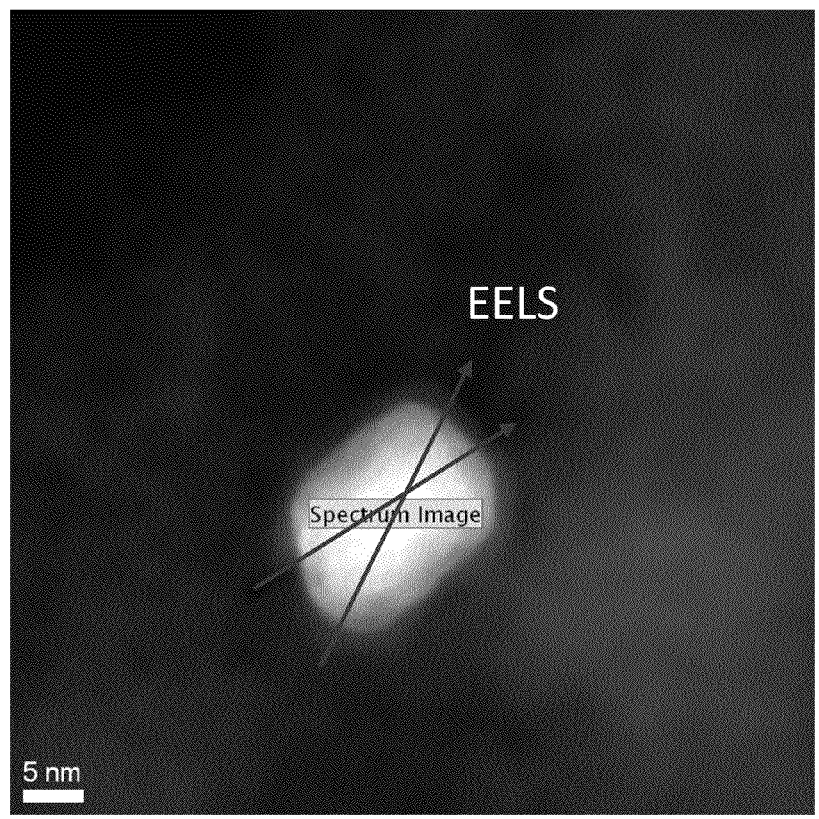
FIG. 143 is an STEM micrograph described in Example 60.
Figure 144:
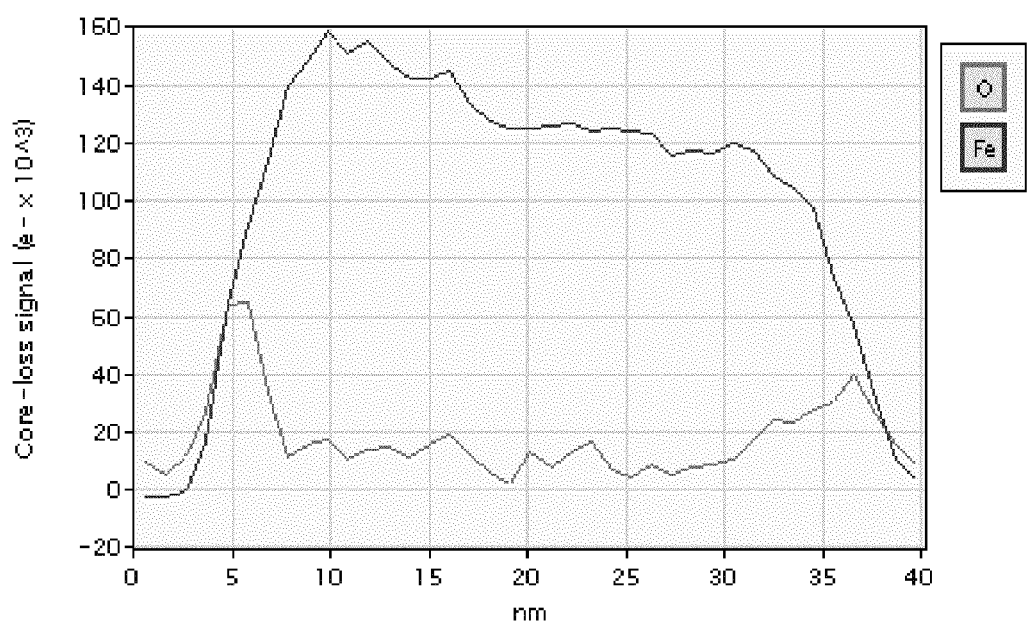
FIG. 144 provides results of EELS line scan analysis described in Example 60.
Figure 145:
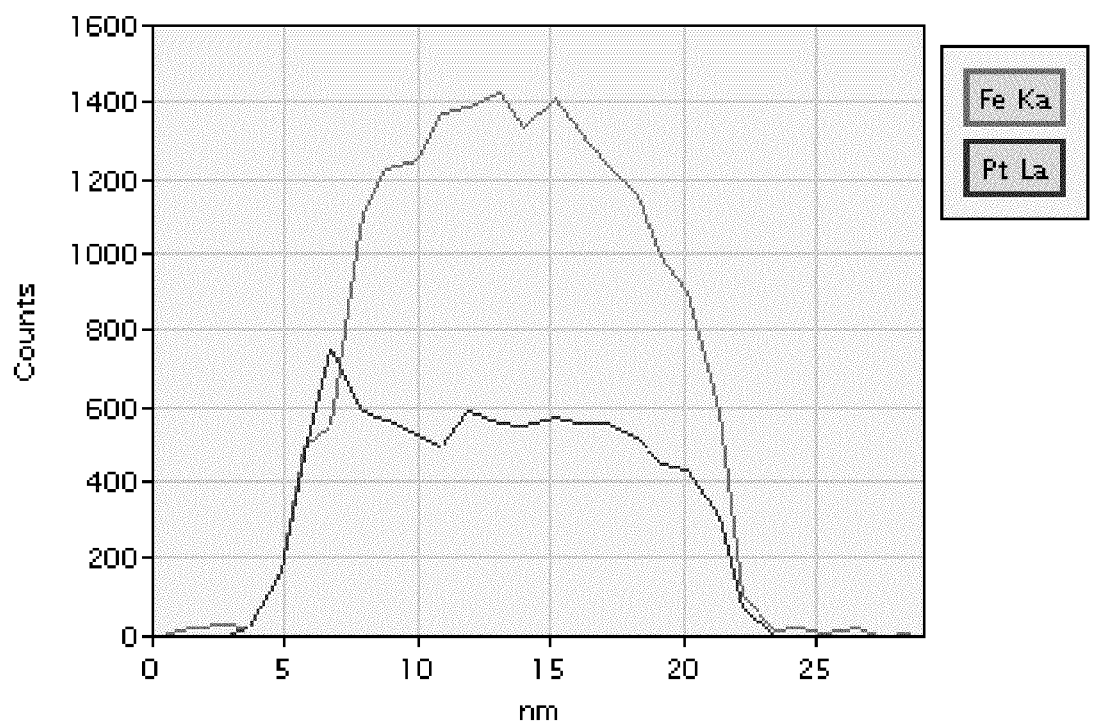
FIG. 145 provides EDX line scan analysis results described in Example 60.

FIG. 143 is an STEM micrograph and FIGS. 144 and 145 the corresponding EELS line scan analysis and EDX line scan analysis, respectively. The EELS line scan results indicate the presence of an iron oxide layer. The EDX line scan results indicate the presence of a thin platinum shell.

Figure 146:
FIG. 146 is an STEM micrograph described in Example 60.
Figure 147:
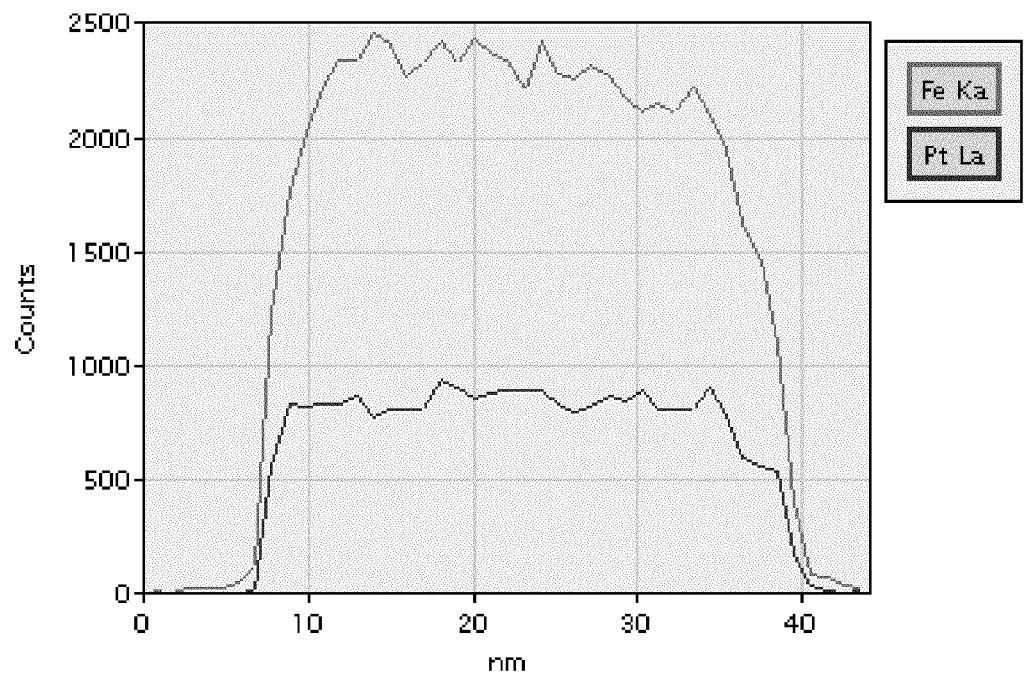
FIG. 147 provides EDX line scan analysis results described in Example 60.

FIG. 146 is an STEM micrograph and FIG. 147 the corresponding EDX line scan analysis. The line scan results indicate a relatively constant platinum signal, i.e., ranging by no more than about 25% during the scan across the particle from about 9 nm to about 35 nm along the scanning line and a greater variation in the magnitude of the iron signal as compared to the variation in the platinum signal (i.e., on the order of about 1.5:1).

Figure 148:
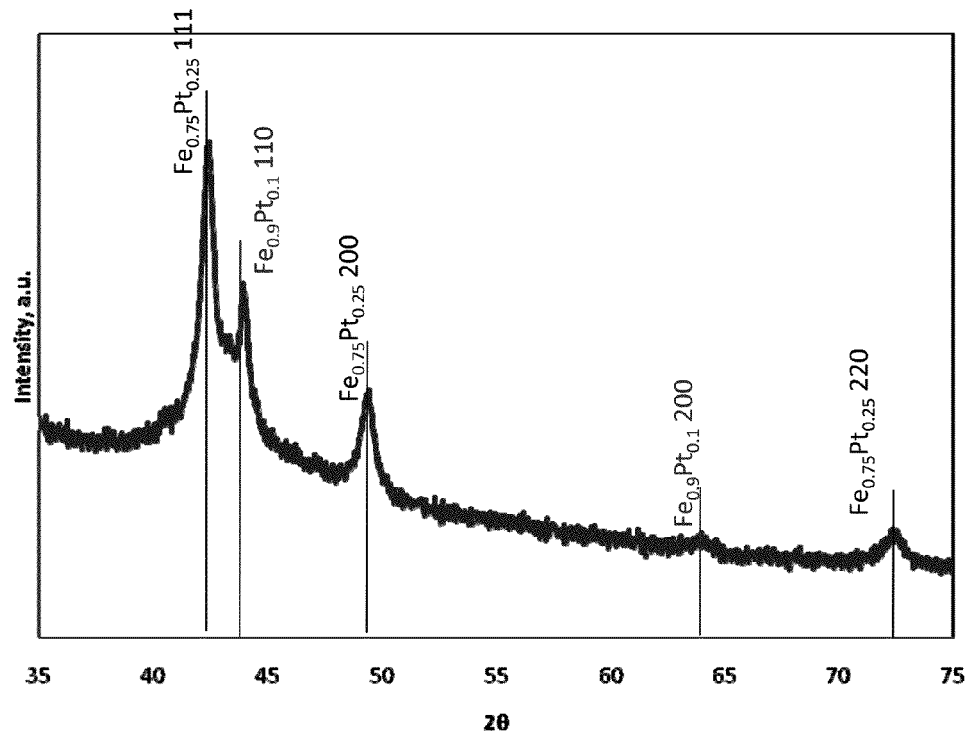
FIG. 148 provides XRD results described in Example 60.

FIG. 148 provides XRD results of analysis conducted as described in Example 69. These results indicate formation of an $Fe_{0.75}Fe_{0.25}$ phase.

FIGS. 149-153 are microscopy results for the spent catalyst (i.e., after testing in PMIDA oxidation).

Figure 149:
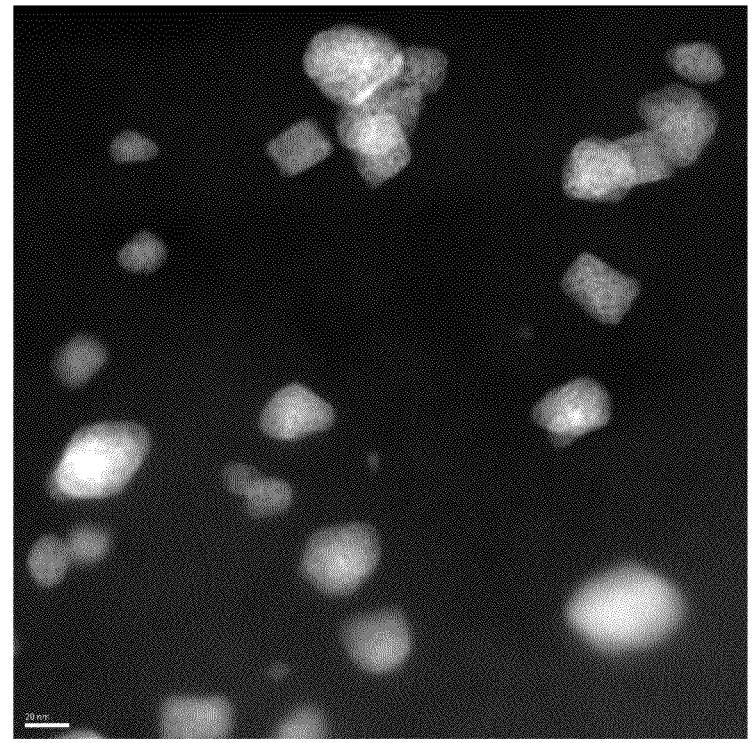
FIGS. 149 and 150 are STEM micrographs described in Example 60.

FIG. 149 is an STEM micrograph showing various porous metal particles at the spent catalyst surface.

Figure 150:
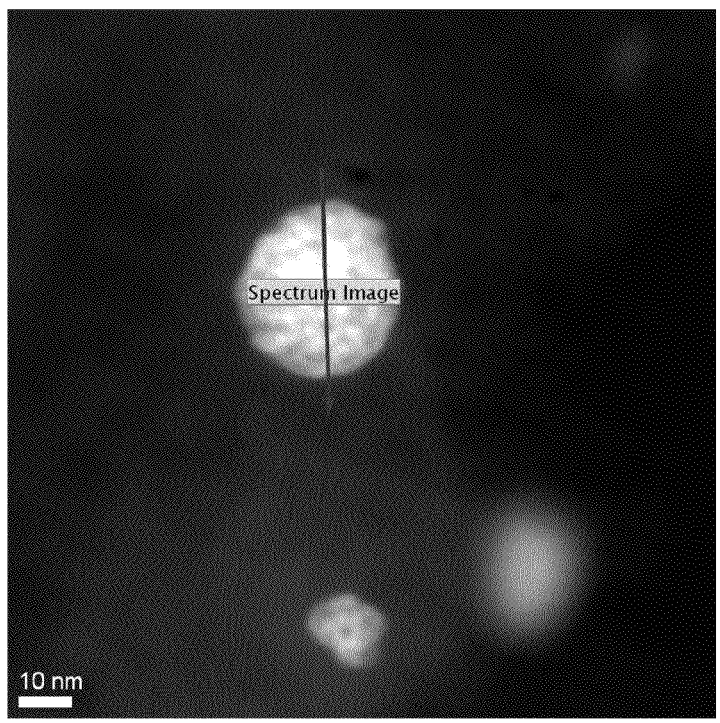
Figure 151:
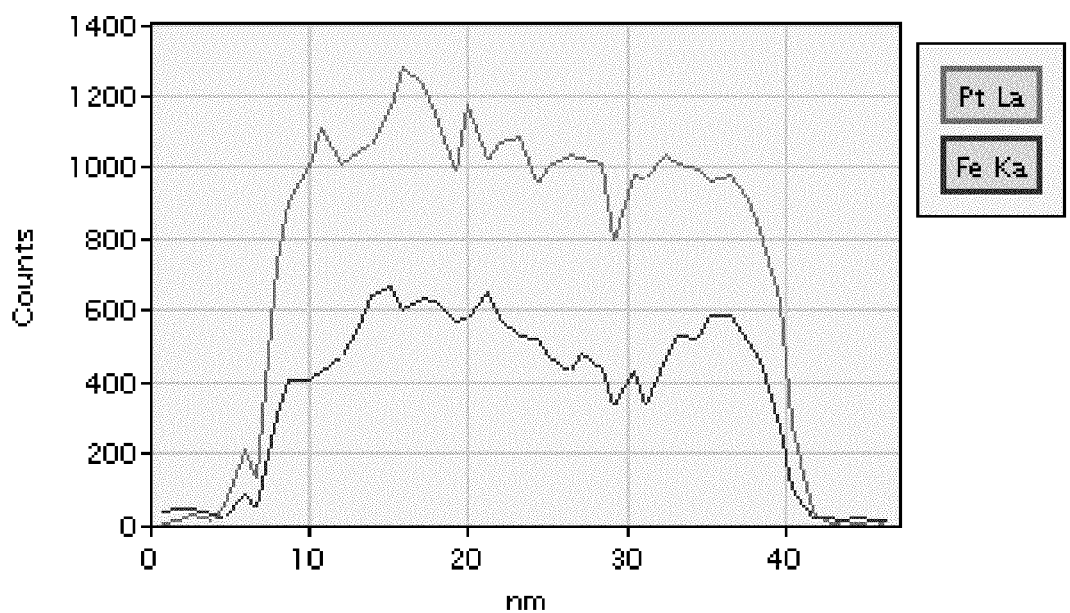
FIG. 151 provides EDX line scan analysis results described in Example 60.
Figure 152:
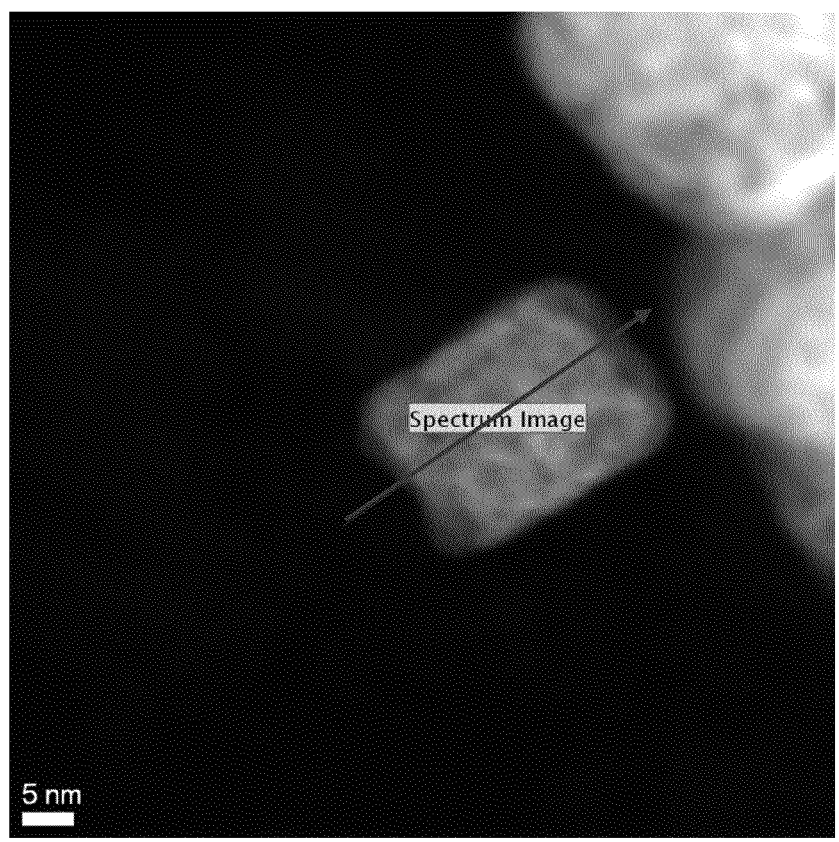
FIG. 152 is an STEM micrograph described in Example 60.
Figure 153:
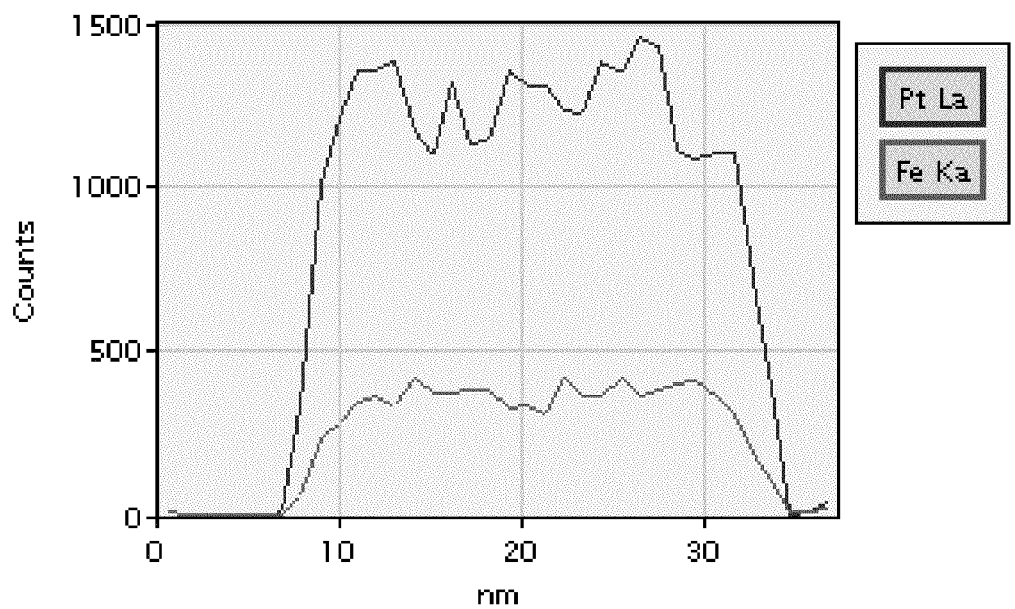
FIG. 153 provides EDX line scan analysis described in Example 60.

FIG. 150 is an STEM micrograph and FIG. 151 the corresponding EDX line scan analysis results. FIG. 152 is an STEM micrograph and FIG. 153 the corresponding EDX line scan analysis results. These results indicate a platinum-rich composition throughout the particles analyzed due to leaching of iron from the core, i.e., inner regions of the particles to form porous platinum-rich particles.

Example 61

This example details preparation of a catalyst precursor having a nominal Pt content of 2 wt. % and a nominal iron content of 3.5 wt. % on an activated carbon support having a Langmuir surface area of approximately 1500 m²/g. The following preparation was conducted under nitrogen protection.

Activated carbon support (approximately 10.457 g) was introduced into a baffled beaker under a nitrogen atmosphere. $FeCl_3.6H_2O$ (approximately 1.753 g) and sucrose (approximately 4.455 g) were dissolved in degassed water (approximately 90 g). 50 wt. % NaOH (approximately 4.613 g) was added to and mixed with the $FeCl_3.6H_2O$-sucrose solution. The $FeCl_3.6H_2O$-sucrose solution was then poured into the baffled beaker, and allowed to mix with the activated carbon support. The slurry was then heated a temperature of approximately 60° C. over a period of 10 minutes.

Ethylene glycol (approximately 1.200 g) was added to the baffled beaker and allowed to mix with the slurry for approximately ten minutes at approximately 60° C. The slurry was then filtered, and the wet cake was then re-slurried in degassed deionized water (90 g) and introduced into the baffled beaker. The pH of the resulting slurry was then lowered to approximately 6 by addition of degassed 1M HCl (3.6 g).

$K_2PtCl_4$ (approximately 0.452 g) was dissolved in degassed water (approximately 20 g) to form a platinum solution that was introduced into the baffled beaker over a period of approximately 3 minutes. The resulting slurry was then allowed to mix at ambient conditions (approximately 22° C.) for approximately 15 minutes, and then heated to a temperature of approximately 40° C. over a period of approximately 12 minutes.

The final slurry was then filtered and the wet cake was hot washed twice by contact with degassed water (approximately 100 g) at a temperature of approximately 60° C. The resulting sample was then dried in a vacuum oven at approximately 110° C. for approximately 12 hours with a small nitrogen stream.

The catalyst precursor was then heated at elevated temperatures up to approximately 755° C. in the presence of a hydrogen/argon stream (4%/96%; v/v) for approximately 120 minutes.

Figure 154:
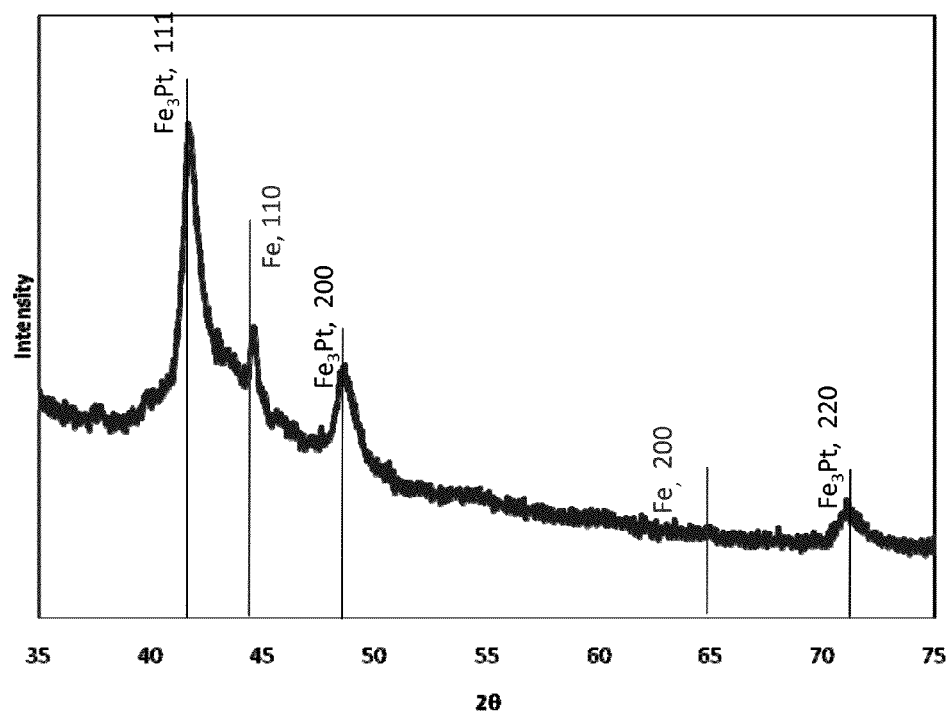
FIGS. 154 and 155 provide XRD results described in Example 61.

FIG. 154 provides XRD analysis results for the finished 2% Pt/3.5% Fe catalyst, which indicate formation of a $Fe_3Pt$ phase.

Figure 155:
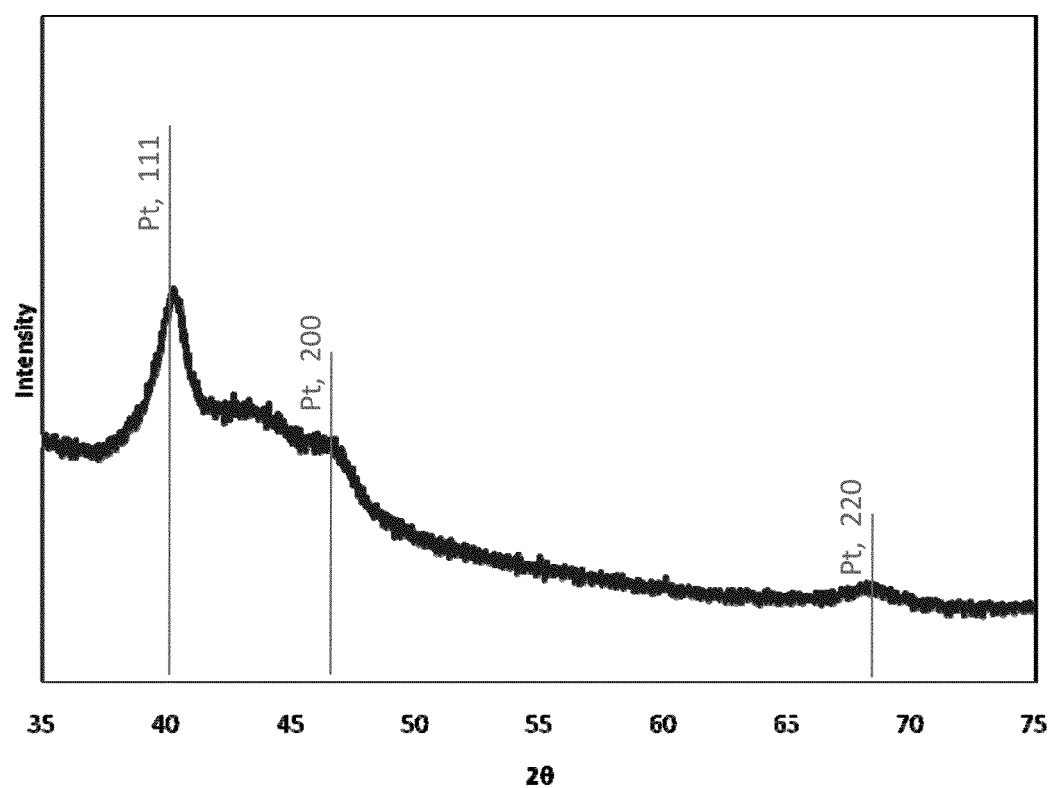

Table 28 sets forth PMIDA reaction testing results, platinum leaching data, and iron leaching data for the finished catalyst. FIG. 155 provides XRD analysis results for the catalyst after reaction testing (i.e., the spent catalyst). These results indicate formation of a Pt phase.

TABLE 28

| Cycle | 1 | 2 | 3 | 4 | 5 | 6 | 7 | 8 | 9 | 10 |
|---|---|---|---|---|---|---|---|---|---|---|
| Total $CO_2$ (cc) | 1785.7 | 1841.8 | 1913.6 | 1928.1 | 1970.6 | 1956.8 | 1956.0 | 1947.8 | 1967.6 | 1602.0 |
| End point(min) | 43.83 | 41.67 | 39.83 | 40.17 | 40.42 | 40.75 | 40.58 | 41.83 | 41.67 | 42.75 |
| Maximum $CO_2$ Concentration (%) | 35.4 | 36.0 | 36.9 | 36.9 | 36.2 | 35.7 | 36.2 | 35.1 | 35.4 | 34.7 |
| PMIDA (wt. %) | ND | | 0.003 | | 0.004 | | 0.004 | | 0.004 | 0.143 |
| Glyphosate(wt. %) | 5.169 | | 5.405 | | 5.405 | | 5.343 | | 5.446 | 5.430 |
| IDA(wt. %) | 0.085 | | 0.045 | | 0.039 | | 0.038 | | 0.036 | 0.036 |
| $CH_2O$(ppm) | 3172 | | 2624 | | 2341 | | 2272 | | 2068 | 2612 |
| HCOOH(ppm) | 6258 | | 6539 | | 6489 | | 6391 | | 6313 | 6465 |
| Pt(ppm) | 0.011 | | 0.013 | | 0.014 | | 0.016 | | 0.016 | 0.022 |
| Fe(ppm) | 24.680 | | 2.502 | | 0.584 | | 0.487 | | 0.363 | 0.362 |

Example 61A

This example details preparation of a catalyst having a nominal Pt content of 2 wt. % and a nominal iron content of 4 wt. % on an activated carbon support having a Langmuir surface area of approximately 1500 m²/g. The following preparation was conducted under nitrogen protection.

Activated carbon (approximately 10.456 g) and degassed water (approximately 90 g) were mixed in a baffled beaker and allowed to mix for 20 minutes.

$FeCl_3.6H_2O$ (approx. 2.009 g) was dissolved in degassed water (40 g) and this solution was then pumped into the baffled beaker over a period of 30 minutes while maintaining the pH of the slurry at 4 with 2.5N NaOH, as necessary. After addition of the $FeCl_3.6H_2O$ solution to the beaker was completed, the pH of the slurry was raised to 4.5 and allowed to mix for 10 minutes.

The slurry was then heated to approximately 60° C. over a period of approximately 30 minutes. During the heating, the pH was maintained at 4.5. The pH of the slurry was then raised to 11 over a period of 30 minutes, and then allowed to mix for 10 minutes. Ethylene glycol (1.388 g) was then added to the slurry, and allowed to mix at approximately 60° C. for approximately 10 minutes. The slurry was then filtered, and the wet cake was then re-slurried in the baffled in degassed deionized water (approx. 90 g).

The pH of the solution was then lowered to 7 by addition of 0.5M degassed HCl. $K_2PtCl_4$ (0.460 g) was dissolved in 20 mL of degassed water. The Pt solution was then pumped into the baffled beaker over a period of 30 minutes. The resulting slurry was then allowed to mix at ambient conditions (approx. 20° C.) for approximately 30 minutes, and then heated to a temperature of approximately 60° C. over a period of 10 minutes.

The resulting slurry was then filtered and washed twice by contact with degassed water (approx. 100 g) at a temperature of approximately 60° C. The sample was then dried in a vacuum oven at approximately 110° C. for 12 hours with a small nitrogen stream to form a Pt/Fe catalyst precursor.

The catalyst precursor was then heated at elevated temperatures up to approximately 650° C. in the presence of a hydrogen/argon stream (4%/96%; v/v) for approximately 120 minutes.

V. Platinum-Cobalt

Example 62

This example details preparation of a catalyst having a nominal platinum content of approximately 2 wt. % and a nominal cobalt content of approximately 4 wt. % on an activated carbon support having a Langmuir surface area of approximately 1500 m$^2$/g. The following preparation was conducted under nitrogen protection.

$CoCl_2$ (1.686 g) and sucrose (4.499 g) were dissolved in degassed water (89.4 mL) in a screw top jar that had been flushed with nitrogen. To this mixture was added 50 wt. % sodium hydroxide (5.209 g), the jar was flushed with nitrogen, and the solution was then mixed for one minute.

Activated carbon support (10.458 g) was added to a 400 mL baffled beaker and the $CoCl_2$ solution was then poured into the baffled beaker, the beaker was flushed with nitrogen, and the components were allowed to mix at room temperature for approximately five minutes. The resulting solution was then heated to approximately 60° C. over a period of approximately forty minutes. Ethylene glycol (approx. 1.272 g) was then added, and the resulting solution was allowed to mix at approximately 60° C. for approximately twenty minutes.

The solution was then filtered on a fritted glass filter, the resulting wet cake was returned to the baffled beaker. The pH of the solution was reduced to approximately 4.7 by addition of HCl (2M).

$K_2PtCl_4$ (approx. 0.460 g) was dissolved in degassed water (20 ml) and the platinum solution was added to the baffled beaker drop-wise over a period of approximately three minutes. The resulting solution was allowed to mix at approximately 25° C. for approximately sixty minutes. The solution was then heated to approximately 60° C. over a period of approximately twenty minutes. The resulting solution was then filtered, and the filtrate was hot washed twice with in degassed water (120 ml) at approximately 60° C. The sample was then dried in a vacuum oven at 110° C. for 12 hours with a nitrogen stream.

The catalyst precursor was then heated at elevated temperatures up to approximately 900° C. in the presence of a hydrogen/argon stream (4%/96%; v/v) for approximately 120 minutes.

Example 63

This example details preparation of a catalyst precursor having a nominal platinum content of 2 wt. % and a cobalt content of 4 wt. % on an activated carbon support having a Langmuir surface area of approximately 1500 m$^2$/g. The following preparation was conducted under nitrogen protection.

Activated carbon (10.458 g) was placed in a baffled beaker. $CoCl_2.6H_2O$ (1.685 g) and sucrose (4.566 g) were mixed with degassed water (89.2 ml) and allowed to dissolve. 5.154 g of 50 wt. % sodium hydroxide was added to the cobalt solution and allowed to mix. The resulting $CoCl_2.6H_2O$ solution was then poured into the baffled beaker with carbon, and allowed to mix.

The resulting slurry was then heated to approximately 60° C. over a period of twenty minutes. Sodium borohydride (approx. 0.558 g) was dissolved in degassed water (20 ml) to which 2.5N degassed NaOH (0.329 g) was then added. The sodium borohydride solution was added to the baffled beaker at approximately 60° C. over a period of approximately twenty minutes, and then allowed to mix for ten additional minutes. The slurry was then filtered, and the wet cake was washed twice at approximately 60° C. The resulting wet cake was then re-slurried in degassed deionized water (90 g).

The pH of the solution was reduced to approximately 5 by addition of degassed 2M HCl. $K_2PtCl_4$ (0.459 g) was dissolved in degassed water (20 ml). The Pt solution was then added to the baffled beaker over a period of approximately three minutes. The slurry was then allowed to mix at approximately 25° C. for approximately 40 minutes, and then heated to a temperature of approximately 40° C.

The resulting slurry was then filtered, and the wet cake was washed twice with hot water (approx. 100 ml) at approx. 60° C. The resulting sample was then dried in a vacuum oven at approximately 110° C. for 12 hours with a small nitrogen stream.

VI. Platinum-Tin

Example 64

The following preparation was conducted under nitrogen protection. Activated carbon (10.457 g) was placed in a baffled beaker and mixed with degassed water (100 ml).

$SnCl_4.5H_2O$ (2.545 g) and $K_2PtCl_4$ (0.463 g) were dissolved in degassed water (20 ml). The Sn/Pt solution was then pumped into the baffled beaker over a period of approximately twenty-three minutes. The temperature and pH of the Sn/Pt solution were raised simultaneously to approximately 60° C. and approximately 7, respectively, over a period of approximately forty five minutes. The solution was allowed to mix for approximately thirty minutes.

$NaBH_4$ (1.310 g) was dissolved in degassed water (10 ml) and this solution was added to the baffled beaker over a twenty minute period. The resulting slurry was then allowed to mix for approximately twenty minutes, the slurry filtered, and the wet cake was hot washed twice with approximately 100 ml of degassed water at approximately 60° C. The resulting sample was then dried in a vacuum oven at 110° C. for 12 hours with a small nitrogen stream.

The catalyst precursor was then heated at elevated temperatures up to approximately 545° C. in the presence of a hydrogen/argon stream (2%/98%; v/v) for approximately 120 minutes.

VII. Platinum-Copper

Example 65

The following preparation was conducted under nitrogen protection.

Preparation of nominal 2% Pt4% Cu on activated carbon: The following was added to a baffled beaker including approx. 10 g of activated carbon: 1.64 g of $CuSO_4 \cdot 5H_2O$ solution, 4.51 g of sucrose, 90 g of degassed deionized water, and 4.63 g of 50 wt. % NaOH. The mixture was heated to approx. 40° C. and stirred for approx. 10 minutes with a mechanical agitator. To this slurry was added 1.71 g of 37% formaldehyde diluted to 17.1 g with degassed deionized water. The resulting slurry was heated to approx. 40° C. along with continued stirring for approx. 30 minutes (or until solution became colorless). Then the slurry was filtered, washed once in the filter, and then re-slurried in water to pH 2.02 by adding 1M degassed HCl. A solution of 0.454 g of $K_2PtCl_4$ in 10 g of degassed water was then added to the slurry, along with continued stirring for approx. 30 minutes at ambient conditions. Then the slurry was heated to approx. 60° C. and stirred for approx. 30 more minutes. This slurry was then filtered and washed with water, and dried under vacuum at approx. 110° C. under a small stream of nitrogen. A total of 11.720 g of dried material was recovered. During heat treatment to a maximum temperature of approximately 950° C. in the presence of an argon/hydrogen atmosphere (2%/98%) (v/v) for approximately 120 minutes, the sample lost 13.5% weight.

$K_2PtCl_4$ (approximately 0.427 g) was dissolved in degassed water (approximately 20 g) to form a platinum solution that was introduced into the baffled beaker over a period of approximately 3 minutes. The resulting slurry was then allowed to mix at ambient conditions (approximately 22° C.) for approximately 30 minutes, and then heated to a temperature of approximately 60° C., and then mixed for approximately an additional 30 minutes.

The final slurry was then filtered and the wet cake was hot washed twice at 60° C. by contact with degassed water (approximately 100 g). The resulting sample was dried in a vacuum oven at approximately 110° C. for approximately 12 hours with a small nitrogen stream.

The catalyst precursor was then heated at elevated temperatures up to approximately 950° C. in the presence of a hydrogen/argon stream (2%/98%; v/v) for approximately 120 minutes.

Table 29 sets forth PMIDA reaction testing results, platinum leaching data, and iron leaching data for the finished catalyst.

TABLE 29

| Cycle | 1 | 2 | 3 | 4 | 5 | 6 | 7 | 8 | 9 | 10 |
|---|---|---|---|---|---|---|---|---|---|---|
| Total $CO_2$ (cc) | 1916.9 | 2049.0 | 2048.7 | 2037.5 | 2010.9 | 1996.5 | 1995.9 | 1918.9 | 1920.4 | 1601.5 |
| End point(min) | 49.00 | 43.50 | 42.00 | 42.17 | 42.33 | 42.33 | 41.58 | 44.42 | 44.92 | 45.07 |
| Maximum $CO_2$ Concentration (%) | 29.8 | 32.6 | 33.7 | 33.9 | 34.6 | 34.9 | 36.9 | 33.9 | 33.8 | 33.9 |
| PMIDA (wt. %) | 0.007 | | 0.004 | | 0.006 | | 0.005 | | 0.005 | 0.217 |
| Glyphosate(wt. %) | 5.476 | | 5.553 | | 5.492 | | 5.511 | | 5.474 | 5.443 |
| IDA(wt. %) | 0.051 | | 0.021 | | 0.018 | | 0.019 | | 0.019 | 0.018 |
| $CH_2O$(ppm) | 2208 | | 2057 | | 1905 | | 2105 | | 1876 | 2517 |
| HCOOH(ppm) | 4743 | | 4945 | | 5234 | | 5567 | | 5780 | 5802 |
| Pt(ppm) | 0.023 | | 0.031 | | 0.033 | | 0.039 | | 0.046 | 0.068 |
| Fe(ppm) | 16.930 | | 0.953 | | 0.553 | | 0.387 | | 0.284 | 0.247 |

Figure 155A:
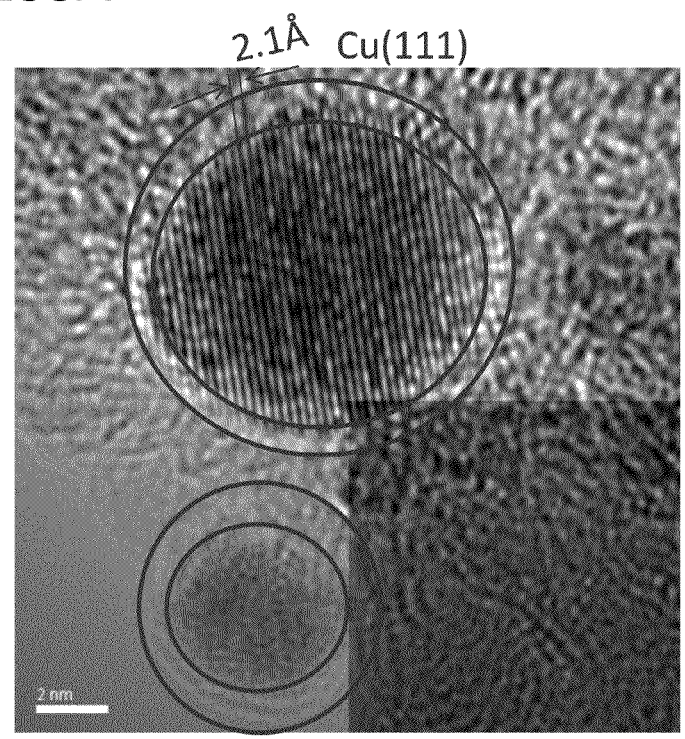
FIGS. 155A and 155B provide microscopy results for a finished catalyst as described in Example 65.
Figure 155B:
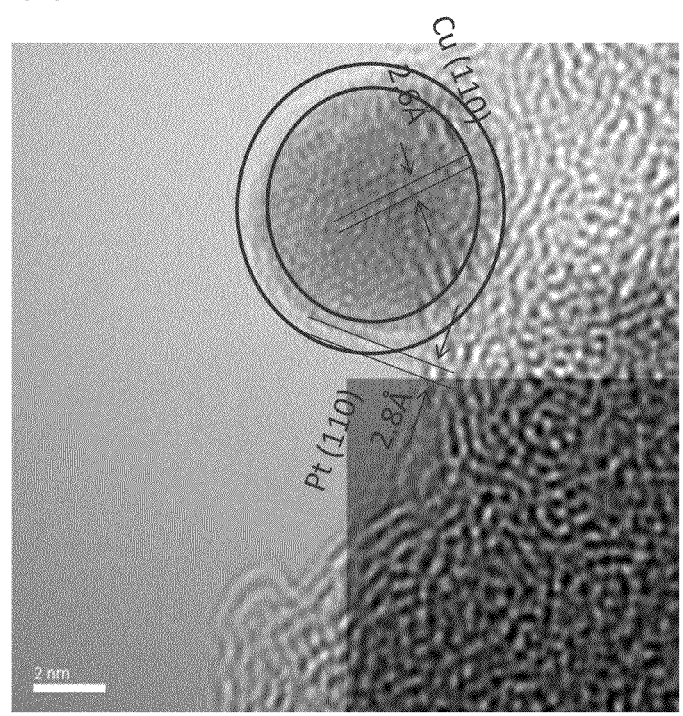
Figure 155C:
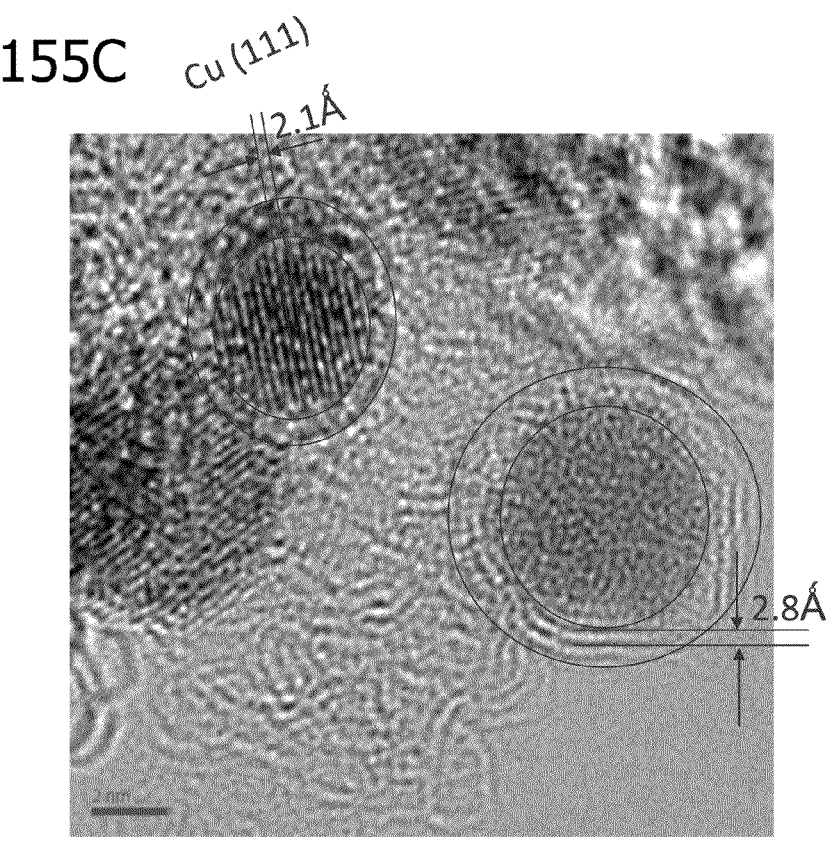
FIGS. 155C-155F provide microscopy results for a finished catalyst described in Example 65.
Figure 155D:
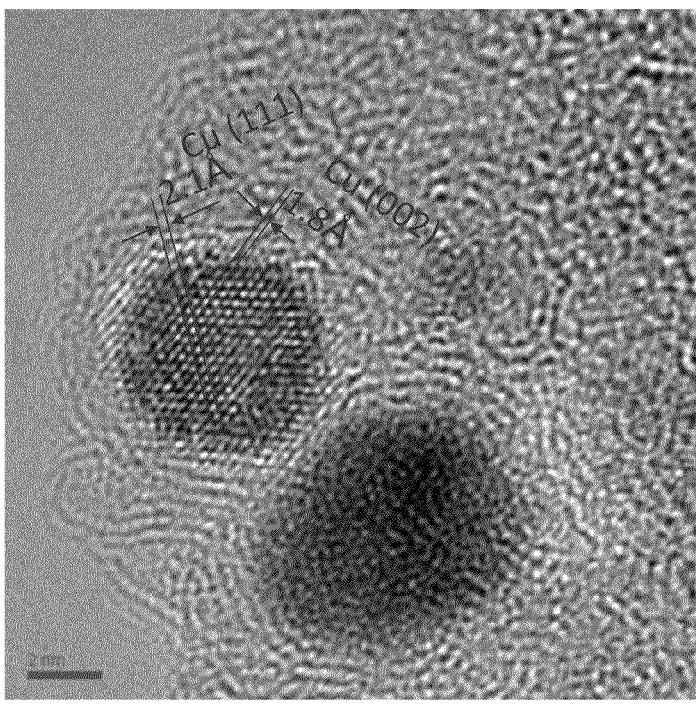
Figure 155E:
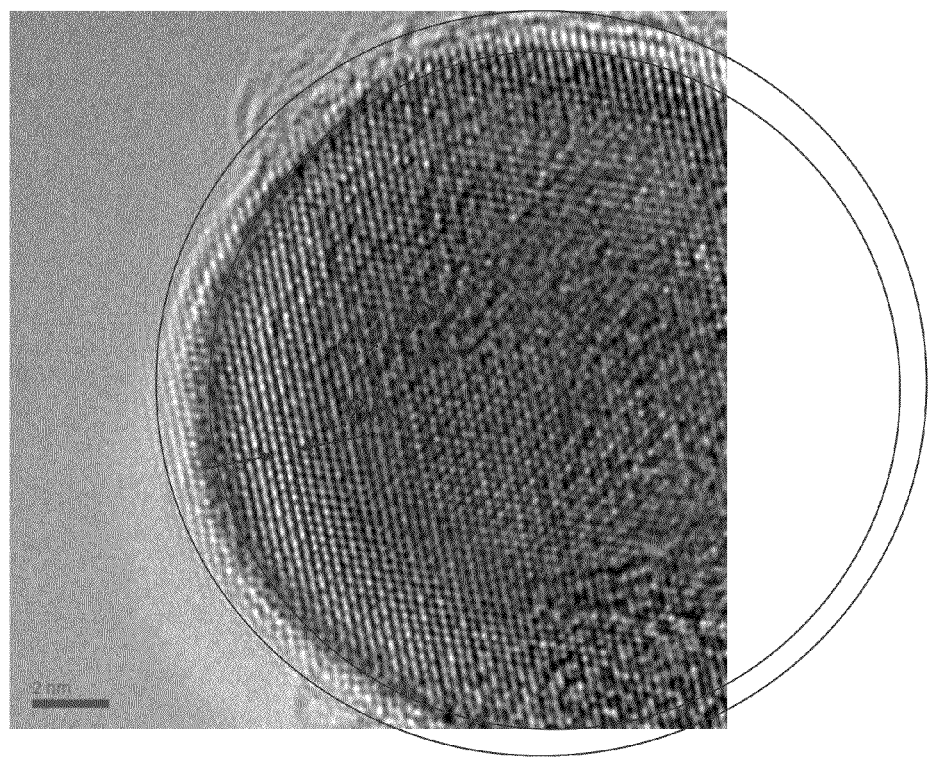
Figure 155F:
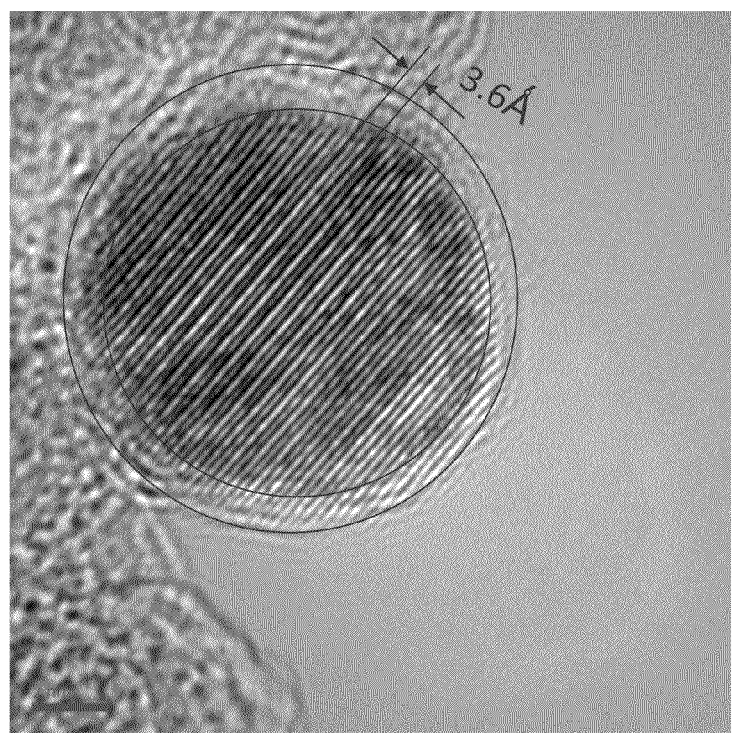

FIGS. 155A and 155B include microscopy results for the finished catalyst. FIGS. 155C-155F include microscopy results for the catalyst after testing in PMIDA oxidation.

Example 66

This example details preparation of a catalyst having a nominal Pt content of 2 wt. % and a nominal copper content of 3.75 wt. % on an activated carbon support having a Langmuir surface area of approximately 1500 $m^2/g$. The following preparation was conducted under nitrogen protection.

Activated carbon support (approximately 10.457 g) was introduced into a baffled beaker under a nitrogen atmosphere. $CuSO_4 \cdot 5H_2O$ (approximately 1.540 g) and sucrose (approximately 4.225 g) were dissolved in degassed water (approximately 91 g). 50 wt. % NaOH (approximately 4.370 g) was added to and mixed with the $CuSO_4 \cdot 5H_2O$-sucrose solution, and the resulting solution was then poured into the baffled beaker, and allowed to mix with the activated carbon support at a temperature of approximately 29° C. for approximately 20 minutes.

Formaldehyde (37%) (approximately 1.604 g) was added to the baffled beaker and allowed to mix with the slurry for approximately eighty four minutes at approximately 29° C. The slurry was then filtered, and the wet cake was then re-slurried in degassed deionized water (90 g) and introduced into the beaker. The pH of the resulting slurry was then lowered to approximately 4 by addition of degassed 1M HCl.

VIII. Testing Protocols

Example 67

Protocol A

The following example details CO chemisorption analysis used to determine the exposed metal surface areas of catalysts prepared as described herein. The method described in this example is referenced in this specification and appended claims as "Protocol A."

This protocol subjects a single sample to two sequential CO chemisorption cycles.

Cycle 1 measures initial exposed noble metal at zero valence state. The sample is vacuum degassed and treated with oxygen. Next, residual, un-adsorbed oxygen is removed and the catalyst is then exposed to CO. The volume of CO taken up irreversibly is used to calculate initial noble metal (e.g., $Pt^0$) site density.

Cycle 2 measures total exposed noble metal. Without disturbing the sample after cycle 1, it is again vacuum degassed and then treated with flowing hydrogen, and again degassed. Next the sample is treated with oxygen. Finally, residual, non-adsorbed oxygen is removed and the catalyst is then again exposed to CO. The volume of CO taken up irreversibly is used to calculate total exposed noble metal (e.g., $Pt^0$) site density. See, for example, Webb et al., *Analytical Methods in*

*Fine Particle Technology*, Micromeritics Instrument Corp., 1997, for a description of chemisorption analysis. Sample preparation, including degassing, is described, for example, at pages 129-130.

Equipment:

Micromeritics (Norcross, Ga.) ASAP 2010~static chemisorption instrument; Required gases: UHP hydrogen; carbon monoxide; UHP helium; oxygen (99.998%); Quartz flow through sample tube with filler rod; two stoppers; two quartz wool plugs; Analytical balance.

Preparation:

Insert quartz wool plug loosely into bottom of sample tube. Obtain tare weight of sample tube with 1st wool plug. Preweigh approximately 0.25 grams of sample then add this on top of the 1st quartz wool plug. Precisely measure initial sample weight. Insert 2nd quartz wool plug above sample and gently press down to contact sample mass, then add filler rod and insert two stoppers. Measure total weight (before degas): Transfer sample tube to degas port of instrument then vacuum to <10 µm Hg while heating under vacuum to 150° C. for approximately 8-12 hours. Release vacuum. Cool to ambient temperature and reweigh. Calculate weight loss and final degassed weight (use this weight in calculations).

Cycle 1:

Secure sample tube on analysis port of static chemisorption instrument. Flow helium (approximately 85 cm/minute) at ambient temperature and atmospheric pressure through sample tube, then heat to 150° C. at 5° C./minute. Hold at 150° C. for 30 minutes. Cool to 30° C.

Evacuate sample tube to <10 µm Hg at 30° C. Hold at 30° C. for 15 minutes. Close sample tube to vacuum pump and run leak test. Evacuate sample tube while heating to 70° C. at 5° C./min. Hold for 20 minutes at 70° C.

Flow oxygen (approximately 75 cm/minute) through sample tube at 70° C. and atmospheric pressure for 50 minutes.

Evacuate sample tube at 70° C. for 5 minutes.

Flow helium (approximately 85 $cm^3$/minute) through sample tube at atmospheric pressure and increase to 80° C. at 5° C./minute. Hold at 80° C. for 15 minutes.

Evacuate sample tube at 80° C. for 60 minutes and hold under vacuum at 80° C. for 60 minutes. Cool sample tube to 30° C. and continue evacuation at 30° C. for 30 minutes. Close sample tube to vacuum pump and run leak test.

Evacuate sample tube at 30° C. for 30 minutes and hold under vacuum at 30° C. for 30 minutes.

For a first CO analysis, CO uptakes are measured under static chemisorption conditions at 30° C. and starting manifold pressures of 50, 100, 150, 200, 250, 300, 350 and 400 mm Hg (gauge) to determine the total amount of CO adsorbed (i.e., both chemisorbed and physisorbed).

Pressurize manifold to the starting pressure (e.g., 50 mm Hg). Open valve between manifold and sample tube allowing CO to contact the sample in the sample tube. Allow the pressure in the sample tube to equilibrate. The reduction in pressure from the starting manifold pressure to equilibrium pressure in the sample tube indicates the volume of CO uptake by the sample.

Close valve between the manifold and sample tube and pressurize the manifold to the next starting pressure (e.g., 100 mm Hg). Open valve between manifold and sample tube allowing CO to contact the sample in the sample tube. Allow the pressure in the sample tube to equilibrate to determine the volume of CO uptake by the sample. Perform for each starting manifold pressure.

Evacuate sample tube at 30° C. for 30 minutes.

For a second CO analysis, CO uptakes are measured under static chemisorption conditions at 30° C. and starting manifold pressures of 50, 100, 150, 200, 250, 300, 350 and 400 mm Hg (gauge) as described above for the first CO analysis to determine the total amount of CO physisorbed.

Cycle 2:

After the second CO analysis of Cycle 1, flow helium (approximately 85 cm/minute) at 30° C. and atmospheric pressure through sample tube then heat to 150° C. at 5° C./minute. Hold at 150° C. for 30 minutes.

Cool to 30° C. Evacuate sample tube to <10 µm Hg at 30° C. for 15 minutes. Hold at 30° C. for 15 minutes.

Close sample tube to vacuum pump and run leak test.

Evacuate sample tube at 30° C. for 20 minutes.

Flow hydrogen (approximately 150 $cm^3$/minute) through sample tube at atmospheric pressure while heating to 150° C. at 10° C./min. Hold at 150° C. for 15 minutes.

Evacuate sample tube at 150° C. for 60 minutes. Cool sample tube to 70° C. Hold at 70° C. for 15 minutes.

Flow oxygen (approximately 75 cm/minute) through sample tube at atmospheric pressure and 70° C. for 50 minutes.

Evacuate sample tube at 70° C. for 5 minutes.

Flow helium (approximately 85 $cm^3$/minute) through sample tube at atmospheric pressure and increase temperature to 80° C. at 5° C./minute. Hold at 80° C. for 15 minutes. Evacuate sample tube at 80° C. for 60 minutes. Hold under vacuum at 80° C. for 60 minutes.

Cool sample tube to 30° C. and continue evacuation at 30° C. for 30 minutes. Close sample tube to vacuum pump and run leak test.

Evacuate sample tube at 30° C. for 30 minutes and hold for 30 minutes.

For a first CO analysis, CO uptakes are measured under static chemisorption conditions at 30° C. and starting manifold pressures of 50, 100, 150, 200, 250, 300, 350 and 400 mm Hg (gauge) to determine the total amount of CO adsorbed (i.e., both chemisorbed and physisorbed).

Pressurize manifold to the starting pressure (e.g., 50 mm Hg). Open valve between manifold and sample tube allowing CO to contact the sample in the sample tube. Allow the pressure in the sample tube to equilibrate. The reduction in pressure from the starting manifold pressure to equilibrium pressure in the sample tube indicates the volume of CO uptake by the sample.

Close valve between the manifold and sample tube and pressurize the manifold to the next starting pressure (e.g., 100 mm Hg). Open valve between manifold and sample tube allowing CO to contact the sample in the sample tube. Allow the pressure in the sample tube to equilibrate to determine the volume of CO uptake by the sample. Perform for each starting manifold pressure.

Evacuate sample tube at 30° C. for 30 minutes.

For a second CO analysis, CO uptakes are measured under static chemisorption conditions at 30° C. and starting manifold pressures of 50, 100, 150, 200, 250, 300, 350 and 400 mm Hg (gauge) as described above for the first CO analysis to determine the total amount of CO physisorbed.

Calculations:

Plot first and second analysis lines in each cycle: volume CO physically adsorbed and chemisorbed (1st analysis) and volume CO physically adsorbed (2nd analysis) ($cm^3$/g at STP) versus target CO pressures (mm Hg). Plot the difference between First and Second analysis lines at each target CO pressure. Extrapolate the difference line to its intercept with the Y-axis. In Cycle 1, total exposed $Pt_0$ (µmole CO/g)=Y- intercept of difference line/22.414×1000. In Cycle 2, total exposed Pt (μmole CO/g)=Y-intercept of difference line/22.414×1000.

Example 68

Microscopy: Protocol B

This Example details microscopy analysis of catalyst samples of the present invention.
High Resolution Electron Micrographs (HREM):
HREM for various catalyst samples were generated using a Jeol 2100 field emission gun (FEG) transmission electron microscope (TEM) operated at an accelerating voltage of 200 keV. Samples were placed in the holder as-is without carbon interference (i.e., the samples were not microtomed and embedded in an organic-containing material such as an epoxy), and under conditions that identified lattice fringe rings.
Atomic Layer Measurements:
Lattice d spacings of catalyst particles identified by TEM were measured. These measurements were calibrated based on the known d spacing (3.84 Å) of single crystal silicon (110) that was also analyzed using the Jeol 2100 FEG TEM at the same magnification and accelerating voltage (200 KeV). The measurements were recorded and analyzed using Digital Micrograph software. The number of atomic layers of platinum for the particles analyzed was determined based from the number of repeating lattice fringe rings observed in the HREM micrographs.
Line Scan Analysis:
Energy dispersive x-ray spectroscopy (EDX) line scan analysis was conducted using the Jeol 2100 FEG TEM operated in scanning transmission electron microscopy (STEM) mode. The probe size was 1 nm.
Electron energy loss spectroscopy (EELS) line scan analysis was conducted using the Jeol 2100 FEG TEM operated in STEM mode with a probe size of 0.5 nm.

Example 69

X-Ray Diffraction

This example details the method utilized for X-Ray Diffraction (XRD) analysis for the results reported herein. Powder samples (less than approx. 0.2 g) were compacted using a pellet press to form sample pellets for analysis. The sample pellet was placed on a plastic sample holder for analysis in a Bruker D8 Discover Diffractometer.
CuK$\alpha$X radiation ($\lambda_{CuK\alpha}$=1.5418 Å) was produced in a sealed Cu tube at 40 kV and 40 mA. Prior to the experiment, a korundum sample was used to adjust any peak misalignments.
The sample holder was placed on the XYZ stage and analyzed in locked coupled scan mode; the gun and detector angles were kept at the same value (i.e., $\theta_1=\theta_2$). XRD data were collected using a LynxEye® Position Sensitive Detector (PSD) which is $10^3$ times more sensitive than regular XRD. For each sample, an XRD spectrum was collected within the 0-90° 2θ range with a step size of 0.02° and a total collection time of approx. 3 hours.

Example 70

Pore Volume and Surface Area Analysis

Various metal-impregnated supports and catalysts were generally analyzed to determine surface area and pore volume data as reported herein using a Micromeritics 2010 Micropore analyzer with a one-torr transducer and a Micromeritics 2020 Accelerated Surface Area and Porosimetry System, also with a one-torr transducer. These analysis methods are described in, for example, Analytical Methods in fine Particle Technology, First Edition, 1997, Micromeritics Instrument Corp.; Atlanta, Ga. (USA); and Principles and Practice of Heterogeneous Catalysis, 1997, VCH Publishers, Inc; New York, N.Y. (USA).

The present invention is not limited to the above embodiments and can be variously modified. The above description of the preferred embodiments, including the Examples, is intended only to acquaint others skilled in the art with the invention, its principles, and its practical application so that others skilled in the art may adapt and apply the invention in its numerous forms, as may be best suited to the requirements of a particular use.

With reference to the use of the word(s) comprise or comprises or comprising in this entire specification (including the claims below), unless the context requires otherwise, those words are used on the basis and clear understanding that they are to be interpreted inclusively, rather than exclusively, and applicants intend each of those words to be so interpreted in construing this entire specification.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

What is claimed is:

1. An oxidation catalyst comprising a particulate carbon support, a first metal, and platinum, the support having at its surface metal particles comprising the first metal and platinum, wherein the first metal is selected from the group consisting of cobalt, copper, iron, and combinations thereof, and:
the platinum distribution within at least one of said first metal and platinum-containing particles as characterized by EDX line scan analysis produces a platinum signal that varies by no more than about 25% across a scanning region having a dimension that is at least about 70% of the largest dimension of the at least one particle and wherein first metal and platinum-containing particles at the surface of the carbon support comprise a core comprising the first metal and a shell at least partially surrounding the core and comprising platinum, the shell having a thickness of no more than two platinum atoms.

2. The oxidation catalyst as set forth in claim 1 wherein the platinum signal varies by no more than about 20% across the scanning region.

3. The oxidation catalyst as set forth in claim 1 wherein the atomic ratio of platinum to first metal of the at least one particle is less than 1:1.

4. The oxidation catalyst as set forth in claim 1 wherein the at least one particle has a largest dimension of at least about 6 nm.

5. The oxidation catalyst as set forth in claim 1 wherein the at least one particle constitutes at least about 1% of the metal particles at the surface of the carbon support.

6. The oxidation catalyst as set forth in claim 1 wherein the first metal distribution of the at least one metal particle as characterized by EDX line scan analysis produces a first metal signal, the ratio of the maximum first metal signal to the maximum platinum signal across the scanning region being at least about 1.5:1.

7. The oxidation catalyst as set forth in claim 1 wherein the first metal is iron.

8. The oxidation catalyst as set forth in claim 1 wherein the first metal is cobalt, copper or a combination thereof.

9. The oxidation catalyst as set forth in claim 1 wherein the first metal constitutes at least about 1% by weight of the catalyst.

10. The oxidation catalyst as set forth in claim 1 wherein the first metal constitutes from about 1% to about 10% by weight of the catalyst.

11. The oxidation catalyst as set forth in claim 1 wherein platinum constitutes at least about 1% by weight of the catalyst.

12. The oxidation catalyst as set forth in claim 1 wherein platinum constitutes less than about 8% by weight of the catalyst.

13. The oxidation catalyst as set forth in claim 1 wherein platinum constitutes from about 1% to about 5% by weight of the catalyst.

14. The oxidation catalyst as set forth in claim 1 wherein at least about 10% of the platinum is present within the shell of the metal particles.

15. The oxidation catalyst as set forth in claim 1 wherein the atom percent of platinum at the surface of first metal and platinum-containing particles at the surface of the carbon support is at least about 2%.

16. An oxidation catalyst comprising a particulate carbon support, a first metal, and platinum, the support having at its surface metal particles comprising the first metal and platinum, wherein the first metal is selected from the group consisting of cobalt, copper, iron, and combinations thereof, and:
 the platinum distribution within at least one of said first metal and platinum-containing particles as characterized by EDX line scan analysis produces a platinum signal that varies by no more than about 20% across a scanning region having a dimension that is at least about 60% of the largest dimension of the at least one particle and wherein first metal and platinum-containing particles at the surface of the carbon support comprise a core comprising the first metal and a shell at least partially surrounding the core and comprising platinum, the shell having a thickness of no more than two platinum atoms.

17. The oxidation catalyst as set forth in claim 16 wherein the platinum signal varies by no more than about 15% across the scanning region.

18. An oxidation catalyst comprising a particulate carbon support, a first metal, and platinum, the support having at its surface metal particles comprising the first metal and platinum, wherein the first metal is selected from the group consisting of cobalt, copper, iron, and combinations thereof, and:
 the platinum distribution within at least one of said first metal and platinum-containing particles as characterized by EDX line scan analysis produces a platinum signal that varies by no more than about 15% across a scanning region having a dimension that is at least about 50% of the largest dimension of the at least one particle and wherein first metal and platinum-containing particles at the surface of the carbon support comprise a core comprising the first metal and a shell at least partially surrounding the core and comprising platinum, the shell having a thickness of no more than two platinum atoms.

19. The oxidation catalyst as set forth in claim 18 wherein the platinum signal varies by no more than about 10% across the scanning region.

20. An oxidation catalyst comprising a particulate carbon support, platinum, and copper, the support having at its surface metal particles comprising platinum and copper, wherein the atom percent of platinum at the surface of the particles is at least about 40% and wherein metal particles comprising platinum and copper at the surface of the carbon support comprise a core comprising copper and a shell at least partially surrounding the core and comprising platinum, the shell having a thickness of no more than two platinum atoms.

\* \* \* \* \*